US009259488B2

(12) United States Patent
Holers et al.

(10) Patent No.: US 9,259,488 B2
(45) Date of Patent: Feb. 16, 2016

(54) ANTI-C3D ANTIBODY CONJUGATES AND METHODS OF DETECTING COMPLEMENT ACTIVATION

(71) Applicant: The Regents of the University of Colorado, a Body Corporate, Denver, CO (US)

(72) Inventors: V. Michael Holers, Denver, CO (US); Joshua M. Thurman, Greenwood Village, CO (US); Liudmila Kulik, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 14/624,347

(22) Filed: Feb. 17, 2015

(65) Prior Publication Data

US 2015/0306254 A1 Oct. 29, 2015

Related U.S. Application Data

(63) Continuation of application No. PCT/US2013/055400, filed on Aug. 16, 2012.

(60) Provisional application No. 61/684,691, filed on Aug. 17, 2012.

(51) Int. Cl.
| | |
|---|---|
| *C07K 16/36* | (2006.01) |
| *C07K 16/18* | (2006.01) |
| *A61K 39/395* | (2006.01) |
| *A61K 39/44* | (2006.01) |
| *A61K 49/00* | (2006.01) |

(52) U.S. Cl.
CPC ............ *A61K 49/0058* (2013.01); *C07K 16/18* (2013.01)

(58) Field of Classification Search
None
See application file for complete search history.

(56) References Cited

U.S. PATENT DOCUMENTS

| | | | |
|---|---|---|---|
| 4,883,784 A | 11/1989 | Kaneko | |
| 5,212,071 A | 5/1993 | Fearon et al. | |
| 5,260,203 A | 11/1993 | Ladner et al. | |
| 5,310,729 A | 5/1994 | Lernhardt | |
| 5,328,470 A | 7/1994 | Nabel et al. | |
| 5,331,090 A | 7/1994 | Lernhardt | |
| 5,472,939 A | 12/1995 | Fearon et al. | |
| 5,679,345 A | 10/1997 | Sanfilippo et al. | |
| 5,679,546 A | 10/1997 | Ko et al. | |
| 5,851,528 A | 12/1998 | Ko et al. | |
| 5,981,481 A | 11/1999 | Fearon et al. | |
| 6,140,472 A | 10/2000 | Rosengard et al. | |
| 6,214,966 B1 | 4/2001 | Harris | |
| 6,224,866 B1 | 5/2001 | Barbera-Guillem | |
| 6,248,365 B1 | 6/2001 | Romisch et al. | |
| 6,291,239 B1 | 9/2001 | Prodinger et al. | |
| 6,355,245 B1 | 3/2002 | Evans et al. | |
| 6,368,596 B1 | 4/2002 | Ghetie et al. | |
| 6,432,679 B1 | 8/2002 | Mond et al. | |
| 6,458,360 B1 | 10/2002 | Fearon et al. | |
| 6,503,947 B1 | 1/2003 | Lipton et al. | |
| 6,521,450 B1 | 2/2003 | Atkinson et al. | |
| 6,572,856 B1 | 6/2003 | Taylor et al. | |
| 6,820,011 B2 | 11/2004 | Chen et al. | |
| 6,897,290 B1 | 5/2005 | Atkinson et al. | |
| 6,962,903 B2 | 11/2005 | Allison | |
| 7,407,475 B2 | 8/2008 | Allison | |
| 7,423,128 B2 | 9/2008 | Gazit-Bornstein et al. | |
| 7,439,331 B2 | 10/2008 | Fung et al. | |
| 7,576,182 B1 | 8/2009 | Goddard et al. | |
| 7,635,676 B2 | 12/2009 | Allison | |
| 7,635,678 B2 | 12/2009 | Allison | |
| 7,635,679 B2 | 12/2009 | Fumero et al. | |
| 7,635,680 B2 | 12/2009 | Allison | |
| 7,645,739 B2 | 1/2010 | Allison | |
| 7,759,304 B2 | 7/2010 | Gilkeson et al. | |
| 7,964,705 B2 | 6/2011 | Emlen et al. | |
| 7,999,082 B2 | 8/2011 | Holers et al. | |
| 8,007,804 B2 | 8/2011 | Tomlinson et al. | |
| 8,124,093 B2 | 2/2012 | Lanzavecchia et al. | |
| 8,840,868 B2 | 9/2014 | Thurman et al. | |
| 2002/0103346 A1 | 8/2002 | Vogel et al. | |
| 2003/0077273 A1 | 4/2003 | Linnik et al. | |
| 2003/0165509 A1 | 9/2003 | Ghetie et al. | |
| 2003/0180292 A1 | 9/2003 | Hanna et al. | |
| 2004/0005538 A1 | 1/2004 | Chen et al. | |
| 2004/0191252 A1 | 9/2004 | Taylor et al. | |
| 2004/0219156 A1 | 11/2004 | Goldenberg et al. | |
| 2004/0229827 A1 | 11/2004 | Steward et al. | |
| 2005/0002128 A1 | 1/2005 | Ito et al. | |
| 2005/0032128 A1 | 2/2005 | Halperin | |

(Continued)

FOREIGN PATENT DOCUMENTS

| | | |
|---|---|---|
| EP | 0 358 130 A2 | 3/1990 |
| EP | 0 402 266 A2 | 12/1990 |

(Continued)

OTHER PUBLICATIONS

[(1991) "Sequences of Proteins of Immunological Interest." NIH Publication No. 91-3242, U.S. Department of Health and Human Services, Bethesda, MD].
Wright A, Morrison SL. Effect of altered CH2-associated carbohydrate structure; on the functional properties and in vivo fate of chimeric mouse-human; immunoglobulin G1. J Exp Med. Sep. 1, 1994;180(3):1087-96.
"Monoclonal antibody to human C3(C3d), Catalog No. A207," Quidel Corporation Product Catalog, <http://www.quidel.com/products/product_detail.php?prod=73&group=2>, retrieved on Apr. 25, 2013 (2 pages).

(Continued)

*Primary Examiner* — Phillip Gambel
(74) *Attorney, Agent, or Firm* — Mintz, Levin, Cohn, Ferris, Glovsky and Popeo, P.C.

(57) ABSTRACT

Provided herein, inter alia, are compositions and methods of using the same for detecting complement activation.

20 Claims, 35 Drawing Sheets

(56) References Cited

U.S. PATENT DOCUMENTS

| | | |
|---|---|---|
| 2005/0232920 A1 | 10/2005 | Fung et al. |
| 2005/0260198 A1 | 11/2005 | Holers et al. |
| 2005/0265995 A1 | 12/2005 | Tomlinson et al. |
| 2006/0002944 A1 | 1/2006 | Ashkenazi et al. |
| 2006/0014681 A1 | 1/2006 | Chen et al. |
| 2006/0178308 A1 | 8/2006 | Schwaeble et al. |
| 2006/0263819 A1 | 11/2006 | Hageman et al. |
| 2006/0276388 A1 | 12/2006 | Christa et al. |
| 2006/0292141 A1 | 12/2006 | Holers et al. |
| 2007/0003544 A1 | 1/2007 | Hanna |
| 2007/0020647 A1 | 1/2007 | Hageman et al. |
| 2007/0134260 A1 | 6/2007 | Feger et al. |
| 2007/0172483 A1 | 7/2007 | Schwaeble et al. |
| 2007/0224197 A1 | 9/2007 | Chen et al. |
| 2008/0029911 A1 | 2/2008 | Jeon et al. |
| 2008/0118506 A1 | 5/2008 | An et al. |
| 2008/0241223 A1 | 10/2008 | Nivaggioli et al. |
| 2008/0267980 A1 | 10/2008 | Tomlinson et al. |
| 2008/0299111 A1 | 12/2008 | Delacourte et al. |
| 2008/0299114 A1 | 12/2008 | Emlen et al. |
| 2009/0081211 A1 | 3/2009 | Campagne |
| 2009/0087907 A1 | 4/2009 | Pebay et al. |
| 2009/0175875 A1 | 7/2009 | Etemad-Gilbertson et al. |
| 2009/0304706 A1 | 12/2009 | Lu et al. |
| 2010/0115639 A1 | 5/2010 | Goetsch |
| 2011/0014614 A1 | 1/2011 | Liew |
| 2011/0015127 A1 | 1/2011 | Gilkeson et al. |
| 2011/0275060 A1 | 11/2011 | Ahearn et al. |
| 2011/0286938 A1 | 11/2011 | Thurman et al. |
| 2011/0293605 A1 | 12/2011 | Sathish et al. |
| 2012/0015871 A1 | 1/2012 | Tomlinson et al. |
| 2012/0015872 A1 | 1/2012 | Tomlinson et al. |
| 2012/0135430 A1 | 5/2012 | Zhang et al. |
| 2012/0171206 A1 | 7/2012 | Tomlinson et al. |
| 2013/0029912 A1 | 1/2013 | Holers et al. |
| 2013/0078245 A1 | 3/2013 | Holers et al. |
| 2013/0129728 A1 | 5/2013 | Holers et al. |

FOREIGN PATENT DOCUMENTS

| | | |
|---|---|---|
| EP | 0402226 A1 | 12/1990 |
| EP | 0 430 539 A2 | 6/1991 |
| EP | 0 488 401 A1 | 6/1992 |
| JP | 09-502985 A | 3/1997 |
| JP | 2002-534959 A | 10/2002 |
| JP | 05-507197 B2 | 5/2014 |
| WO | WO-91/16437 A1 | 10/1991 |
| WO | WO-96/12742 A1 | 5/1996 |
| WO | WO-98/07835 A2 | 2/1998 |
| WO | WO-9824884 A1 | 6/1998 |
| WO | WO-9824893 A2 | 6/1998 |
| WO | WO-99/44625 A1 | 9/1999 |
| WO | WO-00/34317 A2 | 6/2000 |
| WO | WO-00/67796 A1 | 11/2000 |
| WO | WO-02/068579 A2 | 9/2002 |
| WO | WO-2004/045520 A2 | 6/2004 |
| WO | WO-2004/103288 A2 | 12/2004 |
| WO | WO-2005/011735 A1 | 2/2005 |
| WO | WO-2005/014618 A2 | 2/2005 |
| WO | WO-2005/044998 A2 | 5/2005 |
| WO | WO-2005/072479 A2 | 8/2005 |
| WO | WO-2005/077417 A1 | 8/2005 |
| WO | WO-2006/030220 A1 | 3/2006 |
| WO | WO-2006/062716 A2 | 6/2006 |
| WO | WO-2006/083533 A2 | 8/2006 |
| WO | WO-2006/088950 A2 | 8/2006 |
| WO | WO-2006/128006 A1 | 11/2006 |
| WO | WO-2007/029008 A2 | 3/2007 |
| WO | WO-2007/035857 A2 | 3/2007 |
| WO | WO-2007/056227 A2 | 5/2007 |
| WO | WO-2007/112403 A2 | 10/2007 |
| WO | WO-2007/129895 A2 | 11/2007 |
| WO | WO-2007/149567 A2 | 12/2007 |
| WO | WO-2008/024188 A2 | 2/2008 |
| WO | WO-2008/154251 A2 | 12/2008 |
| WO | WO-2009/029669 A1 | 3/2009 |
| WO | WO-2009/056631 A2 | 5/2009 |
| WO | WO-2009/110918 A1 | 9/2009 |
| WO | WO-2010/015608 A1 | 2/2010 |
| WO | WO-2010/091183 A2 | 8/2010 |
| WO | WO-2010/136311 A2 | 12/2010 |
| WO | WO-2011/057158 A1 | 5/2011 |
| WO | WO-2011/143637 A1 | 11/2011 |
| WO | WO-2011/163412 A1 | 12/2011 |
| WO | WO-2013/117035 A1 | 8/2013 |
| WO | WO-2013/177035 A2 | 11/2013 |

OTHER PUBLICATIONS

"Monoclonal antibody to human C3d (neo), Catalog No. A250," Quidel Corporation Product Catalog, <http://www.guidel.com/products/product_detail.php?prod=160&group=2>, retrieved on Dec. 26, 2013 (2 pages).

<http://ibis/IBIS/exam/dbfetch.jsp?id=EM_PAT:CQ729676>retrieved on Jan. 3, 2011(1 page).

Abrahmsen et al., "Engineering subtilisin and its substrates for efficient ligation of peptide bonds in aqueous solution," Biochemistry. 30:4151-4159 (1991).

Aguado et al., "Monoclonal antibodies against complement 3 neoantigens for detection of immune complexes and complement activation. Relationship between immune complex levels, state of C3, and numbers of receptors for C3b," J Clin Invest. 76:1418-26 (1985).

Ahearn et al., "Disruption of the Cr2 locus results in a reduction in B-1a cells and in an imparied B cell response to T-dependent antigen," Immunity. 4(3):251-262 (1996).

Ahearn et al., "Epstein-Barr virus (EBV) infection of murine L cells expressing recombinant human EBV/C3d receptor," Proc Natl Acad Sci USA. 85:9307-11 (1988).

Ahearn et al., "Structure and function of the complement receptors, CR1 (CD35) and CR2 (CD21)," Adv Immunol. 46:183-219 (1989).

Amsterdam et al., "Limitation of reperfusion injury by a monoclonal antibody to C5a during myocardial infarction in pigs," Am J Physiol. 268(1):H448-57 (1995).

Andrews et al., "Spontaneous murine Lupus-like syndromes. Clinical and immunopathological manifestations in several strains," J Exp Med. 148:1198-215 (1978).

Arumugam et al., "Complement mediators in ischemia-reperfusion injury," Clin Chim Acta. 374:33-45 (2006).

Arumugam et al., "Protective effect of a human C5a receptor antagonist against hepatic ischaemia-reperfusion injury to rats," J Hepatol. 40:934-41 (2004).

Aslam et al., "Folded-back solution structure of monomeric factor H of human complement by synchrotron X-ray and neutron scattering, analytical ultracentrifugation and constrained molecular modelling," J Mol Biol. 309(5):1117-1138 (2001).

Asokan et al., "Characterization of human complement receptor type 2 (CR2/CD21) as a receptor for IFN-alpha: a potential role in systemic lupus erythematosus," J Immunol. 177:383-94 (2006).

Atkinson et al., "Complement-dependent P-selectin expression and injury following ischemic stroke," J Immunol. 177:7266-74 (2006).

Atkinson et al., "Targeted complement inhibition by C3d recognition ameliorates tissue injury without apparent increase in susceptibility to infection," J Clin Invest. 115(9):2444-53 (2005).

Atkinson et al., "Targeted complement inhibitors protect against posttransplant cardiac ischemia and reperfusion injury and reveal an important role for the alternative pathway of complement activation," J Immunol. 185:7007-13 (2010).

Atkinson et al., "Targeted inhibition of the alternative complement pathway delays the onset of antibody-mediated rejection in a mouse heterotopic heart transplant model," Mol Immunol. 44:3944, Abstract No. P24 (2007).

Atkinson et al., Targeted complement inhibition by C3d recognition ameliorates tissue injury without apparent increase in susceptibility to infection. J Clin Invest. Sep. 2005;115(9):2444-53. Epub Aug. 25, 2005.

Aubry et al., "CD21 is a ligand for CD23 and regulates IgE production," Nature. 358(6386):505-507 (1992).

(56) References Cited

OTHER PUBLICATIONS

Aubry et al., "CD23 interacts with a new functional extracytoplasmic domain involving N-linked oligosaccharides on CD21," J Immunol. 152:5806-13 (1994).
Author manuscript of Clark et al., "Evidence for non-traditional activation of complement factor C3 during murine liver regeneration," available in PMC Jun. 1, 2009, published in final edited form as: Mol Immunol. 45(11):3125-32 (2008) (15 pages).
Author manuscript of Habermann et al., "Increased serum levels of complement C3a anaphylatoxin indicate the presence of colorectal tumors," available in PMC Sep. 8, 2008, published in final edited form as: Gastroenterol. 131(4):1020-9 (2006) (17 pages).
Author manuscript of Huang et al., "A novel targeted inhibitor of the alternative pathway of complement and its therapeutic application in ischemia/reperfusion injury," available in PMC Nov. 25, 2009, published in final edited form as: J Immunol. 181(11): 8068-8076 (2008) (19 pages).
Baechler et al., "Interferon-inducible gene expression signature in peripheral blood cells of patients with severe lupus," Proc Natl Acad Sci USA. 100:2610-5 (2003).
Bagshawe et al., "A cytotoxic agent can be generated selectively at cancer sites," Br J Cancer. 58:700-703 (1988).
Bagshawe, "Towards generating cytotoxic agents at cancer sites," Br J Cancer. 60:275-281(1989).
Bajaj et al., Serial renal biopsy in systemic lupus erythematosus. J Rheumatol. Dec. 2000;27(12):2822-6.
Baldo et al., "The adipsin-acylation stimulating protein system and regulation of intracellular triglyceride synthesis," J Clin Invest. 92:1543-47 (1993).
Banda et al., "Targeted inhibition of the complement alternative pathway with complement receptor 2 and factor H attenuates collagen antibody-induced arthritis in mice," J Immunol. 183:5928-37 (2009).
Baranyi et al., "Cell-surface bound complement regulatory activity is necessary for the in vivo survival of KDH-8 rat hepatoma," Immunology. 82(4):522-8 (1994).
Barlow et al., "Solution structure of a pair of complement modules by nuclear magnetic resonance," J Mol Biol. 232:268-284 (1993).
Battelli et al., "T lymphocyte killing by a xanthine-oxidase-containing immunotoxin," Cancer Immunol Immunother. 35:421-425 (1992).
Benvenuti et al., "Crystallization of soluble proteins in vapor diffusion for X-ray crystallography," Nat Protoc. 2(7):1633-1651 (2007).
Bergelson et al., "Decay-accelerating factor (CD55), a glycosylphosphatidylinositol-anchored complement regulatory protein, is a receptor for several echoviruses," Proc Nat Acad Sci USA. 91(13):6245-9 (1994).
Blank et al., "Hemoglobin interference from in vivo hemolysis," Clin Chem. 31(9):1566-9 (1985).
Bohnsack et al., "CR2 ligands modulate human B cell activation," J Immunol. 141:2569-76 (1988).
Boross et al., "Boosting antibody therapy with complement," Blood. 119(25):5945-5947 (2012).
Brauer et al., "Functional activity of anti-C6 antibodies elicited in C6-deficient rats reconstituted by liver allografts. Ability to inhibit hyperacute rejection of discordant cardiac xenografts," Transplantation 61(4):588-94 (1996).
Brodsky, "How I treat paroxysmal nocturnal hemoglobinuria," Blood. 1 13(26):6522-7 (2009).
Brown et al., "Molecular and cellular mechanisms of receptor-mediated endocytosis," DNA Cell Biol. 10:399-409 (1991).
Bulte et al., Magnetodendrimers allow endosomal magnetic labeling and in vivo tracking of stem cells. Nat Biotechnol. Dec. 2001;19(12):1141-7.
Bykov, "Complement system and alcoholic liver disease," University of Helsinki 1-69 (2008).
Camargo et al., "Interleukin-6 protects liver against warm ischemia/reperfusion injury and promotes hepatocyte proliferation in the rodent," Hepatology. 26:1513-20 (1997).

Cambier, "Signalling processes in haematopoietic cells: positive and negative signal co-operativity in the immune system: the BCR, Fc gamma RIIB, CR2 paradigm," Biochem Soc Trans. 25(2):441-445 (1997).
Caragine et al., "A tumor-expressed inhibitor of the early but not late complement lytic pathway enhances tumor growth in a rat model of human breast cancer," Cancer Res. 62(4):11 10-5 (2002).
Cardarelli et al., "A nonfucosylated human antibody to CD19 with potent B-cell depletive activity for therapy of B-cell malignancies," Cancer Immunol Immunother. 59(2):257-65 (2010).
Carel et al., "Structural requirements for C3d,g/Epstein-Barr virus receptor (CR2/CD21) ligand binding, internalization, and viral infection," J Biol Chem. 265(21):12293-9 (1990).
Carroll, "The role of complement and complement receptors in induction and regulation of immunity," Annu Rev Immunol. 16:545-568 (1998).
Carroll, The role of complement in B cell activation and tolerance. *Advances in Immunology*. Dixon,74:61-88 (2000).
Carter et al., "CD19: lowering the threshold for antigen receptor stimulation of B lymphocytes," Science. 256:105-7 (1992).
Carter et al., "Polymeric C3dg primes human B lymphocytes for proliferation induced by anti-IgM," J Immunol. 143(6):1755-60 (1989).
Carter et al., "Synergistic interaction between complement receptor type 2 and membrane IgM on B lymphocytes," J Immunol. 141:457-63 (1988).
Casasnovas et al., "Crystal structure of two CD46 domains reveals an extended measles virus-binding surface," EMBO J. 18(11):2911-2922 (1999).
Chavez-Cartaya et al., "Regulation of the complement cascade by soluble complement receptor type 1. Protective effect in experimental liver ischemia and reperfusion," Transplantation. 59:1047-52 (1995).
Chen et al., "CD59 expressed on a tumor cell surface modulates decay-accelerating factor expression and enhances tumor growth in a rat model of human neuroblastoma," Cancer Res. 60(11):3013-8 (2000).
Chen et al., "Gene therapy for brain tumors: regression of experimental gliomas by adenovirus-mediated gene transfer in vivo," Proc Natl Acad Sci USA. 91:3054-3057 (1994).
Chothia et al. Conformations of immunoglobulin hypervariable regions. Nature. Dec. 21-28, 1989;342(6252):877-83.
Christiansen et al., "A functional analysis of recombinant soluble CD46 in vivo and a comparison with recombinant soluble forms of CD55 and CD35 in vitro," Eur J Immunol. 26(3):578-85 (1996).
Clavien et al., "Strategies for safer liver surgery and partial liver transplantation," N Engl J Med. 356:1545-59 (2007).
Clemenza et al., "Structure-guided identification of C3d residues essential for its binding to complement receptor 2 (CD21)," J Immunol. 165:3839-3848 (2000).
Colvin, "Antibody-mediated renal allograft rejection: diagnosis and pathogenesis," J Am Soc Nephrol. 18(4):1046-56 (2007).
Cooper et al., "Immunobiology of CR2, the B lymphocyte receptor for Epstein-Barr virus and the C3d complement fragment," Ann Rev Immunol. 6:85-113 (1988).
Crumm et al., "Adenine necleotide changes in the remnant liver: an early signal for regeneration after partial hepatectomy," Hepatology. 48:898-908 (2008).
Cudney, "Protein crystallization and dumb luck," The Rigaku Journal. 16(1):1-7 (1999).
Daha et al., C3 nephritic factor (C3NeF): stabilization of fluid phase and cell-bound alternative pathway convertase. J Immunol. Jan. 1976;116(1):1-7.
Dahm et al., "Small-for-size syndrome after partial liver transplantation: definition, mechanisms of disease and clinical implications," Am J Transplant. 5:2605-10 (2005).
Davies et al., "CD59, a Ly-6-Like protein expressed in human lymphoid cells, regulates the action of the complement membrane attack complex on homologous cells," J Exp Med. 170(3):637-54 (1989).
de Bruijn et al., Human complement component C3: cDNA coding sequence and ; derived primary structure. Proc Natl Acad Sci U S A. Feb. 1985;82(3):708-12.

(56) References Cited

OTHER PUBLICATIONS

De Cordoba et al., "The human complement factor H: functional roles, genetic variations and disease associations," Molec Immunol. 41:355-67 (2004).
Delaglio et al., "NMRPipe: a multidimensional spectral processing system based on UNIX pipes," J Biomol NMR. 6:277-93 (1995).
Delcayre et al., "Epstein Barr virus/complement C3d receptor is an interferon alpha receptor," EMBO J. 10:919-26 (1991).
Delcayre et al., "Inhibition of Epstein-Barr virus-mediated capping of CD21/CR2 by alpha interferon (IFN-alpha): immediate antiviral activity of IFN-alpha during the early phase of infection," J Virol. 67:2918-21 (1993).
Dempsey et al., "C3d of complement as a molecular adjuvant: bridging innate and acquired immunity," Science. 271:348-350 (1996).
Dev et al., "Electrochemotherapy—A novel method of cancer treatment," Cancer Treat Rev. 20:105-115 (1994).
Diefenbach et al., "Mutation of residues in the C3dg region of human complement component C3 corresponding to a proposed binding site for complement receptor type 2 (CR2, CD21) does not abolish binding of iC3b or C3dg to CR2," J Immunol. 154(5):2303-2320 (1995).
Dierich et al., "Structural and functional relationships among receptors and regulators of the complement system," Mol Immunol. 25(11):1043-1051 (1988).
Dilillo et al., "Selective and efficient inhibition of the alternative pathway of complement by a mAb that recognizes C3b/iC3b," Mol Immunol. 43:1010-9 (2006).
Dobbie et al., Epitope specificities and quantitative and serologic aspects of monoclonal complement (C3c and C3d) antibodies. Transfusion. Nov.-Dec. 1987;27(6):453-9.
Dominguez et al., "HADDOCK: a protein-protein docking approach based on biochemical or biophysical information," J Am Chem Soc. 125:1731-7 (2003).
Dorig et al., "The human CD46 molecule is a receptor for measles virus (Edmonston strain)," Cell. 75(2):295-305 (1993).
Drenth, Crystalling a Protein. Principles of Protein X-Ray Crystallography. Springer-Verlag, 1-21 (1999).
Duits et al., "Selective enhancement of Leu-Cam expression by Interleukin 6 during differentiation of human promonocytic U937 cells," Scand J Immunol. 33(2):151-9 (1991).
Duranski et al., "Cytoprotective effects of nitrite during in vivo ischemia-reperfusion of the heart and liver," J Clin Invest. 115(5):1232-40 (2005).
Dutkowski et al., "Novel short-term hypothermic oxygenated perfusion (HOPE) system prevents injury in rat liver graft from non-heart beating donor," Ann Surg. 244(6):968-76, discussion 976-7 (2006).
EBI Accession No. CQ729676.
Edberg et al, Quantitative analyses of the binding of soluble complement-fixing antibody/dsDNA immune complexes to CR1 on human red blood cells. J Immunol. Dec. 1, 1987;139(11):3739-47.
Edwards et al., "Complement factor H polymorphism and age-related macular degeneration," Science. 308:421-4 (2005).
Elsen, J.M.H. & Isenman, D.E., "A Crystal Structure of the Complex Between Human Complement Receptor 2 and Its Ligand C3d." Science (2011) 332:608-611.
Elvington et al., "A targeted complement-dependent strategy to improve the outcome of mAb therapy, and characterization in a murine model of metastatic cancer," Blood. 119(25):6043-6051 (2012).
Extended European Search Report and Written Opinion for European Application No. 11781394.9, dated Sep. 19, 2013 (11 pages).
Extended European Search Report for European Application No. 10829204.6, dated Mar. 5, 2013 (9 pages).
Fabrikant, "The kinetics of cellular proliferation in regenerating liver," J Cell Biol. 36(3):551-65 (1968).
Fausto, "Involvement of the innate immune system in liver regeneration and injury," J Hepatol. 45:347-9 (2006).
Fearon et al., "The CD19/CR2/TAPA-1 complex of B lymphocytes: Linking natural to acquired immunity," Annu Rev Immunol. 13:127-149 (1995).
Fearon, "The complement system and adaptive immunity," Semin Immunol. 10(5):355-361 (1998).
Ferreira et al., "Factor H-mediated cell surface protection from complement is critical for the survival of PNH erythrocytes," Blood. 110(6):2190-2 (2007).
Fingeroth et al., "Characterization of a T-lymphocyte Epstein-Barr virus/C3d receptor (CD21)," J Virol. 62:1442-7 (1988).
Fingeroth et al., "Epstein-Barr virus receptor of human B lymphocytes is the C3d receptor CR2," Proc Natl Acad Sci USA. 81(14):4510-4514 (1984).
Fingeroth et al., "Identification of murine complement receptor type 2," Proc Natl Acad Sci USA. 86(1):242-246 (1989).
Fiorini et al., "Development of an unbiased method for the estimation of liver steatosis," Clin Transplant. 18:700-6 (2004).
Fishelson et al., "Regulation of the alternative pathway of complement by pH," J Immunol. 138(10):3392-5 (1987).
Fondevila et al., "The membrane attack complex (C5b-9) in liver cold ischemia and reperfusion injury," Liver Transpl. 14:1133-41 (2008).
Franco-Gou et al., "Protection of reduced-size liver for transplantation," Am J Transplant. 4(9):1408-20 (2004).
Fremeaux-Bacchi et al., "Soluble CD21 induces activation and differentiation of human monocytes through binding to membrane CD23," Eur J Immunol. 28:4268-4274 (1998).
Fritzinger et al., "Functional characterization of human C3/cobra venom factor hybrid proteins for therapeutic complement depletion," Develop Comp Immunol. 33(1):105-16 (2009).
Fritzinger et al., "Molecular cloning and derived primary structure of cobra venom factor," Proc Natl Acad Sci USA. 91:12775-12779 (1994); correction 92: 7065 (1995).
Fujisaku et al., "Genomic organization and polymorphisms of the human C3d/Epstein-Barr virus receptor," J Biol Chem. 264:2118-25 (1989).
Fukuoka et al., "Molecular cloning of murine decay accelerating factor by immunoscreening," International Immunology. 8:379-385 (1996).
Girardi et al., Complement C5a receptors and neutrophils mediate fetal injury in the antiphospholipid syndrome. J Clin Invest. Dec. 2003;112(11):1644-54.
Gomez et al., "Role of ischaemic preconditioning in liver regeneration following major liver resection and transplantation," World J Gastroenterol. 13(5):657-70 (2007).
Goodford, "A computational procedure for determining energetically favorable binding sites on biologically important macromolecules," J. Med. Chem. 28: 849-857, 1985.
Gordon, "B-cell signalling via the C-type lectins CD23 and CD72," Immunol Today. 15(9):411-417 (1994).
Greene et al., "Partial hepatectomy in the mouse: technique and perioperative management," J Invest Surg. 16:99-102 (2003).
Greenspan et al., "Defining epitopes: Its not as easy as it seems," Nat Biotechnol. 17:936-937 (1999).
Grzesiek et al., "Improved 3D triple-resonance NMR techniques applied to a 31-kDa protein," J Magn Reson. 96:432-40 (1992).
Guthridge et al., "Epitope mapping using the X-ray crystallographic structure of complement receptor type 2 (CR2)/CD21: Identification of a highly inhibitory monoclonal antibody that directly recognizes the CR2-C3d interface," J Immunol. 167:5758-5766 (2001).
Guthridge et al., Structural studies in solution of the recombinant N-terminal pair of; short consensus/complement repeat domains of complement receptor type 2; (CR2/CD21) and interactions with its ligand C3dg. Biochemistry. May 2001; 22;40(20):5931-41.
Haan et al., "Different functional domains in the cytoplasmic tail of glycoprotein B are involved in Epstein-Barr virus-induced membrane fusion," Virology. 290:106-14 (2001).
Haddad et al., "Depletion of glycoprotein gp85 from virosomes made with Epstein-Barr virus proteins abolishes their ability to fuse with virus receptor-bearing cells," J Virol. 63:4998-5005 (1989).
Hageman et al., An integrated hypothesis that considers drusen as biomarkers of immune-mediated processes at the RPE-Bruch's membrane interface in aging and age-related macular degeneration. Prog Retin Eye Res. Nov. 2001;20(6):705-32.

(56) References Cited

OTHER PUBLICATIONS

Hageman et al., "A common haplotype in the complement regulatory gene factor H (HF1/CFH) predisposes individuals to age-related macular degeneration," Proc Natl Acad Sci USA. 102(20):7227-32 (2005).
Haines et al., "Complement factor H variant increases the risk of age-related macular degeneration," Science. 308(5720):419-21 (2005).
Ham et al., "Studies on destruction of red blood cells. II. Chronic hemolytic anemia with paroxysmal nocturnal hemoglobinuria: certain immunological aspects of the hemolytic mechanism with special reference to serum complement," J Clin Invest. 18:657-72 (1939).
Hampton Research, Catalog, 5 & 7 (2001).
Hampton Research, Crystal Screen User Guide, 27632 El Lazo Road, Laguna Niguel, California, 1991 (4 pages).
Hannan et al., "Mutational analysis of the complement receptor type 2 (CR2/CD21)-C3d interaction reveals a putative charged SCR1 binding site for C3d," J Mol Biol. 346(3):845-58 (2005).
Hannan et al., "Structure of complement receptor (CR) 2 and CR2-C3d complexes," Biochem Soc Trans. 30:983-9 (2002).
Harada et al., "Antithrombin reduces ischemia/reperfusion injury of rat liver by increasing the hepatic level of prostacyclin," Blood. 93:157-64 (1999).
Harlow et al., Proteolytic Fragments of Antibodies. *Antibodies: A Laboratory Manuel*. 626-629 (1988).
Harris et al., "Tailoring anti-complement therapeutics," Biochem Soc Trans. 30(6):1019-26 (2002).
Hautekeete et al., "Microvesicular steatosis of the liver," Acta Clin Belg. 45(5):311-326 (1990). Abstract Only.
Hebell et al., "Delivery of antioxidative enzyme genes protects against ischemia/reperfusion-induced liver injury in mice," Liver Transpl. 12:1869-79 (2006).
Hebell et al., "Suppression of the immune response by a soluble complement receptor of B lymphocytes," Science. 254:102-105 (1991).
Heinen et al., "Factor H-related protein 1 (CFHR-1) inhibits complement C5 convertase activity and terminal complex formation," Blood. 114(12):2439-47 (2009).
Helling et al., "Partial hepatectomy with or without endotoxin does not promote apoptosis in the rat liver," J Surg Res. 116:1-10 (2004).
Helling, "Liver failure following partial hepatectomyn" HPB (Oxford). 8:165-74 (2006).
Heyman, "Regulation of antibody responses via antibodies, complement, and Fc receptors," Ann Rev Immunol. 18:709-737 (2000).
Higgins et al., "A soluble chimeric complement inhibitory protein that possesses both decay-accelerating and factor I cofactor activities," J Immunol. 158(6):2872-81 ( 997).
Higgins et al., "Experimental pathology of the liver. 1. Restoration of the liver of the white rat following partial surgical removal," Arch Pathol. 12:186-202 (1931).
Hill et al., "Sustained response and long-term safety of eculizumab in paroxysmal nocturnal hemoglobinuria," Blood. 106:2559-65 (2005).
Hill, "Eculizumab for the treatment of paroxysmal nocturnal hemoglobinuria," Clin Adv Hematol Oncol. 3(1 1):849-50 (2005).
Hillmen et al., "Effect of eculizumab on hemolysis and transfusion requirements in patients with paroxysmal nocturnal hemoglobinuria," N Engl J Med. 350(6):552-9 (2004).
Holers et al., "The alternative pathway of complement in disease: Opportunities for therapeutic targeting," Mol. Immunol. 41:147-152 (2004).
Holers, "The spectrum of complement alternative pathway-mediated diseases," Immunol Rev. 223:300-316 (2008).
Holers, Complement Receptors. *The Year in Immunology 1988. Cellular, Molecular and Clinical Aspects*. Cruse et al., 4:231-240 (1989).
Holers, Complement. *Clinical Immunology, Principles and Practice*. Mosby ed. 363-91 (1996).
Holliger et al., "Diabodies": small bivalent and bispecific antibody fragments. Proc Natl Acad Sci U S A. Jul. 15, 1993;90(14):6444-8.
Holt et al., Domain antibodies: proteins for therapy. Trends Biotechnol. Nov. 2003;21(11):484-90.

Homeister et al., "Soluble complement receptor type 1 prevents human complement-mediated damage of the rabbit isolated heart," J Immunol. 150(3):1055-1064 (1993).
Hon et al., "Crry, a complement regulatory protein, modulates renal interstitial disease induced by proteinuria," Kidney Int. 56:2096-2106 (1999).
Honegger et al., Yet another numbering scheme for immunoglobulin variable domains: an automatic modeling and analysis tool. J Mol Biol. Jun. 8, 2001;309(3):657-70.
Hsu et al., "Chronic progression of tubulointerstitial damage in proteinuric renal disease is mediated by complement activation: a therapeutic role for complement inhibitors?" J Am Soc Nephrol. 14:S186-91 (2003).
Huang et al., "Insights into the human CD59 complement binding interface toward engineering new therapeutics," J Biol Chem. 280(40):34073-9 (2005).
Hudson et al., High avidity scFv multimers; diabodies and triabodies. J Immunol Methods. Dec. 10, 1999;231(1-2):177-89.
Hughes et al., "Monoclonal antibody targeting of liposomes to mouse lung in vivo," Cancer Res. 49(22):6214-20 (1989).
Huh et al., In vivo magnetic resonance detection of cancer by using multifunctional magnetic nanocrystals. J Am Chem Soc. Sep. 7, 2005;127(35):12387-91.
Humar et al., "Liver regeneration after adult living donor and deceased donor split-liver transplants," Liver Transpl. 10(3):374-8 (2004).
Humblet et al., "3D database searching and docking strategies," Topics in Drug Design and Discovery. *Annual Reports in Medicinal Chemistry*. Bristol et al., 28:275-284 (1993).
International Preliminary Report on Patentability and Written Opinion dated Dec. 28, 2012 for International Application No. PCT/US2011/041517, 11 pages.
International Preliminary Report on Patentability and Written Opinion for International Application No. PCT/US2011/041517, dated Dec. 28, 2012 (11 pages).
International Search Report dated Oct. 11, 2011 for International Application No. PCT/US2011/041517, 8 pages.
International Search Report for International Application No. PCT/US2003/36459, mailed Sep. 15, 2004 (2 pages).
International Search Report for International Application No. PCT/US2007/014602, mailed on Mar. 6, 2008 (5 pages).
International Search Report for International Application No. PCT/US2010/040973, mailed Oct. 14, 2010 (5 pages).
International Search Report for International Application No. PCT/US2010/055745, mailed Feb. 4, 2011 (3 pages).
International Search Report for International Application No. PCT/US2011/036552, mailed Jul. 26, 2011 (7 pages).
Isenman et al., Mutational analyses reveal that the staphylococcal immune evasion molecule Sbi and complement receptor 2 (CR2) share overlapping contact residues on C3d: implications for the controversy regarding the CR2/C3d cocrystal structure. J Immunol. Feb. 15, 2010;184(4):1946-55.
Jackson et al., "PI3K/Akt activation is critical for early hepatic regeneration after partial hepatectomy," Am J Physiol Gastrointest Liver Physiol. 294:G1401-10 (2008).
Jacobson et al., "Clinical and immunologic features of transient cold agglutinin-hemolytic anemia," Am J Med. 54:514-21 (1973).
Janssen et al., "Structure of compstatin in complex with complement component C3c reveals a new mechanism of complement inhibition," J Biol Chem. 282:29241-7 (2007).
Janssen et al., Structure of C3b reveals conformational changes that underlie complement activity. Nature. Nov. 9, 2006;444(7116):213-6. Epub Oct. 15, 2006.
Janzi et al., "Serum microarrays for large scale screening of protein levels," Mol Cell Proteomics. 4(12):1942-7 (2005).
Jin et al., "Interleukin-6 inhibits oxidative injury and necrosis after extreme liver resection," Hepatology. 46:802-12 (2007).
Jin et al., "Paradoxical effects of short- and long-term interleukin-6 exposure on liver injury and repair," Hepatology. 43:474-84 (2006).
Johswich et al., "Ligand specificity of the anaphylatoxin C5L2 receptor and its regulation on myeloid and epithelial cell lines," J Biol Chem. 281(51):39088-95 (2006).

(56) References Cited

OTHER PUBLICATIONS

Jozsi et al., "Attachment of the soluble complement regulator factor H to cell and tissue surfaces: relevance for pathology," Histol Hitopathol. 19:251-8 (2004).
Juhl et al., "Complement killing of human neuroblastoma cells: A cytotoxic monoclonal antibody and its F(ab')2-cobra venom factor conjugate are equally cytotoxic," Mol Immunol. 27(10):957-964 (1990).
Kadry et al., "Liver regeneration after adult living donor and deceased donor split-liver transplants," Liver Transpl. 10(8):1078 (2004).
Kalant et al., "C5L2 is a functional receptor for acylation-stimulating protein," J Biol Chem 208(25):23936-44 (2005).
Kalant et al., "The chemoattractant receptor-like protein C5L2 binds the C3a des-Arg77/acylation-stimulating protein," J Biol Chem 278(13):11123-9 (2003).
Kalli et al., "Interaction of iC3b with recombinant isotypic and chimeric forms of CR2," J Immunol. 147(2):590-594 (1991).
Kaplan et al., "Eculizumab treatment of atypical hemolytic uremic syndrome", Expert Opinion on Orphan Drugs (2013) 1(2):167-176.
Kaplan, "Eculizumab Alexion," Curr Opin Investig Drugs. 3(7):1017-23 (2002).
Khurana et al., "Crystal structure of 2,5-diketo-D-gluconic acid reductase A complexed with NADPH at 2.1-A resolution," Proc Natl Acad Sci 95:6768-6773 (1998).
Kildsgaard et al., "A critical evaluation of the putative role of C3adesArg (ASP) in lipid metabolism and hyperapobetalipoproteinemia," Mol Immunol. 36:869-76 (1999).
Klein et al., "Complement factor H polymorphism in age-related macular degeneration," Science. 308(5720):385-9 (2005).
Koski et al., "Cytolysis of nucleated cells by complement: cell death displays multi-hit characteristics," Proc Natl Acad Sci USA. 80:3816-3820 (1983).
Kovacs et al., "Biophysical investigations of complement receptor 2 (CD21 and CR2)-ligand interactions reveal amino acid contacts unique to each receptor-ligand pair," J Biol Chem. 285:27251-8 (2010).
Kovacs et al., Mapping of the C3d ligand binding site on complement receptor 2 (CR2/CD21) using nuclear magnetic resonance and chemical shift analysis. J Biol Chem. Apr. 3, 2009;284(14):9513-20.
Kroshus et al., "A recombinant soluble chimeric complement inhibitor composed of human CD46 and CD55 reduces acute cardiac tissue injury in models of pig-to-human heart transplantation," Transplantation. 69(1 1):2282-9 (2000).
Kroshus et al., "Complement inhibition with an anti-05 monoclonal antibody prevents acute cardiac tissue injury in an ex vivo model of pig-to-human xenotransplantation," Transplantation. 60(11):1194-202 (1995).
Krushkal et al., "Evolutionary relationships among proteins encoded by the regulator of complement activation gene cluster," Mol Biol Evol. 17(11):1718-30 (2000).
Kuby et al., Antigens. *Immunology (2nd edition)*. W H Freeman and Company, 85-96 (1994).
Kulik et al., Intrinsic B cell hypo-responsiveness in mice prematurely expressing human CR2/CD21 during B cell development. Eur J Immunol. Mar. 2007;37(3):623-33.
Kulik et al., Pathogenic natural antibodies recognizing annexin IV are required to develop intestinal ischemia-reperfusion injury. J Immunol. May 1, 2009;182(9):5363-73.
Kundrot, "Which strategy for a protein crystallization project?" Cell Mol Life Science. 61(5):525-536 (2004).
Kuraya et al., "Expression of the complement regulatory proteins CD21, CD55, and CD59 on Burkitt lymphoma lines: Their role in sensitivity to human serum-meidated lysis," Eur J Immunol. 22(7):1871-1876 (1992).
La Flamme et al., "Lack of C3 affects Th2 response development and the sequelae of chemotherapy in schistosomiasis," J Immunol. 170:470-6 (2003).

Lambris et al., "Mapping of the C3d receptor (CR2)-binding site and a neoantigenic site in the C3d domain of the third component of complement," Proc Natl Acad Sci USA. 82(12):4235-4239 (1985).
Law et al., "Action of the C3b-inactivator of the cell-bound C3b," J Immunol. 122(3):759-65 (1979).
Law et al., Complement. *In Focus*. Male, vii-ix (1995).
Law et al., The internal thioester and the covalent binding properties of the complement proteins C3 and C4. Protein Sci. Feb. 1997;6(2):263-74.
Lehmann et al., "Complement inhibition by soluble complement receptor type 1 improves microcirculation after rat liver transplantation," Transplantation. 66:717-22 (1998).
Lehmann et al., "Impact of inhibition of complement by sCR1 on hepatic microcirculation after warm ischemic," Microvasc Res. 62:284-92 (2001).
Leivo et al., "C3d fragment of complement interacts with laminin and binds to basement membranes of glomerulus and trophoblast," J Cell Biol. 103:1091-100 (1986).
Lemoli et al., "Immunological effects of omalizumab in chronic urticaria: a case report," J Invest Allergol Clin Immunol. 20(3):252-4 (2010).
Leu et al., "Triggering of interferon y-primed macrophages by various known complement activators for nonspecific tumor cytotoxicity," *Cell Immunol.* 106:114-121 (1987).
Leveziel et al., Genetic factors associated with age-related macular degeneration.; Ophthalmologica. 2011;226(3):87-102.
Iida et al., "Identification of the membrane receptor for the complement fragment C3d by means of a monoclonal antibody," J Exp Med. 158:1021-33 (1983).
Iimuro et al., "NFkappaB prevents apoptosis and liver dysfunction during liver regeneration," J Clin Invest. 101(4):802-11 (1998).
Linton et al., "therapeutic efficacy of a novel membrane-targeted complement regulator in antigen-induced arthritis in the rat," Arthritis Rheum. 43(11):2590-7 (2000).
Liszewski et al., "Complement inhibitors as therapeutic agents," Clin Immunol Newsletter. 17(12):168-73 (1997).
Litzinger et al., "Biodistribution and immunotargetability of ganglioside-stabilizeddioleoylphosphatidylethanolamine liposomes," Biochimica et Biophysica Acta. 1104:179-87 (1992).
Imai et al., "Enhancement of antibody-dependent mechanisms of tumor cell lysis by a targeted activator of complement," Cancer Res. 67(19):9535-9541 (2007).
Lowell et al., "Mapping of the Epstein-Barr virus and C3dg binding sites to a common domain on complement receptor type 2," J Exp Med. 170(6):1931-1946 (1989).
Luqman et al., "The antileukemia activity of a human anti-CD40 antagonist antibody, HCD122, on human chronic lymphocytic leukemia cells," Blood. 112(3):711-20 (2008).
Luxembourg et al., "Modulation of signaling via the B cell antigen receptor by CD21, the receptor for C3dg and EBV," J Immunol. 153:4448-57 (1994).
Lyubarsky et al., "Recovery phase of the murine rod photoresponse reconstructed from electroretinographic recordings," J Neurosci. 16(2):563-571 (1996).
Lyubchenko et al., "Coligation of the B cell receptor with complement receptor type 2 (CR2/CD21) using its natural ligand C3dg: activation without engagement of an inhibitory signaling pathway," J Immunol. 174:3264-72 (2005).
Mache et al., "Complement inhibitor eculizumab in atypical hemolytic uremic syndrome," Clin J Am Soc Nephrol. 4(8):1312-6 (2009).
MacLaren et al., "Adipokines and the immune system: an adipocentric view," Adv Exp Med Biol. 632:1-21 (2008).
Markiewski et al., "C3a and C3b activation products of the third component of complement (C3) are critical for normal liver recovery after toxic injury," J Immunol. 173:747-754 (2004).
Martin et al., "Determination of the role for CD21 during Epstein-Barr virus infection of B-lymphoblastoid cells," J Virol. 68(8):4716-4726 (1994).
Martin et al., "Determination of the structural basis for selective binding of Epstein-Barr virus to human complement receptor type 2," J Exp Med. 174:1299-1311 (1991).

(56) References Cited

OTHER PUBLICATIONS

Maslowska et al., "Novel roles for acylation stimulating protein/C3adesArg: a review of recent in vitro and in vivo evidence," Vitam Horm. 70:309-32 (2005).
Mastellos et al., "A novel role of complement: mice deficient in the fifth component of complement (C5) exhibit impaired liver regeneration," J Immunol. 166(4):2479-86 (2001).
Mastellos et al., "Novel monoclonal antibodies against mouse C3 interfering with complement activation: description of fine specificity and applications to various immunoassays," Mol Immunol. 40(16):1213-21 (2004).
Matsumoto et al., "Intersection of the complement and immune systems: A signal transduction complex of the B lymphocyte-containing complement receptor type 2 and CD19," J Exp Med. 173(1):55-64 (1991).
Matsuo et al., "Complement in renal tubulointerstitial injuries," Proceedings of the 35th Complement Symposium 21-22 (1998).
McPherson, "Current approaches to macromolecular crystallization," Eur J Biochem. 189(1):1-23 (1990).
Mendrick et al., "I. induction of proteinuria in the rat by a monoclonal antibody against SGP-115/107," Kidney Int. 33:818-30 (1988).
Mendrick et al., "Monoclonal antibodies against rat glomerular antigens: production and specificity," Lab Invest. 49(1):107-17 (1983).
Meri et al., "Structural composition and functional characterization of soluble CD59: heterogeneity of the oligosaccharide and glycophoshoinositol (GPI) anchor revealed by laser-desorption mass spectrometric analysis," Biochem J. 316(3):923-35 (1996).
Moir et al., "B cells of HIV-1-infected patients bind virions through CD21-complement interactions and transmit infectious virus to activated T cells," J Exp Med. 192(5):637-646 (2000).
Mold et al., "Activation of the alternative complement pathway by EBV and the viral envelope glycoprotein, gp350," J Immunol. 140(11):3867-3874 (1988).
Molesworth et al., "Epstein-Barr virus gH is essential for penetration of B cells but also plays a role in attachment of virus to epithelial cells," J Virol. 74(14):6324-32 (2000).
Molina et al., "Analysis of C3b/C3d binding sites and factor I cofactor regions within mouse complement receptor 1 and 2," J Immunol. 153(2):789-795 (1994).
Molina et al., "Analysis of Epstein-Barr virus-binding sites on complement receptor 2 (CR2/CD21) using human-mouse chimeras and peptides," J Biol Chem. 266(19-20):12173-9 (1991).
Molina et al., "Characterization of a complement receptor 2 (CR2, CD21) ligand binding site for C3. An initial model of ligand interaction with two linked short consensus repeat modules," J Immunol. 154:5426-5435 (1995).
Molina et al., "Markedly impaired humoral immune response in mice deficient in complement receptors 1 and 2," Proc Natl Acad Sci USA. 93:3357-3361 (1996).
Mollnes et al., "Identification of a human C5 beta-chain epitope exposed in the native complement component but concealed in the SC5b-9 complex," Scand J Immunol. 28:307-12 (1988).
Moongkarndi et al., "Immunological and functional properties of two monoclonal antibodies against human C5," Immunobiol. 165:323 (1983).
Moongkarndi et al., "Monoclonal antibodies against the fifth component of human complement," Immunobiol. 162:397 (1982).
Moore et al., "Hydrodynamic, electron microscopic, and ligand-binding analysis of the Epstein-Barr virus/C3dg receptor (CR2)," J Biol Chem. 264:20576-82 (1989).
Moore et al., "Inhibition of Epstein-Barr virus infection In Vitro and In Vivo by soluble CR2 (CD21) containing two short consensus repeats," J Virol. 65(7):3559-3565 (1991).
Moore et al., "Molecular cloning of the cDNA encoding the Epstein-Barr virus/C3d receptor (complement receptor type 2) of human B lymphocytes," Proc Natl Acad Sci USA. 84:9194-8 (1987).
Moran et al., "Human recombinant soluble decay accelerating factor inhibits complement activation in vitro and in vivo," J Immunol. 149:1736-1743 (1992).
Morgan, "Clinical complementology: recent progress and future trends," Eur J Clin Invest. 24(4):219-28 (1994).
Morikis et al., "The electrostatic nature of C3d-complement receptor 2 association," J Immunol. 172:7537-47 (2004).
Mullen et al., "Structure of the Epstein-Barr virus gp42 protein bound to the MHC class II receptor HLA-DR1," Mol Cell. 9:375-85 (2002).
Muller-Eberhard, "Molecular organization and function of the complement system," Ann Rev Biochem. 57:321-47 (1988).
Mulligan et al., "Endothelial targeting and enhanced antiinflammatory effects of complement inhibitors possessing sialyl Lewisx moieties," J Immunol 162(8):4952-9 (1999).
Murray et al., "Functional bioactive recombinant acylation stimulating protein is distinct from C3a anaphylatoxin," J Lipid Res. 38:2492-501 (1997).
Murray et al., "Mice lacking acylation stimulating protein (ASP) have delayed postprandial triglyceride clearance," J Lipid Res. 40:1671-6 (1999).
Murray et al., "Reduced body weight, adipose tissue, and leptin levels despite increased energy intake in female mice lacking acylation-stimulating protein," Endocrinology. 141(3):1041-9 (2000).
Nagar et al., "X-ray crystal structure of C3d: A C3 fragment and ligand for complement receptor 2," Science. 280(5367):1277-81 (1998).
NCBI Blast for Accession No. NP_001006659.1. Retrieved on Dec. 26, 2013 (5 pages).
NCBI Blast for Accession No. NP_031784.1. Retrieved on Dec. 26, 2013 (4 pages).
NCBI Blast for GenBank Accession No. U09969. Retrieved on Nov. 15, 2013 (3 pages).
NCBI Blast for UniProtKB/Swiss-Prot Accession No. O55186. Retrieved on Nov. 13, 2013 (5 pages).
NCBI Blast for UniProtKB/Swiss-Prot Accession No. P00746. Retrieved on Nov. 13, 2013 (14 pages).
NCBI Blast for UniProtKB/Swiss-Prot Accession No. P00751. Retrieved on Nov. 13, 2013 (1 page).
NCBI Blast for UniProtKB/Swiss-Prot Accession No. P01024. Retrieved on Nov. 13, 2013 (29 pages).
NCBI Blast for UniProtKB/Swiss-Prot Accession No. P01027. Retrieved on Nov. 13, 2013 (13 pages).
NCBI Blast for UniProtKB/Swiss-Prot Accession No. P03953. Retrieved on Nov. 13, 2013 (6 pages).
NCBI Blast for UniProtKB/Swiss-Prot Accession No. P04004. Retrieved on Nov. 13, 2013 (14 pages).
NCBI Blast for UniProtKB/Swiss-Prot Accession No. P04186. Retrieved on Nov. 13, 2013 (9 pages).
NCBI Blast for UniProtKB/Swiss-Prot Accession No. P05155. Retrieved on Nov. 13, 2013 (29 pages).
NCBI Blast for UniProtKB/Swiss-Prot Accession No. P06909. Retrieved on Nov. 13, 2013 (19 pages).
NCBI Blast for UniProtKB/Swiss-Prot Accession No. P08173. Retrieved on Nov. 13, 2013 (4 pages).
NCBI Blast for UniProtKB/Swiss-Prot Accession No. P08603. Retrieved on Nov. 13, 2013 (1 page).
NCBI Blast for UniProtKB/Swiss-Prot Accession No. P10909. Retrieved on Nov. 13, 2013 (21 pages).
NCBI Blast for UniProtKB/Swiss-Prot Accession No. P11680. Retrieved on Nov. 13, 2013 (5 pages).
NCBI Blast for UniProtKB/Swiss-Prot Accession No. P13987. Retrieved on Nov. 13, 2013 (16 pages).
NCBI Blast for UniProtKB/Swiss-Prot Accession No. P15529. Retrieved on Nov. 13, 2013 (30 pages).
NCBI Blast for UniProtKB/Swiss-Prot Accession No. P17927. Retrieved on Nov. 13, 2013 (1 page).
NCBI Blast for UniProtKB/Swiss-Prot Accession No. P27918. Retrieved on Nov. 13, 2013 (13 pages).
NCBI Blast for UniProtKB/Swiss-Prot Accession No. P29788. Retrieved on Nov. 13, 2013 (10 pages).
NCBI Blast for UniProtKB/Swiss-Prot Accession No. P58019. Retrieved on Nov. 13, 2013 (5 pages).
NCBI Blast for UniProtKB/Swiss-Prot Accession No. P97290. Retrieved on Nov. 13, 2013 (6 pages).
NCBI Blast for UniProtKB/Swiss-Prot Accession No. Q06890. Retrieved on Nov. 13, 2013 (9 pages).

(56) References Cited

OTHER PUBLICATIONS

NCBI Blast for UniProtKB/Swiss-Prot Accession No. Q61475. Retrieved on Nov. 13, 2013 (11 pages).
NCBI Blast for UniProtKB/Swiss-Prot Accession No. Q9P296. Retrieved on Nov. 13, 2013 (9 pages).
NCBI Protein Database Accession No. P08173. Retrieved Feb. 18, 2014 (4 pages).
NCBI Protein Database Accession No. P13987. Retrieved Feb. 18, 2014 (12 pages).
NCBI Protein Database Accession No. P15529. Retrieved Feb. 18, 2014 (21 pages).
NCBI Protein Database Accession No. P58019. Retrieved Feb. 18, 2014 (4 pages).
Nemerow et al., "Identification and characterization of the Epstein-Barr virus receptor on human B lymphocytes and its relationship to the C3d complement receptor (CR2)," J Virol. 55(2):347-51 (1985).
Nemerow et al., "Identification of an epitope in the major envelope protein of Epstein-Barr virus that mediates viral binding to the B lymphocyte EBV receptor (CR2)," Cell. 56:369-77 (1989).
Nemerow et al., "Identification of gp350 as the viral glycoprotein mediating attachment of Epstein-Barr virus (EBV) to the EBV/C3d receptor of B cells: sequence homology of gp350 and C3 complement fragment C3d," J Virol. 61(5):1416-20 (1987).
Ngo et al., Computational Complexity, Protein Structure Prediction, and the Levinthal Paradox. *The Protein Folding Problem and Tertiary Structure Prediction*. Merz et al., 491-495 (1994).
Niemann et al., "The use of monoclonal antibodies as probes of the three-dimensional structure of human complement factor D," J Immunol. 132(2):809-15 (1984).
Nozaki et al., "Drusen complement components C3a and C5a promote choroidal neovascularization," Proc Natl Acad Sci USA. 103(7):2328-2333 (2006).
Oglesby et al., "Membrane cofactor protein (CD46) protects cells from complement-mediated attack by an intrinsic mechanism," J Exp Med. 175:1547-51 (1992).
Okano, "Epstein-Barr virus infection and its role in the expanding spectrum of human diseases," Acta Paediatr. 87:11-18 (1998).
Paglialunga et al., "Reduced adipose tissue triglyceride synthesis and increased muscle fatty acid oxidation in C5L2 knockout mice," J Endocrinol. 194:293-304 (2007).
Paixao-Cavalcante et al., "Factor H facilitates the clearance of GBM bound iC3b by controlling C3 activation in fluid phase," Mol Immunol. 46:1942-50 (2009).
Pascual et al., "A monoclonal antibody which blocks the function of factor D of human complement," J Immunol Methods. 127:263-9 (1990).
Pascual et al., "Inhibition of complement alternative pathway in mice with Fab antibody to recombinant adipsin/factor D," Eur J Immunol. 23:1389-92 (1993).
Patel et al., "Pexelizumab: a novel therapy for myocardial ischemia-reperfusion," Drugs Today (Barc). 41(3):165-70 (2005).
Pervushin et al., "Attenuated T2 relaxation by mutual cancellation of dipole-dipole coupling and chemical shift anisotropy indicates an avenue to NMR structures of very large biological macromolecules in solution," Proc Natl Acad Sci USA. 94:12366-71 (1997).
Petersen et al., "The mannan-binding lectin pathway of complement activation: biology and disease association," Mol Immunol. 38:133-49 (2001).
Piatesi et al., "Immunological optimization of a generic hydrophobic pocket for high affinity hapten binding and Diels-Alder activity," Chembiochem. 5(4):460-466 (2004).
Pickering et al., Uncontrolled C3 activation causes membranoproliferative glomerulonephritis in mice deficient in complement factor H. Nat Genet. Aug. 2002;31(4):424-8. Epub Jul. 1, 2002.
Pietersz et al., "Antibody conjugates for the treatment of cancer," Immunolog Reviews. 129:57-80 (1992).
Poznansky et al., "The difference between human C3F and C3S results from a single amino acid change from an asparagine to an aspartate residue at position 1216 on the a-chain of the complement component C3," J Immunol. 143(4):1254-1258 (1989).
Preissner, "Structure and biological role of vitronectin," Annu Rev Cell Biol. 7:275-310 (1991).
Prodeus et al., "A critical role for complement in maintenance of self-tolerance," Immunity. 9(5):721-731 (1998).
Prodinger et al., "Characterization of C3dg binding to to a recess formed between short consensus repeats 1 and 2 of complement receptor type 2 (CR2; CD21)," J Immunol. 161:4604-4610 (1998).
Prota et al., "The crystal structure of human CD21: Implications for Epstein-Barr virus and C3d binding," Proc Natl Acad Sci USA. 99:10641-6 (2002).
Quigg et al., "Blockade of antibody-induced glomerulonephritis with Crry-Ig, a soluble murine complement inhibitor," J Immunol. 160(9):4553-60 (1998).
Quigg et al., "Production and fuctional analysis of rat CD59 and chimeric CD59-Crry as active soluble proteins in Pichia pastoris," Immunol. 99(1):46-53 (2000).
Rabinovici et al., "Role of complement in endotoxin/platelet-activating factor-induced lung injury," J Immunol. 149(5):1744-50 (1992).
Ramm et al., "Transmembrane channel formation by complement: functional analysis of the number of C5b6, C7, C8, and C9 molecules required for a single channel," Pro Natl Acad Sci. 79(15):4751-5 (1982).
Rao et al., "OKB7, a monoclonal antibody that reacts at or near the C3d binding site of human CR2," Cell Immunol. 93(2):549-555 (1985).
Reeck et al., "Homology in proteins and nucleic acids: A terminology muddle and a way out of it," Cell. 50:667 (1987).
Rehrig et al., "Complement inhibitor, complement receptor 1-related gene/protein y-Ig attenuates intestinal damage after the onset of mesenteric ischemia/reperfusion injury in mice," J Immunol. 167:5921-7 (2001).
Ricklin et al., "Complement-targeted therapeutics," Nat Biotechnol. 25(11):1265-75 (2007).
Ricklin et al., Complement: a key system for immune surveillance and homeostasis. Nat Immunol. Sep. 2010;11(9):785-97.
Rinder et al., "Blockade of C5a and C5b-9 generation inhibits leukocyte and platelet activation during extracorporeal circulation," J Clin Invest. 96(3):1564-72 (1995).
Rioux, "TP-10 AVANT immunotherapeutics," Curr Opin Invest Drugs 2(3):364-71 (2001).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Paroxysmal nocturnal hemoglobinuria: pathophysiology, natural history and treatment options in the era of biological agents," Biologics. 2(2):205-222 (2008).
Risitano et al., "The complement receptor 2/factor H fusion protein TT30 protects paroxysmal nocturnal hemoglobinuria erythroctyes from complement-mediated hemolysis and C3 fragment opsonization," Blood. 119(26):6307-6316 (2012).
Risitano et al., "TT30, a novel regulator of the complement alternative pathway (CAP), inhibits hemolysis of paroxysmal nocturnal hemoglobinuria (PNH) erythrocytes and prevents upstream C3 binding on their surface in an in vitro model," <https://ash.confex.com/ash/2009/webprogram/Paper19102.html>, retrieved on Dec. 26, 2013 (2 pages).
Rittershaus et al., "Recombinant glycoproteins that inhibit complement activation and also bind the selectin adhesion molecules," J Biol Chem. 274(16):11237-44 (1999).
Roffler et al., "Anti-neoplastic glucuronide prodrug treatment of human tumor cells targeted with a monoclonal antibody-enzyme conjugate," Biochem Pharmacol. 42:2062-2065 (1991).
Rohrer et al., "Eliminating complement factor D reduces photoreceptor susceptibility to light-induced damage," Invest Ophthalmol Vis Sci. 48(11):5282-9 (2007).
Rohrer et al., "Role of neurotrophin receptor TrkB in the maturation of rod photoreceptors and establishment of synaptic transmission to the inner retina," J Neurosci. 19(20):8919-8930 (1999).

(56) References Cited

OTHER PUBLICATIONS

Rohrer et al., A targeted inhibitor of the alternative complement pathway reduces angiogenesis in a mouse model of age-related macular degeneration. Invest Ophthalmol Vis Sci. Jul. 2009;50(7):3056-64.
Rohrer et al., Systemic human CR2-targeted complement alternative pathway inhibitor ameliorates mouse laser-induced choroidal neovascularization. J Ocul Pharmacol Ther. Aug. 2012;28(4):402-9.
Ross et al., "Macrophage cytoskeleton association with CR3 and CR4 regulates receptor mobility and phagocytosis of iC3b-opsonized erythrocytes," J Leukoc Biol. 51(20):109-117 (1992).
Rother et al., Discovery and development of the complement inhibitor eculizumab for the treatment of paroxysmal nocturnal hemoglobinuria. Nat Biotechnol. Nov. 2007;25(11):1256-64.
Rothlein et al., "The requirement for lymphocyte function-associated antigen 1 in homotypic leukocyte adhesion stimulated by phorbol ester," J Exp Med. 163(5):1132-49 (1986).
Rudikoff et al., "Single amino acid subsitution altering antigen-binding specificity," Proc Natl Acad Sci USA. 79(6):1979-19783 (1982).
Rushmere et al., "Production and functional characterization of a soluble recombinant form of mouse CD59," Immunol. 99(2):326-32 (2000).
Sahu et al., "Identification of multiple sites of interaction between heparin and the complement system," Mol Immunol. 30(7):679-84 (1993).
Salerno et al., "A soluble chimeric inhibitor of C3 and C5 convertases, complement activation blocker-2, prolongs graft survival in pig-to-rhesus monkey heart transplantation," Xenotransplantation. 9(2):125-34 (2002).
Santiago-Raber et al., "Type-I interferon receptor deficiency reduces lupus-like disease in NZB mice," J Exp Med. 197:777-88 (2003).
Sargsyan et al., Detection of glomerular complement C3 fragments by magnetic resonance imaging in murine lupus nephritis. Kidney Int. Jan. 2012;81(2):152-9.
Sarnaik et al., "Periodic transfusions for sickle cell anemia and CNS infarction," Am J Dis Child. 133(12):1254-7 (1979).
Satoh et al., "Energy metabolism regeneration in transgenic mouse liver expressing creatine kinase after major hepatectomy," Gastroenterology. 101:1166-74 (1996).
Schoonooghe et al., Efficient production of human bivalent and trivalent anti-MUC1; Fab-scFv antibodies in Pichia pastoris. BMC Biotechnol. Aug. 11, 2009;9:70.
Schulze et al., Glomerular C3c localization indicates ongoing immune deposit formation and complement activation in experimental glomerulonephritis. Am J Pathol. Jan. 1993;142(1):179-87.
Schwarzenbacher et al., "Crystal structure of human b2-glycoprotein I: implications for phospholipid binding and the antiphospholipid syndrome," EMBO J. 18:6228-39 (1999).
Scola et al., "The human complement fragment receptor, C5L2, is a recycling decoy receptor," Mol Immunol. 46:1149-62 (2009).
Selzner et al., "Failure of regeneration of the steatotic rat liver: disruption at two different levels in the regeneration pathway," Hepatology. 31:35-42 (2000).
Senter et al., "Generation of 5-fluorouracil from 5-fluorocytosine by monoclonal antibody-cytosine deaminase conjugates," Bioconjugate Chem. 2:447-451 (1991).
Senter et al., "Generation of cytotoxic agents by targeted enzymes," Bioconjugate Chem. 4:3-9 (1993).
Serkova et al., Renal inflammation: targeted iron oxide nanoparticles for molecular MR imaging in mice. Radiology. May 2010;255(2):517-26.
Seya et al., "Limited proteolysis of complement protein C3b by regulatory enzyme C3b inactivator: Isolation and characterization of a biologically active fragment, C3d,g," J Biochem. 97(1):373-382 (1985).
Sharkey et al., "Biodistribution and radiation dose estimates for yttrium- and iodine-labeled monoclonal antibody IgG and fragments in nude mice bearing human colonic tumor xenografts," Cancer Res. 50:2330-2336 (1990).
Sharkey et al., "Rapid blood clearance of immunoglobulin G2a and immunoglobulin G2b in nude mice," Cancer Res. 51:3102-3107 (1991).
Sharma et al., "Identification of three physically and functionally distinct binding sites for C3b in human complement Factor H by deletion mutagenesis," Proc Natl Aced Sci USA. 93(20):10996-11001 (1996).
Sheerin et al., "Leaked protein and interstitial damage in the kidney: is complement the missing link?" Clin Exp Immunol. 130(1):1-3 (2002).
Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. Epub Nov. 28, 2000.
Shinkawa et al., The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73. Epub Nov. 8, 2002.
Sigala et al., "Histological and lipid peroxidation changes after administration of 2-acetylaminofluorene in a rat liver injury model following selective periportal and pericentral damage," Toxicology. 196:155-63 (2004).
Skjodt et al., "MBL/Ficolin assocaited protein-1 (MAP-1) may function as a local lectin pathway specific complement inhibitor," Mol Immunol. 47:2229-30 (2010).
Smith et al., "Membrane-targeted complement inhibitors," Mol Immunol. 38:249-55 (2001).
Sokoloff et al., "Targeting of cancer cells with monoclonal antibodies specific for C3b(ii)," Cancer Immunol and Immunother. 49(10):551-62 (2000).
Song et al., "Complement receptor 2-mediated targeting of complement inhibitors to sites of complement activation," J Clin Invest. 11 1(12):1875-1885 (2003).
Song et al., Complement receptor 2-mediated targeting of complement inhibitors to sites of complement activation. J Clin Invest. Jun. 2003;111(12):1875-85.
Spriggs et al., "The extracellular domain of the Epstein-Barr virus BZLF2 protein binds the HLA-DR beta chain and inhibits antigen presentation," J Virol. 70:5557-63 (1996).
Strey et al., "The proinflammatory mediators C3a and C5a are essential for liver regeneration," J Exp Med. 198(6):913-23 (2003).
Strunk et al., Human peripheral blood monocyte-derived macrophages produce haemolytically active C3 in vitro. Immunology. May 1983;49(1):169-74.
Stryer et al., Levels of Structure in Protein Architecture. *Biochemistry* (*3rd edition*). W H Freeman Company, 31-33 (1998).
Sugita et al., "Recombinant soluble CD59 inhibits reative haemolysis with complement," Immunol. 82(1):34-41 (1994).
Supplementary European Search Report for European Patent Application No. EP1 1798880.8, dated Jan. 7, 2014 (13 pages).
Supplementary Partial European Search Report for European Application No. 03796403.8, mailed Apr. 3, 2006 (3 pages).
Supplementary Partial European Search Report for European Application No. 03796403.8, mailed Jul. 3, 2006 (4 pages).
Szakonyi et al., "Structure of complement receptor 2 in complex with its C3d ligand," Science. 292:1725-1728 (2001).
Szakonyi et al., "Structure of the Epstein-Barr virus major envelope glycoprotein," Nature Struct Mol Biol. 13:996-1001 (2006).
Takahashi et al., "Mouse complement receptors type 1 (CR1 ;CD35) and type 2 (CR2;CD21): expression on normal B cell subpopulations and decreased levels during the development of autoimmunity in MRL/lpr mice," J Immunol. 159:1557-69 (1997).
Takeda et al., "Number of hits necessary for complement-mediated hemolysis," Microbiol Immunol. 30(5):461-8 (1986).
Tamerius et al., Detection of a neoantigen on human C3bi and C3d by monoclonal antibody. J Immunol. Sep. 1985;135(3):2015-9.
Tanhehco et al., "The anti-factor D antibody, MAb 166-32, inhibits the alternative pathway of the human complement system," Transplant Proc. 31(55):2168-71 (1999).
Tanner et al., "Epstein-Barr virus gp350/220 binding to the B lymphocyte C3d receptor mediates adsorption, capping, and endocytosis," Cell. 50:203-13 (1987).

(56) References Cited

OTHER PUBLICATIONS

Taub, "Liver regeneration: from myth to mechanism," Nat Rev Mol Cell Biol. 5:836-47 (2004).
Ten et al., "The signal transduction pathway of CD23 (FceRIIb) targets IkB kinase," J Immunol. 163(7):3851-7 (1999).
Teoh et al., "Dual role of tumor necrosis factor-alpha in hepatic ischemia-reperfusion injury: studies in tumor necrosis factor-alpha gene knockout mice," Hepatology. 39:412-21 (2004).
Thomas et al., Inhibition of complement activity by humanized anti-C5 antibody and single-chain Fv. Mol Immunol. Dec. 1996;33(17-18):1389-401.
Thurman et al., A novel inhibitor of the alternative complement pathway prevents antiphospholipid antibody-induced pregnancy loss in mice. Mol Immunol. Jan. 2005;42(1):87-97.
Thurman et al., Lack of a functional alternative complement pathway ameliorates ischemic acute renal failure in mice. J Immunol. Feb. 1, 2003;170(3):1517-23.
Tian et al., "Kupffer cell-dependent TNF-alpha signaling mediates injury in the arterialized small-for-size liver transplantation in the mouse," Proc Natl Acad Sci USA. 103(12):4598-603 (2006).
Tolnay et al., "Complement receptor 2 in the regulation of the immune response," Clin Immunol Immunopathol. 88:123-32 (1998).
Tosic et al., "Preparation of monoclonal antibodies to C3b by immunization with C3b(i)-sepharose," J Immunol Methods. 120:241-9 (1989).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," Proc Natl Acad Sci USA. 97(15):8548-53 (2000).
Tutt et al., Trispecific F(ab')3 derivatives that usecooperative signaling via the TCR/CD3 complex and CD2 to activate and redirect resting cytotoxic T cells. J Immunol. Jul. 1, 1991;147(1):60-9.
Tuveson et al., "Molecular interactions of complement receptors on B lymphocytes: a CR1/CR2 complex distinct from the CR2/CD19 complex," J Exp Med. 173:1083-9 (1991).
Ueda et al., "Probing Functional Sites on Complement Protein B with Monoclonal Antibodies," J. Immunol. 138(4):1143-1149(1987).
van der Eisen et al., "A crystal structure of the complex between human complement receptor 2 and its ligand C3d," Science. 332:608-611 (2011).
Van Harmelen et al., "Mechanisms involved in the regulation of free fatty acid release from isolated human fat cells by acylation-stimulating protein and insulin," J Biol Chem. 274(26):18243-51 (1999).
Vranken et al., "The CCPN data model for NMR spectroscopy: development of a software pipeline," Proteins. 59:687-96 (2005).
Walport MJ. Complement. Second of two parts. N Engl J Med. Apr. 12, 2001;344(15):1140-4.
Wang et al., "Amelioration of Lupus-like autoimmune disease in NZB/W F1 mice after treatment with a blocking monoclonal antibody specific for complement component C5," Proc Natl Acad Sci USA. 93(16):8563-8 (1996).
Wang et al., "Anti-05 monoclonal antibody therapy prevents collagen-induced arthritis and ameoliorates established disease," Proc Natl Acad Sci USA. 92(19):8955-9 (1995).
Ward et al., "Decay-accelerating factor CD55 is identified as the receptor for echovirus 7 using CELICS, a rapid immuno-focal cloning method," EMBO J. 13(21):5070-4 (1994).
Watanabe et al., "Co-protective effect of Crry and CD59 in rat kidney against complement attack," Proceedings of the Joint Academic Meeting of the Complement Symposium and Japanese Society for Host Defense Research, 37(11):19-20 (2000).
Weening et al., The classification of glomerulonephritis in systemic lupus rythematosus revisited. J Am Soc Nephrol. Feb. 2004;15(2):241-50.
Weis et al., "Identification of a 145,000 Mr membrane protein as the C3d receptor (CR2) of human B lymphocytes," Proc Natl Acad Sci USA. 81:881-5 (1984).
Weis et al., "Identification of a partial cDNA clone for the C3d/Epstein-Barr virus receptor of human B lymphocytes: homology with the receptor for fragments C3b and C4b of the third and fourth components of complement," Proc Natl Acad Sci USA. 83:5639-43 (1986).
Weis et al., "Structure of the human B lymphocyte receptor for C3d and the Epstein-Barr virus and relatedness to other members of the family of C3/C4 binding proteins," J Exp Med. 167:1047-66 (1988).
Weisman et al., "Soluble human complement receptor type 1: in vivo inhibitor of complement suppressing post-ischemic myocardial inflammation and necrosis," Science. 249(4965):146-151 (1990).
Weissleder et al., Superparamagnetic iron oxide: pharmacokinetics and toxicity. AJR Am J Roentgenol. Jan. 1989;152(1):167-73.
Wessels et al., Studies of group B streptococcal infection in mice deficient in complement component C3 or C4 demonstrate an essential role for complement in both innate and acquired immunity. Proc Natl Acad Sci USA. Dec. 1995 ;92(25):11490-4.
Whiss, "Pexelizumab Alexion," Curr Opin Investig Drugs. 3(6):870-7 (2002).
Whittier WL, Korbet SM. Timing of complications in percutaneous renal biopsy. ; J Am Soc Nephrol. Jan. 2004;15(1):142-7.
Wiles et al., "NMR studies of a viral protein that mimics the regulators of complement activation," J Mol Biol. 272(2):253-265 (1997).
Wiseman et al., "Rapid measurement of binding constants and heats of binding using a new titration calorimeter," Anal Biochem. 179:131-7 (1989).
Wittekind et al., "A high sensitivity 3D NMR experiment to correlate amide-proton and nitrogen resonances with the alpha-carbon and beta-carbon resonances in proteins," J Magn Reson. 101:201-5 (1993).
Wright A, Morrison Sl. Effect of glycosylation on antibody function: implications for genetic engineering. Trends Biotechnol. Jan. 1997;15(1):26-32.
Wu et al., Simultaneous targeting of multiple disease mediators by a dual-variable-domain immunoglobulin. Nat Biotechnol. Nov. 2007;25(11):1290-7. Epub Oct. 14, 2007.
Wu et al., Structure of complement fragment C3b-factor H and implications for host protection by complement regulators. Nat Immunol. Jul. 2009;10(7):728-33.
Wullaert et al., "Hepatic tumor necrosis factor signaling and nuclear factor-kappaB: effects on liver homeostasis and beyond," Endocr Rev. 28(4):365-86 (2007).
Xia et al., "Acylation-stimulating protein (ASP) deficiency induces obesity resistance and increased energy expenditure in ob/ob mice," J Biol Chem. 277:45874-9 (2002).
Yamaji et al., "Up-regulation of hepatic heme oxygenase-1 expression by locally induced interleukin-6 in rats administered carbon tetrachloride intraperitoneally," Toxicol Lett. 179:124-9 (2008).
Yang et al., "An engineered complement receptor 1 composed of two functional domains can protect against immune-mediated hemolysis," Protein Expr Purif. 66(1):28-34 (2009).
Young et al., "Molecular basis of the interaction between complement receptor type 2 (CR2/CD21) and Epstein-Barr virus glycoprotein gp350," J Virol. 82:11217-27 (2008).
Yu et al., "Protection of human breast cancer cells from complement-mediated lysis by expression of heterologous CD59," Clin Exp Immunol. 115(1):13-8 (1999).
Zapata et al., Engineering linear F(ab')2 fragments for efficient production in *Escherichia coli* and enhanced antiproliferative activity. Protein Eng. Oct. 1995;8(10):1057-62.
Zhang et al., "Immunophysical exploration of C3d-CR2(CCP1-2) interaction using molecular dynamics and electrostatics," J Mol Biol. 369:567-83 (2007).
Zhang et al., "Targeting of functional antibody-CD59 fusion proteins to a cell surface," J Clin Invest. 103(1):55-61 (1999).
Zhang et al., "Targeting of functional antibody-decay-accelerating factor fusion proteins to a cell surface," J Biol Chem. 276(29):27290-5 (2001).

(56) References Cited

OTHER PUBLICATIONS

Zhao et al., Non-invasive detection of apoptosis using magnetic resonance imaging and a targeted contrast agent. Nat Med. Nov. 2001;7(11):1241-4.

Zhong et al., "NIM811, a mitochondrial permeability transition inhibitor, prevents mitochondrial depolarization in small-for-size rat liver grafts," Am J Transplant. 7:1103-11 (2007).

Zhu et al., "Inhibition of tumor growth and metastasis by targeting tumor-associated angiogenesis with antagonists to the receptors of vascular endothelial growth factor," Invest New Drugs. 17(3):195-212 (1999).

Zipfel PF. Complement factor H: physiology and pathophysiology. Semin Thromb; Hemost. Jun. 2001;27(3):191-9.

Zuiderweg et al., "Heteronuclear three-dimensional NMR spectroscopy of the inflammatory protein C5a," Biochemistry. 28:2387-91 (1989).

Fig. 3
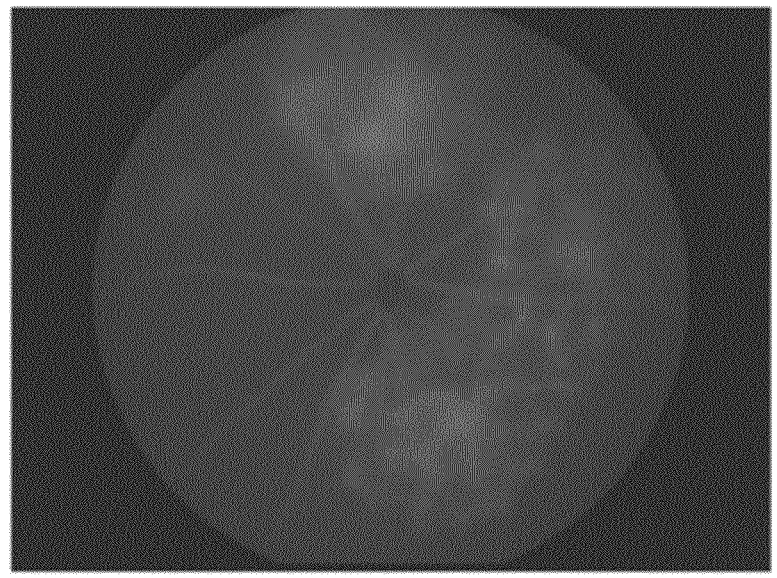
HB5 (control)
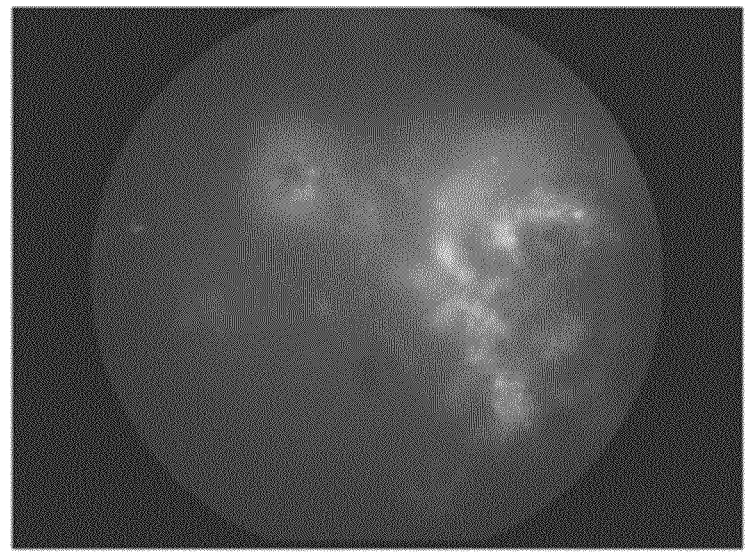
3d29 (anti-C3d)

Fig. 4
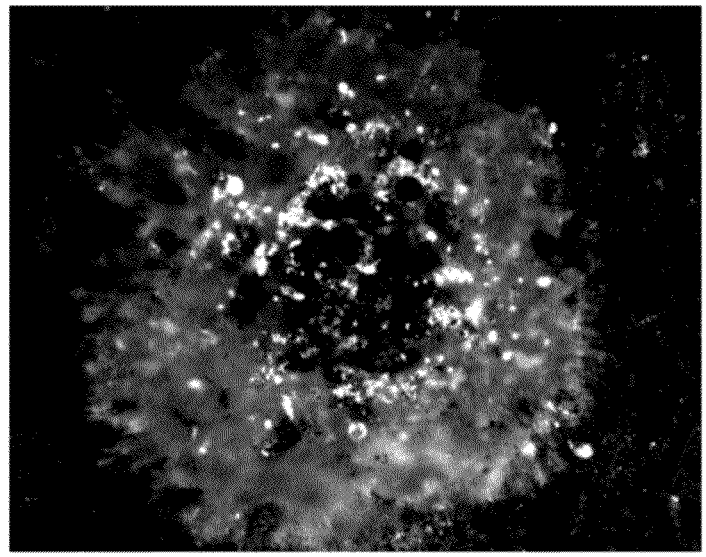
HB5 (control)
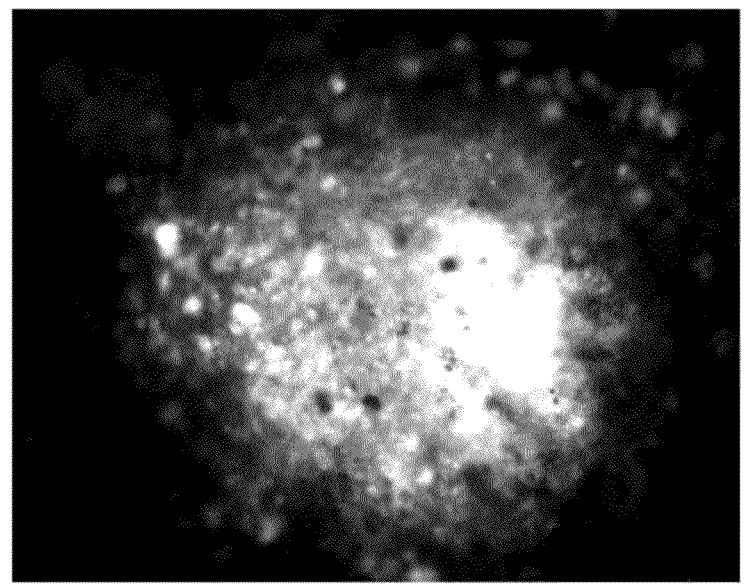
3d29 (anti-C3d)

Fig. 22

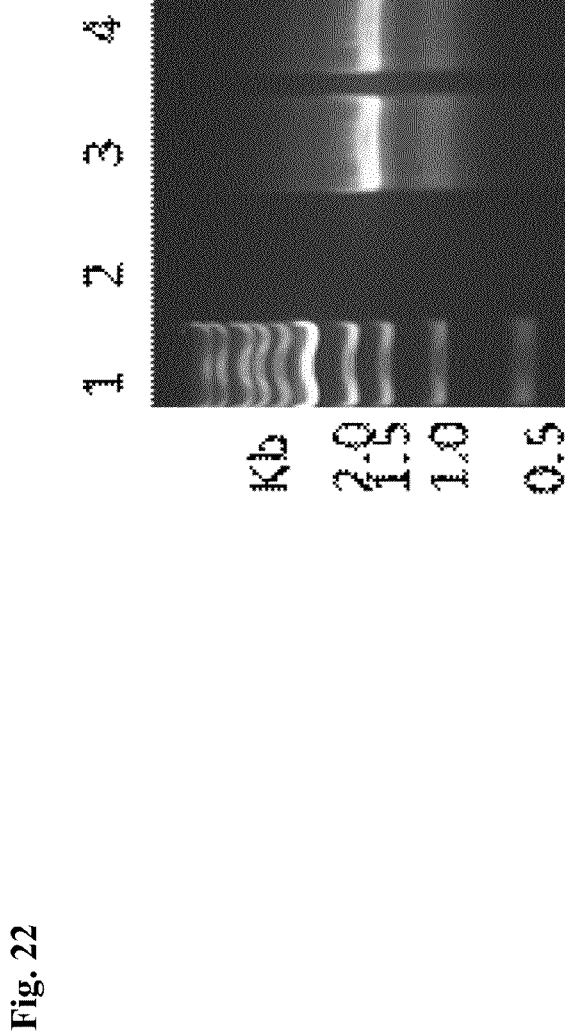

MPMGSLQPLATLYLLGMLVASVLAHHHHHHIEGREVKLVESGGLVQPGSSMKLSCTTSGFTFSDYYMAWVRQVPEK
<u>SP sq</u>    <u>His Tag</u>   <u>Factor Xa</u>
GLEWVANINYDGSSAYYLDSFKSRFTISRDNEKNILYLQMSSLKSEDTATYYCARGDWFVYWGQGTLVTVSAGGGGSGGGGSGGGGSDIQMTQSPSSMSASLGERVTITCKASQDIN
SYLNWFQQKPGKSPKTLIFRANRLVDGVPSRFSGSGSGQDYSLTISSLEFEDVGIYYCLQYAEPPTFGSGTKLEIKIEGRGGGGSGGGGSGGGGSCPAPSQLPSAKPINLTDESMFPIGTYLLYECL
                                                                                      <u>Linker</u>
PGYIKRQFSITCKQDSTWTSAEDKCIRKQCKTPSDPENGLVHVHTGIQFGSRINYTCNQGYRLIGSSSAVCVITDQSVDWDTEAPICEWIPCEIPP
GIPNGDFFSSTREDFHYGMVVTYRCNTDARGKALFNLVGEPSLYCTSNDGEIGVWSGPPQCIELNKCTPPPYVENAVMLSENRSLFSLRDIVE
FRCHPGFIMKGASSVHCQSLNKWEPELPSCFKGVICRLPQEMSGFQKGLGMKKEYYYGENVTLECEDGYTLEGSSQSQCQSDGSWNPLLAKC
VSRSI

SEQUENCE LISTING

<160> NUMBER OF SEQ ID NOS: 54

<210> SEQ ID NO 1
<211> LENGTH: 392
<212> TYPE: PRT
<213> ORGANISM: Homo sapiens

<400> SEQUENCE: 1

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Asp Ala Cys Tyr Arg
                85                  90                  95

```
Glu Thr Cys Pro Tyr Ile Arg Asp Pro Leu Asn Gly Gln Ala Val Pro
                100                 105                 110

Ala Asn Gly Thr Tyr Glu Phe Gly Tyr Gln Met His Phe Ile Cys Asn
            115                 120                 125

Glu Gly Tyr Tyr Leu Ile Gly Glu Glu Ile Leu Tyr Cys Glu Leu Lys
        130                 135                 140

Gly Ser Val Ala Ile Trp Ser Gly Lys Pro Pro Ile Cys Glu Lys Val
145                 150                 155                 160

Leu Cys Thr Pro Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285

Pro Ser Ser Thr Lys Pro Pro Ala Leu Ser His Ser Val Ser Thr Ser
290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
            340                 345                 350

Ala Ile Val Val Gly Val Ala Val Ile Cys Val Val Pro Tyr Arg Tyr
        355                 360                 365

Leu Gln Arg Arg Lys Lys Lys Gly Thr Tyr Leu Thr Asp Glu Thr His
370                 375                 380

Arg Glu Val Lys Phe Thr Ser Leu
385                 390

<210> SEQ ID NO 2
<211> LENGTH: 381
<212> TYPE: PRT
<213> ORGANISM: Homo sapiens

<400> SEQUENCE: 2

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Val
            20                  25                  30

Trp Gly Asp Cys Gly Leu Pro Pro Asp Val Pro Asn Ala Gln Pro Ala
        35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
```

```
            65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Glu Tyr Glu
            115                 120                 125

Cys Arg Pro Gly Tyr Arg Glu Pro Ser Leu Ser Pro Lys Leu Thr
            130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
                180                 185                 190

Gly Tyr Lys Leu Phe Gly Ser Thr Ser Ser Phe Cys Leu Ile Ser Gly
                195                 200                 205

Ser Ser Val Gln Trp Ser Asp Pro Leu Pro Glu Cys Arg Glu Ile Tyr
            210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
                260                 265                 270

Glu Gly Glu Trp Ser Gly Pro Pro Glu Cys Arg Gly Lys Ser Leu
            275                 280                 285

Thr Ser Lys Val Pro Pro Thr Val Gln Lys Pro Thr Thr Val Asn Val
            290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
                340                 345                 350

Ser Gly Thr Thr Arg Leu Leu Ser Gly His Thr Cys Phe Thr Leu Thr
            355                 360                 365

Gly Leu Leu Gly Thr Leu Val Thr Met Gly Leu Leu Thr
            370                 375                 380

<210> SEQ ID NO 3
<211> LENGTH: 390
<212> TYPE: PRT
<213> ORGANISM: Mus musculus

<400> SEQUENCE: 3

Met Ile Arg Gly Arg Ala Pro Arg Thr Arg Pro Ser Pro Pro Pro Pro
1               5                   10                  15

Leu Leu Pro Leu Leu Ser Leu Ser Leu Leu Leu Ser Pro Thr Val
            20                  25                  30

Arg Gly Asp Cys Gly Pro Pro Asp Ile Pro Asn Ala Arg Pro Ile
            35                  40                  45

Leu Gly Arg His Ser Lys Phe Ala Glu Gln Ser Lys Val Ala Tyr Ser
            50                  55                  60
```

Cys Asn Asn Gly Phe Lys Gln Val Pro Asp Lys Ser Asn Ile Val Val
65                  70                  75                  80

Cys Leu Glu Asn Gly Gln Trp Ser Ser His Glu Thr Phe Cys Glu Lys
                85                  90                  95

Ser Cys Val Ala Pro Glu Arg Leu Ser Phe Ala Ser Leu Lys Lys Glu
            100                 105                 110

Tyr Leu Asn Met Asn Phe Phe Pro Val Gly Thr Ile Val Glu Tyr Glu
            115                 120                 125

Cys Arg Pro Gly Phe Arg Lys Gln Pro Pro Leu Pro Gly Lys Ala Thr
        130                 135                 140

Cys Leu Glu Asp Leu Val Trp Ser Pro Val Ala Gln Phe Cys Lys Lys
145                 150                 155                 160

Lys Ser Cys Pro Asn Pro Lys Asp Leu Asp Asn Gly His Ile Asn Ile
                165                 170                 175

Pro Thr Gly Ile Leu Phe Gly Ser Glu Ile Asn Phe Ser Cys Asn Pro
            180                 185                 190

Gly Tyr Arg Leu Val Gly Val Ser Ser Thr Phe Cys Ser Val Thr Gly
        195                 200                 205

Asn Thr Val Asp Trp Asp Asp Glu Phe Pro Val Cys Thr Glu Ile His
210                 215                 220

Cys Pro Glu Pro Pro Lys Ile Asn Asn Gly Ile Met Arg Gly Glu Ser
225                 230                 235                 240

Asp Ser Tyr Thr Tyr Ser Gln Val Val Thr Tyr Ser Cys Asp Lys Gly
                245                 250                 255

Phe Ile Leu Val Gly Asn Ala Ser Ile Tyr Cys Thr Val Ser Lys Ser
            260                 265                 270

Asp Val Gly Gln Trp Ser Ser Pro Pro Pro Arg Cys Ile Glu Lys Ser
        275                 280                 285

Lys Val Pro Thr Lys Lys Pro Thr Ile Asn Val Pro Ser Thr Gly Thr
290                 295                 300

Pro Ser Thr Pro Gln Lys Pro Thr Thr Glu Ser Val Pro Asn Pro Gly
305                 310                 315                 320

Asp Gln Pro Thr Pro Gln Lys Pro Ser Thr Val Lys Val Ser Ala Thr
                325                 330                 335

Gln His Val Pro Val Thr Lys Thr Thr Val Arg His Pro Ile Arg Thr
            340                 345                 350

Ser Thr Asp Lys Gly Glu Pro Asn Thr Gly Gly Asp Arg Tyr Ile Tyr
        355                 360                 365

Gly His Thr Cys Leu Ile Thr Leu Thr Val Leu His Val Met Leu Ser
370                 375                 380

Leu Ile Gly Tyr Leu Thr
385                 390

<210> SEQ ID NO 4
<211> LENGTH: 128
<212> TYPE: PRT
<213> ORGANISM: Homo sapiens

<400> SEQUENCE: 4

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
            50                  55                  60

Trp Lys Phe Glu His Cys Asn Phe Asn Asp Val Thr Thr Arg Leu Arg
 65                  70                  75                  80

Glu Asn Glu Leu Thr Tyr Tyr Cys Cys Lys Lys Asp Leu Cys Asn Phe
                    85                  90                  95

Asn Glu Gln Leu Glu Asn Gly Gly Thr Ser Leu Ser Glu Lys Thr Val
                100                 105                 110

Leu Leu Leu Val Thr Pro Phe Leu Ala Ala Ala Trp Ser Leu His Pro
            115                 120                 125

<210> SEQ ID NO 5
<211> LENGTH: 123
<212> TYPE: PRT
<213> ORGANISM: Mus musculus

<400> SEQUENCE: 5

Met Arg Ala Gln Arg Gly Leu Ile Leu Leu Leu Leu Leu Ala Val
 1               5                  10                  15

Phe Cys Ser Thr Ala Val Ser Leu Thr Cys Tyr His Cys Phe Gln Pro
                    20                  25                  30

Val Val Ser Ser Cys Asn Met Asn Ser Thr Cys Ser Pro Asp Gln Asp
                35                  40                  45

Ser Cys Leu Tyr Ala Val Ala Gly Met Gln Val Tyr Gln Arg Cys Trp
            50                  55                  60

Lys Gln Ser Asp Cys His Gly Glu Ile Ile Met Asp Gln Leu Glu Glu
 65                  70                  75                  80

Thr Lys Leu Lys Phe Arg Cys Cys Gln Phe Asn Leu Cys Asn Lys Ser
                    85                  90                  95

Asp Gly Ser Leu Gly Lys Thr Pro Leu Leu Gly Thr Ser Val Leu Val
                100                 105                 110

Ala Ile Leu Asn Leu Cys Phe Leu Ser His Leu
            115                 120

<210> SEQ ID NO 6
<211> LENGTH: 129
<212> TYPE: PRT
<213> ORGANISM: Mus musculus

<400> SEQUENCE: 6

Met Arg Ala Gln Arg Gly Leu Ile Leu Leu Leu Leu Leu Ala Val
 1               5                  10                  15

Phe Cys Ser Thr Ala Val Ser Leu Lys Cys Tyr Asn Cys Phe Gln Phe
                    20                  25                  30

Val Ser Ser Cys Lys Ile Asn Thr Thr Cys Ser Pro Asn Leu Asp Ser
                35                  40                  45

Cys Leu Tyr Ala Val Ala Gly Arg Gln Val Tyr Gln Gln Cys Trp Lys
            50                  55                  60

Leu Ser Asp Cys Asn Ser Asn Tyr Ile Met Ser Arg Leu Asp Val Ala
 65                  70                  75                  80

Gly Ile Gln Ser Lys Cys Cys Gln Trp Gly Leu Cys Asn Lys Asn Leu
                    85                  90                  95

Asp Gly Leu Glu Glu Pro Asn Asn Ala Glu Thr Ser Ser Leu Arg Lys
                100                 105                 110

Thr Ala Leu Leu Gly Thr Ser Val Leu Val Ala Ile Leu Lys Phe Cys
            115                 120                 125

Phe

<210> SEQ ID NO 7
<211> LENGTH: 483
<212> TYPE: PRT
<213> ORGANISM: Mus musculus

<400> SEQUENCE: 7

```
Met Glu Val Ser Ser Arg Ser Ser Glu Pro Leu Asp Pro Val Trp Leu
  1               5                  10                  15
Leu Val Ala Phe Gly Arg Gly Val Lys Leu Glu Val Leu Leu Leu
             20                  25                  30
Phe Leu Leu Pro Phe Thr Leu Gly Glu Leu Arg Gly Gly Leu Gly Lys
         35                  40                  45
His Gly His Thr Val His Arg Glu Pro Ala Val Asn Arg Leu Cys Ala
     50                  55                  60
Asp Ser Lys Arg Trp Ser Gly Leu Pro Val Ser Ala Gln Arg Pro Phe
 65                  70                  75                  80
Pro Met Gly His Cys Pro Ala Pro Ser Gln Leu Pro Ser Ala Lys Pro
                 85                  90                  95
Ile Asn Leu Thr Asp Glu Ser Met Phe Pro Ile Gly Thr Tyr Leu Leu
            100                 105                 110
Tyr Glu Cys Leu Pro Gly Tyr Ile Lys Arg Gln Phe Ser Ile Thr Cys
        115                 120                 125
Lys Gln Asp Ser Thr Trp Thr Ser Ala Glu Asp Lys Cys Ile Arg Lys
    130                 135                 140
Gln Cys Lys Thr Pro Ser Asp Pro Glu Asn Gly Leu Val His Val His
145                 150                 155                 160
Thr Gly Ile Gln Phe Gly Ser Arg Ile Asn Tyr Thr Cys Asn Gln Gly
                165                 170                 175
Tyr Arg Leu Ile Gly Ser Ser Ala Val Cys Val Ile Thr Asp Gln
            180                 185                 190
Ser Val Asp Trp Asp Thr Glu Ala Pro Ile Cys Glu Trp Ile Pro Cys
        195                 200                 205
Glu Ile Pro Pro Gly Ile Pro Asn Gly Asp Phe Phe Ser Ser Thr Arg
    210                 215                 220
Glu Asp Phe His Tyr Gly Met Val Val Thr Tyr Arg Cys Asn Thr Asp
225                 230                 235                 240
Ala Arg Gly Lys Ala Leu Phe Asn Leu Val Gly Glu Pro Ser Leu Tyr
                245                 250                 255
Cys Thr Ser Asn Asp Gly Glu Ile Gly Val Trp Ser Gly Pro Pro Pro
            260                 265                 270
Gln Cys Ile Glu Leu Asn Lys Cys Thr Pro Pro Tyr Val Glu Asn
        275                 280                 285
Ala Val Met Leu Ser Glu Asn Arg Ser Leu Phe Ser Leu Arg Asp Ile
    290                 295                 300
Val Glu Phe Arg Cys His Pro Gly Phe Ile Met Lys Gly Ala Ser Ser
305                 310                 315                 320
Val His Cys Gln Ser Leu Asn Lys Trp Glu Pro Glu Leu Pro Ser Cys
                325                 330                 335
Phe Lys Gly Val Ile Cys Arg Leu Pro Gln Glu Met Ser Gly Phe Gln
            340                 345                 350
Lys Gly Leu Gly Met Lys Lys Glu Tyr Tyr Tyr Gly Glu Asn Val Thr
        355                 360                 365
```

```
Leu Glu Cys Glu Asp Gly Tyr Thr Leu Glu Gly Ser Gln Ser Gln
        370                 375                 380

Cys Gln Ser Asp Gly Ser Trp Asn Pro Leu Leu Ala Lys Cys Val Ser
385                 390                 395                 400

Arg Ser Ile Ser Gly Leu Ile Val Gly Ile Phe Ile Gly Ile Ile Val
            405                 410                 415

Phe Ile Leu Val Ile Ile Val Phe Ile Trp Met Ile Leu Lys Tyr Lys
        420                 425                 430

Lys Arg Asn Thr Thr Asp Glu Lys Tyr Lys Glu Val Gly Ile His Leu
    435                 440                 445

Asn Tyr Lys Glu Asp Ser Cys Val Arg Leu Gln Ser Leu Leu Thr Ser
    450                 455                 460

Gln Glu Asn Ser Ser Thr Thr Ser Pro Ala Arg Asn Ser Leu Thr Gln
465                 470                 475                 480

Glu Val Ser

<210> SEQ ID NO 8
<211> LENGTH: 2039
<212> TYPE: PRT
<213> ORGANISM: Homo sapiens

<400> SEQUENCE: 8

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65              70                  75                  80

Pro Phe Ser Ile Ile Cys Leu Lys Asn Ser Val Trp Thr Gly Ala Lys
            85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
            165                 170                 175

Phe Ile Ser Thr Asn Arg Glu Asn Phe His Tyr Gly Ser Val Val Thr
        180                 185                 190

Tyr Arg Cys Asn Pro Gly Ser Gly Gly Arg Lys Val Phe Glu Leu Val
    195                 200                 205

Gly Glu Pro Ser Ile Tyr Cys Thr Ser Asn Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
            245                 250                 255
```

```
Ser Leu Asn Glu Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
        355                 360                 365

Arg Val Leu Phe Pro Val Asn Leu Gln Leu Gly Ala Lys Val Asp Phe
    370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Pro Val Ile Pro Asn Gly Arg His
            420                 425                 430

Thr Gly Lys Pro Leu Glu Val Phe Pro Phe Gly Lys Ala Val Asn Tyr
        435                 440                 445

Thr Cys Asp Pro His Pro Asp Arg Gly Thr Ser Phe Asp Leu Ile Gly
    450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
    530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
    610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
                645                 650                 655

Leu Val Gly Glu Pro Ser Ile Tyr Cys Thr Ser Asn Asp Asp Gln Val
            660                 665                 670
```

-continued

```
Gly Ile Trp Ser Gly Pro Ala Pro Gln Cys Ile Ile Pro Asn Lys Cys
                675                 680                 685

Thr Pro Pro Asn Val Glu Asn Gly Ile Leu Val Ser Asp Asn Arg Ser
690                 695                 700

Leu Phe Ser Leu Asn Glu Val Glu Phe Arg Cys Gln Pro Gly Phe
705                 710                 715                 720

Val Met Lys Gly Pro Arg Val Lys Cys Gln Ala Leu Asn Lys Trp
                725                 730                 735

Glu Pro Glu Leu Pro Ser Cys Ser Arg Val Cys Gln Pro Pro Asp
                740                 745                 750

Val Leu His Ala Glu Arg Thr Gln Arg Asp Lys Asp Asn Phe Ser Pro
                755                 760                 765

Gly Gln Glu Val Phe Tyr Ser Cys Glu Pro Gly Tyr Asp Leu Arg Gly
                770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val
                820                 825                 830

Asp Phe Val Cys Asp Glu Gly Phe Gln Leu Lys Gly Ser Ser Ala Ser
                835                 840                 845

Tyr Cys Val Leu Ala Gly Met Glu Ser Leu Trp Asn Ser Ser Val Pro
                850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
                885                 890                 895

Asn Tyr Thr Cys Asp Pro His Pro Asp Arg Gly Thr Ser Phe Asp Leu
                900                 905                 910

Ile Gly Glu Ser Thr Ile Arg Cys Thr Ser Asp Pro Gln Gly Asn Gly
                915                 920                 925

Val Trp Ser Ser Pro Ala Pro Arg Cys Gly Ile Leu Gly His Cys Gln
930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
                980                 985                 990

Ser Ser Pro Lys Asp Val Cys Lys Arg Lys Ser Cys Lys Thr Pro Pro
                995                 1000                1005

Asp Pro Val Asn Gly Met Val His Val Ile Thr Asp Ile Gln Val
        1010                1015                1020

Gly Ser Arg Ile Asn Tyr Ser Cys Thr Thr Gly His Arg Leu Ile
        1025                1030                1035

Gly His Ser Ser Ala Glu Cys Ile Leu Ser Gly Asn Thr Ala His
        1040                1045                1050

Trp Ser Thr Lys Pro Pro Ile Cys Gln Arg Ile Pro Cys Gly Leu
        1055                1060                1065

Pro Pro Thr Ile Ala Asn Gly Asp Phe Ile Ser Thr Asn Arg Glu
        1070                1075                1080

Asn Phe His Tyr Gly Ser Val Val Thr Tyr Arg Cys Asn Leu Gly
```

```
                     1085                1090                1095
Ser Arg Gly Arg Lys Val Phe Glu Leu Val Gly Glu Pro Ser Ile
    1100                1105                1110
Tyr Cys Thr Ser Asn Asp Asp Gln Val Gly Ile Trp Ser Gly Pro
    1115                1120                1125
Ala Pro Gln Cys Ile Ile Pro Asn Lys Cys Thr Pro Pro Asn Val
    1130                1135                1140
Glu Asn Gly Ile Leu Val Ser Asp Asn Arg Ser Leu Phe Ser Leu
    1145                1150                1155
Asn Glu Val Val Glu Phe Arg Cys Gln Pro Gly Phe Val Met Lys
    1160                1165                1170
Gly Pro Arg Arg Val Lys Cys Gln Ala Leu Asn Lys Trp Glu Pro
    1175                1180                1185
Glu Leu Pro Ser Cys Ser Arg Val Cys Gln Pro Pro Glu Ile
    1190                1195                1200
Leu His Gly Glu His Thr Pro Ser His Gln Asp Asn Phe Ser Pro
    1205                1210                1215
Gly Gln Glu Val Phe Tyr Ser Cys Glu Pro Gly Tyr Asp Leu Arg
    1220                1225                1230
Gly Ala Ala Ser Leu His Cys Thr Pro Gln Gly Asp Trp Ser Pro
    1235                1240                1245
Glu Ala Pro Arg Cys Ala Val Lys Ser Cys Asp Asp Phe Leu Gly
    1250                1255                1260
Gln Leu Pro His Gly Arg Val Leu Phe Pro Leu Asn Leu Gln Leu
    1265                1270                1275
Gly Ala Lys Val Ser Phe Val Cys Asp Glu Gly Phe Arg Leu Lys
    1280                1285                1290
Gly Ser Ser Val Ser His Cys Val Leu Val Gly Met Arg Ser Leu
    1295                1300                1305
Trp Asn Asn Ser Val Pro Val Cys Glu His Ile Phe Cys Pro Asn
    1310                1315                1320
Pro Pro Ala Ile Leu Asn Gly Arg His Thr Gly Thr Pro Ser Gly
    1325                1330                1335
Asp Ile Pro Tyr Gly Lys Glu Ile Ser Tyr Thr Cys Asp Pro His
    1340                1345                1350
Pro Asp Arg Gly Met Thr Phe Asn Leu Ile Gly Glu Ser Thr Ile
    1355                1360                1365
Arg Cys Thr Ser Asp Pro His Gly Asn Gly Val Trp Ser Ser Pro
    1370                1375                1380
Ala Pro Arg Cys Glu Leu Ser Val Arg Ala Gly His Cys Lys Thr
    1385                1390                1395
Pro Glu Gln Phe Pro Phe Ala Ser Pro Thr Ile Pro Ile Asn Asp
    1400                1405                1410
Phe Glu Phe Pro Val Gly Thr Ser Leu Asn Tyr Glu Cys Arg Pro
    1415                1420                1425
Gly Tyr Phe Gly Lys Met Phe Ser Ile Ser Cys Leu Glu Asn Leu
    1430                1435                1440
Val Trp Ser Ser Val Glu Asp Asn Cys Arg Arg Lys Ser Cys Gly
    1445                1450                1455
Pro Pro Pro Glu Pro Phe Asn Gly Met Val His Ile Asn Thr Asp
    1460                1465                1470
Thr Gln Phe Gly Ser Thr Val Asn Tyr Ser Cys Asn Glu Gly Phe
    1475                1480                1485
```

-continued

```
Arg Leu Ile Gly Ser Pro Ser Thr Thr Cys Leu Val Ser Gly Asn
    1490            1495                1500

Asn Val Thr Trp Asp Lys Lys Ala Pro Ile Cys Glu Ile Ile Ser
    1505            1510                1515

Cys Glu Pro Pro Pro Thr Ile Ser Asn Gly Asp Phe Tyr Ser Asn
    1520            1525                1530

Asn Arg Thr Ser Phe His Asn Gly Thr Val Val Thr Tyr Gln Cys
    1535            1540                1545

His Thr Gly Pro Asp Gly Glu Gln Leu Phe Glu Leu Val Gly Glu
    1550            1555                1560

Arg Ser Ile Tyr Cys Thr Ser Lys Asp Asp Gln Val Gly Val Trp
    1565            1570                1575

Ser Ser Pro Pro Pro Arg Cys Ile Ser Thr Asn Lys Cys Thr Ala
    1580            1585                1590

Pro Glu Val Glu Asn Ala Ile Arg Val Pro Gly Asn Arg Ser Phe
    1595            1600                1605

Phe Ser Leu Thr Glu Ile Ile Arg Phe Arg Cys Gln Pro Gly Phe
    1610            1615                1620

Val Met Val Gly Ser His Thr Val Gln Cys Gln Thr Asn Gly Arg
    1625            1630                1635

Trp Gly Pro Lys Leu Pro His Cys Ser Arg Val Cys Gln Pro Pro
    1640            1645                1650

Pro Glu Ile Leu His Gly Glu His Thr Leu Ser His Gln Asp Asn
    1655            1660                1665

Phe Ser Pro Gly Gln Glu Val Phe Tyr Ser Cys Glu Pro Ser Tyr
    1670            1675                1680

Asp Leu Arg Gly Ala Ala Ser Leu His Cys Thr Pro Gln Gly Asp
    1685            1690                1695

Trp Ser Pro Glu Ala Pro Arg Cys Thr Val Lys Ser Cys Asp Asp
    1700            1705                1710

Phe Leu Gly Gln Leu Pro His Gly Arg Val Leu Leu Pro Leu Asn
    1715            1720                1725

Leu Gln Leu Gly Ala Lys Val Ser Phe Val Cys Asp Glu Gly Phe
    1730            1735                1740

Arg Leu Lys Gly Arg Ser Ala Ser His Cys Val Leu Ala Gly Met
    1745            1750                1755

Lys Ala Leu Trp Asn Ser Ser Val Pro Val Cys Glu Gln Ile Phe
    1760            1765                1770

Cys Pro Asn Pro Pro Ala Ile Leu Asn Gly Arg His Thr Gly Thr
    1775            1780                1785

Pro Phe Gly Asp Ile Pro Tyr Gly Lys Glu Ile Ser Tyr Ala Cys
    1790            1795                1800

Asp Thr His Pro Asp Arg Gly Met Thr Phe Asn Leu Ile Gly Glu
    1805            1810                1815

Ser Ser Ile Arg Cys Thr Ser Asp Pro Gln Gly Asn Gly Val Trp
    1820            1825                1830

Ser Ser Pro Ala Pro Arg Cys Glu Leu Ser Val Pro Ala Ala Cys
    1835            1840                1845

Pro His Pro Pro Lys Ile Gln Asn Gly His Tyr Ile Gly Gly His
    1850            1855                1860

Val Ser Leu Tyr Leu Pro Gly Met Thr Ile Ser Tyr Thr Cys Asp
    1865            1870                1875
```

-continued

```
Pro Gly Tyr Leu Leu Val Gly Lys Gly Phe Ile Phe Cys Thr Asp
    1880            1885                1890

Gln Gly Ile Trp Ser Gln Leu Asp His Tyr Cys Lys Glu Val Asn
    1895            1900                1905

Cys Ser Phe Pro Leu Phe Met Asn Gly Ile Ser Lys Glu Leu Glu
    1910            1915                1920

Met Lys Lys Val Tyr His Tyr Gly Asp Tyr Val Thr Leu Lys Cys
    1925            1930                1935

Glu Asp Gly Tyr Thr Leu Glu Gly Ser Pro Trp Ser Gln Cys Gln
    1940            1945                1950

Ala Asp Asp Arg Trp Asp Pro Pro Leu Ala Lys Cys Thr Ser Arg
    1955            1960                1965

Ala His Asp Ala Leu Ile Val Gly Thr Leu Ser Gly Thr Ile Phe
    1970            1975                1980

Phe Ile Leu Leu Ile Ile Phe Leu Ser Trp Ile Ile Leu Lys His
    1985            1990                1995

Arg Lys Gly Asn Asn Ala His Glu Asn Pro Lys Glu Val Ala Ile
    2000            2005                2010

His Leu His Ser Gln Gly Gly Ser Ser Val His Pro Arg Thr Leu
    2015            2020                2025

Gln Thr Asn Glu Glu Asn Ser Arg Val Leu Pro
    2030            2035

<210> SEQ ID NO 9
<211> LENGTH: 1231
<212> TYPE: PRT
<213> ORGANISM: Homo sapiens

<400> SEQUENCE: 9

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205
```

```
Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
            355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
    435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
    515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
    595                 600                 605

Val Gln Cys Tyr His Phe Gly Leu Ser Pro Asp Leu Pro Ile Cys Lys
610                 615                 620
```

```
Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
        645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
        1010                1015                1020

Met Asp Gly Ala Ser Asn Val Thr Cys Ile Asn Ser Arg Trp Thr
        1025                1030                1035

Gly Arg Pro Thr Cys Arg Asp Thr Ser Cys Val Asn Pro Pro Thr
```

```
                    1040                1045                1050
Val Gln Asn Ala Tyr Ile Val Ser Arg Gln Met Ser Lys Tyr Pro
        1055                1060                1065

Ser Gly Glu Arg Val Arg Tyr Gln Cys Arg Ser Pro Tyr Glu Met
        1070                1075                1080

Phe Gly Asp Glu Val Met Cys Leu Asn Gly Asn Trp Thr Glu
        1085                1090                1095

Pro Pro Gln Cys Lys Asp Ser Thr Gly Lys Cys Gly Pro Pro Pro
        1100                1105                1110

Pro Ile Asp Asn Gly Asp Ile Thr Ser Phe Pro Leu Ser Val Tyr
        1115                1120                1125

Ala Pro Ala Ser Ser Val Glu Tyr Gln Cys Gln Asn Leu Tyr Gln
        1130                1135                1140

Leu Glu Gly Asn Lys Arg Ile Thr Cys Arg Asn Gly Gln Trp Ser
        1145                1150                1155

Glu Pro Pro Lys Cys Leu His Pro Cys Val Ile Ser Arg Glu Ile
        1160                1165                1170

Met Glu Asn Tyr Asn Ile Ala Leu Arg Trp Thr Ala Lys Gln Lys
        1175                1180                1185

Leu Tyr Ser Arg Thr Gly Glu Ser Val Glu Phe Val Cys Lys Arg
        1190                1195                1200

Gly Tyr Arg Leu Ser Ser Arg Ser His Thr Leu Arg Thr Thr Cys
        1205                1210                1215

Trp Asp Gly Lys Leu Glu Tyr Pro Thr Cys Ala Lys Arg
        1220                1225                1230

<210> SEQ ID NO 10
<211> LENGTH: 1234
<212> TYPE: PRT
<213> ORGANISM: Mus musculus

<400> SEQUENCE: 10

Met Arg Leu Ser Ala Arg Ile Ile Trp Leu Ile Leu Trp Thr Val Cys
1               5                   10                  15

Ala Ala Glu Asp Cys Lys Gly Pro Pro Arg Glu Asn Ser Glu Ile
            20                  25                  30

Leu Ser Gly Ser Trp Ser Glu Gln Leu Tyr Pro Glu Gly Thr Gln Ala
        35                  40                  45

Thr Tyr Lys Cys Arg Pro Gly Tyr Arg Thr Leu Gly Thr Ile Val Lys
    50                  55                  60

Val Cys Lys Asn Gly Lys Trp Val Ala Ser Asn Pro Ser Arg Ile Cys
65                  70                  75                  80

Arg Lys Lys Pro Cys Gly His Pro Gly Asp Thr Pro Phe Gly Ser Phe
                85                  90                  95

Arg Leu Ala Val Gly Ser Gln Phe Glu Phe Gly Ala Lys Val Val Tyr
            100                 105                 110

Thr Cys Asp Asp Gly Tyr Gln Leu Leu Gly Glu Ile Asp Tyr Arg Glu
        115                 120                 125

Cys Gly Ala Asp Gly Trp Ile Asn Asp Ile Pro Leu Cys Glu Val Val
    130                 135                 140

Lys Cys Leu Pro Val Thr Glu Leu Glu Asn Gly Arg Ile Val Ser Gly
145                 150                 155                 160

Ala Ala Glu Thr Asp Gln Glu Tyr Tyr Phe Gly Gln Val Val Arg Phe
                165                 170                 175
```

-continued

```
Glu Cys Asn Ser Gly Phe Lys Ile Glu Gly His Lys Glu Ile His Cys
                180                 185                 190
Ser Glu Asn Gly Leu Trp Ser Asn Glu Lys Pro Arg Cys Val Glu Ile
            195                 200                 205
Leu Cys Thr Pro Pro Arg Val Glu Asn Gly Asp Gly Ile Asn Val Lys
        210                 215                 220
Pro Val Tyr Lys Glu Asn Glu Arg Tyr His Tyr Lys Cys Lys His Gly
225                 230                 235                 240
Tyr Val Pro Lys Glu Arg Gly Asp Ala Val Cys Thr Gly Ser Gly Trp
                245                 250                 255
Ser Ser Gln Pro Phe Cys Glu Glu Lys Arg Cys Ser Pro Pro Tyr Ile
            260                 265                 270
Leu Asn Gly Ile Tyr Thr Pro His Arg Ile Ile His Arg Ser Asp Asp
        275                 280                 285
Glu Ile Arg Tyr Glu Cys Asn Tyr Gly Phe Tyr Pro Val Thr Gly Ser
290                 295                 300
Thr Val Ser Lys Cys Thr Pro Thr Gly Trp Ile Pro Val Pro Arg Cys
305                 310                 315                 320
Thr Leu Lys Pro Cys Glu Phe Pro Gln Phe Lys Tyr Gly Arg Leu Tyr
                325                 330                 335
Tyr Glu Glu Ser Leu Arg Pro Asn Phe Pro Val Ser Ile Gly Asn Lys
            340                 345                 350
Tyr Ser Tyr Lys Cys Asp Asn Gly Phe Ser Pro Ser Gly Tyr Ser
        355                 360                 365
Trp Asp Tyr Leu Arg Cys Thr Ala Gln Gly Trp Glu Pro Glu Val Pro
        370                 375                 380
Cys Val Arg Lys Cys Val Phe His Tyr Val Glu Asn Gly Asp Ser Ala
385                 390                 395                 400
Tyr Trp Glu Lys Val Tyr Val Gln Gly Gln Ser Leu Lys Val Gln Cys
                405                 410                 415
Tyr Asn Gly Tyr Ser Leu Gln Asn Gly Gln Asp Thr Met Thr Cys Thr
            420                 425                 430
Glu Asn Gly Trp Ser Pro Pro Pro Lys Cys Ile Arg Ile Lys Thr Cys
        435                 440                 445
Ser Ala Ser Asp Ile His Ile Asp Asn Gly Phe Leu Ser Glu Ser Ser
450                 455                 460
Ser Ile Tyr Ala Leu Asn Arg Glu Thr Ser Tyr Arg Cys Lys Gln Gly
465                 470                 475                 480
Tyr Val Thr Asn Thr Gly Glu Ile Ser Gly Ser Ile Thr Cys Leu Gln
                485                 490                 495
Asn Gly Trp Ser Pro Gln Pro Ser Cys Ile Lys Ser Cys Asp Met Pro
            500                 505                 510
Val Phe Glu Asn Ser Ile Thr Lys Asn Thr Arg Thr Trp Phe Lys Leu
        515                 520                 525
Asn Asp Lys Leu Asp Tyr Glu Cys Leu Val Gly Phe Glu Asn Glu Tyr
        530                 535                 540
Lys His Thr Lys Gly Ser Ile Thr Cys Thr Tyr Tyr Gly Trp Ser Asp
545                 550                 555                 560
Thr Pro Ser Cys Tyr Glu Arg Glu Cys Ser Val Pro Thr Leu Asp Arg
                565                 570                 575
Lys Leu Val Val Ser Pro Arg Lys Glu Lys Tyr Arg Val Gly Asp Leu
            580                 585                 590
Leu Glu Phe Ser Cys His Ser Gly His Arg Val Gly Pro Asp Ser Val
```

```
                    595                 600                 605
Gln Cys Tyr His Phe Gly Trp Ser Pro Gly Phe Pro Thr Cys Lys Gly
            610                 615                 620

Gln Val Ala Ser Cys Ala Pro Pro Leu Glu Ile Leu Asn Gly Glu Ile
625                 630                 635                 640

Asn Gly Ala Lys Lys Val Glu Tyr Ser His Gly Glu Val Val Lys Tyr
                645                 650                 655

Asp Cys Lys Pro Arg Phe Leu Leu Lys Gly Pro Asn Lys Ile Gln Cys
            660                 665                 670

Val Asp Gly Asn Trp Thr Thr Leu Pro Val Cys Ile Glu Glu Glu Arg
            675                 680                 685

Thr Cys Gly Asp Ile Pro Glu Leu Glu His Gly Ser Ala Lys Cys Ser
690                 695                 700

Val Pro Pro Tyr His His Gly Asp Ser Val Glu Phe Ile Cys Glu Glu
705                 710                 715                 720

Asn Phe Thr Met Ile Gly His Gly Ser Val Ser Cys Ile Ser Gly Lys
                725                 730                 735

Trp Thr Gln Leu Pro Lys Cys Val Ala Thr Asp Gln Leu Glu Lys Cys
            740                 745                 750

Arg Val Leu Lys Ser Thr Gly Ile Glu Ala Ile Lys Pro Lys Leu Thr
            755                 760                 765

Glu Phe Thr His Asn Ser Thr Met Asp Tyr Lys Cys Arg Asp Lys Gln
770                 775                 780

Glu Tyr Glu Arg Ser Ile Cys Ile Asn Gly Lys Trp Asp Pro Glu Pro
785                 790                 795                 800

Asn Cys Thr Ser Lys Thr Ser Cys Pro Pro Pro Gln Ile Pro Asn
                805                 810                 815

Thr Gln Val Ile Glu Thr Val Lys Tyr Leu Asp Gly Glu Lys Leu
            820                 825                 830

Ser Val Leu Cys Gln Asp Asn Tyr Leu Thr Gln Asp Ser Glu Glu Met
            835                 840                 845

Val Cys Lys Asp Gly Arg Trp Gln Ser Leu Pro Arg Cys Ile Glu Lys
850                 855                 860

Ile Pro Cys Ser Gln Pro Pro Thr Ile Glu His Gly Ser Ile Asn Leu
865                 870                 875                 880

Pro Arg Ser Ser Glu Glu Arg Arg Asp Ser Ile Glu Ser Ser Ser His
                885                 890                 895

Glu His Gly Thr Thr Phe Ser Tyr Val Cys Asp Asp Gly Phe Arg Ile
            900                 905                 910

Pro Glu Glu Asn Arg Ile Thr Cys Tyr Met Gly Lys Trp Ser Thr Pro
            915                 920                 925

Pro Arg Cys Val Gly Leu Pro Cys Gly Pro Pro Ser Ile Pro Leu
            930                 935                 940

Gly Thr Val Ser Leu Glu Leu Glu Ser Tyr Gln His Gly Glu Glu Val
945                 950                 955                 960

Thr Tyr His Cys Ser Thr Gly Phe Gly Ile Asp Gly Pro Ala Phe Ile
                965                 970                 975

Ile Cys Glu Gly Gly Lys Trp Ser Asp Pro Pro Lys Cys Ile Lys Thr
            980                 985                 990

Asp Cys Asp Val Leu Pro Thr Val  Lys Asn Ala Ile Ile Arg Gly Lys
            995                 1000                1005

Ser Lys  Lys Ser Tyr Arg Thr  Gly Glu Gln Val Thr  Phe Arg Cys
    1010                1015                1020
```

```
Gln Ser Pro Tyr Gln Met Asn Gly Ser Asp Thr Val Thr Cys Val
    1025                1030                1035

Asn Ser Arg Trp Ile Gly Gln Pro Val Cys Lys Asp Asn Ser Cys
    1040                1045                1050

Val Asp Pro Pro His Val Pro Asn Ala Thr Ile Val Thr Arg Thr
    1055                1060                1065

Lys Asn Lys Tyr Leu His Gly Asp Arg Val Arg Tyr Glu Cys Asn
    1070                1075                1080

Lys Pro Leu Glu Leu Phe Gly Gln Val Glu Val Met Cys Glu Asn
    1085                1090                1095

Gly Ile Trp Thr Glu Lys Pro Lys Cys Arg Asp Ser Thr Gly Lys
    1100                1105                1110

Cys Gly Pro Pro Pro Ile Asp Asn Gly Asp Ile Thr Ser Leu
    1115                1120                1125

Ser Leu Pro Val Tyr Glu Pro Leu Ser Ser Val Glu Tyr Gln Cys
    1130                1135                1140

Gln Lys Tyr Tyr Leu Leu Lys Gly Lys Lys Thr Ile Thr Cys Thr
    1145                1150                1155

Asn Gly Lys Trp Ser Glu Pro Pro Thr Cys Leu His Ala Cys Val
    1160                1165                1170

Ile Pro Glu Asn Ile Met Glu Ser His Asn Ile Ile Leu Lys Trp
    1175                1180                1185

Arg His Thr Glu Lys Ile Tyr Ser His Ser Gly Glu Asp Ile Glu
    1190                1195                1200

Phe Gly Cys Lys Tyr Gly Tyr Tyr Lys Ala Arg Asp Ser Pro Pro
    1205                1210                1215

Phe Arg Thr Lys Cys Ile Asn Gly Thr Ile Asn Tyr Pro Thr Cys
    1220                1225                1230

Val

<210> SEQ ID NO 11
<211> LENGTH: 1642
<212> TYPE: PRT
<213> ORGANISM: Naja kaouthia

<400> SEQUENCE: 11

Met Glu Arg Met Ala Leu Tyr Leu Val Ala Ala Leu Leu Ile Gly Phe
1               5                   10                  15

Pro Gly Ser Ser His Gly Ala Leu Tyr Thr Leu Ile Thr Pro Ala Val
                20                  25                  30

Leu Arg Thr Asp Thr Glu Glu Gln Ile Leu Val Glu Ala His Gly Asp
            35                  40                  45

Ser Thr Pro Lys Gln Leu Asp Ile Phe Val His Asp Phe Pro Arg Lys
        50                  55                  60

Gln Lys Thr Leu Phe Gln Thr Arg Val Asp Met Asn Pro Ala Gly Gly
65                  70                  75                  80

Met Leu Val Thr Pro Thr Ile Glu Ile Pro Ala Lys Glu Val Ser Thr
                85                  90                  95

Asp Ser Arg Gln Asn Gln Tyr Val Val Val Gly Val Thr Gly Pro Gln
                100                 105                 110

Val Arg Leu Glu Lys Val Val Leu Leu Ser Tyr Gln Ser Ser Phe Leu
            115                 120                 125

Phe Ile Gln Thr Asp Lys Gly Ile Tyr Thr Pro Gly Ser Pro Val Leu
        130                 135                 140
```

```
Tyr Arg Val Phe Ser Met Asp His Asn Thr Ser Lys Met Asn Lys Thr
145                 150                 155                 160

Val Ile Val Glu Phe Gln Thr Pro Glu Gly Ile Leu Val Ser Ser Asn
            165                 170                 175

Ser Val Asp Leu Asn Phe Phe Trp Pro Tyr Asn Leu Pro Asp Leu Val
        180                 185                 190

Ser Leu Gly Thr Trp Arg Ile Val Ala Lys Tyr Glu His Ser Pro Glu
    195                 200                 205

Asn Tyr Thr Ala Tyr Phe Asp Val Arg Lys Tyr Val Leu Pro Ser Phe
210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
                245                 250                 255

Val Glu Gly Val Ala Phe Val Leu Phe Gly Val Lys Ile Asp Asp Ala
            260                 265                 270

Lys Lys Ser Ile Pro Asp Ser Leu Thr Arg Ile Pro Ile Ile Asp Gly
        275                 280                 285

Asp Gly Lys Ala Thr Leu Lys Arg Asp Thr Phe Arg Ser Arg Phe Pro
    290                 295                 300

Asn Leu Asn Glu Leu Val Gly His Thr Leu Tyr Ala Ser Val Thr Val
305                 310                 315                 320

Met Thr Glu Ser Gly Ser Asp Met Val Val Thr Glu Gln Ser Gly Ile
                325                 330                 335

His Ile Val Ala Ser Pro Tyr Gln Ile His Phe Thr Lys Thr Pro Lys
            340                 345                 350

Tyr Phe Lys Pro Gly Met Pro Tyr Glu Leu Thr Val Tyr Val Thr Asn
        355                 360                 365

Pro Asp Gly Ser Pro Ala Ala His Val Pro Val Val Ser Glu Ala Phe
    370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
                405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
        435                 440                 445

Ile Thr Ser Thr Glu Ile Lys Pro Gly Asp Asn Leu Pro Val Asn Phe
    450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
                485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Tyr Gln Val Gly Asn
        515                 520                 525

Asn Glu Ile Val Ala Asp Ser Val Trp Val Asp Val Lys Asp Thr Cys
    530                 535                 540

Met Gly Thr Leu Val Val Lys Gly Asp Asn Leu Ile Gln Met Pro Gly
545                 550                 555                 560
```

```
Ala Ala Met Lys Ile Lys Leu Glu Gly Asp Pro Gly Ala Arg Val Gly
            565                 570                 575
Leu Val Ala Val Asp Lys Ala Val Tyr Val Leu Asn Asp Lys Tyr Lys
        580                 585                 590
Ile Ser Gln Ala Lys Ile Trp Asp Thr Ile Glu Lys Ser Asp Phe Gly
    595                 600                 605
Cys Thr Ala Gly Ser Gly Gln Asn Asn Leu Gly Val Phe Glu Asp Ala
610                 615                 620
Gly Leu Ala Leu Thr Thr Ser Thr Asn Leu Asn Thr Lys Gln Arg Ser
625                 630                 635                 640
Ala Ala Lys Cys Pro Gln Pro Ala Asn Arg Arg Arg Ser Ser Val
        645                 650                 655
Leu Leu Leu Asp Ser Asn Ala Ser Lys Ala Ala Glu Phe Gln Asp Gln
            660                 665                 670
Asp Leu Arg Lys Cys Cys Glu Asp Val Met His Glu Asn Pro Met Gly
        675                 680                 685
Tyr Thr Cys Glu Lys Arg Ala Lys Tyr Ile Gln Glu Gly Asp Ala Cys
    690                 695                 700
Lys Ala Ala Phe Leu Glu Cys Cys Arg Tyr Ile Lys Gly Val Arg Asp
705                 710                 715                 720
Glu Asn Gln Arg Glu Ser Glu Leu Phe Leu Ala Arg Asp Asp Asn Glu
                725                 730                 735
Asp Gly Phe Ile Ala Asp Ser Asp Ile Ile Ser Arg Ser Asp Phe Pro
            740                 745                 750
Lys Ser Trp Leu Trp Leu Thr Lys Asp Leu Thr Glu Glu Pro Asn Ser
        755                 760                 765
Gln Gly Ile Ser Ser Lys Thr Met Ser Phe Tyr Leu Arg Asp Ser Ile
    770                 775                 780
Thr Thr Trp Val Val Leu Ala Val Ser Phe Thr Pro Thr Lys Gly Ile
785                 790                 795                 800
Cys Val Ala Glu Pro Tyr Glu Ile Arg Val Met Lys Val Phe Phe Ile
                805                 810                 815
Asp Leu Gln Met Pro Tyr Ser Val Val Lys Asn Glu Gln Val Glu Ile
            820                 825                 830
Arg Ala Ile Leu His Asn Tyr Val Asn Glu Asp Ile Tyr Val Arg Val
        835                 840                 845
Glu Leu Leu Tyr Asn Pro Ala Phe Cys Ser Ala Ser Thr Lys Gly Gln
    850                 855                 860
Arg Tyr Arg Gln Gln Phe Pro Ile Lys Ala Leu Ser Ser Arg Ala Val
865                 870                 875                 880
Pro Phe Val Ile Val Pro Leu Glu Gln Gly Leu His Asp Val Glu Ile
                885                 890                 895
Lys Ala Ser Val Gln Glu Ala Leu Trp Ser Asp Gly Val Arg Lys Lys
            900                 905                 910
Leu Lys Val Val Pro Glu Gly Val Gln Lys Ser Ile Val Thr Ile Val
        915                 920                 925
Lys Leu Asp Pro Arg Ala Lys Gly Val Gly Gly Thr Gln Leu Glu Val
    930                 935                 940
Ile Lys Ala Arg Lys Leu Asp Asp Arg Val Pro Asp Thr Glu Ile Glu
945                 950                 955                 960
Thr Lys Ile Ile Ile Gln Gly Asp Pro Val Ala Gln Ile Ile Glu Asn
                965                 970                 975
Ser Ile Asp Gly Ser Lys Leu Asn His Leu Ile Ile Thr Pro Ser Gly
```

-continued

```
               980             985              990
Cys Gly Glu Gln Asn Met Ile Arg  Met Ala Ala Pro Val  Ile Ala Thr
                995               1000             1005

Tyr Tyr Leu Asp Thr Thr Glu  Gln Trp Glu Thr Leu  Gly Ile Asn
    1010              1015              1020

Arg Arg Thr Glu Ala Val Asn  Gln Ile Val Thr Gly  Tyr Ala Gln
    1025              1030              1035

Gln Met Val Tyr Lys Lys Ala  Asp His Ser Tyr Ala  Ala Phe Thr
    1040              1045              1050

Asn Arg Ala Ser Ser Ser Trp  Leu Thr Ala Tyr Val  Val Lys Val
    1055              1060              1065

Phe Ala Met Ala Ala Lys Met  Val Ala Gly Ile Ser  His Glu Ile
    1070              1075              1080

Ile Cys Gly Gly Val Arg Trp  Leu Ile Leu Asn Arg  Gln Gln Pro
    1085              1090              1095

Asp Gly Ala Phe Lys Glu Asn  Ala Pro Val Leu Ser  Gly Thr Met
    1100              1105              1110

Gln Gly Gly Ile Gln Gly Ala  Glu Glu Glu Val Tyr  Leu Thr Ala
    1115              1120              1125

Phe Ile Leu Val Ala Leu Leu  Glu Ser Lys Thr Ile  Cys Asn Asp
    1130              1135              1140

Tyr Val Asn Ser Leu Asp Ser  Ser Ile Lys Lys Ala  Thr Asn Tyr
    1145              1150              1155

Leu Leu Lys Lys Tyr Glu Lys  Leu Gln Arg Pro Tyr  Thr Thr Ala
    1160              1165              1170

Leu Thr Ala Tyr Ala Leu Ala  Ala Ala Asp Gln Leu  Asn Asp Asp
    1175              1180              1185

Arg Val Leu Met Ala Ala Ser  Thr Gly Arg Asp His  Trp Glu Glu
    1190              1195              1200

Tyr Asn Ala His Thr His Asn  Ile Glu Gly Thr Ser  Tyr Ala Leu
    1205              1210              1215

Leu Ala Leu Leu Lys Met Lys  Lys Phe Asp Gln Thr  Gly Pro Ile
    1220              1225              1230

Val Arg Trp Leu Thr Asp Gln  Asn Phe Tyr Gly Glu  Thr Tyr Gly
    1235              1240              1245

Gln Thr Gln Ala Thr Val Met  Ala Phe Gln Ala Leu  Ala Glu Tyr
    1250              1255              1260

Glu Ile Gln Met Pro Thr His  Lys Asp Leu Asn Leu  Asp Ile Thr
    1265              1270              1275

Ile Glu Leu Pro Asp Arg Glu  Val Pro Ile Arg Tyr  Arg Ile Asn
    1280              1285              1290

Tyr Glu Asn Ala Leu Leu Ala  Arg Thr Val Glu Thr  Lys Leu Asn
    1295              1300              1305

Gln Asp Ile Thr Val Thr Ala  Ser Gly Asp Gly Lys  Ala Thr Met
    1310              1315              1320

Thr Ile Leu Thr Phe Tyr Asn  Ala Gln Leu Gln Glu  Lys Ala Asn
    1325              1330              1335

Val Cys Asn Lys Phe His Leu  Asn Val Ser Val Glu  Asn Ile His
    1340              1345              1350

Leu Asn Ala Met Gly Ala Lys  Gly Ala Leu Met Leu  Lys Ile Cys
    1355              1360              1365

Thr Arg Tyr Leu Gly Glu Val  Asp Ser Thr Met Thr  Ile Ile Asp
    1370              1375              1380
```

```
Ile Ser Met Leu Thr Gly Phe Leu Pro Asp Ala Glu Asp Leu Thr
    1385                1390                1395

Arg Leu Ser Lys Gly Val Asp Arg Tyr Ile Ser Arg Tyr Glu Val
    1400                1405                1410

Asp Asn Asn Met Ala Gln Lys Val Ala Val Ile Ile Tyr Leu Asn
    1415                1420                1425

Lys Val Ser His Ser Glu Asp Glu Cys Leu His Phe Lys Ile Leu
    1430                1435                1440

Lys His Phe Glu Val Gly Phe Ile Gln Pro Gly Ser Val Lys Val
    1445                1450                1455

Tyr Ser Tyr Tyr Asn Leu Asp Glu Lys Cys Thr Lys Phe Tyr His
    1460                1465                1470

Pro Asp Lys Gly Thr Gly Leu Leu Asn Lys Ile Cys Ile Gly Asn
    1475                1480                1485

Val Cys Arg Cys Ala Gly Glu Thr Cys Ser Ser Leu Asn His Gln
    1490                1495                1500

Glu Arg Ile Asp Val Pro Leu Gln Ile Glu Lys Ala Cys Glu Thr
    1505                1510                1515

Asn Val Asp Tyr Val Tyr Lys Thr Lys Leu Leu Arg Ile Glu Glu
    1520                1525                1530

Gln Asp Gly Asn Asp Ile Tyr Val Met Asp Val Leu Glu Val Ile
    1535                1540                1545

Lys Gln Gly Thr Asp Glu Asn Pro Arg Ala Lys Thr His Gln Tyr
    1550                1555                1560

Ile Ser Gln Arg Lys Cys Gln Glu Ala Leu Asn Leu Lys Val Asn
    1565                1570                1575

Asp Asp Tyr Leu Ile Trp Gly Ser Arg Ser Asp Leu Leu Pro Thr
    1580                1585                1590

Lys Asp Lys Ile Ser Tyr Ile Ile Thr Lys Asn Thr Trp Ile Glu
    1595                1600                1605

Arg Trp Pro His Glu Asp Glu Cys Gln Glu Glu Phe Gln Lys
    1610                1615                1620

Leu Cys Asp Asp Phe Ala Gln Phe Ser Tyr Thr Leu Thr Glu Phe
    1625                1630                1635

Gly Cys Pro Thr
    1640

<210> SEQ ID NO 12
<211> LENGTH: 112
<212> TYPE: PRT
<213> ORGANISM: Artificial sequence
<220> FEATURE:
<223> OTHER INFORMATION: Synthetic polypeptide.

<400> SEQUENCE: 12

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110
```

<210> SEQ ID NO 13
<211> LENGTH: 111
<212> TYPE: PRT
<213> ORGANISM: Artificial sequence
<220> FEATURE:
<223> OTHER INFORMATION: Synthetic polypeptide.

<400> SEQUENCE: 13

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asn Tyr
            20                  25                  30

Tyr Ile Asn Trp Val Lys Gln Ser His Gly Lys Ser Leu Glu Trp Ile
        35                  40                  45

Gly Val Ile Asn Pro Tyr Asn Gly Gly Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Phe Cys
                85                  90                  95

Ser Ser Pro Tyr Trp Gly Gln Gly Thr Ser Val Thr Val Ser Ser
            100                 105                 110
```

<210> SEQ ID NO 14
<211> LENGTH: 11
<212> TYPE: PRT
<213> ORGANISM: Artificial sequence
<220> FEATURE:
<223> OTHER INFORMATION: Synthetic polypeptide.

<400> SEQUENCE: 14

```
Gln Ser Leu Leu Asp Ser Asp Gly Lys Thr Tyr
1               5                   10
```

<210> SEQ ID NO 15
<211> LENGTH: 3
<212> TYPE: PRT
<213> ORGANISM: Artificial sequence
<220> FEATURE:
<223> OTHER INFORMATION: Synthetic polypeptide.

<400> SEQUENCE: 15

```
Leu Val Ser
1
```

<210> SEQ ID NO 16
<211> LENGTH: 9
<212> TYPE: PRT
<213> ORGANISM: Artificial sequence
<220> FEATURE:
<223> OTHER INFORMATION: Synthetic polypeptide.

<400> SEQUENCE: 16

```
Trp Gln Gly Thr His Phe Pro Arg Thr
1               5
```

<210> SEQ ID NO 17

```
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 17

Gly Tyr Thr Phe Thr Asn Tyr Tyr
1               5

<210> SEQ ID NO 18
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 18

Ile Asn Pro Tyr Asn Gly Gly Thr
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic polypeptide.

<400> SEQUENCE: 19

Ser Ser Pro Tyr
1

<210> SEQ ID NO 20
<211> LENGTH: 336
<212> TYPE: DNA
<213> ORGANISM: Artificial sequence
<220> FEATURE:
<223> OTHER INFORMATION: Synthetic polynucleotide.

<400> SEQUENCE: 20
gatgttttga tgacccaaac tccactcact ttgtcggtta ccattggaca accagcctcc      60
atctcttgca agtcaagtca gagcctctta gatagtgatg aaagacata tttgaattgg     120 ttgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acatttttcct   300 cggacgttcg gtggaggcac caagctggaa atcaaa                              336

<210> SEQ ID NO 21
<211> LENGTH: 333
<212> TYPE: DNA
<213> ORGANISM: Artificial sequence
<220> FEATURE:
<223> OTHER INFORMATION: Synthetic polynucleotide.

<400> SEQUENCE: 21
gaggttcagc ttcagcagtc tggacctgtg ctggtgaagc ctggggcttc agtgaagatg      60
tcctgtaagg cttctggata cacattcact aactactata aaactgggt gaagcagagc     120 catggaaaga gccttgagtg gattggagtt attaatcctt acaacggtgg tactagctac    180
aaccagaagt tcaagggcaa ggccacattg actgttgaca gtcctccag cacagcctac    240 atggagctca acagcctgac atctgaggac tctgcagtct atttctgttc aagtccctac    300
```
tggggtcaag gaacctcagt caccgtctcc tca                                    333

<210> SEQ ID NO 22
<211> LENGTH: 112
<212> TYPE: PRT
<213> ORGANISM: Artificial sequence
<220> FEATURE:
<223> OTHER INFORMATION: Synthetic polypeptide.

<400> SEQUENCE: 22

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Glu Ser Gly Val Pro
    50                  55                  60

Asp Arg Phe Thr Gly Ser Gly Ser Gly Thr Asp Phe Thr Leu Glu Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 23
<211> LENGTH: 113
<212> TYPE: PRT
<213> ORGANISM: Artificial sequence
<220> FEATURE:
<223> OTHER INFORMATION: Synthetic polypeptide.

<400> SEQUENCE: 23

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Asn Ser Leu Thr Ser Glu Asp Ser Ala Val Tyr Tyr Cys
                85                  90                  95

Ser Arg Gly Gly Pro Tyr Trp Gly Gln Gly Thr Thr Leu Thr Val Ser
            100                 105                 110

Ser

<210> SEQ ID NO 24
<211> LENGTH: 11
<212> TYPE: PRT
<213> ORGANISM: Artificial sequence
<220> FEATURE:
<223> OTHER INFORMATION: Synthetic polypeptide.

<400> SEQUENCE: 24

Gln Ser Leu Leu Asp Ser Asp Gly Lys Thr Tyr
1               5                   10

<210> SEQ ID NO 25
<211> LENGTH: 3
<212> TYPE: PRT
<213> ORGANISM: Artificial sequence
<220> FEATURE:
<223> OTHER INFORMATION: Synthetic polypeptide.

<400> SEQUENCE: 25

Leu Val Ser
1

<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide.

<400> SEQUENCE: 26

Trp Gln Gly Thr His Phe Pro Arg Thr
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 27

Gly Tyr Thr Phe Thr Asp Tyr Tyr
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 28

Ile Asn Pro Tyr Asn Gly Gly Thr
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic polypeptide.

<400> SEQUENCE: 29

Ser Arg Gly Gly Pro Tyr
1               5

<210> SEQ ID NO 30
<211> LENGTH: 336
<212> TYPE: DNA
<213> ORGANISM: Artificial sequence
<220> FEATURE:
<223> OTHER INFORMATION: Synthetic polynucleotide.

<400> SEQUENCE: 30
gatgttttga tgacccaaac tccactcact tgtcggtta ccattggaca accagcctcc      60
atctcttgca agtcaagtca gagcctctta gatagtgatg aaagacata tttgaattgg    120

```
ttgttacaga ggccaggcca gtctccaaag cgcctaatct atctggtgtc taaactggaa    180
tctggagtcc ctgacaggtt cactggcagt ggatcaggga cagatttcac actggaaatc    240
agcagagtgg aggctgagga tttgggagtt tattattgct ggcaaggtac acattttcct    300
cggacgttcg gtggaggcac caagctggaa atcaaa                              336
```

<210> SEQ ID NO 31
<211> LENGTH: 339
<212> TYPE: DNA
<213> ORGANISM: Artificial sequence
<220> FEATURE:
<223> OTHER INFORMATION: Synthetic polynucleotide.

<400> SEQUENCE: 31

```
gaggttcagc tgcagcagtc tggacctgtg ctggtgaagc ctggggcttc agtgaagatg     60
tcctgtaagg cttctggata cacattcact gactactata tgaattgggt gaagcagagc    120
catggaaaga gccttgagtg gattggagtt attaatcctt acaacggtgg tactagttac    180
aatcagaagt tcaagggcaa ggccacattg actgttgata agtcctcccg cacagcctac    240
atggagctca acagcctgac atctgaggac tctgcagtct attattgttc aagagggggc    300
ccctactggg gccaaggcac cactctcaca gtctcctca                            339
```

<210> SEQ ID NO 32
<211> LENGTH: 604
<212> TYPE: PRT
<213> ORGANISM: Artificial sequence
<220> FEATURE:
<223> OTHER INFORMATION: Synthetic polypeptide.

<400> SEQUENCE: 32

```
Met Pro Met Gly Ser Leu Gln Pro Leu Ala Thr Leu Tyr Leu Leu Gly
1               5                   10                  15

Met Leu Val Ala Ser Val Leu Ala His His His His His Ile Glu
                20                  25                  30

Gly Arg Glu Val Lys Leu Val Glu Ser Gly Gly Gly Leu Val Gln Pro
            35                  40                  45

Gly Ser Ser Met Lys Leu Ser Cys Thr Thr Ser Gly Phe Thr Phe Ser
        50                  55                  60

Asp Tyr Tyr Met Ala Trp Val Arg Gln Val Pro Glu Lys Gly Leu Glu
65                  70                  75                  80

Trp Val Ala Asn Ile Asn Tyr Asp Gly Ser Ser Ala Tyr Tyr Leu Asp
                85                  90                  95

Ser Phe Lys Ser Arg Phe Thr Ile Ser Arg Asp Asn Glu Lys Asn Ile
            100                 105                 110

Leu Tyr Leu Gln Met Ser Ser Leu Lys Ser Glu Asp Thr Ala Thr Tyr
        115                 120                 125

Tyr Cys Ala Arg Gly Asp Trp Phe Val Tyr Trp Gly Gln Gly Thr Leu
    130                 135                 140

Val Thr Val Ser Ala Gly Gly Gly Gly Ser Gly Gly Gly Gly Ser Gly
145                 150                 155                 160

Gly Gly Gly Ser Asp Ile Gln Met Thr Gln Ser Pro Ser Ser Met Ser
                165                 170                 175

Ala Ser Leu Gly Glu Arg Val Thr Ile Thr Cys Lys Ala Ser Gln Asp
            180                 185                 190

Ile Asn Ser Tyr Leu Asn Trp Phe Gln Gln Lys Pro Gly Lys Ser Pro
        195                 200                 205
```

-continued

Lys Thr Leu Ile Phe Arg Ala Asn Arg Leu Val Asp Gly Val Pro Ser
    210                 215                 220

Arg Phe Ser Gly Ser Gly Ser Gly Gln Asp Tyr Ser Leu Thr Ile Ser
225                 230                 235                 240

Ser Leu Glu Phe Glu Asp Val Gly Ile Tyr Tyr Cys Leu Gln Tyr Ala
                245                 250                 255

Glu Phe Pro Phe Thr Phe Gly Ser Gly Thr Lys Leu Glu Ile Lys Ile
            260                 265                 270

Glu Gly Arg Gly Gly Gly Ser Gly Gly Gly Ser Cys Pro Ala
            275                 280                 285

Pro Ser Gln Leu Pro Ser Ala Lys Pro Ile Asn Leu Thr Asp Glu Ser
    290                 295                 300

Met Phe Pro Ile Gly Thr Tyr Leu Leu Tyr Glu Cys Leu Pro Gly Tyr
305                 310                 315                 320

Ile Lys Arg Gln Phe Ser Ile Thr Cys Lys Gln Asp Ser Thr Trp Thr
                325                 330                 335

Ser Ala Glu Asp Lys Cys Ile Arg Lys Gln Cys Lys Thr Pro Ser Asp
            340                 345                 350

Pro Glu Asn Gly Leu Val His Val His Thr Gly Ile Gln Phe Gly Ser
    355                 360                 365

Arg Ile Asn Tyr Thr Cys Asn Gln Gly Tyr Arg Leu Ile Gly Ser Ser
370                 375                 380

Ser Ala Val Cys Val Ile Thr Asp Gln Ser Val Asp Trp Asp Thr Glu
385                 390                 395                 400

Ala Pro Ile Cys Glu Trp Ile Pro Cys Glu Ile Pro Pro Gly Ile Pro
                405                 410                 415

Asn Gly Asp Phe Phe Ser Ser Thr Arg Glu Asp Phe His Tyr Gly Met
            420                 425                 430

Val Val Thr Tyr Arg Cys Asn Thr Asp Ala Arg Gly Lys Ala Leu Phe
    435                 440                 445

Asn Leu Val Gly Glu Pro Ser Leu Tyr Cys Thr Ser Asn Asp Gly Glu
    450                 455                 460

Ile Gly Val Trp Ser Gly Pro Pro Pro Gln Cys Ile Glu Leu Asn Lys
465                 470                 475                 480

Cys Thr Pro Pro Tyr Val Glu Asn Ala Val Met Leu Ser Glu Asn
                485                 490                 495

Arg Ser Leu Phe Ser Leu Arg Asp Ile Val Glu Phe Arg Cys His Pro
            500                 505                 510

Gly Phe Ile Met Lys Gly Ala Ser Ser Val His Cys Gln Ser Leu Asn
    515                 520                 525

Lys Trp Glu Pro Glu Leu Pro Ser Cys Phe Lys Gly Val Ile Cys Arg
530                 535                 540

Leu Pro Gln Glu Met Ser Gly Phe Gln Lys Gly Leu Gly Met Lys Lys
545                 550                 555                 560

Glu Tyr Tyr Tyr Gly Glu Asn Val Thr Leu Glu Cys Glu Asp Gly Tyr
                565                 570                 575

Thr Leu Glu Gly Ser Ser Gln Ser Gln Cys Gln Ser Asp Gly Ser Trp
            580                 585                 590

Asn Pro Leu Leu Ala Lys Cys Val Ser Arg Ser Ile
    595                 600

<210> SEQ ID NO 33
<211> LENGTH: 348
<212> TYPE: DNA

<213> ORGANISM: Artificial sequence
<220> FEATURE:
<223> OTHER INFORMATION: Synthetic polynucleotide.

<400> SEQUENCE: 33

```
gaggtccagc tgcagcaatc tggagctgag ctggtaaggc ctgggacttc agtgaaggtg      60
tcctgcaagg cttctggata cgccttcgct cactacttga taaatgggt aaagcagagg      120
cctggacagg gccttgagtg gattggcgtg attaatcctg gaactgatgg cactaactac     180
aatgagaagt tcaagggcaa ggcaacactg actgcagaca atcctccag cactgcctac      240
atgcacctca gcagcctgac atctgaggac tctgcggtct atttctgtgc aagagaggaa     300
ctggggtttg cttactgggg ccaagggact ctggtcactg tctctgca                 348
```

<210> SEQ ID NO 34
<211> LENGTH: 116
<212> TYPE: PRT
<213> ORGANISM: Artificial sequence
<220> FEATURE:
<223> OTHER INFORMATION: Synthetic polypeptide.

<400> SEQUENCE: 34

```
Glu Val Gln Leu Gln Gln Ser Gly Ala Glu Leu Val Arg Pro Gly Thr
1               5                   10                  15
Ser Val Lys Val Ser Cys Lys Ala Ser Gly Tyr Ala Phe Ala His Tyr
            20                  25                  30
Leu Ile Glu Trp Val Lys Gln Arg Pro Gly Gln Gly Leu Glu Trp Ile
        35                  40                  45
Gly Val Ile Asn Pro Gly Thr Asp Gly Thr Asn Tyr Asn Glu Lys Phe
    50                  55                  60
Lys Gly Lys Ala Thr Leu Thr Ala Asp Lys Ser Ser Ser Thr Ala Tyr
65                  70                  75                  80
Met His Leu Ser Ser Leu Thr Ser Glu Asp Ser Ala Val Tyr Phe Cys
                85                  90                  95
Ala Arg Glu Glu Leu Gly Phe Ala Tyr Trp Gly Gln Gly Thr Leu Val
            100                 105                 110
Thr Val Ser Ala
        115
```

<210> SEQ ID NO 35
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 35

```
Gly Tyr Ala Phe Ala His Tyr Leu
1               5
```

<210> SEQ ID NO 36
<211> LENGTH: 8
<212> TYPE: PRT
<213> ORGANISM: Artificial sequence
<220> FEATURE:
<223> OTHER INFORMATION: Synthetic polypeptide.

<400> SEQUENCE: 36

```
Ile Asn Pro Gly Thr Asp Gly Thr
1               5
```

```
<210> SEQ ID NO 37
<211> LENGTH: 9
<212> TYPE: PRT
<213> ORGANISM: Artificial sequence
<220> FEATURE:
<223> OTHER INFORMATION: Synthetic polypeptide.

<400> SEQUENCE: 37

Ala Arg Glu Glu Leu Gly Phe Ala Tyr
1               5

<210> SEQ ID NO 38
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(4)
<223> OTHER INFORMATION: Residues 3 and 4 may be absent
<220> FEATURE:
<221> NAME/KEY: MISC_FEATURE
<222> LOCATION: (5)..(6)
<223> OTHER INFORMATION: Residues 5 and 6 may be absent
<220> FEATURE:
<221> NAME/KEY: MISC_FEATURE
<222> LOCATION: (7)..(8)
<223> OTHER INFORMATION: Residues 7 and 8 may be absent
<220> FEATURE:
<221> NAME/KEY: MISC_FEATURE
<222> LOCATION: (9)..(10)
<223> OTHER INFORMATION: Residues 9 and 10 may be absent
<220> FEATURE:
<221> NAME/KEY: MISC_FEATURE
<222> LOCATION: (11)..(12)
<223> OTHER INFORMATION: Residues 11 and 12 may be absent
<220> FEATURE:
<221> NAME/KEY: MISC_FEATURE
<222> LOCATION: (13)..(14)
<223> OTHER INFORMATION: Residues 13 and 14 may be absent
<220> FEATURE:
<221> NAME/KEY: MISC_FEATURE
<222> LOCATION: (15)..(16)
<223> OTHER INFORMATION: Residues 15 and 16 may be absent

<400> SEQUENCE: 38

Gly Ser Gly Ser Gly Ser Gly Ser Gly Ser Gly Ser Gly Ser Gly Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(8)
<223> OTHER INFORMATION: Residues 5 through 8 may be absent
<220> FEATURE:
<221> NAME/KEY: MISC_FEATURE
<222> LOCATION: (9)..(12)
<223> OTHER INFORMATION: Residues 9 through 12 may be absent
<220> FEATURE:
<221> NAME/KEY: MISC_FEATURE
<222> LOCATION: (13)..(16)
<223> OTHER INFORMATION: Residues 13 through 16 may be absent

<400> SEQUENCE: 39

Gly Gly Gly Ser Gly Gly Gly Ser Gly Gly Gly Ser Gly Gly Gly Ser
1               5                   10                  15
```

```
<210> SEQ ID NO 40
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(10)
<223> OTHER INFORMATION: Residues 6 through 10 may be absent
<220> FEATURE:
<221> NAME/KEY: MISC_FEATURE
<222> LOCATION: (11)..(15)
<223> OTHER INFORMATION: Residues 11 through 15 may be absent
<220> FEATURE:
<221> NAME/KEY: MISC_FEATURE
<222> LOCATION: (16)..(20)
<223> OTHER INFORMATION: Residues 16 through 20 may be absent
<220> FEATURE:
<221> NAME/KEY: MISC_FEATURE
<222> LOCATION: (21)..(25)
<223> OTHER INFORMATION: Residues 21 through 25 may be absent
<220> FEATURE:
<221> NAME/KEY: MISC_FEATURE
<222> LOCATION: (26)..(30)
<223> OTHER INFORMATION: Residues 26 through 30 may be absent
<220> FEATURE:
<221> NAME/KEY: MISC_FEATURE
<222> LOCATION: (31)..(35)
<223> OTHER INFORMATION: Residues 31 through 35 may be absent
<220> FEATURE:
<221> NAME/KEY: MISC_FEATURE
<222> LOCATION: (36)..(40)
<223> OTHER INFORMATION: Residues 36 through 40 may be absent

<400> SEQUENCE: 40

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 41
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(8)
<223> OTHER INFORMATION: Residues 5 through 8 may be absent
<220> FEATURE:
<221> NAME/KEY: MISC_FEATURE
<222> LOCATION: (9)..(12)
<223> OTHER INFORMATION: Residues 9 through 12 may be absent
<220> FEATURE:
<221> NAME/KEY: MISC_FEATURE
<222> LOCATION: (13)..(16)
<223> OTHER INFORMATION: Residues 13 through 16 may be absent

<400> SEQUENCE: 41

Gly Ser Ser Gly Gly Ser Ser Gly Gly Ser Ser Gly Gly Ser Ser Gly
1               5                   10                  15

<210> SEQ ID NO 42
<211> LENGTH: 5
<212> TYPE: PRT
<213> ORGANISM: Artificial Sequence
<220> FEATURE:
<223> OTHER INFORMATION: Synthetic polypeptide
```

```
<400> SEQUENCE: 42

Gly Gly Gly Gly Ser
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 43

Gly Gly Gly Gly Ser Gly Gly Gly Gly Ser
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 44

Gly Gly Gly Gly Ser Gly Gly Gly Gly Ser Gly Gly Gly Gly Ser
1               5                   10                  15

<210> SEQ ID NO 45
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 45

Gly Gly Gly Gly Ser Gly Gly Gly Gly Ser Gly Gly Gly Gly Ser Gly
1               5                   10                  15

Gly Gly Gly Ser
            20

<210> SEQ ID NO 46
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 46

Ser Gly Gly Gly Gly
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 47

Ser Gly Gly Gly Gly Ser Gly Gly Gly Gly
1               5                   10

<210> SEQ ID NO 48
<211> LENGTH: 15
<212> TYPE: PRT
<213> ORGANISM: Artificial Sequence
<220> FEATURE:
```

```
<223> OTHER INFORMATION: Synthetic polypeptide

<400> SEQUENCE: 48

Ser Gly Gly Gly Gly Ser Gly Gly Gly Gly Ser Gly Gly Gly Gly
1               5                   10                  15

<210> SEQ ID NO 49
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 49

Ser Gly Gly Gly Gly Ser Gly Gly Gly Ser Gly Gly Gly Gly Ser
1               5                   10                  15

Gly Gly Gly Gly
            20

<210> SEQ ID NO 50
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 50

Val Ser Val Phe Pro Leu Glu
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 51

Glu Tyr Phe Asn Lys Tyr Ser Ser
1               5

<210> SEQ ID NO 52
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 52

Glu Glu Ile Phe
1

<210> SEQ ID NO 53
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 53
cgcggatccg cggctgtgga cggggag                                              27

<210> SEQ ID NO 54
<211> LENGTH: 33
<212> TYPE: DNA
<213> ORGANISM: Artificial Sequence
```

```
<220> FEATURE:
<223> OTHER INFORMATION: Synthetic polynucleotide

<400> SEQUENCE: 54
ccggaattcc ggtcatcaac ggctggggag gtg                                    33
```

ANTI-C3D ANTIBODY CONJUGATES AND METHODS OF DETECTING COMPLEMENT ACTIVATION

CROSS-REFERENCE TO RELATED APPLICATIONS

This application is a continuation of International Application No. PCT/US2013/055400, filed Aug. 16, 2013, which claims the benefit of U.S. Provisional Patent Application No. 61/684,691, filed Aug. 17, 2012, each of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48498-549C01US_ST25.TXT, created on Jul. 9, 2015, 93,812 bytes, machine format IBM-PC, MS-Windows operating system, is hereby incorporated by reference.

BACKGROUND OF THE INVENTION

Complement is the collective term for a series of blood proteins that constitute a major effector mechanism of the immune system. The complement system plays an important role in the pathology of many autoimmune, inflammatory and ischemic diseases. Inappropriate complement activation and its deposition on host cells can lead to complement-mediated lysis and/or injury of cells and target tissues, as well as tissue destruction due to the generation of powerful mediators of inflammation. Key to the activity of the complement system is the covalent attachment of processed protein fragments derived from a serum protein, complement C3, to tissue sites of complement activation. This unusual property is due to the presence of a thioester bond in C3 that, when cleaved during C3 activation, converts C3 to a form designated C3b which can then utilize ester or amide bonds to link to cell and tissue-attached molecules. Once C3b is covalently attached, it is rapidly processed to the iC3b, C3dg and C3d forms, each of which remain covalently attached to the target tissue site. This process results in the "marking" of the tissue as one in which an inflammatory injury or other complement-related process is underway.

Complement can be activated by any of three pathways: the classical, lectin and alternative pathways. The classical pathway is activated through the binding of the complement system protein C1q to antigen-antibody complexes, pentraxins or apoptotic cells. The pentraxins include C-reactive protein and serum amyloid P component. The lectin pathway is initiated by binding of microbial carbohydrates to mannose-binding lectin or by the binding of ficolins to carbohydrates or acetylated molecules.

The alternative pathway is activated on surfaces of pathogens that have neutral or positive charge characteristics and do not express or contain complement inhibitors. This results from the process termed 'tickover' of C3 that occurs spontaneously, involving the interaction of conformationally altered C3 with factor B, and results in the fixation of active C3b on pathogens or other surfaces. The alternative pathway can also be initiated when certain antibodies block endogenous regulatory mechanisms, by IgA-containing immune complexes, or when expression of complement regulatory proteins is decreased. In addition, the alternative pathway is activated by a mechanism called the 'amplification loop' when C3b that is deposited onto targets via the classical or lectin pathway, or indeed through the tickover process itself, binds factor B. See Muller-Eberhard (1988) *Ann. Rev. Biochem.* 57:321. For example, Holers and colleagues have shown that the alternative pathway is amplified at sites of local injury when inflammatory cells are recruited following initial complement activation. Girardi et al., *J. Clin. Invest.* 2003, 112:1644. Dramatic complement amplification through the alternative pathway then occurs through a mechanism that involves either the additional generation of injured cells that fix complement, local synthesis of alternative pathway components, or more likely because infiltrating inflammatory cells that carry preformed C3 and properdin initiate and/or greatly increase activation specifically at that site.

Alternative pathway amplification is initiated when circulating factor B binds to activated C3b. This complex is then cleaved by circulating factor D to yield an enzymatically active C3 convertase complex, C3bBbn. C3bBb cleaves additional C3 generating C3b, which drives inflammation and also further amplifies the activation process, generating a positive feedback loop. Factor H is a key regulator (inhibitor) of the alternative complement pathway activation and initiation mechanisms that competes with factor B for binding to conformationally altered C3 in the tickover mechanism and to C3b in the amplification loop. Binding of C3b to Factor H also leads to degradation of C3b by factor I to the inactive form iC3b (also designated C3bi), thus exerting a further check on complement activation. Factor H regulates complement in the fluid phase, circulating at a plasma concentration of approximately 500 µg/ml, but its binding to cells is a regulated phenomenon enhanced by the presence of a negatively charged surface as well as fixed C3b, iC3b, C3dg or C3d. Jozsi et al., *Histopathol.* (2004) 19:251-258.

Complement activation, C3 fragment fixation and complement-mediated inflammation are involved in the etiology and progression of numerous diseases. The down-regulation of complement activation has been shown to be effective in treating several diseases in animal models and in ex vivo studies, including, for example, systemic lupus erythematosus and glomerulonephritis (Y. Wang et al., *Proc. Nat'l Acad. Sci. USA* (1996) 93:8563-8568), rheumatoid arthritis (Y. Wang et al., *Proc. Nat'l Acad. Sci. USA* (1995) 92:8955-8959), cardiopulmonary bypass and hemodialysis (C. S. Rinder, *J. Clin. Invest.* (1995) 96:1564-1572), hyperacute rejection in organ transplantation (T. J. Kroshus et al., *Transplantation* (1995) 60:1194-1202), myocardial infarction (J. W. Homeister et al., *J. Immunol.* (1993) 150:1055-1064; H. F. Weisman et al., *Science* (1990) 249:146-151), ischemia/reperfusion injury (E. A. Amsterdam et al., *Am. J. Physiol.* (1995) 268:H448-H457), antibody-mediated allograft rejection, for example, in the kidneys (J. B. Colvin, *J. Am. Soc. Nephrol.* (2007) 18(4):1046-56), and adult respiratory distress syndrome (R. Rabinovici et al., *J. Immunol.* (1992) 149:1744-1750).

Moreover, other inflammatory conditions and autoimmune/immune complex diseases are also closely associated with complement activation (B. P. Morgan. *Eur. J. Clin. Invest.* (1994) 24:219-228), including, but not limited to, thermal injury, severe asthma, anaphylactic shock, bowel inflammation, urticaria, angioedema, vasculitis, multiple sclerosis, myasthenia gravis, myocarditis, membranoproliferative glomerulonephritis, atypical hemolytic uremic syndrome, Sjögren's syndrome, renal and pulmonary ischemia/reperfusion, and other organ-specific inflammatory disorders. It is currently uncertain whether complement activation is essential to the pathogenesis and injury of all diseases in which local tissue C3 activation and inflammatory injury occurs; nevertheless, C3 fragment fixation is almost universally found as an associated event.

A variety of disorders are associated with inflammation, however, so definitive diagnosis of complement-mediated inflammation typically requires confirmation via immunostaining or other in vitro analysis performed on tissue samples retrieved by biopsy. While biopsies are in many respects routine, they have their limitations and are not risk-free. Because commonly used needle or punch biopsies sample only a small portion of the target organ, there is a risk of sample error leading to an incorrect diagnosis. Furthermore, although biopsy is a generally safe procedure, major complications such as internal bleeding may occur in a significant number of cases.

In some cases, because of the difficulties in diagnosing disease or monitoring disease progression, for example, in patients with systemic lupus erythematosus or lupus nephritis, repeat renal biopsies are therefore frequently necessary to assess the response to therapy or to diagnose disease relapse. See e.g., S. Bajaj et al., 2000, *J. Rheumatol.* 27:2822-2826. Although renal biopsy is generally a safe procedure, complications may occur in 6% or more of biopsies and intra-renal bleeding and hematuria are common Patients requiring repeat biopsies are at concomitantly greater risk of complications. See e.g., W. L. Whittier et al., 2004, *J. Am. Soc. Nephrol.* 15:142-147; D. C. Mendelssohn et al., 1995, *Am. J. Kidney Dis.* 26:580-585. Thus, a non-invasive method of detecting or accurately assessing the presence, degree and/or extent of complement-mediated inflammation would be of significant value in diagnosing disease, formulating treatment strategies and monitoring their efficacy for many inflammatory diseases, including lupus nephritis.

The use of complement receptor 2 (CR2), or functional fragments thereof, to target complement modulators to tissues which exhibit or express C3, or fragments of C3 to which the CR2 is able to bind, including C3b, iC3b, C3d and C3dg, is described in US 2008/0267980 and US 2008/0221011, the disclosures of which are hereby incorporated herein by reference. Such CR2 molecules, and functional fragments thereof, can be used for targeting because the first two N-terminal short consensus repeat domains (SCRs) comprise an active binding site for the exposed C3d domain that is contained within iC3b, C3dg, and C3d.

The present invention provides solutions to these and other problems in the art. The disclosures of all publications, patents, patent applications and published patent applications referred to herein are hereby incorporated herein by reference in their entirety.

BRIEF SUMMARY OF THE INVENTION

In a first aspect is provided an antibody conjugate including an antibody, or antigen binding fragment thereof, and a detectable moiety.

In a second aspect is provided a method of detecting complement-mediated inflammation in an individual including: (a) administering to the individual an effective amount of an anti-C3d antibody conjugate as described herein; (b) allowing the anti-C3d antibody conjugate to bind to a C3 protein fragment within the individual thereby forming an anti-C3d antibody conjugate-C3 protein fragment complex; and (c) detecting the anti-C3d antibody conjugate-C3 protein fragment complex in the individual.

In a third aspect is provided a method of detecting complement activation in an individual including: (a) administering to the individual an effective amount of an anti-C3d antibody conjugate as described herein; (b) allowing the anti-C3d antibody conjugate to bind to a C3 protein fragment within the individual thereby forming an anti-C3d antibody conjugate-C3 protein fragment complex; and (c) detecting the anti-C3d antibody conjugate-C3 protein fragment complex in the individual.

In a fourth aspect is provided a method of detecting complement activation including (a) administering to a biological sample (e.g. biopsy, tissue, blood, blood fraction, serum, or cells, all optionally from a subject or patient) an effective amount of an anti-C3d antibody conjugate as described herein; (b) allowing the anti-C3d antibody conjugate to bind to a C3 protein fragment within the biological sample thereby forming an anti-C3d antibody conjugate-C3 protein fragment complex; and (c) detecting the anti-C3d antibody conjugate-C3 protein fragment complex in the biological sample. In some embodiments, the C3 protein fragment is C3d or C3dg or iC3b.

BRIEF DESCRIPTION OF THE DRAWINGS

FIG. 3. Specific and durable in vivo binding of monoclonal antibody 3d29 to the site of complement C3 fixation at 48 hours following injection the day after laser-induced CNV injury. In vivo imaging was performed using a Micron III retinal imaging microscope (Phoenix Research Laboratories).

FIG. 4. Specific and durable in vitro binding of monoclonal antibody 3d29 to the site of complement C3 fixation at 48 hours following injection the day after induction of laser-induced CNV injury. In vitro imaging was performed using a flat mount and B×W image capture system.

(FIG. 5A) FACS analysis was used to determine the efficacy of the reactions. Unconjugated SPIO are represented by filled gray curves, and conjugated are represented by black line curves. (FIG. 5B) The percentage of antibody-positive SPIO obtained using each method of conjugation and for each protein are shown. Data are mean±SEM from three independent conjugations per method per protein species.

(FIG. 7A) zeta potential of unconjugated and conjugated SPIO. The conjugated proteins change the negative zeta potential of the NH2-SPIO from slightly negative to positive, and reduce the negative zeta potential of COOH-SPIO. Data are mean±SEM from three independent conjugations per method per protein species. (FIG. 7B) mean diameter and percent distribution of unconjugated and conjugated SPIO. All conjugates species of SPIO show an increase in hydrodynamic size from that of unconjugated SPIO. C3d29-SPIO of EDC/NHS method shows properties of aggregation (greater increase in hydrodynamic size and a greater reduction of the negative zeta potential). Data are mean±SD from three independent conjugations per method per protein species. (FIG. 7C) Estimated nmoles of protein per nmole of conjugated SPIO for three different methods of conjugation with three different proteins. Data are mean±SEM per conjugation method per protein.

(FIG. 9A) reduction of $T_2$-relaxation time of opsonized CHO cell pellets incubated with CR2-Fc-SPIO or C3d29-SPIO was seen relative to those incubated with control 171-SPIO. Three different methods of SPIO conjugation were tested. Data are mean±SEM from conjugated SPIO obtained from three independent conjugations per method per protein. (FIG. 9B) images from $T_2$-weighted MRI scans of the cell pellets. Images were obtained at TE=48 ms for all three methods of conjugation. Targeting proteins conjugated to SPIO are indicated on the left. Darkening of the pellets reflects binding of the SPIO to the opsonized cells. *p<0.05, p<0.01, and *p<0.001 by one-way ANOVA followed by Dunnett's post-test where data from 171-SPIO was used as control.

FIG. 10A. Schematic demonstration of cleavage of soluble C3 initially to the C3b and C3a forms through the activity of C3 convertases (activating enzymes), followed by the sequential processing to iC3b, C3dg and C3d (latter not shown) through the activity of cofactors and proteases. The iC3b, C3dg and C3d proteins exhibit durable tissue and cell binding properties FIG. 10B. Illustration of the molecular entities (iC3b, C3dg (not shown) and C3d) to which the anti-C3d monoclonal antibodies described herein specifically bind.

(FIG. 11A) The hybridomas were screened against recombinant human C3d by ELISA, and nine of the clones bound to the protein (clone 7C10 was used as a positive control, and the remaining clones were newly identified). (FIG. 11B) Reactivity of the clones against intact C3 and recombinant C3d by Western blot analysis was tested. Three patterns of reactivity were seen: Group 1 clones bound strongly to C3d, Group 2 clones bound to the α chain of intact C3, and Group 3 clones did not bind well to either moiety. The * denotes the clone whose results are shown. (FIG. 11C) Clone 3d11 recognized all of the C3 fragments by Western blot analysis. The appearance of the α, α', α1, α2, C3dg, and C3d fragments from purified proteins and from mouse plasma are shown. (FIG. 11D) Immunoprecipitation of C3 fragments in plasma demonstrated that the Group 1 clones recognize the iC3b form (α1 chain) and C3dg, but do not bind to the C3 and C3b (α and α' chains). Clone 3d16 demonstrated some binding to the C3dg and C3d fragments.

(FIG. 13A) When guinea pig serum was added to the erythrocytes as a source of membrane attack complex (MAC) and the average number of MAC complexes was calculated, cells treated with clones 3d3, 3d15, and 3d16 demonstrated a greater MAC formation than control treated cells. (FIG. 13B) When the cells were incubated two hours prior to addition of the guinea pig serum the same three clones showed greater Z values, indicating that these clones stabilize the C3 convertase on the cell surface. (FIG. 13C and FIG. 13D) the experiment was repeated for clones 3d3, 3d15, and 3d16 in the presence or absence of factor B. In the absence of factor B MAC formation was eliminated, demonstrating that the reaction required formation of the alternative pathway C3 convertase. (FIG. 3E) The same reaction was repeated but with the addition of 400 ng of factor H. The reaction was incubated for 30 minutes and the Z values were measured. None of the antibodies tested interfered with the ability of factor H to dissociated the C3 convertase and prevent MAC formation. Antibodies 3d8b, 3d9a, 3d29a, and 3d16 were added to sheep erythrocytes in an alternative pathway lysis assay. Varying concentrations of the anti-C3d antibodies were added, and the percent of cells lysed by the serum were calculated for each reaction. The addition of clone 3d16 caused an increase in the percentage of cells lysed using a fixed concentration of serum.

(FIG. 15A) A competition ELISA was performed to test whether the anti-C3d mAbs interfere with the binding of a recombinant construct of the two N-terminal domains of CR2 (MBP-CR2) and plate-bound C3d. The percentage binding of MBP-CR2 at a concentration of 10 µg/ml (y-axis) was determined in the presence of individual anti-C3d mAbs (x-axis) at a concentration of 26 µg/ml. Values are normalized to a positive control in which C3d-coated wells were incubated with MBP-CR2 in the absence of anti-C3d mAbs (not shown). Also shown for each sample is a negative control in which the wells were coated with BSA instead of C3d. (FIG. 15B-D) Capacity of the Group 1 mAbs (3d8b [FIG. 15B], 3d9a [FIG. 15C] and 3d29 [FIG. 15D]) to block MBP-CR2 binding to plate-bound C3d, at mAb concentrations ranging from 1.625 to 26 µg/ml.

(FIG. 16A) Normal mouse serum was activated on zymosan particles, and binding of the antibodies to the C3-opsonized particles was tested. The opsonized particles were incubated with 1 µg of each antibody, and bound antibody was detected by flow cytometry. Polyclonal anti-mouse C3 was used as a positive control. Clones 3d8b, 3d9, and 3d29 bound to the opsonized particles. (FIG. 16B) Kidney tissue sections from factor H deficient mice were used to test binding of the antibodies to C3 tissue deposits. Factor H mice are known to have abundant deposition of C3 fragments along the glomerular capillaries without IgG at this location. This was confirmed by immunostaining using a polyclonal antibody to mouse C3. Kidney tissue sections were then incubated with 5 µg/mL of each clone. Clones 3d8b, 3d9, and 3d29 bound to the capillaries in a pattern identical to that of C3. The remaining 6 clones did not demonstrate substantive binding (results for clone 3d31 are shown). Original magnification ×400.

(FIG. 17A) Factor H deficient mice were injected with 0.5 mg of each antibody. After 24 hours the mice were sacrificed, and immunofluorescence microscopy was performed to detect glomerular IgG. Mice injected with clones 3d8b, 3d9, and 3d29 demonstrated IgG deposition along the capillary walls in a pattern indistinguishable from that of C3 deposition. These mice do not have detectable C3 deposits along the tubules, and no IgG was seen in the tubulointerstitium. To confirm that the detection antibody was not binding to endogenous IgG, clone 3d29 was biotinylated and the experiment was repeated. Streptavidin-FITC was used to detect the injected antibody, and again it could be seen along the capillary loops. (FIG. 17B) Wild-type C57BL/6 mice demonstrate C3 deposits along the basolateral aspect of the tubules. Unmanipulated C57BL/6 mice were injected with biotinylated 3d29 or with a biotinylated control antibody. The mice were sacrificed after 24 hours, and 3d29 was detected in the kidneys using strepatavidin-PE. The antibody was detected along the tubules, in a pattern indistinguishable from the C3 deposits. Original magnification ×400.

(FIG. 18A) FITC-3d29 strongly bound to CNV lesions in flatmounts made from wild-type mice. (FIG. 18B) Low intensity staining was observed for HB5, a control antibody, to edge of the CNV lesions in flatmounts made from wild-type mice. (FIG. 18C) Low intensity staining of FITC-3d29 was observed in CNV lesions in flatmounts made from fβ$^{-/-}$ mice. Clones 3d29 targets tissue-bound C3 fragments in vivo in the retina in a model of choroidal neovascularization. Four laser spots in each eye were created by Argon laser photocoagulation. (FIG. 18D) Brightfield image revealing four depigmented CNV lesions in a wild-type mouse injected with FITC-HB5. (FIG. 18E) Fluorescent image of the same fundus demonstrating that no fluorescence is detectable in live CNV mice injected with FITC-HB5. (FIG. 18F) Brightfield image revealing four depigmented CNV lesions in a wild-type mouse injected with FITC-3d29. (FIG. 18G) Fluorescent image of the same fundus, demonstrating that fluorescence is clearly detectable in live CNV mice injected with FITC-3d29.

FIG. 22. 3d8bCrry Protein sequence. Overlapping PCR to amplify. 3d8bCrry and pselko12Crry. Lane 1: 1 kB DNA ladder; Lane2: blanket. Lane 3: 3d8bscFvCrry; Lane 4: PselKO12scFv Crry, amino acid sequence of 3d scFv Crry fusion with Sp sq sequence underlined, His Tag labeled, Factor Xa recognition sequence underlined, and linker underlined. Sequence legend: SEQ ID NO:32.

DETAILED DESCRIPTION OF THE INVENTION

Definitions

Figure 1:
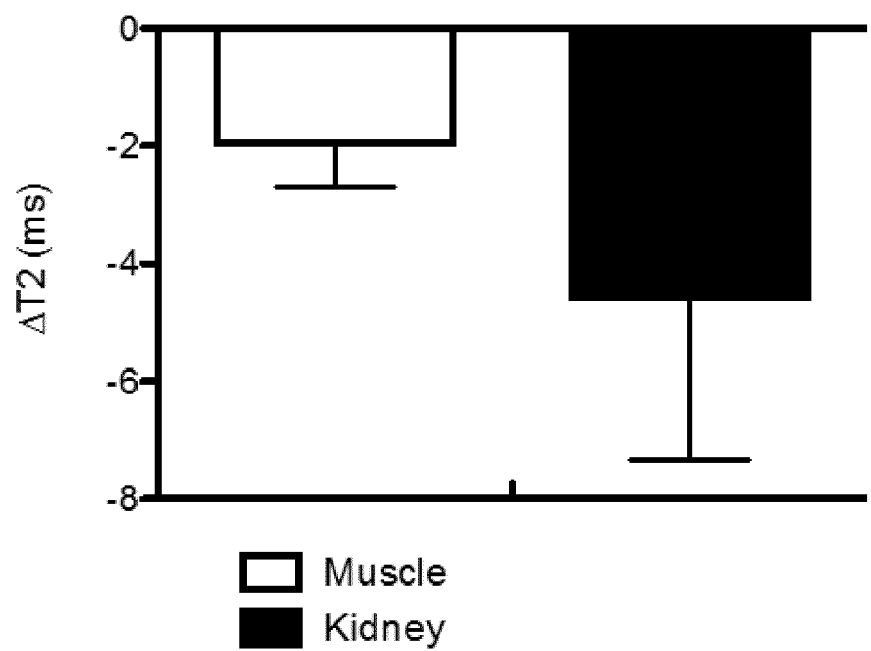
FIG. 1. Changes in T2 relaxation as measured by MRI in muscle and kidney following administration of the 3d29 antibody conjugated to the surface of iron-oxide nanoparticles to factor H knockout mice (that have abundant target C3 fragment deposits (i.e. iC3b, C3dg, and C3d) in the glomeruli of their kidneys).
Figure 2:
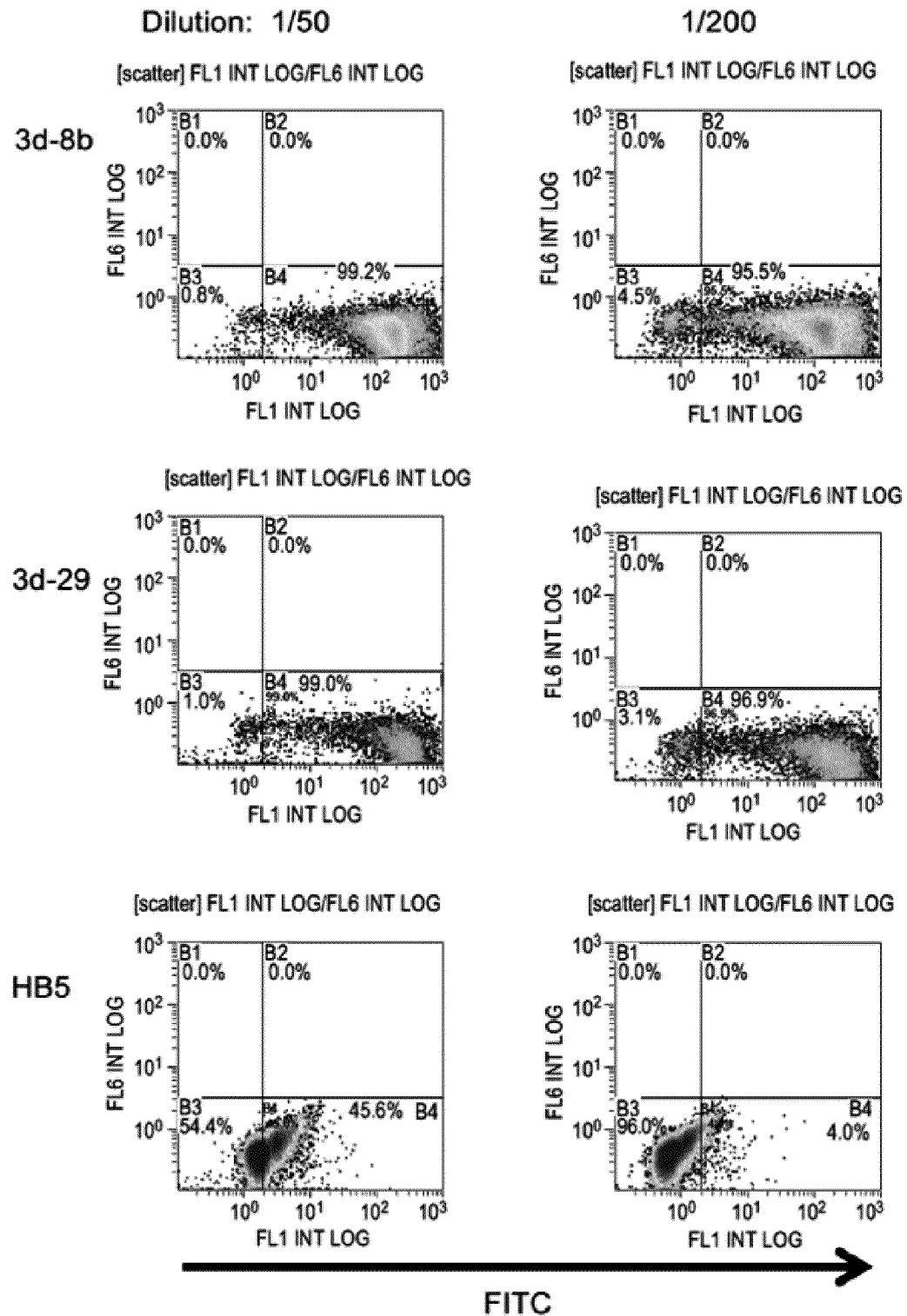
FIG. 2. Specific binding by flow cytometry of FITC-labelled Group 1 monoclonal antibodies 3d29 and 3d8, but not control monoclonal Antibody HB5, to C3d-coated zymosan particles. These monoclonal antibodies also retained binding to C3d following biotinylation and other techniques.
Figure 5A:
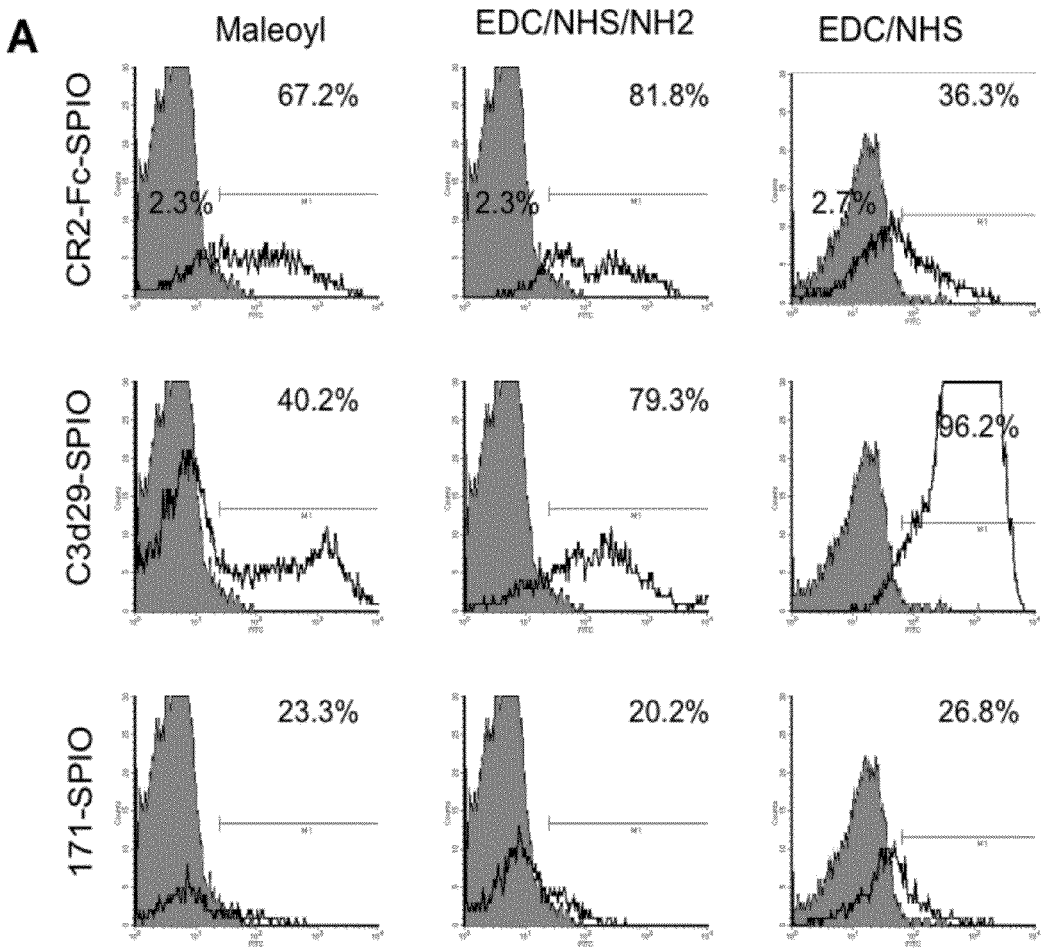
FIGS. 5A-5B. Conjugation of anti-C3d antibodies to the surface of superparamagnetic iron-oxide nanoparticles (SPIO). Three different methods of conjugating antibodies to the surface of SPIO were tested using three different proteins: C3d29 anti-C3d, CR2-Fc, and 171 (as a control antibody).
Figure 5B:
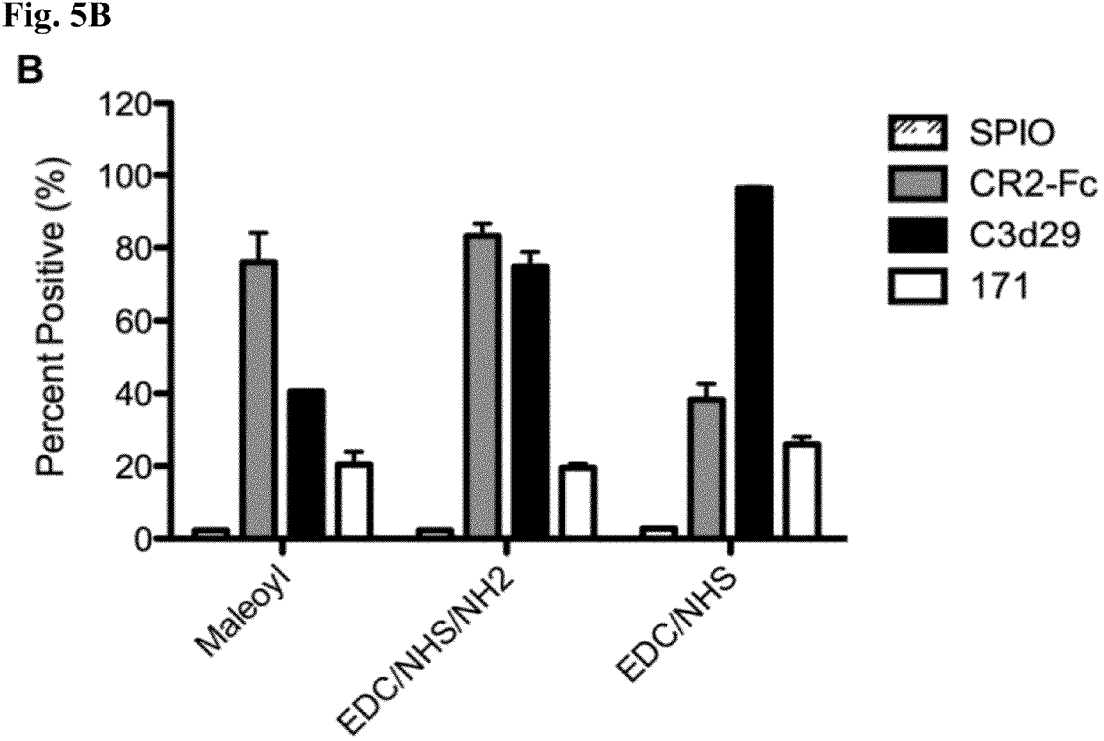
Figure 6A:
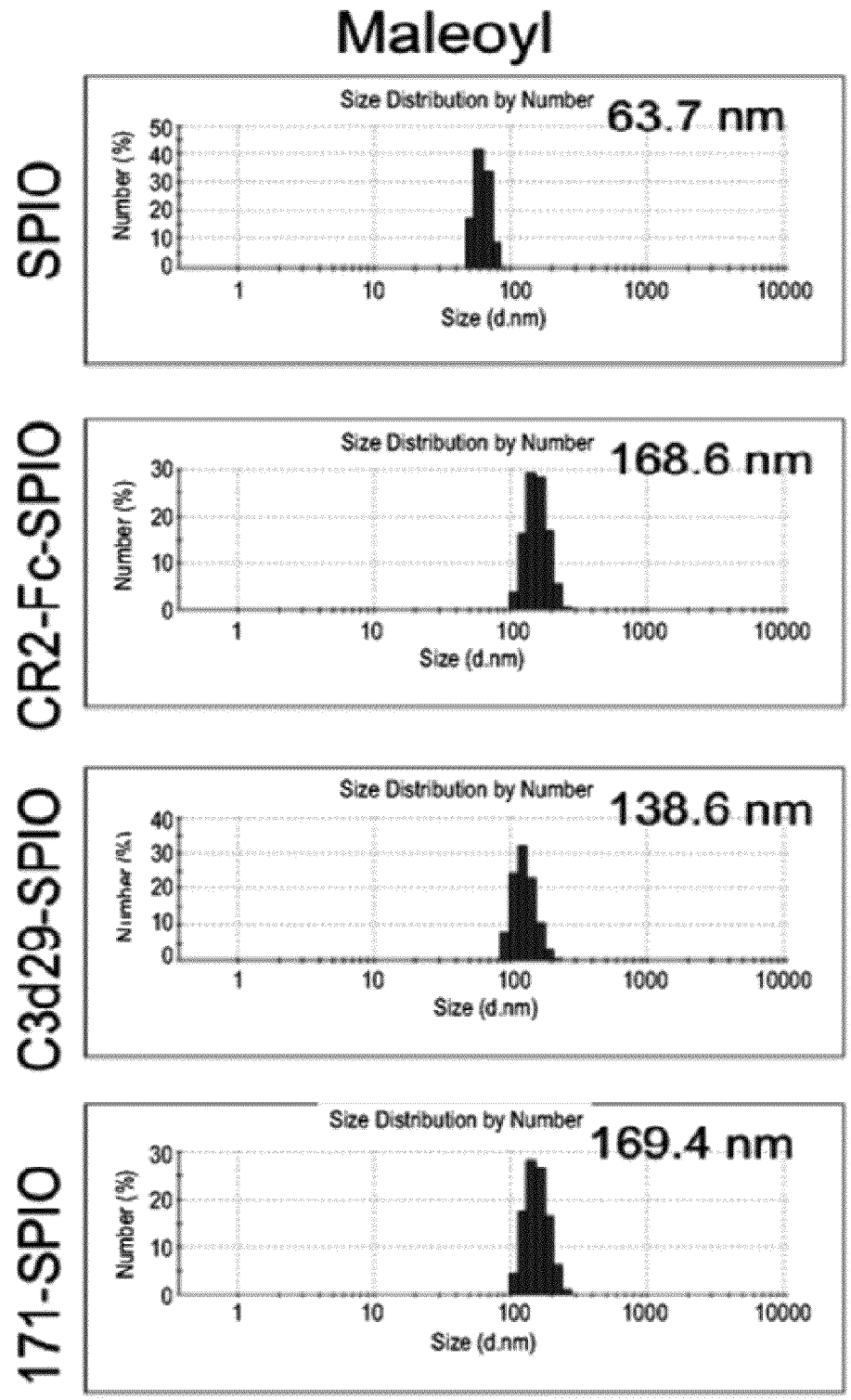
FIGS. 6A-6C. Analysis of conjugated SPIO size as determined by dynamic light scattering (DLS). Representative histograms of the dominant peak of number-weighted size distribution are presented for maleoyl (FIG. 6A), EDC/NHS/NH2 (FIG. 6B), and EDC/NHS (FIG. 6C) conjugation methods for unconjugated SPIO, and CR2-Fc-, C3d29-, and 171-conjugated SPIO. The mean diameter (nm) for the dominant peak of size distribution is indicated in the top right corner of every sample. An increase in size following conjugation of SPIO with proteins was observed for all conjugated samples.
Figure 6B:
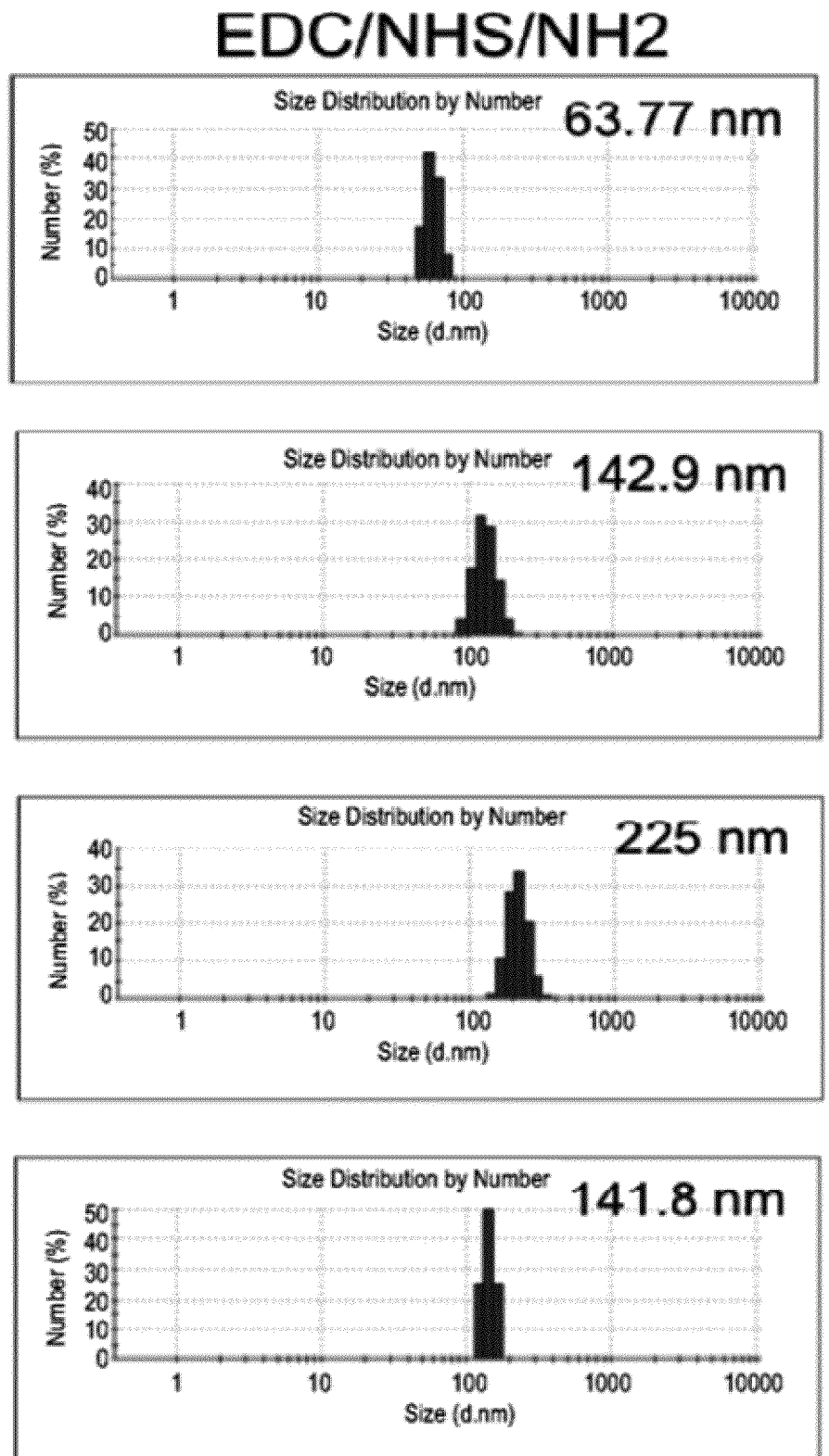
Figure 6C:
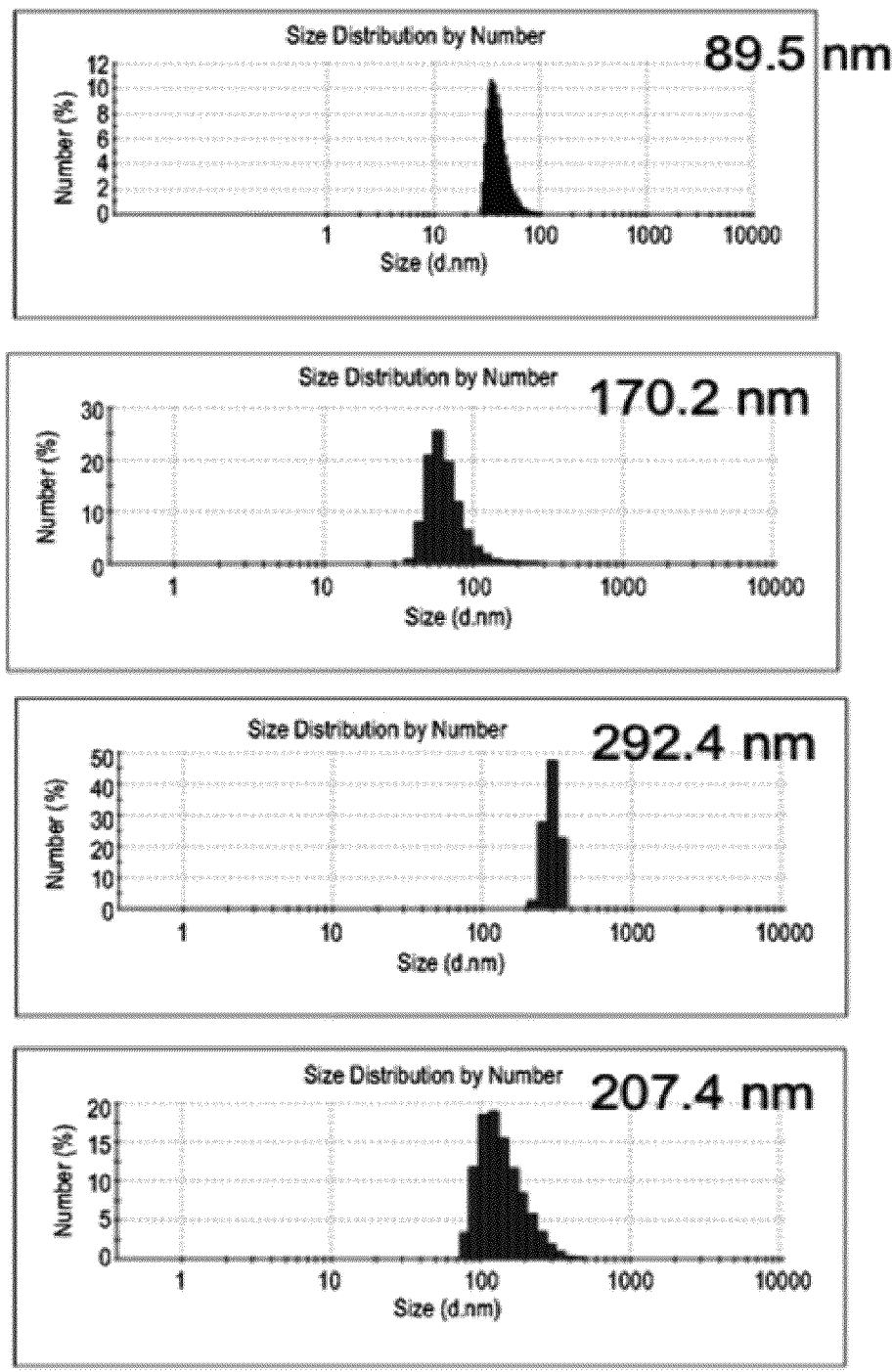
Figure 7A:
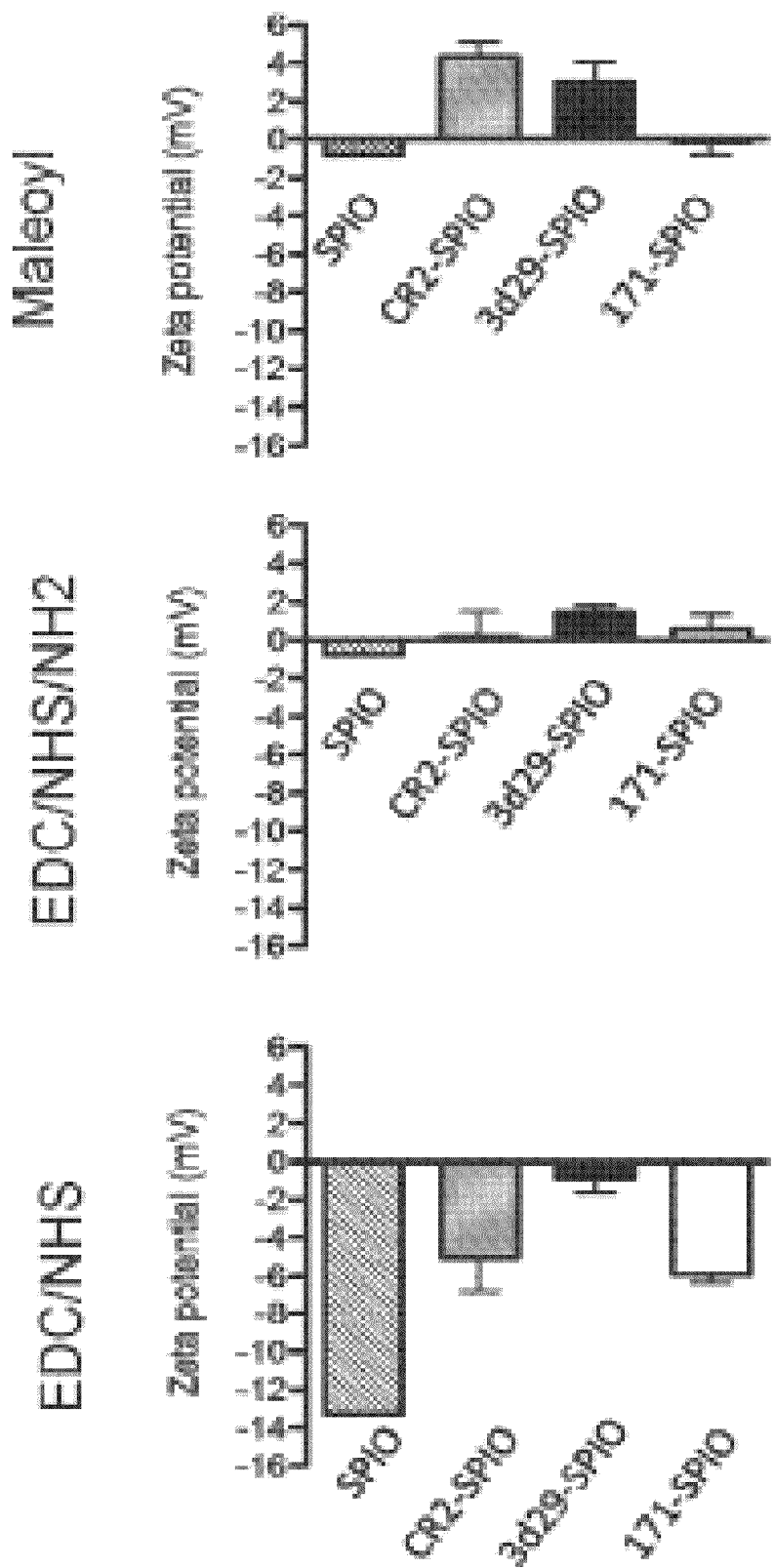
FIGS. 7A-7C. Hydrodynamic size and surface characteristics of conjugated SPIO.
Figure 7B:
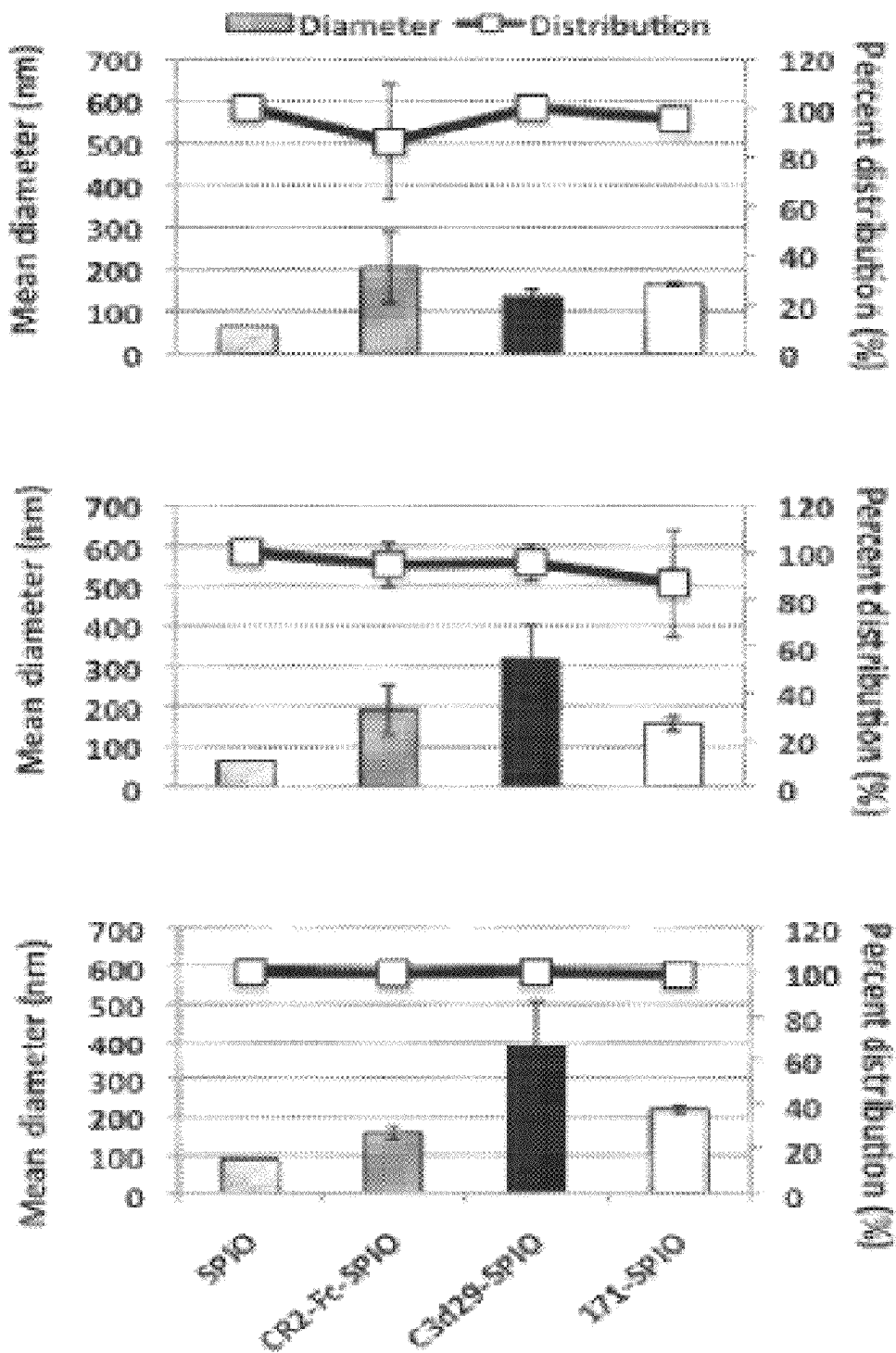
Figure 7C:
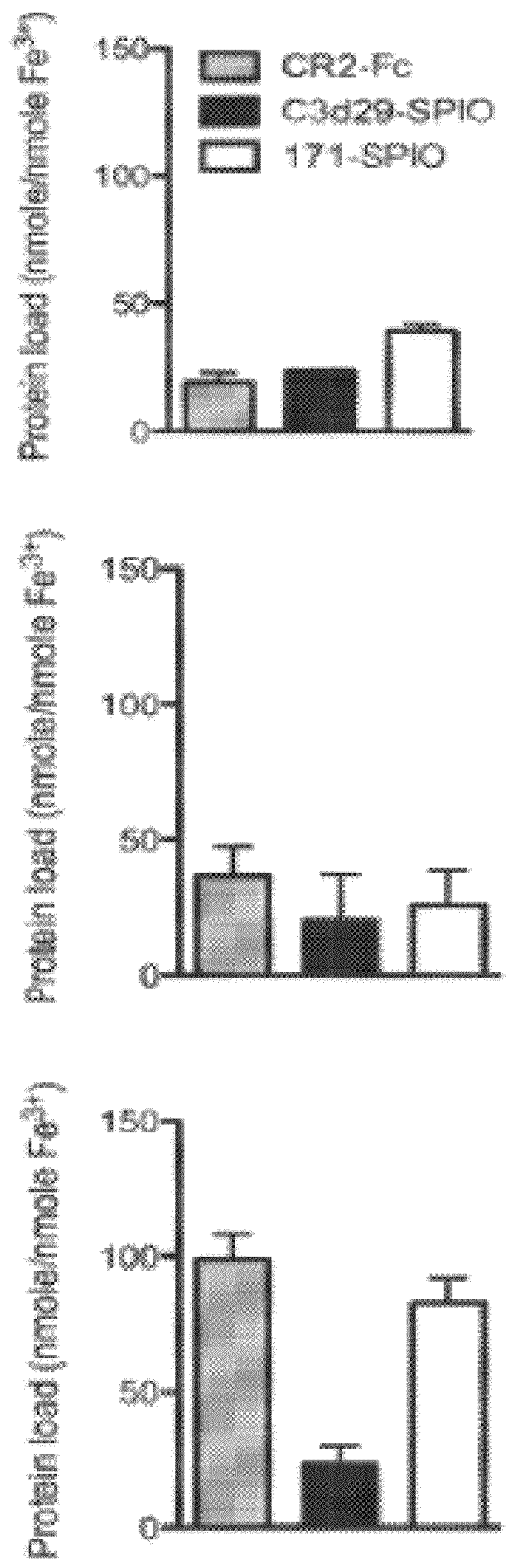
Figure 8A:
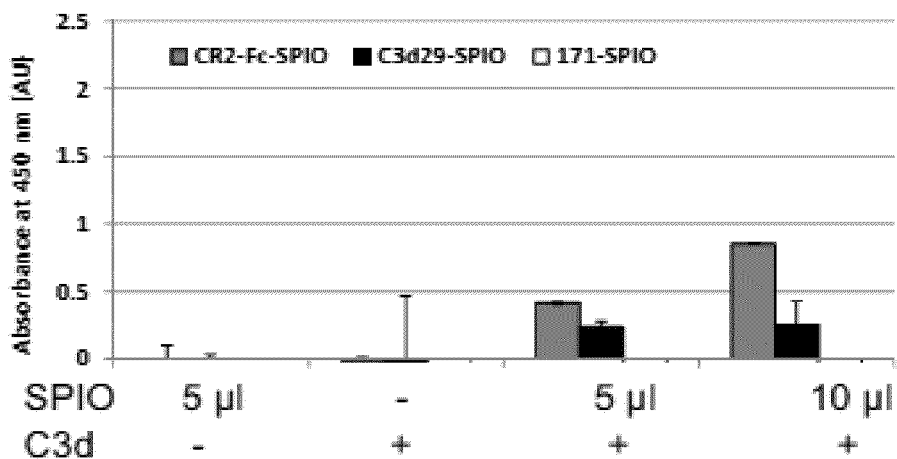
FIGS. 8A-8C. Binding of conjugated SPIO with the target C3d antigen in ELISA. Detection of SPIO binding to the target C3d antigen by ELISA for SPIO conjugated with maleoyl (FIG. 8A), EDC/NHS/NH2 (FIG. 8B) and EDC/NHS (FIG. 8C) methods. Specific, C3d-dependent, binding was detected for CR2-Fc-SPIO and C3d29-SPIO conjugated with all three methods. Data are mean±SD for samples tested in duplicates from two independent experiments. Differences in the absorbance values between CR2-Fc-SPIO and C3d29-SPIO may be due to the use of two different secondary antibodies.
Figure 8B:
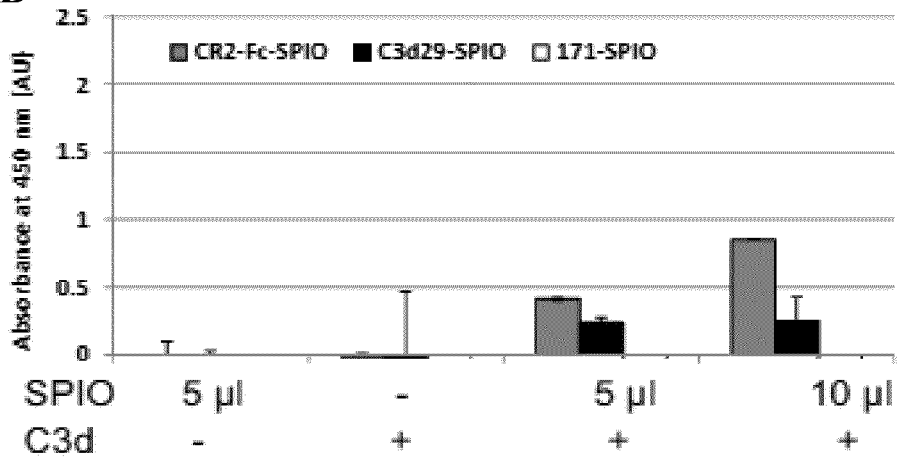
Figure 8C:
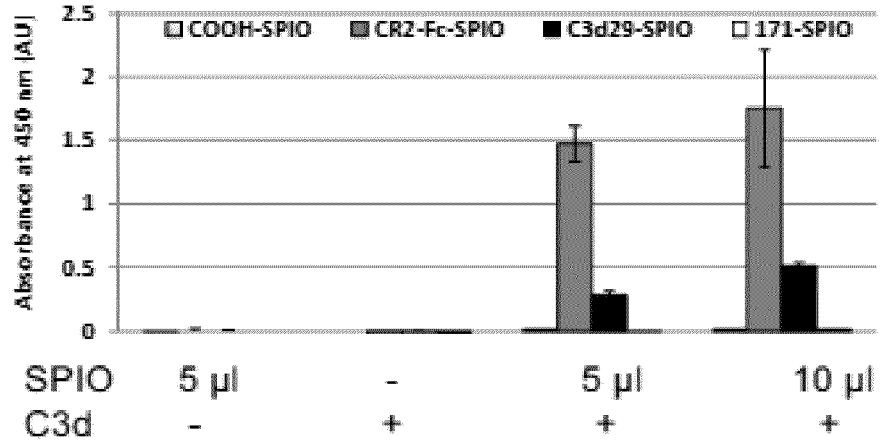
Figure 9A:
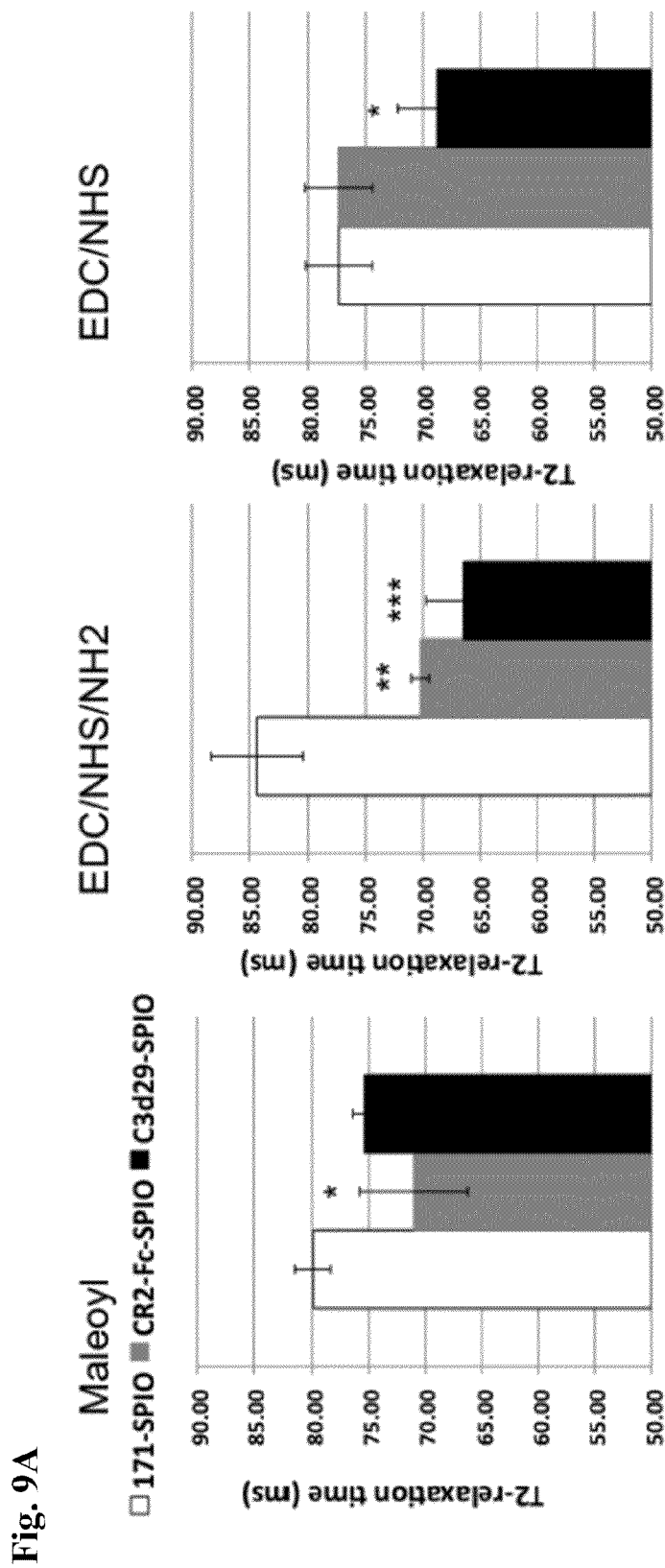
FIGS. 9A-9B. Target-specific MRI signal reduction by conjugated SPIO.
Figure 9B:
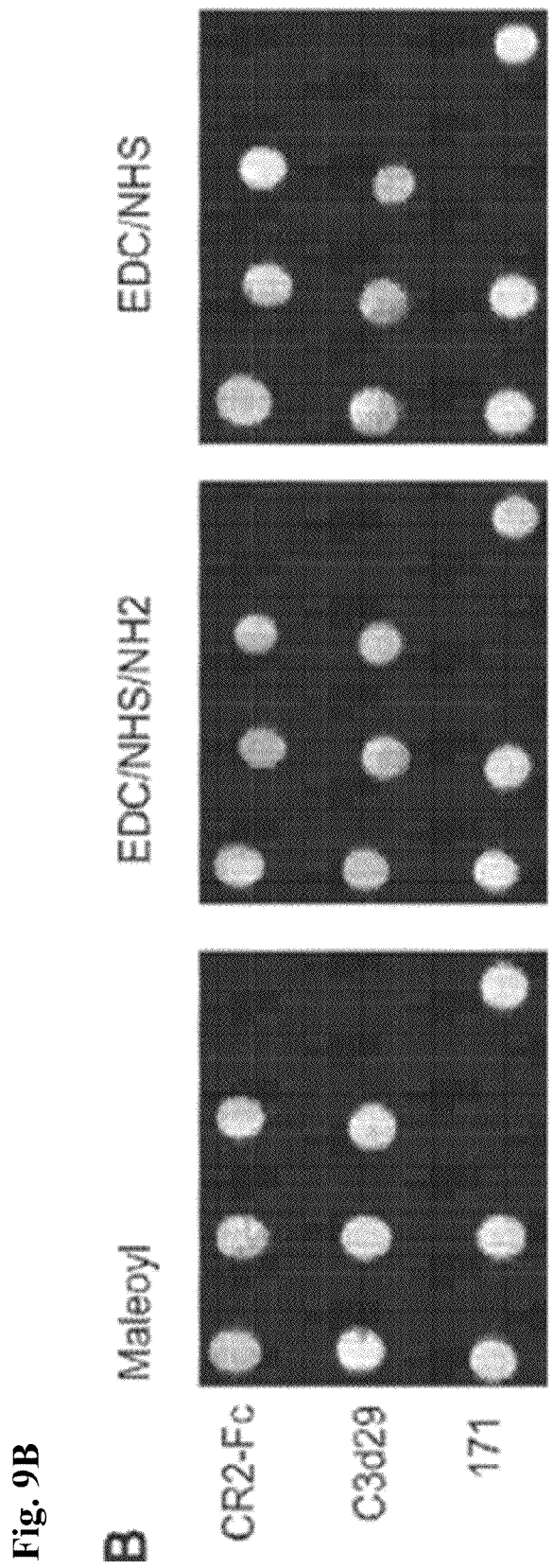

As used herein, the terms "treat" and "prevent" may refer to any delay in onset, reduction in the frequency or severity of symptoms, amelioration of symptoms, improvement in patient comfort or function (e.g. joint function), decrease in severity of the disease state, etc. The effect of treatment can be compared to an individual or pool of individuals not receiving a given treatment, or to the same patient prior to, or after cessation of, treatment. The term "prevent" generally refers to a decrease in the occurrence of a given disease (e.g. an autoimmune, inflammatory autoimmune, cancer, infectious, immune, or other disease) or disease symptoms in a patient. As indicated above, the prevention may be complete (no detectable symptoms) or partial, such that fewer symptoms are observed than would likely occur absent treatment.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The term "diagnosis" refers to a relative probability that a disease (e.g. an autoimmune, inflammatory autoimmune, cancer, infectious, immune, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. an autoimmune, inflammatory autoimmune, cancer, infectious, immune, or other disease), or the likely severity of the disease (e.g., duration of disease). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments. the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

TABLE 1

Example of amino acid classification

| | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20): 11882-11886).

In some embodiments, the non-conservative amino acid substitution comprises substituting any of glycine (G), alanine (A), isoleucine (I), valine (V), and leucine (L) for any of serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of serine (S) and threonine (T) for any of glycine (G), alanine (A), isoleucine (I), valine (V), leucine (L), aspartic acid (D), glutamic acid (E), glutamine (Q), asparagine (N), lysine (K), arginine (R), phenylalanine (F), tyrosine (Y), tryptophan (W), methionine (M), cysteine (C), histidine (H) and proline (P). In some embodiments, the non-conservative amino acid substitution comprises substituting any of aspartic acid (D) and glutamic acid (E) for any of glycine (G), alanine (A), isoleucine (I), valine (V), leucine (L), serine (S), threonine (T), glutamine (Q), asparagine (N), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of glutamine (Q) and asparagine (N) for any of glycine (G), alanine (A), isoleucine (I), valine (V), leucine (L), serine (S), threonine (T), aspartic acid (D), glutamic acid (E), lysine (K), arginine (R), phenylalanine (F), tyrosine (Y), tryptophan (W), methionine (M), cysteine (C), histidine (H), and proline (P). In some embodiments, the non-conservative amino acid substitution comprises substituting any of lysine (K) and arginine (R) for any of glycine (G), alanine (A), isoleucine (I), valine (V), leucine (L), serine (S), threonine (T), aspartic acid (D), glutamic acid (E), glutamine (Q), asparagine (N), phenylalanine (F), tyrosine (Y), tryptophan (W), methionine (M), cysteine (C), histidine (H), and proline (P). In some embodiments, the non-conservative amino acid substitution comprises substituting any of phenylalanine (F), tyrosine (Y), and tryptophan (W) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), methionine (M), cysteine (C), histidine (H), and proline (P). In some embodiments, the non-conservative amino acid substitution comprises substituting any of methionine (M) and cysteine (C) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), histidine (H), and proline (P). In some embodiments, the non-conservative amino acid substitution comprises substituting histidine (H) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and proline (P). In some embodiments, the non-conservative amino acid substitution comprises substituting proline (P) for any of glycine (G), alanine (A), isoleucine (I), valine (V), leucine (L), serine (S), threonine (T), aspartic acid (D), glutamic acid (E), glutamine (Q), asparagine (N), lysine (K), arginine (R), phenylalanine (F), tyrosine (Y), tryptophan (W), methionine (M), cysteine (C), and histidine (H).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative. In some embodiments, conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Following expression, the proteins (e.g. antibodies, antigen-binding fragments thereof, conjugates, antibody-conjugates) can be isolated. The term "purified" or "isolated" as applied to any of the proteins described herein (e.g., a conjugate described herein, antibody or antigen-binding fragment thereof described herein) refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

A "label" or a "detectable moiety" is a composition detectable by spectroscopic, photochemical, biochemical, immunochemical, chemical, magnetic resonance imaging, or other physical means. For example, useful detectable moieties include $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, standard superparamagnetic iron oxide ("SSPIO"), SSPIO nanoparticle aggregates, polydisperse superparamagnetic iron oxide ("PSPIO"), PSPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. antibody or antigen binding fragment). Any method known in the art for conjugating an antibody to the label may be employed, e.g., using methods described in Hermanson, *Bioconjugate Techniques* 1996, Academic Press, Inc., San Diego.

An "anti-C3d antibody" is an antibody, or antigen binding fragment thereof, that binds human C3d. An antigen binding fragment of an anti-C3d antibody is any fragment of an anti-C3d antibody capable of binding human C3d (e.g. as described herein). In some embodiments, an anti-C3d antibody or antigen binding fragment thereof also binds human C3dg and/or human iC3b. In some embodiments, an anti-C3d antibody or antigen binding fragment thereof specifically binds human C3d. In some embodiments, an anti-C3d antibody or antigen binding fragment thereof preferentially binds human C3d. In some embodiments, an anti-C3d antibody or antigen binding fragment thereof binds C3d with higher affinity than it binds human C3.

An "anti-C3dg antibody" is an antibody, or antigen binding fragment thereof, that binds human C3dg. An antigen binding fragment of an anti-C3dg antibody is any fragment of an anti-C3dg antibody capable of binding human C3dg (e.g. as described herein). In some embodiments, an anti-C3dg antibody or antigen binding fragment thereof also binds human C3d and/or human iC3b. In some embodiments, an anti-C3dg antibody or antigen binding fragment thereof specifically binds human C3dg. In some embodiments, an anti-C3d antibody or antigen binding fragment thereof preferentially binds human C3dg. In some embodiments, an anti-C3dg antibody or antigen binding fragment thereof binds C3dg with higher affinity than it binds human C3.

An "anti-iC3b antibody" is an antibody, or antigen binding fragment thereof, that binds human iC3b. An antigen binding fragment of an anti-iC3b antibody is any fragment of an anti-iC3b antibody capable of binding human iC3b (e.g. as described herein). In some embodiments, an anti-iC3b antibody or antigen binding fragment thereof also binds human C3dg and/or human C3d. In some embodiments, an anti-iC3b antibody or antigen binding fragment thereof specifically binds human iC3b. In some embodiments, an anti-iC3b antibody or antigen binding fragment thereof preferentially binds human iC3b. In some embodiments, an anti-iC3b antibody or antigen binding fragment thereof binds iC3b with higher affinity than it binds human C3.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration. The term "diagnostically acceptable" is used synonymously with "physiologically acceptable" and "pharmacologically acceptable" and refers to diagnostic compositions.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

Unless indicated otherwise, the term "about" in the context of a numeric value indicated the nominal value±10% of the nominal value.

Antibody Compositions and Uses

As used herein, the term "antibody" or "immunoglobulin" refers to proteins (including glycoproteins) of the immunoglobulin (Ig) superfamily of proteins. An antibody or immunoglobulin (Ig) molecule may be tetrameric, comprising two identical light chain polypeptides and two identical heavy chain polypeptides. The two heavy chains are linked together by disulfide bonds, and each heavy chain is linked to a light chain by a disulfide bond. Each full-length Ig molecule contains at least two binding sites for a specific target or antigen.

The immune system produces several different classes of Ig molecules (isotypes), including IgA, IgD, IgE, IgG, and IgM, each distinguished by the particular class of heavy chain polypeptide present: alpha (α) found in IgA, delta (δ) found in IgD, epsilon (ε) found in IgE, gamma (γ) found in IgG, and mu (μ) found in IgM. There are at least five different γ heavy chain polypeptides (isotypes) found in IgG. In contrast, there are only two light chain polypeptide isotypes, referred to as kappa (κ) and lambda (λ) chains. The distinctive characteristics of antibody isotypes are defined by sequences of the constant domains of the heavy chain.

An IgG molecule comprises two light chains (either κ or λ form) and two heavy chains (γ form) bound together by disulfide bonds. The κ and λ forms of IgG light chain each contain a domain of relatively variable amino acid sequences, called the variable region (variously referred to as a "$V_L$-," "$V_\kappa$-," or "$V_\lambda$-region") and a domain of relatively conserved amino acid sequences, called the constant region ($C_L$-region). Similarly, each IgG heavy chain contains a variable region ($V_H$-region) and one or more conserved regions: a complete IgG heavy chain contains three constant domains ("$C_H1$-," "$C_H2$-," and "$C_H3$-regions") and a hinge region. Within each $V_L$- or $V_H$-region, hypervariable regions, also known as complementarity-determining regions ("CDR"), are interspersed between relatively conserved framework regions ("FR"). Generally, the variable region of a light or heavy chain polypeptide contains four FRs and three CDRs arranged in the following order along the polypeptide: $NH_2$—FR1-CDR1-FR2-CDR2-FR3-CDR3-FR4-COOH. Together the CDRs and FRs determine the three-dimensional structure of the IgG binding site and thus, the specific target protein or antigen to which that IgG molecule binds. Each IgG molecule is dimeric, able to bind two antigen molecules. Cleavage of a dimeric IgG with the protease papain produces two identical antigen-binding fragments ("Fab'") and an "Fc" fragment or Fc domain, so named because it is readily crystallized.

As used throughout the present disclosure, the term "antibody" further refers to a whole or intact antibody (e.g., IgM, IgG, IgA, IgD, or IgE) molecule that is generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "epitope" refers to the site on a protein (e.g., a human complement component C3d or C3dg or iC3b protein) that is bound by an antibody. "Overlapping epitopes" include at least one (e.g., two, three, four, five, or six) common amino acid residue(s).

As used herein, the terms "specific binding" or "specifically binds" refer to two molecules forming a complex (e.g., a complex between an antibody and a complement component C3d or C3dg or iC3b protein) that is relatively stable under physiologic conditions. Typically, binding is considered specific when the association constant ($K_a$) is higher than $10^6$ M−1. Thus, an antibody can specifically bind to a C3d or C3dg or iC3b protein with a Ka of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ or higher) $M^{-1}$.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) J. Immunol. Meth. 160:191-198; Jonsson et al. (1993) Ann. Biol. Clin. 51:19-26; and Jonsson et al. (1991) Biotechniques 11:620-627. See also, U.S. Pat. No. 6,355,245.

Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

Antibodies can also be assayed using any surface plasmon resonance (SPR)-based assays known in the art for characterizing the kinetic parameters of the interaction of the antibody with C3d or C3dg or a C3 protein fragment. Any SPR instrument commercially available including, but not limited to, BIAcore Instruments (Biacore AB; Uppsala, Sweden); IAsys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) Methods 22: 77-91; Dong et al. (2002) Reviews in Mol Biotech 82: 303-323; Fivash et al. (1998) Curr Opin Biotechnol 9: 97-101; and Rich et al. (2000) Curr Opin Biotechnol 11: 54-61.

In some embodiments, the present disclosure provides an anti-C3d antibody or anti-C3dg antibody or anti-iC3b antibody, or antigen-binding fragments thereof, which specifically bind to human C3d with a $K_D$ value of $1.1 \times 10^{-9}$ M or better. In some embodiments, such a $K_D$ value is in the range from $1.1 \times 10^{-9}$ M to $3.6 \times 10^{-10}$ M. In some embodiments, the antibody or antigen-binding fragment thereof binds to human C3d with an affinity about $K_D=1.06 \times 10^{-9}$ M. In some embodiments, the antibody is mAb 3d29. In some embodiments, the antibody or antigen-binding fragment thereof binds to human C3d with an affinity about $K_D=4.65 \times 10^{-10}$ M. In some embodiments, the antibody is mAb 3d8b. In some embodiments, the antibody or antigen-binding fragment thereof binds to human C3d with an affinity about $K_D=3.67 \times 10^{-10}$ M. In some embodiments, the antibody is mAb 3d9a. In embodiments, the antibody is a derivative (e.g. humanized, chimerized, antigen-binding fragment thereof) of mAb 3d29. In embodiments, the antibody is a derivative (e.g. humanized, chimerized, antigen-binding fragment thereof) of mAb 3d8b. In embodiments, the antibody is a derivative (e.g. humanized, chimerized, antigen-binding fragment thereof) of mAb 3d9a.

Measurements to determine antibody affinity are standard and well known techniques. As an exemplary method to measure affinity, BIAcore analysis was used to quantify humanized antibodies' respective affinities for human C5a. See, e.g., Karlsson and Larsson (2004) Methods Mol Biol 248:389-415. Briefly, each of the humanized antibodies was screened with 3-4 concentrations of human C5a (antigen) using a capture technique. The antibodies were captured by an anti-Fc (human) directly immobilized on a CM5 sensor chip with various concentrations in the range from 0.6 nM to 5.9 nM of human C5a passed over the sensor chip surface. The surface was regenerated with 20 mM HCl, 0.02% P20 after each cycle to remove bound antibody and antigen. The data were evaluated using Biacore BIA evaluation software using a 1:1 Langmuir Model Fit (Rmax:Global Fit; RI:Local Fit). Kinetics information such as ($k_a$: Association Rate constant), ($k_d$:Dissociation Rate constant) and $K_D$ (Equilibrium Dissociation constant) was obtained from the fit. These and similar techniques are applicable to other antibodies such as those that bind to C3d or C3dg or iC3b.

In some embodiments, the disclosure provides an antibody, or antigen-binding fragment thereof, which preferably binds to C3d or C3dg or iC3b compared to binding to complement component proteins C3, C3a, C3b, C3c, or C3f. In some embodiments, the antibody is 3d8b, 3d9a, or 3d29. In some embodiments, an anti-C3d antibody or anti-C3dg antibody or anti-iC3b antibody described herein binds to C3d or C3dg or iC3b but not to any one of complement component proteins C3, C3a, C3b, C3c, or C3f. The complement C3 protein and the nucleic acid encoding the protein are well known within the fields of Immunology and Biology and the amino acid and nucleic acid sequences of C3 and the C3 fragments described herein are well known or easily obtained by one of ordinary skill in the art related to the subject matter of the disclosure herein. For example, the human C3 amino acid and nucleic acid sequences may be found in the UniProtKB/Swiss-Prot under accession number P01024 and GenBank database under accession number NM_000064.2. Accession number P01024 and NM_000064.2 also provide sequence information for C3 fragments (e.g. C3dg, C3d, iC3b formed by cleavage of C3b) and additional references related to the proteins and nucleic acids. The identity and sequence of C3 fragments is also discussed in De Bruijn, M. H. L. and Fey G. H., *Proc Natl Acad Sci USA* (1985) February; 82(3):708-12. In some embodiments, the present disclosure provides an antibody, or antigen-binding fragment thereof, which binds to C3d or C3dg or iC3b at a comparable affinity as its binding to complement component proteins C3, C3a, C3b, C3c, or C3f. In some embodiments, the antibody is 3d11, or 3d31. In some embodiments, the present disclosure provides an antibody, or antigen-binding fragment thereof, which binds weakly to C3d or C3dg or iC3b but not to any one of complement component proteins C3, C3a, C3b, C3c, or C3f. In some embodiments, the antibody is 3d3, or 3d15.

Thus, in some embodiments, an antibody or antigen-binding fragment thereof binds to free C3d or C3dg or iC3b (e.g. human proteins such as hC3d or hC3dg or hiC3b) with an affinity that is at least 2 (e.g. at least 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, 400, 500, 600, 700, 800, 900, 1000, 2000, 3000, 4000, 5000, 6000, 7000, 8000, 9000, or 10000)-fold greater than its corresponding affinity for uncleaved, native C3 protein. In some embodiments, the preferential binding is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000 fold, 100,000-fold, or 1,000,000-fold greater for free C3d or C3dg or iC3b than for uncleaved, native C3 protein.

In some embodiments, the disclosure provides an antibody, or antigen-binding fragment thereof, which preferably binds to deposited or opsonized C3 fragments, e.g., C3d or C3dg or iC3b, compared to binding to free or circulating or undeposited C3 fragments. In some embodiments, such an antibody or antigen-binding fragment thereof only binds to deposited C3 fragments but not free C3 or C3 fragments. In other embodiments, the present disclosure includes antibodies which bind to complement fragment C3d or C3dg or iC3b and are able to discriminate between tissue bound C3 fragments from circulating C3 (e.g., C3, C3b, or (C3H$_2$O). In some embodiments, such antibodies include mAbs 3d9a, 3d29 and 3d8b. In some embodiments, such antibodies include an antibody selected from the antibodies described herein. In some embodiments, such antigen-binding fragments include an antigen-binding fragment described herein. In some embodiments, antibodies of the invention bind to C3d or C3dg or iC3b with greater specificity than commercially available anti-C3d antibodies. In some embodiments, the commercially available anti-C3d antibodies are designated by the Quidel catalog numbers A207 and A250, and are commercially available from the Quidel Corporation (Quidel Corp., San Diego and Santa Clara, Calif.).

In some embodiments, the present disclosure also provides antibodies, or antigen-binding fragments thereof, which are variants of mouse monoclonal antibodies 3d8b, 3d9a, 3d29, 3d11, 3d31, 3d3, 3d15, 3d10, and 3d16 and maintain the C3d or C3dg or iC3b binding ability of these mouse antibodies. For example, the present disclosure provides an anti-C3d or anti-C3dg antibody or anti-iC3b antibody, or antigen-binding fragments thereof, which is a polyclonal antibody, a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, single chain antibody, single chain Fv fragment (scFv), Fv, Fd fragment, Fab fragment, Fab' fragment, F(ab')$_2$ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, phage-displayed antibody or antigen-binding fragment thereof, or antibody, or antigen-binding fragment thereof, identified with a repetitive backbone array (e.g. repetitive antigen display). For example, the present disclosure provides chimerized, humanized, or single-chain versions of 3d8b, 3d9a, 3d29, etc.

Methods for preparing a hybridoma cell line include immunizing C57Bl/6 mice by injecting subcutaneously and/or intraperitoneally an immunogenic composition containing human C3d or C3dg or iC3b protein (or an immunogenic fragment thereof) several times, e.g., four to six times, over several months, e.g., between two and four months. Spleen cells from the immunized mice are taken two to four days after the last injection and fused with cells of the myeloma cell line Sp2/0 in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be, in some embodiments, "chimeric." Chimeric antibodies and antigen-binding fragments thereof comprise portions from two or more different species (e.g., mouse and human). Chimeric antibodies can be produced with mouse variable regions of desired specificity spliced onto human constant domain gene segments (see, for example, U.S. Pat. No. 4,816,567). In this manner, non-human antibodies can be modified to make them more suitable for human clinical application (e.g., methods for treating or preventing a complement associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc. Natl. Acad. Sci. USA* 90:2551; Jakobovits et al. (1993) *Nature* 362:255-258; Bruggemann et al. (1993) *Year in Immunol.* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a complement component C3d or C3dg or iC3b protein, fragments thereof, or cells expressing C3d or C3dg or iC3b protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

Thus, in some embodiments, the disclosure provides, e.g., humanized, deimmunized or primatized antibodies comprising one or more of the complementarity determining regions (CDRs) of the mouse monoclonal antibodies described herein, which retain the ability (e.g., at least 50, 60, 70, 80, 90, or 100%, or even greater than 100%) of the mouse monoclonal antibody counterpart to bind to its antigen (e.g., C3d or C3dg or iC3b). For example, the disclosure features a humanized antibody comprising the set of six CDRs (e.g., heavy chain CDR1, heavy chain CDR2, heavy chain CDR3, light chain CDR1, light chain CDR2, and light chain CDR3) of any one of mouse monoclonal antibodies 3d8b, 3d9a, 3d29, 3d11, 3d31, 3d3, 3d15, 3d10, or 3d16 and human framework regions (with or without human constant or Fc regions).

The exact boundaries of CDRs and framework regions have been defined differently according to different methods and are well known to one of ordinary skill in the art of antibody engineering. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1") and the framework regions can be referred to as "Kabat framework regions," (e.g., "Kabat LFR1" or "Kabat HFR3"). In some embodiments, the positions of the CDRs or framework regions of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3") or "Chothia framework regions" (e.g., "Chothia LFR1" or "Chothia LFR3"), respectively. In some embodiments, the positions of the CDRs or framework regions of the light and heavy chain variable regions can be as defined by a Kabat-Chothia combined definition. In such embodiments, these regions can be referred to as "combined Kabat-Chothia CDRs" or "combined Kabat-Chothia framework regions," respectively. Thomas et al. [(1996) Mol Immunol 33(17/18): 1389-1401] exemplifies the identification of CDRs and framework region boundaries according to Kabat and Chothia definitions.

In some embodiments, the positions of the CDRs and/or framework regions with a light or heavy chain variable domain can be as defined by Honnegger and Plückthun [(2001) J Mol Biol 309: 657-670].

In addition, human antibodies can be derived from phage-display libraries (Hoogenboom et al. (1991) *J. Mol. Biol.* 227:381; Marks et al. (1991) *J. Mol. Biol.*, 222:581-597; and Vaughan et al. (1996) Nature Biotech 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132, 6,680,209, 4,634,666, and Ostberg et al. (1983), Hybridoma 2:361-367, the contents of each of which are incorporated herein by reference in their entirety.

For the generation of human antibodies, also see Mendez et al. (1998) *Nature Genetics* 15:146-156 and Green and Jakobovits (1998) *J. Exp. Med.* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 2003-0229905 A1, 2004-0010810 A1, US 2004-0093622 A1, 2006-0040363 A1, 2005-0054055 A1, 2005-0076395 A1, and 2005-0287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res.* 20: 6287; Chen et al. (1993) *Int. Immunol.* 5: 647; Tuaillon et al. (1993) *Proc. Natl. Acad. Sci. USA* 90: 3720-4; Choi et al. (1993) *Nature Genetics* 4: 117; Lonberg et al. (1994) *Nature* 368: 856-859; Taylor et al. (1994) International Immunology 6: 579-591; Tuaillon et al. (1995) *J. Immunol.* 154: 6453-65; Fishwild et al. (1996) *Nature Biotechnology* 14: 845; and Tuaillon et al. (2000) *Eur. J. Immunol.* 10: 2998-3005, the disclosures of each of which are hereby incorporated by reference in their entirety.

In some embodiments, de-immunized antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-C3d antibodies or anti-C3dg antibodies or anti-iC3b antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In some embodiments, the present disclosure also provides bispecific antibodies. Bispecific antibodies are monoclonal, preferably human or humanized, antibodies that have binding specificities for at least two different antigens. In the present case, one of the binding specificities is for C3d or C3dg or iC3b, the other one is for any other antigen than the first one.

Methods for making bispecific antibodies are within the purview of those skilled in the art. Traditionally, the recombinant production of bispecific antibodies is based on the co-expression of two immunoglobulin heavy-chain/light-chain pairs, where the two heavy chain/light-chain pairs have different specificities (Milstein and Cuello (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al., *J Exp Med* (1992) 175:217-225; Kostelny et al. (1992) *J Immunol* 148(5):1547-1553; Hollinger et al. (1993) *Proc Natl Acad Sci USA* 90:6444-6448; Gruber et al. (1994) *J Immunol* 152:5368; and Tutt et al. (1991) *J Immunol* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

Antibodies with more than two valencies (e.g., trispecific antibodies) are contemplated and described in, e.g., Tutt et al. (1991) *J Immunol* 147:60.

The disclosure also embraces variant forms of multi-specific antibodies such as the dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715.

The disclosure also provides camelid or dromedary antibodies (e.g., antibodies derived from *Camelus bactrianus, Calelus dromaderius,* or *lama paccos*). Such antibodies, unlike the typical two-chain (fragment) or four-chain (whole antibody) antibodies from most mammals, generally lack light chains. See U.S. Pat. No. 5,759,808; Stijlemans et al. (2004) *J Biol Chem* 279:1256-1261; Dumoulin et al. (2003) *Nature* 424:783-788; and Pleschberger et al. (2003) *Bioconjugate Chem* 14:440-448.

Engineered libraries of camelid antibodies and antibody fragments are commercially available, for example, from Ablynx (Ghent, Belgium). As with other antibodies of non-human origin, an amino acid sequence of a camelid antibody can be altered recombinantly to obtain a sequence that more closely resembles a human sequence, i.e., the nanobody can be "humanized" to thereby further reduce the potential immunogenicity of the antibody.

In some embodiments, the present disclosure also provides antibodies, or antigen-binding fragments thereof, which are mutants of mouse monoclonal antibodies 3d8b, 3d9a, 3d29, 3d11, 3d31, 3d3, 3d15, 3d10, and 3d16, or their variant antibodies, or antigen-binding fragments thereof, as described above and therein. Preferably, such a mutant antibody or antigen-binding fragments thereof maintain the C3d or C3dg or iC3b binding ability of the parent mouse mAbs. Such mutations and the methods to prepare these mutants are standard practices and well known in the art. In some embodiments, such a mutation introduces at least a single amino acid substitution, deletion, insertion, or other modification. In some embodiments, an antibody or antigen-binding fragment thereof described herein (e.g., mouse monoclonal antibodies 3d8b, 3d9a, 3d29, 3d11, 3d31, 3d3, 3d15, 3d10, or 3d16) comprises no more than 20 (e.g., no more than 19, 18, 17, 16, 15, 14, 13, 12, 11, 10, nine, eight, seven, six, five, four, three, two, or one) amino acid modifications (e.g., amino acid substitutions, deletions, or additions). In some embodiments, an antibody or antigen-binding fragment thereof described herein does not contain an amino acid modification in its CDRs. In some embodiments, an antibody or antigen-binding fragment thereof described herein does not contain an amino acid modification in the CDR3 of the heavy chain. In some embodiments, an antibody or antigen-binding fragment thereof described herein does contain one or more (e.g. 1, 2, 3, 4, 5, 6, 7, 8, 9, 10, 11, 12, 13, 14, 15, 16, 17, 18, 19, or 20) amino acid modifications in its CDRs. In some embodiments, an antibody or antigen-binding fragment thereof described herein does contain one or more (e.g. 1, 2, 3, 4, 5, 6, 7, 8, 9, 10, 11, 12, 13, 14, 15, 16, 17, 18, 19, or 20) amino acid modifications in the CDR3 of the heavy chain.

As used herein, the term "antibody fragment", "antigen-binding fragment", "antigen binding fragment", or similar terms refer to fragment of an antibody that retains the ability to bind to an antigen (e.g., a C3 protein fragment or a complement component C3dg, C3d, or iC3b) wherein the antigen binding fragment may optionally include additional compositions not part of the original antibody (e.g. different framework regions or mutations) as well as the fragment(s) from the original antibody. Examples include, but are not limited to, a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, diabodies (Poljak (1994) *Structure* 2(12):1121-1123; Hudson et al. (1999) *J. Immunol. Methods* 23(1-2):177-189, the disclosures of each of which are incorporated herein by reference in their entirety), minibodies, triabodies (Schoonooghe et al. (2009) *BMC Biotechnol* 9:70), and domain antibodies (also known as "heavy chain immunoglobulins" or camelids; Holt et al. (2003) *Trends Biotechnol* 21(11):484-490), (the disclosures of each of which are incorporated herein by reference in their entirety) that bind to a complement component C3d or C3dg or iC3b protein can be incorporated into the compositions, and used in the methods, described herein. In some embodiments, any of the antigen binding fragments described herein may be included under "antigen binding fragment thereof" or equivalent terms, when referring to fragments related to an antibody, whether such fragments were actually derived from the antibody or are antigen binding fragments that bind the same epitope or an overlapping epitope or an epitope contained in the antibody's epitope. For example, a 3d8a murine monoclonal antibody or antigen binding fragment thereof, may include any of the antigen binding fragments described herein even if, for example, such camelid antibody is not entirely a fragment of the 3d8a murine monoclonal antibody. An antigen binding fragment thereof may include antigen-binding fragments that bind the same, or overlapping, antigen as the original antibody and wherein the antigen binding fragment includes a portion (e.g. one or more CDRs, one or more variable regions, etc.) that is a fragment of the original antibody.

In some embodiments, the anti-C3d antibodies or anti-C3dg antibodies or anti-iC3b antibodies described herein comprise an altered or mutated sequence that leads to altered stability or half-life compared to parent antibodies. This includes, for example, an increased stability or half-life for higher affinity or longer clearance time in vitro or in vivo, or a decreased stability or half-life for lower affinity or quicker removal. Additionally, the altered anti-C3d antibodies or anti-C3dg antibodies or anti-iC3b antibodies described herein may contain one or more (e.g. 1, 2, 3, 4, 5, 6, 7, 8, 9, 10, 11, 12, 13, 14, 15, 16, 17, 18, 19, or 20) amino acid substitutions, deletions, or insertions (e.g. in one or more CDRs, one or more framework regions, and/or constant region) that result in altered post-translational modifications, including, for example, an altered glycosylation pattern (e.g., the addition of one or more sugar components, the loss of one or more sugar components, or a change in composition of one or more sugar components relative to the unaltered constant region).

In some embodiments, the anti-C3d antibodies or anti-C3dg antibodies or anti-iC3b antibodies described herein comprise an altered heavy chain constant region that has reduced (e.g. or no) effector function relative to its corresponding unaltered constant region. That is, in some embodiments, an antibody described herein comprises an altered constant region that exhibits approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the effector function of the corresponding unaltered (native) form of the constant region. Effector functions involving the constant region of the anti-C3d antibody or anti-C3dg antibody or anti-iC3b antibodies may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-C3d antibody or anti-C3dg antibody or anti-iC3b antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-C3d antibody or anti-C3dg antibody or anti-iC3b antibody described herein comprising an altered constant region displaying reduced ADCC and/or CDC may exhibit reduced or no ADCC and/or CDC activity as exemplified herein.

In some embodiments, the altered constant region has at least one amino acid substitution, insertion, and/or deletion, compared to a native sequence constant region or to the unaltered constant region, e.g., from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that result in altered post-translational modifications, including, for example, an altered glycosylation pattern (e.g., the addition of one or more sugar components, the loss of one or more sugar components, or a change in composition of one or more sugar components relative to the unaltered constant region).

Antibodies with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988), supra; Borrebaek (1992), supra; Johne et al. (1993), supra; PCT publication no. WO 06/53301; and U.S. Pat. No. 7,704,497.

In some embodiments, an anti-C3d antibody or anti-C3dg antibody or anti-iC3b antibody described herein exhibits reduced or no effector function. In some embodiments, an anti-C3d antibody or anti-C3dg antibody or anti-iC3b antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In addition to using a G2/G4 construct as described above, an anti-C3d antibody or anti-C3dg antibody or anti-iC3b antibody described herein having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, an anti-C3d antibody or anti-C3dg antibody or anti-iC3b antibody with one or more mutations within the constant region including the Ala-Ala mutation has reduced or no effector function. According to these embodiments, the constant region of the antibody can comprise a substitution to an alanine at position 234 or a mutation to an alanine at position 235. Additionally, the altered constant region may contain a double mutation: a mutation to an alanine at position 234 and a second mutation to an alanine at position 235. In some embodiments, an anti-C3d antibody or anti-C3dg antibody or anti-iC3b antibody comprises an IgG4 framework, wherein the Ala-Ala mutation would describe a mutation(s) from phenylalanine to alanine at position 234 and/or a mutation from leucine to alanine at position 235. In some embodiments, the anti-C3d antibody or anti-C3dg antibody or anti-iC3b antibody comprises an $IgG_1$ framework, wherein the Ala-Ala mutation would describe a mutation(s) from leucine to alanine at position 234 and/or a mutation from leucine to alanine at position 235. An anti-C3d antibody or anti-C3dg antibody or anti-iC3b antibody may alternatively or additionally carry other mutations, including the point mutation K322A in the CH2 domain (Hezareh et al. (2001) *J Virol* 75:12161-12168). An antibody with said mutation(s) in the constant region may furthermore be a blocking or non-blocking antibody.

Additional substitutions that, when introduced into a heavy chain constant region, result in decreased effector function are set forth in, e.g., Shields et al. (2001) *J Biol Chem* 276 (9):6591-6604. See particularly Table 1 ("Binding of human $IgG_1$ variants to human FcRn and FcγR") of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an anti-C3d antibody or anti-C3dg antibody or anti-iC3b antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) TIBTECH 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-264. Differences in effector function may be related to the IgG's ability to bind to the Fcγ receptors (FcγRs) on the effector cells. Shields et al. have shown that IgG, with alterations in amino acid sequence that have improved binding to FcγR, can exhibit up to 100% enhanced ADCC using human effector cells. (2001) *J Biol Chem* 276(9):6591-6604. While these alterations include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30): 26733-26740. An IgG that lacked a fucosylated carbohydrate linked to Asn297 exhibited normal receptor binding to the FcγRI receptor. In contrast, binding to the FcγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) *J Biol Chem* 278(5):3466-73). Monosaccharide composition and oligosaccharide profiling showed that the rat hybridoma-produced IgG had a lower content of fucose than the CHO-produced protein. The authors concluded that the lack of fucosylation of an IgG$_1$ has a critical role in enhancement of ADCC activity.

A different approach was taken by Umana et al. who changed the glycosylation pattern of chCE7, a chimeric IgG$_1$ anti-neuroblastoma antibody. (1999) *Nat Biotechnol* 17(2): 176-180). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis. (1994) *J Exp Med* 180: 1087-1096. Thus, as known alterations that affect effector function include modifications in the glycosylation pattern or a change in the number of glycosylated residues, the present disclosure relates to an anti-C3d antibody or anti-C3dg antibody or anti-iC3b antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s). Additional details of molecular biology techniques useful for preparing an antibody or antigen-binding fragment thereof described herein are set forth below.

In some embodiments, an antibody or an antigen-binding fragment thereof includes light chain complementarity determining regions (CDR) 1, 2 and 3, wherein light chain CDR 1 is SEQ ID NO:14 including three or less amino acid mutations (e.g. 3, 2, 1, or 0) or SEQ ID NO:24 including three or less amino acid mutations (e.g. 3, 2, 1, or 0), light chain CDR 2 is SEQ ID NO:15 including three or less amino acid mutations (e.g. 3, 2, 1, or 0) or SEQ ID NO:25 including three or less amino acid mutations (e.g. 3, 2, 1, or 0) and light chain CDR 3 is SEQ ID NO:16 including three or less amino acid mutations (e.g. 3, 2, 1, or 0) or SEQ ID NO:26 including three or less amino acid mutations (e.g. 3, 2, 1, or 0); or heavy chain complementarity determining regions (CDR) 1, 2 and 3, wherein heavy chain CDR 1 is SEQ ID NO:17 including three or less amino acid mutations (e.g. 3, 2, 1, or 0) or SEQ ID NO:27 including three or less amino acid mutations (e.g. 3, 2, 1, or 0) or SEQ ID NO:35 including three or less amino acid mutations (e.g. 3, 2, 1, or 0), heavy chain CDR 2 is SEQ ID NO:18 including three or less amino acid mutations (e.g. 3, 2, 1, or 0) or SEQ ID NO:28 including three or less amino acid mutations (e.g. 3, 2, 1, or 0) or SEQ ID NO:36 including three or less amino acid mutations (e.g. 3, 2, 1, or 0) and heavy chain CDR 3 is SEQ ID NO:19 including three or less amino acid mutations (e.g. 3, 2, 1, or 0) or SEQ ID NO:29 including three or less amino acid mutations (e.g. 3, 2, 1, or 0) or SEQ ID NO:37 including three or less amino acid mutations (e.g. 3, 2, 1, or 0). In some embodiments, the mutations are non-conservative and/or conservative amino acid substitutions. In some embodiments, the mutations are conservative amino acid substitutions. In some embodiments, the mutations are non-conservative amino acid substitutions.

In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; or heavy chain complementarity determining regions (CDR) 1, 2 and 3, wherein heavy chain CDR 1 is SEQ ID NO:17 or SEQ ID NO:27 or SEQ ID NO:35, heavy chain CDR 2 is SEQ ID NO:18 or SEQ ID NO:28 or SEQ ID NO:36 and heavy chain CDR 3 is SEQ ID NO:19 or SEQ ID NO:29 or SEQ ID NO:37. In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; or heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or SEQ ID NO:29.

In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; and heavy chain complementarity determining regions (CDR) 1, 2 and 3, wherein heavy chain CDR 1 is SEQ ID NO:17 or SEQ ID NO:27 or SEQ ID NO:35, heavy chain CDR 2 is SEQ ID NO:18 or SEQ ID NO:28 or SEQ ID NO:36 and heavy chain CDR 3 is SEQ ID NO:19 or SEQ ID NO:29 or SEQ ID NO:37. In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or SEQ ID NO:29.

In some embodiments of the antibody or antigen-binding fragment thereof, light chain CDR 1 is SEQ ID NO:14 including three or less amino acid mutations (e.g. 3, 2, 1, or 0), light chain CDR 2 is SEQ ID NO:15 including three or less amino acid mutations (e.g. 3, 2, 1, or 0), light chain CDR 3 is SEQ ID NO:16 including three or less amino acid mutations (e.g. 3, 2, 1, or 0), heavy chain CDR 1 is SEQ ID NO:17 including three or less amino acid mutations (e.g. 3, 2, 1, or 0), heavy chain CDR 2 is SEQ ID NO:18 including three or less amino acid mutations (e.g. 3, 2, 1, or 0), and heavy chain CDR 3 is SEQ ID NO:19 including three or less amino acid mutations (e.g. 3, 2, 1, or 0). In some embodiments of the antibody or antigen-binding fragment thereof, light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19.

In some embodiments of the antibody or antigen-binding fragment thereof, light chain CDR 1 is SEQ ID NO:24 including three or less amino acid mutations (e.g. 3, 2, 1, or 0), light chain CDR 2 is SEQ ID NO:25 including three or less amino acid mutations (e.g. 3, 2, 1, or 0), light chain CDR 3 is SEQ ID NO:26 including three or less amino acid mutations (e.g. 3, 2, 1, or 0), heavy chain CDR 1 is SEQ ID NO:27 including three or less amino acid mutations (e.g. 3, 2, 1, or 0), heavy chain CDR 2 is SEQ ID NO:28 including three or less amino acid mutations (e.g. 3, 2, 1, or 0), and heavy chain CDR 3 is SEQ ID NO:29 including three or less amino acid mutations (e.g. 3, 2, 1, or 0). In some embodiments of the antibody or antigen-binding fragment thereof, light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29.

In some embodiments, an antibody or an antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; or a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23 or SEQ ID NO:34. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23 or SEQ ID NO:34. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; or a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23.

In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:22. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:23. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:34. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:23. In some embodiments, the antibody, or an antigen-binding fragment thereof, is selected from the group consisting of: a polyclonal antibody a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, a bispecific antibody or antibody fragment, a monovalent antibody or antibody fragment, single chain antibody, single chain Fv fragment (scFv), Fv, Fd fragment, Fab fragment, Fab' fragment, F(ab')$_2$ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, CDR-grafted antibody or antigen-binding fragment thereof, synthetic antibody or antigen-binding fragment thereof, semi-synthetic antibody or antigen-binding fragment thereof, phage-displayed antibody or antigen-binding fragment thereof, and antibody, or antigen-binding fragment thereof, identified with a repetitive backbone array (e.g. repetitive antigen display).

In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 or SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 75, 100, 125, 150 nucleotides or over all of SEQ ID NO: 20 or SEQ ID NO:30 respectively). In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20). In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 30), In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 or SEQ ID NO:31 or SEQ ID NO:33, over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21 or SEQ ID NO:31 or SEQ ID NO:33 respectively). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:31 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 31). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:33 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 33).

In some embodiments, the antibody or antigen-binding fragment thereof includes a light chain variable region amino acid sequence expressed from a nucleic acid sequence that hybridizes to the nucleic acid consisting of SEQ ID NO:20 or SEQ ID NO:30 under moderately stringent hybridization conditions. In some embodiments, the nucleic acid sequence hybridizes to the nucleic acid consisting of SEQ ID NO:20 or SEQ ID NO:30 under stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:20 under moderately stringent hybridization conditions. In some embodiments, the nucleic acid sequence hybridizes to the nucleic acid consisting of SEQ ID NO:20 under stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:30 under moderately stringent hybridization conditions. In some embodiments, the nucleic acid sequence hybridizes to the nucleic acid consisting of SEQ ID NO:30 under stringent hybridization conditions.

In some embodiments, the antibody or antigen-binding fragment thereof includes a heavy chain variable region amino acid sequence expressed from a nucleic acid sequence that hybridizes to the nucleic acid consisting of SEQ ID NO:21 or SEQ ID NO:31 or SEQ ID NO:33 under moderately stringent hybridization conditions. In some embodiments, the nucleic acid sequence hybridizes to the nucleic acid consisting of SEQ ID NO:21 or SEQ ID NO:31 or SEQ ID NO:33 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:21 under moderately stringent hybridization conditions. In some embodiments, the nucleic acid sequence hybridizes to the nucleic acid consisting of SEQ ID NO:21 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:31 under moderately stringent hybridization conditions. In some embodiments, the nucleic acid sequence hybridizes to the nucleic acid consisting of SEQ ID NO:31 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:33 under moderately stringent hybridization conditions. In some embodiments, the nucleic acid sequence hybridizes to the nucleic acid consisting of SEQ ID NO:33 under stringent hybridization conditions.

In some embodiments, the antibody or antigen-binding fragment thereof includes one or more (e.g. one, two, three, four, five, or six) CDRs encoded by the nucleic acid sequences of SEQ ID NO:20, SEQ ID NO:21, SEQ ID NO:30, or SEQ ID NO:31, having six or less (six, five, four, three, two, one, or zero) nucleotide mutations in the nucleic acid sequences encoding the one or more CDRs (e.g. one, two, three, four, five, or six). In some embodiment, the antibody or antigen-binding fragment thereof includes one or more (e.g. one, two, three, four, five, or six) CDRs encoded by the nucleic acid sequences of SEQ ID NO:20, SEQ ID NO:21, SEQ ID NO:30, or SEQ ID NO:31. In some embodiment, the antibody or antigen-binding fragment thereof includes one or more (e.g. one, two, three, four, five, or six) CDRs encoded by the CDR nucleic acid sequences of SEQ ID NO:20, SEQ ID NO:21, SEQ ID NO:30, or SEQ ID NO:31.

In some embodiments, the antibody or antigen-binding fragment thereof includes one or more (e.g. one, two, or three) light chain variable region CDRs encoded by the nucleic acid sequences of SEQ ID NO:20 or SEQ ID NO:30, having six or less (six, five, four, three, two, one, or zero) nucleotide mutations in the nucleic acid sequences encoding the one or more CDRs (e.g. one, two, or three). In some embodiment, the antibody or antigen-binding fragment thereof includes one or more (e.g. one, two, or three) light chain variable region CDRs encoded by the nucleic acid sequences of SEQ ID NO:20 or SEQ ID NO:30. In some embodiment, the antibody or antigen-binding fragment thereof includes one or more (e.g. one, two, or three) light chain variable region CDRs encoded by the CDR nucleic acid sequences of SEQ ID NO:20 or SEQ ID NO:30.

In some embodiments, the antibody or antigen-binding fragment thereof includes one or more (e.g. one, two, or three) heavy chain variable region CDRs encoded by the nucleic acid sequences of SEQ ID NO:21 or SEQ ID NO:31, having six or less (six, five, four, three, two, one, or zero) nucleotide mutations in the nucleic acid sequences encoding the one or more CDRs (e.g. one, two, or three). In some embodiment, the antibody or antigen-binding fragment thereof includes one or more (e.g. one, two, or three) heavy chain variable region CDRs encoded by the nucleic acid sequences of SEQ ID NO:21 or SEQ ID NO:31. In some embodiment, the antibody or antigen-binding fragment thereof includes one or more (e.g. one, two, or three) heavy chain variable region CDRs encoded by the CDR nucleic acid sequences of SEQ ID NO:21 or SEQ ID NO:31. In some embodiments, the antibody or antigen-binding fragment thereof includes one or more (e.g. one, two, or three) heavy chain variable region CDRs encoded by the nucleic acid sequence of SEQ ID NO:33, having six or less (six, five, four, three, two, one, or zero) nucleotide mutations in the nucleic acid sequences encoding the one or more CDRs (e.g. one, two, or three). In some embodiments, the antibody or antigen-binding fragment thereof includes one or more (e.g. one, two, or three) heavy chain variable region CDRs encoded by the nucleic acid sequence of SEQ ID NO:33. In some embodiments, the antibody or antigen-binding fragment thereof includes one or more (e.g. one, two, or three) heavy chain variable region CDRs encoded by the CDR nucleic acid sequence of SEQ ID NO:33. As used herein, a CDR nucleic acid sequence refers to a nucleic acid sequence included in SEQ ID NO:20, SEQ ID NO:21, SEQ ID NO:30, SEQ ID NO:31, SEQ ID NO:33, which encodes a CDR having an amino acid sequence selected from SEQ ID NO:14 to SEQ ID NO:19, SEQ ID NO:24 to SEQ ID NO:29, and SEQ ID NO:35 to SEQ ID NO:37. CDR nucleic acid sequences (nucleic acid sequences encoding CDRs) are underlined in each of SEQ ID NO:20, 21, 30, 31, and 33 in consecutive order (e.g. CDR 1, then CDR 2, then CDR 3).

In some embodiments, an antibody or antigen-binding fragment thereof described herein and including all or a portion of an amino acid sequence selected from SEQ ID NO: 12-19, 22-29, and 34-37 or expressed from a nucleic acid sequence including all or a portion of a sequence selected from SEQ ID NO: 20, 21, 30, 31, and 33 (including any of the antibodies or antigen-binding fragments thereof described herein and above) is an anti-C3d antibody or antigen-binding fragment thereof, anti-C3dg antibody or antigen-binding fragment thereof, anti-C3d/C3dg antibody or antigen-binding fragment thereof, anti-iC3b antibody or antigen-binding fragment thereof, antibody or antigen-binding fragment described herein, antibody described herein or antigen-binding fragment thereof, fragment described herein, antibody or antigen-binding fragment thereof provided by the disclosure, antibody or antigen-binding fragment thereof that the disclosures comprises, anti-C3d antibody or anti-C3dg antibody or anti-iC3b antibody, antigen-binding fragment thereof provided by the present disclosure, antibody or fragment thereof, antibody which binds a binding partner selected from the group consisting of C3dg and C3d and iC3b or fragments of such antibody which retain the ability to bind to its respective binding partner that is a suitable targeting moiety, antibody of the present invention or fragment thereof which retain the ability to bind to their respective binding partner and are suitable targeting moieties, isolated antibody or antigen-binding fragment thereof, as these terms are used herein, or equivalent terms used herein to describe an antibody or antigen-binding fragment of the invention (e.g. as isolated compositions, included in a conjugate, included in an antibody conjugate).

SEQ ID NO: 12-21 are amino acid or nucleic acid sequences, as appropriate, of the mouse antibody 3d8b. SEQ ID NO: 22-31 are amino acid or nucleic acid sequences, as appropriate, of the mouse antibody 3d29. SEQ ID NO: 33-37 are amino acid or nucleic acid sequences, as appropriate, of the mouse antibody 3d16. SEQ ID NO: 32 is the amino acid sequence of a 3d scFv Crry fusion protein (e.g. a construct).

In some embodiments, a pharmaceutical composition includes an antibody or antigen-binding fragment thereof described herein and a pharmaceutically-acceptable excipient.

In some embodiments, the isolated anti-C3d antibody or antigen-binding fragment thereof, the isolated anti-C3dg antibody or antigen-binding fragment thereof, the isolated anti-iC3b antibody or antigen-binding fragment thereof, described in the present disclosure includes, but is not limited to, a polyclonal antibody a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, a bispecific antibody or antibody fragment, a monovalent antibody or antibody fragment, single chain antibody, single chain Fv fragment (scFv), Fv, Fd fragment, Fab fragment, Fab' fragment, F(ab')₂ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, CDR-grafted antibody or antigen-binding fragment thereof, synthetic antibody or antigen-binding fragment thereof, semi-synthetic antibody or antigen-binding fragment thereof, phage-displayed antibody or antigen-binding fragment thereof, or antibody, or antigen-binding fragment thereof, identified with a repetitive backbone array (e.g. repetitive antigen display. In some embodiments, the antibody described herein is a monoclonal antibody. In some embodiments, the antibody described herein is the mAb 3d8b, produced by hybridoma cell line 3d-8b/2 (ATCC Deposit PTA-10999). In some embodiments, the antibody described herein is mAb 3d9a, produced by hybridoma cell line 3d-9a/25 (ATCC Deposit PTA-10998). In some embodiments, the antibody described herein is mAb 3d29, produced by hybridoma cell line 3d-29/5/2 (ATCC Deposit PTA-11000). In some embodiments, the antibody or antigen-binding fragment thereof described in the present disclosure includes, but is not limited to, any engineered or recombinant antibody or antigen-binding fragment thereof originated from mAb 3d8b, 3d9a, 3d29, or other mAb described in this disclosure, which can be easily screened or produced by standard methods well known in the art, many of which are discussed in this disclosure. Generally, all these antibodies or fragments originating from mAbs in this disclosure may be designed, screened, produced and/or tested to modify, without being limiting, their binding affinity, avidity, or cross-species activity to the C3d/C3dg protein and/or iC3b protein, selectivity over C3 or other C3 fragments, or their expression pattern and solubility, stability, half-life, cross-reactivity to other proteins/targets, or other inherent activities or characteristics of these antibodies or fragments, such as the effector activity.

Described herein is a hybridoma cell selected from the group consisting of: 3d-8b/2 (ATCC Deposit PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d-3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026).

In some embodiments, the present disclosure provides an isolated antibody produced by a hybridoma cell described above. In yet another aspect, the disclosure features a humanized, primatized, or chimerized antibody comprising the set of six (6) CDRs of any of the antibodies produced by the above-listed hybridomas.

In some embodiments, the present disclosure provides an isolated nucleic acid molecule encoding the antibody or antigen-binding fragment thereof described in this disclosure. In some embodiments, the isolated nucleic acid molecule includes a nucleic acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 or SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20 or SEQ ID NO:30 respectively). In some embodiments, the isolated nucleic acid molecule includes a nucleic acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 or SEQ ID NO:31 or SEQ ID NO:33, over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21 or SEQ ID NO:31 or SEQ ID NO:33 respectively). In some embodiments, the isolated nucleic acid molecule includes a nucleic acid sequence that hybridizes to the nucleic acid consisting of SEQ ID NO:20 or SEQ ID NO:30 under moderately stringent hybridization conditions. In some embodiments, the nucleic acid sequence hybridizes to the nucleic acid consisting of SEQ ID NO:20 or SEQ ID NO:30 under stringent hybridization conditions. In some embodiments, the isolated nucleic acid molecule includes a nucleic acid sequence that hybridizes to the nucleic acid consisting of SEQ ID NO:21 or SEQ ID NO:31 or SEQ ID NO:33 under moderately stringent hybridization conditions. In some embodiments, the nucleic acid sequence hybridizes to the nucleic acid consisting of SEQ ID NO:21 or SEQ ID NO:31 or SEQ ID NO:33 under stringent hybridization conditions. In some embodiments, is provided a nucleic acid encoding a CDR having an amino acid sequence identical to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, or SEQ ID NO:29. In some embodiments, is provided a nucleic acid encoding a CDR having an amino acid sequence having three or less (three, two, one, or zero) amino acid mutations when compared to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, or SEQ ID NO:29. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a light chain variable region CDR having an amino acid sequence identical to SEQ ID NO:14, SEQ ID NO:15, SEQ ID NO:16, SEQ ID NO:24, SEQ ID NO:25, or SEQ ID NO:26. In some embodiments, is provided a nucleic acid encoding a light chain variable region CDR having an amino acid sequence having three or less (three, two, one, or zero) amino acid mutations when compared to SEQ ID NO:14, SEQ ID NO:15, SEQ ID NO:16, SEQ ID NO:24, SEQ ID NO:25, or SEQ ID NO:26. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a heavy chain variable region CDR having an amino acid sequence identical to SEQ ID NO:17, SEQ ID NO:18, SEQ ID NO:19, SEQ ID NO:27, SEQ ID NO:28, or SEQ ID NO:29. In some embodiments, is provided a nucleic acid encoding a heavy chain variable region CDR having an amino acid sequence having three or less (three, two, one, or zero) amino acid mutations when compared to SEQ ID NO:17, SEQ ID NO:18, SEQ ID NO:19, SEQ ID NO:27, SEQ ID NO:28, or SEQ ID NO:29. In some embodiments, the amino acid mutations are conservative and non-conservative. In some embodiments, the amino acid mutations are conservative. In some embodiments, the amino acid mutations are non-conservative.

In another embodiment, the present disclosure provides a vector containing the nucleic acid sequence of an antibody, or antigen-binding fragment thereof, or CDR, all as described herein. Such vector includes, but is not limited to, a plasmid vector, a cosmid vector, a viral vector, a shuttle vector, or any vector well known in the art for expression in prokaryotic or eukaryotic cells.

In another embodiment, the present disclosure provides a cell containing a vector containing the nucleic acid sequence of an isolated nucleic acid encoding an antibody, or antigen-binding fragment thereof, or CDR described herein. Such cell includes, for example, a prokaryotic cell or a eukaryotic cell.

In another embodiment, the disclosure features: (a) a nucleic acid encoding any one of the antibodies, antigen-binding fragments, or CDRs or constructs (e.g. conjugates, anti-C3d antibody-conjugates) described herein; (b) a vector (e.g., an expression vector) including the nucleic acid; and (c) a cell (e.g., a bacterial, plant, fungal, insect, or mammalian cell) including the vector or expression vector.

In yet another embodiment, the disclosure features a method for producing an antibody, an antigen-binding fragment of the antibody, or a CDR, or a construct (e.g. conjugates, anti-C3d antibody-conjugates) described herein. The method includes culturing the aforementioned cell under conditions suitable to allow for expression of the antibody, fragment, or construct (e.g. conjugates, anti-C3d antibody-conjugates) by the cell. The method can optionally include purifying the antibody, fragment, or construct from the cell or from the media in which the cell is cultured.

In some embodiments, the present disclosure provides a pharmaceutical composition including any of the isolated antibodies or antigen-binding fragments thereof described in this disclosure. In some embodiments, the present disclosure provides a pharmaceutical composition including a nucleic acid encoding an antibody or antigen-binding fragment thereof described in this disclosure. In some embodiments, the present disclosure provides a pharmaceutical composition including a vector containing the nucleic acid sequence of an isolated nucleic acid encoding the antibody or antigen-binding fragment thereof described in this disclosure. In some embodiments, the present disclosure provides a pharmaceutical composition including a cell containing such vector described herein.

In some embodiments, the present disclosure provides a pharmaceutical composition including any of the constructs described in this disclosure. In some embodiments, the present disclosure provides a pharmaceutical composition including a conjugate described in this disclosure. In some embodiments, the present disclosure provides a pharmaceutical composition including any of the antibody conjugates described in this disclosure. In some embodiments, the present disclosure provides a pharmaceutical composition including any of the anti-C3d antibody conjugates described in this disclosure. In some embodiments, the pharmaceutical compositions include a pharmaceutically acceptable excipient.

In some embodiments, the present disclosure provides a pharmaceutical composition including any of the isolated antibodies or antigen-binding fragments thereof described in this disclosure and a therapeutically acceptable excipient. Suitable excipients are well known in the art and recited herein.

The present inventors have found that targeting of diagnostic agents or detectable moieties to particular epitopes present on the C3d and/or C3dg and/or iC3b fragment of complement is surprisingly effective in terms of localizing diagnostic agents such that they can exert optimal effects at tissue or cells which are the site of complement activation. Thus, the present inventors have isolated antibodies which bind to the C3d and/or C3dg and/or iC3b fragment of complement and used them for the targeting of diagnostic agents and detectable moieties.

In some embodiments, the disclosure features an antibody, or antigen-binding fragment thereof, that binds to an epitope in the human C3d protein. In some embodiments, the disclosure features an antibody, or antigen-binding fragment thereof, that binds to an epitope in the human C3dg protein. In some embodiments, the disclosure features an antibody, or antigen-binding fragment thereof, that binds to an epitope in the human iC3b protein. For example, the anti-C3d antibody or anti-C3dg antibody or anti-iC3b antibody can bind to an epitope within, or overlapping with, an antigenic peptide fragment of a human complement component C3d protein, or to an epitope in the human complement component C3dg protein, or to an epitope in the human complement component iC3b protein. In some embodiments, these anti-C3d antibodies or anti-C3dg antibodies or anti-iC3b antibody are monoclonal antibodies or antibody fragments maintaining the antigen-binding activity. In some embodiments, these monoclonal antibodies include those produced by hybridoma cells 3d-8b/2 (ATCC Deposit number: PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026). In some embodiments, the present disclosure provides antibodies, or antigen-binding fragments thereof, that bind to an epitope within, or overlapping with, an epitope recognized by any one of antibodies 3d8b, 3d9a, 3d29, 3d11, 3d31, 3d3, 3d15, 3d10, and 3d16. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, do not compete with at least one of antibodies 3d8b, 3d9a, 3d29, 3d11, 3d31, 3d3, 3d15, 3d10, and 3d16 for binding to C3d or C3dg or iC3b. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, compete with at least one (e.g. 1, 2, 3, 4, 5, 6, 7, 8, or 9) of antibodies including 3d8b, 3d9a, 3d29, 3d11, 3d31, 3d3, 3d15, 3d10, and 3d16 for binding to C3d or C3dg or iC3b. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, inhibit at least one of antibodies 3d8b, 3d9a, 3d29, 3d11, 3d31, 3d3, 3d15, 3d10, and 3d16 from binding to C3d or C3dg or iC3b. In some embodiments, an antibody, or antigen binding fragment thereof, is an scFv. In some embodiments, the scFv is derived from any one of the antibodies 3d8b, 3d9a, 3d29, 3d11, 3d31, 3d3, 3d15, 3d10, and 3d16 (a 3d scFv). In some embodiments the scFv is a 3d8b scFv. In some embodiments, the scFv is a 3d29 scFv.

In some embodiments, the anti-C3d antibody or anti-C3dg antibody or anti-iC3b antibody, or antigen-binding fragment thereof, provided in the present disclosure can crossblock binding of another antibody or binding partner that binds to an epitope within, or overlapping with, a human complement component C3d or C3dg protein or iC3b protein. In some embodiments, the anti-C3d antibody or anti-C3dg antibody or anti-iC3b antibody, or antigen-binding fragment thereof, can crossblock binding of an antibody that binds to an epitope within, or overlapping with, a peptide fragment of a human complement component C3d protein or C3dg protein or iC3b protein. As used herein, the term "crossblocking antibody" refers to an antibody, or antibody fragment thereof maintaining its antigen-binding activity, that lowers the amount of binding of anti-C3d antibody or anti-C3dg antibody or anti-iC3b antibody, or antibody fragment thereof maintaining its antigen-binding activity, to an epitope on a complement component C3d protein or C3dg protein or iC3b protein relative to the amount of binding of the anti-C3d antibody or anti-C3dg antibody or anti-iC3b antibody, or antibody fragment thereof maintaining its antigen-binding activity, to the epitope in the absence of the crossblocking antibody, or antibody fragment thereof maintaining its antigen-binding activity. Suitable methods for determining whether a first antibody, or antibody fragment thereof, crossblocks binding of a second antibody, or antibody fragment thereof, to an epitope are known in the art. For example, crossblocking antibodies can be identified by comparing the binding of the 3d-9a/25anti-C3d monoclonal antibody (produced by the hybridoma cell line ATCC designation PTA-11025) to C3d in the presence and absence of a test antibody. In such a case, decreased binding of the 3d-9a/25 antibody in the presence of the test antibody as compared to binding of the 3d-9a/25 antibody in the absence of the test antibody indicates that the test antibody is a crossblocking antibody.

In another embodiment, provided herein are articles of manufacture or kits containing diagnostic compositions including an effective amount of any of the targeted diagnostic agent moieties (e.g. constructs, conjugates, anti-C3d antibody-conjugates) and instructions for their use in the methods described herein. Thus, in some embodiments, the article of manufacture comprises instructions for the use of diagnostic compositions including an effective amount of a anti-C3d antibody-conjugate comprising a monoclonal antibody which binds to a binding partner selected from C3d and C3dg and iC3b, joined to a detectable moiety. The diagnostic compositions may further include one or more pharmaceutically acceptable excipients formulated for administration to an individual as described herein. The kit may further include means for administration, such as a syringe, inhaler or other device useful for systemic administration or local administration.

In yet another embodiment, the disclosure features an article of manufacture including: a container including a label; and a composition including any of the antibodies or antigen-binding fragments or constructs (e.g. conjugates, anti-C3d antibody-conjugates) described herein, wherein the label indicates that the composition is to be administered to a human having, suspected of having, or at risk for developing, a complement-associated disorder, disease, or condition. The article of manufacture can include one or more additional agents.

In another aspect, the disclosure features a diagnostic or monitoring kit including: (i) any of the antibodies or antigen-binding fragments thereof described herein and (ii) means for delivering the antibody or antigen-binding fragment to a human; or (ii) any of the constructs (e.g. conjugates, anti-C3d antibody-conjugates) described herein and (iv) means for delivering the construct to a human. The means can be suitable for subcutaneous delivery of the construct (e.g. conjugates, anti-C3d antibody-conjugates) to the human. The means can be suitable for intraocular delivery of the construct (e.g. conjugates, anti-C3d antibody-conjugates), or the antibody or antigen-binding fragment thereof, to the human. The means can be suitable for intraarticular delivery of the construct (e.g. conjugates, anti-C3d antibody-conjugates), or the antibody or antigen-binding fragment thereof, to the human.

Detectable Moieties

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can image cell migration (J. W. Bulte et al., 2001, *Nat. Biotechnol.* 19:1141-1147), apoptosis (M. Zhao et al., 2001, *Nat. Med.* 7:1241-1244), and can detect small foci of cancer. See e.g., Y. W. Jun et al., 2005, *J. Am. Chern. Soc.* 127:5732-5733; Y. M. Huh et al., 2005, *J. Am. Chern. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscropy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound (ultrasonography) and contrast enhanced ultrasound (contrast enhanced ultrasonography) can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates. These detection methods and instruments and detectable moieties capable of being measured or detected by the corresponding method are non-limiting examples.

As used herein, the term "ultrasmall superparamagnetic iron oxide nanoparticle" or "USPIO nanoparticle" refers to superparamagnetic iron oxide particles ranging from 1 to 50 nm in diameter, more typically between 5 and 40 nm in diameter (excluding any coating applied after synthesis). USPIO nanoparticles are commonly made of maghemite ($Fe_2O_3$) or magnetite ($Fe_3O_4$) having crystal-containing regions of unpaired spins. Those magnetic domains are disordered in the absence of a magnetic field, but when a field is applied (i.e., while taking an MRI), the magnetic domains align to create a magnetic moment much greater than the sum of the individual unpaired electrons without resulting in residual magnetization of the particles. When injected into the blood stream, USPIO nanoparticles are taken up by macrophages and accumulate in inflamed tissues. Their iron moiety negatively enhances signal attenuation on $T_2$-weighted images, and their relative concentrations can be assessed by decreased $T_2$-signal intensity or, more precisely, by decreased spin-spin $T_2$-relaxation time. The decreased $T_2$-relaxation time (the transverse relaxation time) can thus be used to detect inflammation. The shortened $T_2$ relaxation time results in a darkening of the magnetic resonance image where the particles are located, thereby generating "negative contrast." This approach has been successfully utilized to detect renal inflammation in several models. In some cases, USPIO nanoparticles may be aggregated after synthesis to produce aggregates thereof (referred to herein as "ultrasmall superparamagnetic iron oxide ("USPIO") nanoparticle aggregates" or "USPIO nanoparticle aggregates") of 25 nm, 50 nm, 75 nm, 100 nm, or 150 nm, in diameter, or even larger.

The USPIO nanoparticles or aggregates thereof may be coated with a wide variety of materials, including natural or synthetic polymers, surfactants, phospholipids, or inorganic materials, any of which may be modified or derivatized to permit attachment of targeting groups, either directly or via different types of linkers, including peptides, polypeptides, proteins, or other chemical groups, or uncoated. Possible coatings include synthetic polymers, such as those based on poly(ethylene-co-vinyl acetate), polyvinylpyrrolidone ("PYP"), poly(lactic-co-glycolic acid) ("PLGA"), polyethylene glycol ("PEG"), polyvinyl alcohol ("PYA"), polyacrylic acid, and the like; natural polymers, such as gelatin, dextran, chitosan, pullulan, and the like; surfactants, such as sodium oleate, dodecylamine, sodium carboxymethylcellulose, and the like; inorganic materials, such as gold or silica; and biological materials, such as phospholipids.

Also provided herein are non-invasive methods of detecting complement-mediated inflammation in an individual using the antibody-targeted USPIO nanoparticle or nanoparticle aggregate compositions provided herein. In certain embodiments, the invention provides non-invasive methods of detecting complement-mediated inflammation in an individual, the methods comprising: (a) administering to the individual a composition comprising an effective amount of antibody-targeted ultrasmall superparamagnetic iron oxide ("USPIO") nanoparticles or aggregates thereof; and (2) taking a magnetic resonance image of the individual. In some of the embodiments described herein, the complement-mediated inflammation is alternative complement-mediated inflammation.

In some of the embodiments described herein, the composition administered to the individual is a pharmaceutical composition comprising any of the antibody-targeted USPIO nanoparticle compositions described herein. In some of the embodiments described herein, the composition administered to the individual is a pharmaceutical composition comprising any of the antibody-targeted USPIO nanoparticle aggregate compositions described herein.

As used herein, the term "magnetic resonance imaging" or "MRI" refers to a non-invasive medical imaging technique commonly used to visualize the structure and function of the body that provides detailed images of the body in any plane. MRI provides much greater contrast between the different soft tissues of the body than other non-invasive imaging methods, such as computed tomography (CT), making it especially useful in neurological, musculoskeletal, cardiovascular, and oncological (cancer) imaging. Unlike CT, it does not require ionizing radiation, instead using a powerful magnetic field to align the nuclear magnetization of hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to reconstruct an image of the body or a portion thereof.

When an individual lies in a scanner, the hydrogen nuclei (i.e., protons) found in abundance in water molecules throughout the individual's body, align with the strong main magnetic field. A second electromagnetic field, which oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different body tissues (e.g., fat vs. muscle) realign at different speeds, different body structures can be imaged. Contrast agents may be injected intravenously to enhance the appearance of blood vessels, organs, tumors or sites of inflammation.

As used herein, an "effective amount" or "diagnostically effective amount" of an antibody-targeted ultrasmall superparamagnetic iron oxide ("USPIO") nanoparticle or nanoparticle aggregate composition (including any of the pharmaceutical compositions described herein) is an amount sufficient to produce a clinically useful magnetic resonance image of complement-mediated inflammation. A clinically useful magnetic resonance image is one containing sufficient detail to enable an experienced clinician to assess the degree and/or extent of inflammation for purposes of diagnosis, monitoring the efficacy of a therapeutic intervention, and the like. As used herein, an "effective amount" or "diagnostically effective amount" of an antibody-targeted detectable moiety or antibody conjugate or anti-C3d antibody conjugate (including any of the pharmaceutical compositions described herein) is an amount sufficient to produce a clinically useful characterization or measurement of complement-mediated inflammation or complement activation (e.g. in an individual, patient, human, mammal, clinical sample, tissue, or biopsy) when coupled with a detection method capable of detecting the antibody-targeted detectable moiety or antibody conjugate or anti-C3d antibody conjugate. A clinically useful characterization or measurement of complement-mediated inflammation or complement activation is one containing sufficient detail to enable an experienced clinician to assess the degree and/or extent of inflammation or complement activation for purposes of diagnosis, monitoring the efficacy of a therapeutic intervention, and the like.

Delivery of ultrasmall superparamagnetic iron oxide ("USPIO") nanoparticles, USPIO nanoparticle aggregates, superparamagnetic iron oxide ("SPIO") nanoparticles, SPIO nanoparticle aggregates or other nanoparticle contrast agents (examples of detectable moieties) to the sites of active inflammation via antibody-targeting to sites of complement activation permits non-invasive magnetic resonance imaging of such inflammation, enabling the specific detection of complement activation throughout the body, and distinguishing complement-mediated inflammation from other types of inflammation.

Accordingly, in one aspect, the invention provides compositions comprising antibody-targeted nanoparticle contrast agents for non-invasive medical or diagnostic imaging applications. In certain embodiments, the antibody-targeted nanoparticle contrast agent compositions include USPIO nanoparticles or aggregates thereof. In certain embodiments, the antibody-targeted nanoparticle contrast agent compositions include antibody-targeted liposomes or other antibody-targeted delivery vehicles containing Gadolinium chelate ("Gd-chelate") molecules. Antibody-targeted nanoparticle contrast agents or compositions and antibody targeted ultrasmall super paramagnetic iron oxide ("USPIO") nanoparticles or aggregates are examples of antibody conjugates.

At least two physicochemical characteristics of ultrasmall super paramagnetic iron oxide ("USPIO") nanoparticles or aggregates thereof vary with the size of the individual nanoparticles or nanoparticle aggregates. First, the ability of USPIO nanoparticle preparations to enhance contrast in MRI imaging and the degree of contrast enhancement both vary with nanoparticle diameter, because the magnetic moment of individual USPIO nanoparticles also varies with particle diameter. Iron oxide nanoparticles with diameters up to approximately 15 nm (preferably less than 10 nm) remain super paramagnetic, but larger iron oxide nanoparticles lose their superparamagnetic properties. Thus, there is an upper limit to the diameter of USPIO nanoparticles suitable for use as MRI contrast reagents. This limitation can be overcome by use of multiparticle aggregates of smaller individual USPIO nanoparticles. Such USPIO nanoparticle aggregates effectively enhance MRI contrast because the magnetic moments of the individual nanoparticles within each nanoparticle aggregate are additive. Unlike individual iron oxide nanoparticles, aggregates of ultra small super paramagnetic iron oxide nanoparticles do not lose their paramagnetic properties with increased size.

Second, the in vivo half-life (e.g., circulating plasma or blood half-life and tissue half-life) and biodistribution of USPIO nanoparticles or aggregates thereof varies with nanoparticle or aggregate size. For example, USPIO nanoparticles ~10 nm or less in diameter (monochrystalline iron oxide nanoparticles) have a circulating blood half-life of ~81 minutes (R. Weissleder et al., 1990, *Radial.* 175(2):489-493), USPIO nanoparticles ~50 nm in diameter have a circulating half-life of ~30 minutes (D. Pouliquen et al., 1991, *Magnet. Resonance Imag.* 9(3):275-283), USPIO nanoparticles ~150 nm in diameter are thought to have a circulating half-life of less than ~30 minutes, and USPIO nanoparticles ~80 nm in diameter have a tissue half-life on the order of one to several days (e.g., 1, 2, 3, 4, 5, 6, 7, 8, 9, or more days) and a whole body half-life of ~45 days (R. Weissleder et al., 1989, *Am. J. Roentgenol.* 152(1):167-173). Effective targeted MRI contrast-enhancing reagents must circulate in the vasculature long enough to recognize and bind the desired target (e.g., renal deposits of C3 breakdown products) while still being cleared quickly enough to minimize any potential toxicity. Optimal USPIO nanoparticle or nanoparticle aggregate sizes for generating clinically useful magnetic resonance images vary depending on the organ (e.g., the kidney, eye, retina), tissue, and/or physiological phenomenon (e.g., complement-mediated inflammation) to be imaged.

The circulating half-life of USPIO nanoparticles or nanoparticle aggregates can also be altered (i.e., reduced or extended) by coating them with different materials. For instance, USPIO nanoparticles or nanoparticle aggregates can be coated with natural or synthetic polymers, surfactants, or phospholipids, among other materials, any of which may be modified or derivatized to permit attachment of targeting groups, either directly or indirectly via different types of linkers, including peptides, polypeptides, proteins, or other chemical groups. In some cases, the coatings may be further modified to incorporate synthetic polymers, natural polymers, aphiphilic polymers, or other molecules (e.g., polyvinylpyrrolidone ("PVP"), poly (lactic-co-glycolic acid) ("PLGA"), polyethylene glycol ("PEG"), polyvinyl alcohol ("PYA"), polyacrylic acid, and the like) suitable for stabilizing the aggregates or minimizing their susceptibility to extravasation, opsonization, phagocytosis, endocytosis or other modes of physiological clearance. As with USPIO nanoparticle or nanoparticle aggregate size, the particular coating, modification or derivatization suitable for targeting the nanoparticles or nanoparticle aggregates to a desired organ (e.g., the kidney, eye, retina), tissue, and/or physiological phenomenon (e.g., complement-mediated inflammation) may be determined empirically. Disclosed herein is identification of an optimal USPIO nanoparticle aggregate size range and coating type suitable for production of stable targeted USPIO nanoparticle aggregates with a circulating half-life long enough that the aggregates reach their targets, permitting detection of complement-mediated inflammation in particular tissues, while not being cleared so quickly that they cannot find and bind to their targets.

In embodiments, the disclosure features a diagnostic or monitoring kit including: (i) any of the antibodies or antigen-binding fragments thereof described herein and means for delivering the antibody or antigen-binding fragment to a human; or (ii) any of the constructs (e.g. conjugates, anti-C3d antibody-conjugates) and means for delivering the constructs (e.g. conjugates, anti-C3d antibody-conjugates) to a human.

In certain embodiments, the USPIO nanoparticles or aggregates thereof are between about 1 nm and about 1000 nm in diameter. In certain embodiments, the USPIO nanoparticles or aggregates thereof are between about 5 nm and about 500 nm in diameter. In certain embodiments, the USPIO nanoparticles or aggregates thereof are between about 10 nm and about 100 nm in diameter. In certain embodiments, the USPIO nanoparticles or aggregates thereof are between about 50 nm and about 150 nm in diameter. In certain embodiments, the USPIO nanoparticles or aggregates thereof are between about 65 nm and about 85 nm in diameter. In certain embodiments, the USPIO nanoparticles or aggregates thereof are about 75 nm in diameter. In certain embodiments, the USPIO nanoparticles or aggregates thereof are about 150 nm in diameter. In certain embodiments, the USPIO nanoparticles or aggregates thereof are between about 1 nm and about 1000 nm in diameter and coated with amphiphilic polymer. In certain embodiments, the USPIO nanoparticles or aggregates thereof are between about 5 nm and about 500 nm in diameter and coated with amphiphilic polymer. In certain embodiments, the USPIO nanoparticles or aggregates thereof are between about 10 nm and about 100 nm in diameter and coated with amphiphilic polymer. In certain embodiments, the USPIO nanoparticles or aggregates thereof are between about 50 nm and about 150 nm in diameter and coated with amphiphilic polymer. In certain embodiments, the USPIO nanoparticles or aggregates thereof are between about 65 nm and about 85 nm in diameter and coated with amphiphilic polymer. In certain embodiments, the USPIO nanoparticles or aggregates thereof are about 75 nm in diameter and coated with amphiphilic polymer. In certain embodiments, the USPIO nanoparticles or aggregates thereof are about 150 nm in diameter and coated with amphiphilic polymer. In certain embodiments, the USPIO nanoparticles or aggregates thereof are between about 1 nm and about 1000 nm in diameter and phospholipid-encapsulated. In certain embodiments, the USPIO nanoparticles or aggregates thereof are between about 5 nm and about 500 nm in diameter and phospholipid-encapsulated. In certain embodiments, the USPIO nanoparticles or aggregates thereof are between about 10 nm and about 100 nm in diameter and phospholipid-encapsulated. In certain embodiments, the USPIO nanoparticles or aggregates thereof are between about 50 nm and about 150 nm in diameter and phospholipid-encapsulated. In certain embodiments, the USPIO nanoparticles or aggregates thereof are between about 65 nm and about 85 nm in diameter and phospholipid-encapsulated. In certain embodiments, the USPIO nanoparticles or aggregates thereof are about 75 nm in diameter and phospholipid-encapsulated. In certain embodiments, the USPIO nanoparticles or aggregates thereof are about 150 nm in diameter and phospholipid-encapsulated. In some of the embodiments described herein, the phospholipid comprises 1,2-distearoyl-sn-glycero-3-phosphoethanolamine ("DSPE"). In some of the embodiments described herein, the phospholipid is PEGylated. The term "PEGylated" refers in the customary sense to conjugation with polyethylene glycol (PEG). In certain embodiments described herein, the PEGylated phospholipid further comprises a functional group suitable for cross-linking with an antibody- or bacterial-targeting group. In certain embodiments described herein, the PEGylated phospholipid further comprises a functional group suitable for cross-linking an antibody directed to C3 or fragment thereof, including but not limited to C3b, iC3b, C3dg, C3d and the like. In certain embodiments described herein, the functional group is an amine. In some of the embodiments described herein, the functional group is maleimide. In any of the embodiments described herein, the functional group is a thiol. In some of the embodiments described herein, the PEGylated phospholipid includes polyethylene glycol ("PEG") at a molecular weight ranging from PEG100 to PEG5000, from PEG 500 to PEG5000, from PEG1000 to PEG5000, or from PEG2000 to PEG4000. In some of the embodiments described herein, the PEGylated phospholipid includes PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In some of the embodiments described herein, the phospholipid includes DSPE-PEG2000. In some of the embodiments described herein, the phospholipid includes amine-functionalized DSPE-PEG2000. In some of the embodiments described herein, the phospholipid includes amine-functionalized DSPE-PEG2000. In some of the embodiments described herein, the phospholipid includes maleimide-functionalized DSPE-PEG2000. In some of the embodiments described herein, the USPIO nanoparticle aggregates are antibody-targeted, phospholipid-encapsulated, have a circulating plasma half-life of between about 20 minutes and about 40 minutes, and have a tissue half life of one to several days (e.g., 1, 2, 3, 4, 5, 6, 7, 8, 9, or more days).

In certain embodiments, the USPIO nanoparticles or aggregates thereof are between about 1 nm and about 1000 nm in diameter and coated with dextran. In certain embodiments, the USPIO nanoparticles or aggregates thereof are between about 5 nm and about 500 nm in diameter and coated with dextran. In certain embodiments, the USPIO nanoparticles or aggregates thereof are between about 10 nm and about 100 nm in diameter and coated with dextran. In certain embodiments, the USPIO nanoparticles or aggregates thereof are between about 50 nm and about 150 nm in diameter and coated with dextran. In certain embodiments, the USPIO nanoparticles or aggregates thereof are between about 65 nm and about 85 nm in diameter and coated with dextran. In certain embodiments, the USPIO nanoparticles or aggregates thereof are about 75 nm in diameter and coated with dextran. In certain embodiments, the USPIO nanoparticles or aggregates thereof are about 150 nm in diameter and coated with dextran.

In certain embodiments, the phospholipid-encapsulated antibody-targeted USPIO nanoparticles or aggregates thereof are between about 1 nm and about 1000 nm in diameter and include an antibody-targeting group attached to the phospholipid coating. In certain embodiments, the phospholipid-encapsulated antibody-targeted USPIO nanoparticles or aggregates thereof are between about 5 nm and about 500 nm in diameter and include an antibody-targeting group attached to the phospholipid coating. In certain embodiments, the phospholipid-encapsulated antibody-targeted USPIO nanoparticles or aggregates thereof are between about 10 nm and about 100 nm in diameter and include an antibody-targeting group attached to the phospholipid coating. In certain embodiments, the phospholipid-encapsulated antibody-targeted USPIO nanoparticles or aggregates thereof are between about 50 nm and about 150 nm in diameter and include an antibody-targeting group attached to the phospholipid coating. In certain embodiments, the phospholipid-encapsulated antibody-targeted USPIO nanoparticles or aggregates thereof are between about 65 nm and about 85 nm in diameter and include an antibody-targeting group attached to the phospholipid coating. In certain embodiments, the phospholipid-encapsulated antibody-targeted USPIO nanoparticles or aggregates thereof are about 75 nm in diameter and include an antibody-targeting group attached to the phospholipid coating. In certain embodiments, the phospholipid-encapsulated antibody-targeted USPIO nanoparticles or aggregates thereof are about 150 nm in diameter and include an antibody-targeting group attached to the phospholipid coating. In some of the embodiments described herein, the phospholipid includes 1,2-distearoyl-sn-glycero-3-phosphoethanolamine ("DSPE"). In some of the embodiments described herein, the phospholipid is PEGylated. In some of the embodiments described herein, the PEGylated phospholipid further includes a functional group suitable for cross-linking with a antibody-targeting group. In some of the embodiments described herein, the functional group is an amine. In some of the embodiments described herein, the functional group is maleimide. In some of the embodiments described herein, the functional group is a thiol. In some of the embodiments described herein, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In some of the embodiments described herein, the PEGylated phospholipid includes PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In some of the embodiments described herein, the phospholipid includes DSPE-PEG2000. In some of the embodiments described herein, the phospholipid includes amine-functionalized DSPE-PEG2000. In some of the embodiments described herein, the phospholipid includes amine-functionalized DSPE- PEG2000. In some of the embodiments described herein, the phospholipid includes maleimide-functionalized DSPE-PEG2000.

An antibody-targeted detectable moiety is a detectable moiety (e.g. USPIO, fluorophore, fluorescent moiety, paramagnetic species, radioisotope, other detectable moiety as described herein) connected to any antibody or antigen binding fragment described herein (e.g. directly bonded, covalently bonded, bonded through a linker, reversibly bonded), wherein the target is the antigen recognized by the antibody or antigen-binding fragment thereof. Antibody-targeted detectable moieties include detectable moieties connected to antigen-binding fragments of antibodies and such moieties are included in the definition of an antibody-targeted moiety or antibody-targeted detectable molecule or antibody-targeted detectable composition. An antibody-targeted detectable moiety is an antibody conjugate. An antibody-targeted detectable moiety wherein the antibody is an anti-C3d, anti-C3dg, or anti-iC3b antibody or antigen binding fragment thereof, is an anti-C3d antibody-conjugate.

In some embodiments, the antibody-targeted USPIO nanoparticle aggregates have a circulating plasma half-life of between about 20 minutes and about 40 minutes, and have a tissue halflife of one to several days (e.g., 1, 2, 3, 4, 5, 6, 7, 8, 9, or more days).

In certain embodiments, the dextran-coated antibody-targeted USPIO nanoparticles or aggregates thereof are between about 1 nm and about 1000 nm in diameter and include an antibody-targeting group attached to the dextran coating. In certain embodiments, the dextran-coated antibody-targeted USPIO nanoparticles or aggregates thereof are between about 5 nm and about 500 nm in diameter and include an antibody-targeting group attached to the dextran coating. In certain embodiments, the dextran-coated antibody-targeted USPIO nanoparticles or aggregates thereof are between about 10 nm and about 100 nm in diameter and include an antibody-targeting group attached to the dextran coating. In certain embodiments, the dextran-coated antibody-targeted USPIO nanoparticles or aggregates thereof are between about 50 nm and about 150 nm in diameter and include an antibody-targeting group attached to the dextran coating. In certain embodiments, the dextran-coated antibody-targeted USPIO nanoparticles or aggregates thereof are between about 65 nm and about 85 nm in diameter and include an antibody-targeting group attached to the dextran coating. In certain embodiments, the dextran-coated antibody-targeted USPIO nanoparticles or aggregates thereof are about 75 nm in diameter and include an antibody-targeting group attached to the dextran coating. In certain embodiments, the dextran-coated antibody-targeted USPIO nanoparticles or aggregates thereof are about 150 nm in diameter and include an antibody-targeting group attached to the dextran coating.

In certain embodiments, the USPIO nanoparticles or aggregates thereof are between 1 nm and 1000 nm in diameter. In certain embodiments, the USPIO nanoparticles or aggregates thereof are between 5 nm and 500 nm in diameter. In certain embodiments, the USPIO nanoparticles or aggregates thereof are between 10 nm and 100 nm in diameter. In certain embodiments, the USPIO nanoparticles or aggregates thereof are between 50 nm and 150 nm in diameter. In certain embodiments, the USPIO nanoparticles or aggregates thereof are between 65 nm and 85 nm in diameter. In certain embodiments, the USPIO nanoparticles or aggregates thereof are 75 nm in diameter. In certain embodiments, the USPIO nanoparticles or aggregates thereof are 150 nm in diameter. In certain embodiments, the USPIO nanoparticles or aggregates thereof are between 1 nm and 1000 nm in diameter and coated with amphiphilic polymer. In certain embodiments, the USPIO nanoparticles or aggregates thereof are between 5 nm and 500 nm in diameter and coated with amphiphilic polymer. In certain embodiments, the USPIO nanoparticles or aggregates thereof are between 10 nm and 100 nm in diameter and coated with amphiphilic polymer. In certain embodiments, the USPIO nanoparticles or aggregates thereof are between 50 nm and 150 nm in diameter and coated with amphiphilic polymer. In certain embodiments, the USPIO nanoparticles or aggregates thereof are between 65 nm and 85 nm in diameter and coated with amphiphilic polymer. In certain embodiments, the USPIO nanoparticles or aggregates thereof are 75 nm in diameter and coated with amphiphilic polymer. In certain embodiments, the USPIO nanoparticles or aggregates thereof are 150 nm in diameter and coated with amphiphilic polymer. In certain embodiments, the USPIO nanoparticles or aggregates thereof are between 1 nm and 1000 nm in diameter and phospholipid-encapsulated. In certain embodiments, the USPIO nanoparticles or aggregates thereof are between 5 nm and 500 nm in diameter and phospholipid-encapsulated. In certain embodiments, the USPIO nanoparticles or aggregates thereof are between 10 nm and 100 nm in diameter and phospholipid-encapsulated. In certain embodiments, the USPIO nanoparticles or aggregates thereof are between 50 nm and 150 nm in diameter and phospholipid-encapsulated. In certain embodiments, the USPIO nanoparticles or aggregates thereof are between 65 nm and 85 nm in diameter and phospholipid-encapsulated. In certain embodiments, the USPIO nanoparticles or aggregates thereof are 75 nm in diameter and phospholipid-encapsulated. In certain embodiments, the USPIO nanoparticles or aggregates thereof are 150 nm in diameter and phospholipid-encapsulated.

In certain embodiments, the USPIO nanoparticles or aggregates thereof are between 1 nm and 1000 nm in diameter and coated with dextran. In certain embodiments, the USPIO nanoparticles or aggregates thereof are between 5 nm and 500 nm in diameter and coated with dextran. In certain embodiments, the USPIO nanoparticles or aggregates thereof are between 10 nm and 100 nm in diameter and coated with dextran. In certain embodiments, the USPIO nanoparticles or aggregates thereof are between 50 nm and 150 nm in diameter and coated with dextran. In certain embodiments, the USPIO nanoparticles or aggregates thereof are between 65 nm and 85 nm in diameter and coated with dextran. In certain embodiments, the USPIO nanoparticles or aggregates thereof are 75 nm in diameter and coated with dextran. In certain embodiments, the USPIO nanoparticles or aggregates thereof are 150 nm in diameter and coated with dextran.

In certain embodiments, the phospholipid-encapsulated antibody-targeted USPIO nanoparticles or aggregates thereof are between 1 nm and 1000 nm in diameter and include an antibody-targeting group attached to the phospholipid coating. In certain embodiments, the phospholipid-encapsulated antibody-targeted USPIO nanoparticles or aggregates thereof are between 5 nm and 500 nm in diameter and include an antibody-targeting group attached to the phospholipid coating. In certain embodiments, the phospholipid-encapsulated antibody-targeted USPIO nanoparticles or aggregates thereof are between 10 nm and 100 nm in diameter and include an antibody-targeting group attached to the phospholipid coating. In certain embodiments, the phospholipid-encapsulated antibody-targeted USPIO nanoparticles or aggregates thereof are between 50 nm and 150 nm in diameter and include an antibody-targeting group attached to the phospholipid coating. In certain embodiments, the phospholipid-encapsulated antibody-targeted USPIO nanoparticles or aggregates thereof are between 65 nm and 85 nm in diameter and include an antibody-targeting group attached to the phospholipid coating. In certain embodiments, the phospholipid-encapsulated antibody-targeted USPIO nanoparticles or aggregates thereof are 75 nm in diameter and include an antibody-targeting group attached to the phospholipid coating. In certain embodiments, the phospholipid-encapsulated antibody-targeted USPIO nanoparticles or aggregates thereof are 150 nm in diameter and include an antibody-targeting group attached to the phospholipid coating.

In certain embodiments, the dextran-coated antibody-targeted USPIO nanoparticles or aggregates thereof are between 1 nm and 1000 nm in diameter and include an antibody-targeting group attached to the dextran coating. In certain embodiments, the dextran-coated antibody-targeted USPIO nanoparticles or aggregates thereof are between 5 nm and 500 nm in diameter and include an antibody-targeting group attached to the dextran coating. In certain embodiments, the dextran-coated antibody-targeted USPIO nanoparticles or aggregates thereof are between 10 nm and 100 nm in diameter and include an antibody-targeting group attached to the dextran coating. In certain embodiments, the dextran-coated antibody-targeted USPIO nanoparticles or aggregates thereof are between 50 nm and 150 nm in diameter and include an antibody-targeting group attached to the dextran coating. In certain embodiments, the dextran-coated antibody-targeted USPIO nanoparticles or aggregates thereof are between 65 nm and 85 nm in diameter and include an antibody-targeting group attached to the dextran coating. In certain embodiments, the dextran-coated antibody-targeted USPIO nanoparticles or aggregates thereof are 75 nm in diameter and include an antibody-targeting group attached to the dextran coating. In certain embodiments, the dextran-coated antibody-targeted USPIO nanoparticles or aggregates thereof are 150 nm in diameter and include an antibody-targeting group attached to the dextran coating.

In embodiments, the USPIO has a diameter selected from the group consisting of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nm. In emboments, the USPIO has a diameter selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nm. In embodiments, the USPIO has a diameter selected from the group consisting of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nm. In embodiments, the USPIO has a diameter selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nm. In embodiments, the USPIO aggregate has a diameter selected from the group consisting of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nm. In embodiments, the USPIO aggregate has a diameter selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nm. In embodiments, the USPIO aggregate has a diameter selected from the group consisting of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1000 nm. In embodiments, the USPIO aggregate has a diameter selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1000 nm.

In embodiments, the USPIO has a diameter selected from the group consisting of 1, 2, 3, 4, 5, 6, 7, 8, 9, 10, 11, 12, 13, 14, and 15 nm. In embodiments, the USPIO has a diameter selected from the group consisting of about 1, 2, 3, 4, 5, 6, 7, 8, 9, 10, 11, 12, 13, 14, and 15 nm. In embodiments, the USPIO has a diameter selected from the group consisting of 1, 2, 3, 4, 5, 6, 7, 8, 9, and 10 nm. In embodiments, the USPIO has a diameter selected from the group consisting of about 1, 2, 3, 4, 5, 6, 7, 8, 9, and 10 nm. In embodiments, the USPIO has a diameter between about 1 and 15 nm. In embodiments, the USPIO has a diameter between 1 and 15 nm. In embodiments, the USPIO has a diameter between about 1 and 10 nm. In embodiments, the USPIO has a diameter between 1 and 10 nm. In embodiments, any of the USPIOs described herein may be modified as described above for USPIOs of different sizes (e.g. coated with an amphiphilic polymer, phospholipid encapsulated, coated with dextran, etc., or combinations thereof).

Diagnostic Compositions and Methods

Complement-mediated inflammation associated with many diseases in which any of the three complement pathways is implicated can be detected by the non-invasive methods of the present invention. Such diseases include, for example: (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membranous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. Complement-mediated inflammation associated with autoimmune disorders including, but not limited to, myasthenia gravis, Alzheimer's disease, multiple sclerosis, rheumatoid arthritis, systemic lupus erythematosus, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barre syndrome, Hashimoto's disease, idiopathic thrombocytopenic purpura, pemphigus, Sjogren's syndrome, and Takayasu's arteritis, may also be detected with the methods described herein.

In certain embodiments, the complement-mediated inflammation to be detected by the methods provided herein is associated with a disorder selected from the following group: post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukopheresis; extracorporeal membrane oxygenation (ECMO); heparin-induced extracorporeal LDL precipitation (HELP); radiographic contrast media-induced allergic response; transplant rejection; other inflammatory conditions, autoimmune disorders, and autoimmune/immune complex diseases such as multiple sclerosis, myasthenia gravis, pancreatitis, rheumatoid arthritis, IgG4-mediated/associated diseases, Alzheimer's disease, asthma, thermal injury, anaphylactic shock, bowel inflammation, urticaria, angioedema, vasculitis, glomerulonephritis, Sjogren's syndrome, systemic lupus erythromatosus and lupus nephritis.

Membranoproliferative glomerulonephritis type II (MPGN II) is a rare kidney disease leading to persistent proteinuria, hematuria, and nephritic syndrome. FH deficiency and dysfunction in MPGN II have been reported in several cases. For example, mutations in FH have been found in human patients with MPGN II. Pigs of the Norwegian Yorkshire breed have FH defects that are inherited in a recessive pattern. These animals develop MPGN II, show massive complement deposits in the renal glomeruli and die at an early age because of the renal failure. Furthermore, an autoantibody that recognizes FH has been described in a patient with hypocomplementemic MPGN II. Thus, evidence suggests that the alternative complement pathway is involved in the development and progression of MPGN II.

Hemolytic uremic syndrome (HUS) is a disease characterized by microangiopathic hemolytic anemia and thrombocytopenia, ultimately resulting in acute renal failure, caused by continuous platelet degradation in the periphery and platelet thrombin in the microcirculation of the kidney. See e.g., Zipfel, 2001, *Seminars in Thrombosis Hemostasis* 27(3):191-199. There is now considerable evidence that the nondiarrheal form of HUS (also known as atypical HUS, or aHUS) is associated with alternations and mutations of FH. In addition, autoantibodies to FH have been reported in aHUS patients. Thus, evidence suggests that the alternative complement pathway is involved in the development and progression of HUS and aHUS.

Rheumatoid arthritis is a chronic disease which can exhibit a variety of systemic manifestations. This disease has an unknown etiology and characteristically exhibits a persistent inflammatory synovitis which usually involves peripheral joints in a symmetric distribution. The most important feature of this incurable condition is complement-mediated inflammation which causes cartilage destruction, bone erosions and, ultimately, joint deformities that are the hallmark of the disease.

As used herein, the term "ischemia/reperfusion (I/R) injury" refers to inflammatory injury to the endothelium and underlying parenchymal tissues following reperfusion of hypoxic tissues. It is a general syndrome that is responsible for both acute and chronic injury to various tissues including, for example, myocardium, central nervous system, hind limb and intestine. Ischemia reperfusion injury can result in necrosis and irreversible cell injury. The complement pathway (including the alternative complement pathway) is a major mediator of I/R injury. The non-invasive methods provided herein are thus useful for detection of complement-mediated inflammation associated with ischemia reperfusion that occurs in any organ or tissue, including, but not limited to, intestinal ischemia-reperfusion injury, renal ischemia-reperfusion injury, cardiac ischemia-reperfusion injury, ischemia-reperfusion injury of other internal organs such as the lung or liver, central nervous system ischemia-reperfusion injury, ischemia-reperfusion injury of the limbs or digits, trauma-induced hypovolemia, or ischemia-reperfusion injury of any transplanted organ or tissue. Ischemia-reperfusion injury can also occur in conjunction with a variety of other conditions including, but not limited to, stroke, spinal cord injury, trauma-induced hypovolemic shock, and autoimmune diseases such as rheumatoid arthritis (e.g., which can be greatly worsened by ischemic injury of the synovium) or a variety of other inflammatory diseases (diseases mediated by inflammation or wherein inflammation is a symptom that may result in or be associated with ischemic events and reperfusion). Other conditions and diseases in which ischemia-reperfusion injury occurs will be known to those of skill in the art.

The non-invasive methods provided herein may also be used to detect complement-mediated inflammation in drusen-associated diseases. As used herein, the term "drusen-associated disease" refers to any disease in which formation of drusen or drusen-like extracellular disease plaque takes place, and for which drusen or drusen-like extracellular disease plaque causes or contributes to thereto or represents a sign thereof. For example, age-related macular degeneration (AMD), characterized by the formation of macular drusen, is considered a drusen-associated disease. Non-ocular drusen-related diseases include, but are not limited to, amyloidosis, elastosis, dense deposit disease, and/or atherosclerosis. The term "drusen-related disease" also includes glomerulonephritis, such as MPGN II.

In another embodiment, the present disclosure provides a method of monitoring or diagnosing complement activation in a subject, the method including administering to the subject an effective amount of a construct (e.g. conjugates, anti-C3d antibody-conjugates) described herein.

In another embodiment, provided herein is the use of any of the compositions as described herein in connection with the methods as described herein, unless otherwise noted or as is clear from the specific context.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. An antibody or construct (e.g. conjugates, anti-C3d antibody-conjugates) described herein can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, the means can be a syringe, e.g., a double-barreled syringe. In some embodiments, the means can be a trans-scleral patch or a contact lens including the construct (e.g. conjugates, anti-C3d antibody-conjugates) or the antibody or antigen-binding fragment thereof.

In some embodiments, the means is suitable for intrapulmonary delivery of the construct (e.g. conjugates, anti-C3d antibody-conjugates), or the antibody or antigen-binding fragment thereof, to the human. For example, the means can be an inhaler or a nebulizer.

In some embodiments, the kits include at least one additional active agent for use in monitoring or diagnosing a complement-associated disorder in a human.

In yet another embodiment, the disclosure features a pre-filled syringe including: (a) any of the antibodies or antigen-binding fragments thereof described herein or any of the constructs (e.g. conjugates, anti-C3d antibody-conjugates) described herein. The construct (e.g. conjugates, anti-C3d antibody-conjugates), or the antibody or antigen-binding fragment thereof, can be formulated for intraocular, intravitreal, or intraarticular administration.

In some embodiments, the construct (e.g. conjugates, anti-C3d antibody-conjugates), or the antibody or antigen-binding fragment thereof, is formulated for intramuscular or subcutaneous administration.

In some embodiments, an antibody, or antigen-binding fragment thereof, or conjugate or construct (e.g. conjugates, anti-C3d antibody-conjugates) described herein is delivered to a subject by way of local administration. As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

In some embodiments, an antibody, or antigen-binding fragment thereof, or conjugate or construct (e.g. conjugates, anti-C3d antibody-conjugates) described herein can be locally administered to a joint (e.g., an articulated joint). For example, in embodiments where the complement-associated disorder is arthritis, an antibody, or antigen-binding fragment thereof, or conjugate or construct (e.g. conjugates, anti-C3d antibody-conjugates) described herein can be administered directly to a joint (e.g., into a joint space) or in the vicinity of a joint. Examples of intraarticular joints to which, an antibody, or antigen-binding fragment thereof, or conjugate or construct (e.g. conjugates, anti-C3d antibody-conjugates) described herein can be locally administered include, e.g., the hip, knee, elbow, wrist, sternoclavicular, temperomandibular, carpal, tarsal, ankle, and any other joint subject to arthritic conditions. An antibody, or antigen-binding fragment thereof, or conjugate or construct (e.g. conjugates, anti-C3d antibody-conjugates) described herein can also be administered to bursa such as, e.g., acromial, bicipitoradial, cubitoradial, deltoid, infrapatellar, ischial, and any other bursa known in the art of medicine.

In some embodiments, an antibody, or antigen-binding fragment thereof, or conjugate or construct (e.g. conjugates, anti-C3d antibody-conjugates) described herein can be locally administered to the eye. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, an antibody, or antigen-binding fragment thereof, or conjugate or construct (e.g. conjugates, anti-C3d antibody-conjugates) described herein is administered to the posterior chamber of the eye. In some embodiments, an antibody, or antigen-binding fragment thereof, or conjugate or construct (e.g. conjugates, anti-C3d antibody-conjugates) described herein is administered intravitreally. In some embodiments, an antibody, or antigen-binding fragment thereof, or conjugate or construct (e.g. conjugates, anti-C3d antibody-conjugates) described herein is administered trans-sclerally.

In some embodiments, an antibody, or antigen-binding fragment thereof, or conjugate or construct (e.g. conjugates, anti-C3d antibody-conjugates) described herein can be administered to a subject by way of the lung. Pulmonary drug delivery may be achieved by inhalation, and administration by inhalation herein may be oral and/or nasal. Examples of pharmaceutical devices for pulmonary delivery include metered dose inhalers, dry powder inhalers (DPIs), and nebulizers. For example, an antibody, or antigen-binding fragment thereof, or conjugate or construct (e.g. conjugates, anti-C3d antibody-conjugates) described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TurboHaler® (AstraZeneca; London, England) the AIR® inhaler (Alkermes®; Cambridge, Mass.); Rotahaler® (GlaxoSmithKline; London, England); and Eclipse™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, an antibody, or antigen-binding fragment thereof, or conjugate or construct (e.g. conjugates, anti-C3d antibody-conjugates) described herein can be intrapulmonarily administered by way of a metered dose inhaler. These inhalers rely on a propellant to deliver a discrete dose of a compound to the lungs. Examples of compounds administered by metered dose inhalers include, e.g., Astovent® (Boehringer-Ingelheim; Ridgefield, Conn.) and Flovent® (GlaxoSmithKline). See also, e.g., U.S. Pat. Nos. 6,170,717; 5,447,150; and 6,095,141.

In some embodiments, an antibody, or antigen-binding fragment thereof, or conjugate or construct (e.g. conjugates, anti-C3d antibody-conjugates) described herein can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, an antibody, or antigen-binding fragment thereof, or conjugate or construct (e.g. conjugates, anti-C3d antibody-conjugates) described herein is present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

A "subject," as used herein, can be any mammal. For example, a subject can be a human, a non-human primate (e.g., orangutan, gorilla, macaque, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject is a patient. In some embodiments, the subject is a human.

In some embodiments, the present disclosure provides a method of specifically targeting a detectable moiety or portion of a construct (e.g. conjugates, anti-C3d antibody-conjugates) to a pre-defined area or compartment in vivo, thus increasing the local concentration of such detectable moiety or portion in such area or compartment but not in other areas or compartments or increasing the accessibility of such detectable moiety or portion to at least one pre-defined molecule located in such area or compartment, by the specific interaction between a targeting moiety or portion of such construct (e.g. conjugates, anti-C3d antibody-conjugates) and a target molecule located in such area or compartment. In some embodiments, the present disclosure provides a method of specifically targeting an active or detectable moiety or portion of a construct (e.g. conjugates, anti-C3d antibody-conjugates) to a surface of complement activation by an antibody or antigen-binding fragment thereof which is fused (e.g. directly or through one or more linkers) to such active or detectable moiety or portion and is able to specifically bind to a complement component protein. In some embodiments, such complement component protein is C3d or C3dg or iC3b.

Monitoring a subject (e.g., a human patient) for an improvement in a complement-associated disorder (e.g., sepsis, severe burn, RA, lupus nephritis, Goodpasture's syndrome, or asthma), as defined herein, means evaluating the subject for a change in a disease parameter, e.g., an improvement in one or more symptoms of a given disorder. The symptoms of complement-associated disorders are well known in the art of medicine. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a complement-associated disorder described herein. In some embodiments, monitoring a subject (e.g. patient) includes use of any of the constructs or conjugates described herein in any of the methods described herein.

Also provided are articles of manufacture including the compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present disclosure also provides kits including compositions (or unit dosage forms and/or articles of manufacture) described herein and may further include instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

The compositions and formulations of the present disclosure are useful for the diagnosis, prognosis, monitoring, or identification of conditions associated with complement activation, preferably those which involve the complement alternative pathway, which is largely unaffected by terminal complement inhibitors (e.g., inhibitors of steps of the complement pathway subsequent to the activation of C3).

In certain embodiments, the invention provides non-invasive methods of detecting complement-mediated inflammation in an individual in need thereof including: (a) administering to the individual a composition including an effective amount of antibody-targeted ultrasmall superparamagnetic iron oxide ("USPIO") nanoparticles or aggregates thereof and (b) taking a magnetic resonance image of the individual. In certain embodiments, the composition is any of the pharmaceutical compositions including antibody-targeted USPIO nanoparticles or aggregates thereof or other antibody-targeted detectable moiety or antibody conjugate described herein. In certain embodiments, the individual is a mammal. In certain embodiments, the mammal is a human, a mouse, or a rat. In certain embodiments, the compositions including antibody-targeted USPIO nanoparticles or aggregates thereof or other antibody-targeted detectable moieties or antibody conjugates are administered by injection. In certain embodiments, the injection is parenteral, intravenous, subcutaneous, or intramuscular. In some of the embodiments described herein, the complement-mediated inflammation is alternative complement-mediated inflammation. In some embodiments, provided herein are non-invasive methods of detecting complement-mediated inflammation or complement activation in an individual in need thereof including: (a) administering to the individual a composition including an effective amount of an antibody-targeted detectable moiety (i.e. antibody conjugate) and (b) measuring the presence of the antibody-targeted detectable moiety (i.e. antibody conjugate) using an instrument and/or method (e.g. MRI, CT, SPECT, radiography, spectroscopy, microscopy, PET, ultrasound, or any other detection method described herein) capable of detecting the presence of the detectable moiety.

The antibody-targeted USPIO nanoparticle or nanoparticle aggregate compositions or other antibody-targeted detectable moieties or antibody conjugates described herein can be administered to an individual via any route, including, but not limited to, intravenous (e.g., by infusion pumps), intraperitoneal, intraocular, intraarterial, intravesicular, intramuscular, subcutaneous, intrathecal, transpleural, intraarterial, subcutaneous, intraarticular, intracisternal, intraventricular, intracranial, intraurethral, intrahepatic, and intratumoral. In certain embodiments, the antibody-targeted USPIO nanoparticle or nanoparticle aggregate compositions or other antibody-targeted detectable moieties or antibody conjugates are administered systemically (for example, by intravenous injection). In some embodiments, the antibody-targeted USPIO nanoparticle or nanoparticle aggregate compositions or other antibody-targeted detectable moieties or antibody conjugates are administered locally (for example, by intraarterial or intraocular injection).

In certain embodiments, the compositions are administered directly to the eye or the eye tissue. In certain embodiments, the compositions are administered by injection to the eye (intraocular injection) or to the tissues associated with the eye. The antibody-targeted USPIO nanoparticle or nanoparticle aggregate compositions or other antibody-targeted detectable moieties or antibody conjugates can be administered, for example, by intraocular injection, periocular injection, subretinal injection, intravitreal injection, transseptal injection, subscleral injection, intrachoroidal injection, intracameral injection, subconjunctival injection, subtenon injection, retrobulbar injection, or peribulbar injection. These methods are known in the art. For example, exemplary periocular routes for retinal drug delivery are disclosed in "Periocular routes for retinal drug delivery," Raghava et al., 2004, Exp. Opin. Drug Deliv. 1(1):99-114. The antibody-targeted USPIO nanoparticle or nanoparticle aggregate compositions or other antibody-targeted detectable moieties or antibody conjugates may be administered, for example, to the vitreous humor, aqueous humor, sclera, conjunctiva, the area between the sclera and conjunctiva, the retina, the choroid, the macula, to any other area in or proximate to the eye of an individual.

In certain embodiments, the antibody-targeted compositions are administered intravascularly, such as intravenously (IV) or intraarterially. In certain embodiments (for example for the treatment of renal diseases), the compositions are administered directly into arteries (such as renal arteries).

In certain embodiments, the complement-mediated inflammation is associated with tissue damage resulting from ischemia reperfusion injury, inflammatory disorders, transplant rejection, pregnancy-related diseases, adverse drug reactions, and autoimmune or immune complex disorders. In certain embodiments, the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In certain embodiments, the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In certain embodiments, the transplant rejection is hyperacute xenograft rejection. In certain embodiments, the pregnancy-related disease is selected from the group consisting of recurrent fetal loss and pre-eclampsia. In certain embodiments, the adverse drug reaction is selected from the group consisting of drug allergy and IL-2 induced vascular leakage syndrome. In certain embodiments, the autoimmune or immune complex disorder is selected from the group consisting of myasthenia gravis, Alzheimer's disease, multiple sclerosis, rheumatoid arthritis, IgG4 mediated/associated diseases, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndromes, Graves' disease, Guillain-Barre syndrome, Hashimoto's disease, idiopathic thrombocytopenic purpura, pemphigus, Sjogren's syndrome, Takayasu's arteritis, autoimmune glomerulonephritis, membranoproliferative glomerulonephritis type II, hemolytic uremic syndrome, and atypical hemolytic uremic syndrome. In certain embodiments, the autoimmune glomerulonephritis is associated with immunoglobulin A nephropathy or membranoproliferative glomerulonephritis type I.

Also provided herein are non-invasive methods of detecting complement-mediated inflammation associated with systemic lupus erythematosus (SLE), membranous glomerulonephritis, or lupus nephritis in an individual in need thereof using the antibody-targeted USPIO nanoparticle or nanoparticle aggregate compositions provided herein. In certain embodiments, the complement-mediated inflammation is alternative complement-mediated inflammation.

As used herein, the term "systemic lupus erythematosus" or "lupus" or "SLE" refers to a chronic, occasionally fatal, autoimmune disease. As with other autoimmune diseases, in SLE, the immune system attacks the body's cells and tissue, resulting in inflammation and tissue damage. SLE can affect any part of the body, but most often harms the heart, joints, skin, lungs, blood vessels, liver, kidneys, and nervous system. The course of the disease is unpredictable, with periods of illness, or flares, alternating with periods of remission. Diagnosis can be elusive, with patients sometimes suffering unexplained symptoms and untreated SLE for years. Common initial and chronic complaints are fever, malaise, joint pains, myalgias, fatigue and temporary loss of cognitive abilities. In some cases, the disease is accompanied by chronic renal dysfunction, including the development of lupus nephritis.

As used herein, the term "membranous glomerulonephritis" or "lupus nephritis" refers to an inflammation of the kidney caused by the chronic autoimmune disease SLE. Those afflicted with lupus nephritis may or may not have renal symptoms, but the disease can manifest itself through weight gain, high blood pressure, darker foamy urine or swelling around the eyes, legs, ankles or fingers.

SLE is a complex autoimmune disease with pleiotropic clinical manifestations. Up to 80% of patients with lupus develop renal abnormalities, but the renal prognosis varies greatly within this population. C. Parikh et al., (2006) "The Long Term Outcome of Glomerular Diseases, in DISEASES OF THE KIDNEY AND Urinary TRACT: CLINICO-PATHO-LOGIC FOUNDATIONS OF MEDICINE (R. W. Schrier ed., 8th ed., Lippincott Williams & Wilkins, Philadelphia, Pa.). Furthermore, in individual patients the disease may transform from one pattern to another. In some cases, the only renal manifestation of the disease is painless hematuria or proteinuria, but in some cases patients develop lupus nephritis, leading to acute or end-stage renal failure. Patients with active proliferative nephritis are usually treated with steroids in combination with cytotoxic agents or mycophenolate mofetil. Waldman, M. et al., 2006, *Kidney Int.* 70:1403-1412. Because of the significant morbidity associated with these agents, however, careful consideration is necessary to identify patients who require aggressive therapy. The duration and intensity of therapy are also frequently adjusted according to how well a patient is responding. Thus, one of the great challenges to treating SLE patients with lupus nephritis is assessing the activity of the disease, and tailoring pharmacologic therapy to achieve remission while minimizing toxicity.

The most commonly used system for classifying the different histologic patterns of lupus nephritis was originally developed by the World Health Organization ("WHO"), and is based upon the appearance of glomeruli by light microscopy. J. J. Weening et al., 2004, *J. Am. Soc. Nephrol.* 15:241-250. Proliferative lupus nephritis (WHO class III or IV) has the worst prognosis and most large clinical trials have focused on the response of these patients to therapy. The histologic pattern of disease may change over time or in response to treatment, however, and clinical parameters do not correlate well with disease activity. Serologic studies, such as measurement of perturbations in circulating levels of C3 and C4, are also poor markers of disease activity and are not specific to renal disease activity.

Histologically, a hallmark of SLE is membranous glomerulonephritis (also referred to as "lupus nephritis") with "wire loop" abnormalities, comprising a glomerular capillary loop with a circumferential, subendothelial immune complex deposit around the loop. The wire loop lesion results from immune complex deposition along the glomerular basement membrane, which leads to a characteristic granular appearance in immunofluorescence images. Thus, the diagnosis of active lupus nephritis is founded upon the presence of mesangial, subendothelial, and/or subepithelial immune-complexes. Complement activation is an essential prerequisite to active immune complex disease such as lupus nephritis.

Because effective treatment of proliferative lupus nephritis often requires treatment with potent immunosuppressive agents such as cyclophosphamide or mycophenolate mofetil, treatment is usually guided by examination of a renal biopsy. Definitive diagnosis of glomerular diseases such as active lupus nephritis is based upon the examination of renal biopsy tissue by light microscopy, electron microscopy, and immunofluorescence staining for clinical markers of inflammation, including, but not limited to, IgM, IgA, IgG, C3, C4, and C1q.

Percutaneous renal biopsy is the gold standard for the definitive diagnosis of lupus nephritis and for monitoring the course of disease. As discussed herein, however, renal biopsies have their limitations and risks. Because a needle biopsy samples only a small portion of the kidney, there is a risk of sample error leading to an incorrect diagnosis. Furthermore, although biopsy is a generally safe procedure, major complications may occur in a significant percentage of biopsies and intra-renal bleeding and hematuria are common W. L. Whittier et al., 2004, *I. Am. Soc. Nephrol.* 15:142-147; D. C. Mendelssohn et al., 1995, *Am. J. Kidney Disease* 26:580-585. Therefore, there is a need to develop accurate, safe, and non-invasive methods to image and diagnose renal inflammation, including lupus nephritis associated with SLE.

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can image cell migration (J. W. Bulte et al., 2001, *Nat. Biotechnol.* 19:1141-1147), apoptosis (M. Zhao et al., 2001, *Nat. Med.* 7:1241-1244), and can detect small foci of cancer. See e.g., Y. W. Jun et al., 2005, *J. Am. Chern. Soc.* 127:5732-5733; Y. M. Huh et al., 2005, *J. Am. Chern. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscropy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound and contrast enhanced ultrasound can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates.

Because complement (e.g., the alternative complement pathway) is known to be involved in etiology and progression of renal inflammation and lupus nephritis associated with SLE, a ligand capable of targeting components of the complement pathway (e.g., the alternative complement pathway) would be useful in targeted delivery of USPIO nanoparticles or aggregates thereof to sites of renal inflammation in SLE patients. For example, specific antibodies (or antigen-binding fragment thereof) could be used, which bind C3b, iC3b, and C3d cleavage products of alternative complement protein C3. Phospholipid-encapsulated or dextran-coated USPIO nanoparticles or aggregates thereof can be covalently conjugated to a protein ligand such as an antibody or antibody fragment by linkage to thiol, amine, or carboxyl groups, either directly or through an antibody or antibody fragment. The labeled protein can then be used to target the USPIO nanoparticles or aggregates thereof or other antibody-targeted detectable moieties or antibody conjugates to sites of complement-mediated (e.g., alternative complement-mediated) inflammation.

Thus, in certain embodiments, the invention provides non-invasive methods of detecting complement-mediated inflammation associated with systemic lupus erythematosus (SLE), membranous glomerulonephritis, or lupus nephritis in an individual in need thereof, the methods comprising: (1) administering to the individual a composition comprising an effective amount of antibody-targeted USPIO nanoparticles or aggregates thereof or other antibody-targeted detectable moiety or antibody conjugate; and (2) taking a magnetic resonance image of the individual or measurement capable of detecting the detectable moiety administered in step (1). In certain embodiments, the complement-mediated inflammation is alternative complement-mediated inflammation. In certain embodiments, the individual is a mammal. In certain embodiments, the mammal is a human, a mouse, or a rat. In certain embodiments, the compositions comprising antibody-targeted USPIO nanoparticles or aggregates thereof or other antibody-targeted detectable moiety or antibody conjugate are administered by injection. In certain embodiments, the injection is parenteral, intravenous, subcutaneous, or intramuscular.

Diagnostic Conjugate Compositions

In an aspect is provided a construct including: (a) a C3d binding portion; and (b) a complement diagnostic portion, wherein (a) and (b) are joined (a "conjugate" or "conjugate molecule").

In some embodiments, the C3d binding portion includes an anti-C3d antibody or anti-C3dg antibody or anti-iC3b antibody, or antigen-binding fragment thereof, including any of the anti-C3d/C3dg antibodies or antigen-binding fragments thereof described herein, anti-C3d antibodies or antigen-binding fragments thereof described herein, anti-C3dg antibodies or antigen-binding fragments thereof described herein, or anti-iC3b antibodies or antigen-binding fragments thereof described herein. In embodiments, the complement diagnostic portion includes a detectable moiety described herein. In embodiments, the complement diagnostic portion is a detectable moiety described herein. An "anti-C3d antibody-conjugate" or "anti-C3d antibody conjugate" is a conjugate or conjugate molecule wherein the C3d binding portion is an anti-C3d antibody or anti-C3dg antibody or anti-iC3b antibody, or antigen-binding fragment thereof of any of these antibodies. In embodiments, the anti-C3d antibody-conjugate includes an anti-C3d antibody, or antigen-binding fragment thereof. In embodiments, the anti-C3d antibody-conjugate includes an anti-C3dg antibody, or antigen-binding fragment thereof. In embodiments, the anti-C3d antibody-conjugate includes an anti-iC3b antibody, or antigen-binding fragment thereof.

In some embodiments, the anti-C3d antibody-conjugate includes an antibody, or antigen binding fragment thereof, selected from the group consisting of any of the antibodies or antigen binding fragments described herein (e.g. including aspects, embodiments, antibody compositions and uses section above, examples, tables, figures, claims). In some embodiments, the anti-C3d antibody-conjugate includes a detectable moiety selected from the group consisting of any of the detectable moieties or labels described herein (e.g. including aspects, embodiments, detectable moieties section above, examples, tables, figures, claims). In embodiments, the anti-C3d antibody-conjugate includes an antibody, or antigen binding fragment thereof, including at least one CDR described herein. In embodiments, the anti-C3d antibody-conjugate includes an antibody, or antigen binding fragment thereof, including six CDRs described herein. In embodiments, the anti-C3d antibody-conjugate includes an antibody, or antigen binding fragment thereof, including an amino acid sequence encoded by a nucleic acid described herein. In embodiments, the anti-C3d antibody-conjugate includes an antibody, or antigen binding fragment thereof, including an amino acid sequence described herein. In embodiments, the anti-C3d antibody-conjugate includes an amino acid sequence encoded by a nucleic acid described herein. In embodiments, the anti-C3d antibody-conjugate includes an amino acid sequence described herein.

In some embodiments, the complement diagnostic portion is a compound, composition, or protein. In some embodiments, the complement diagnostic portion is any label or detectable moiety described herein. In some embodiments, the C3d binding portion (e.g. anti-C3d or anti-C3dg, or anti-iC3b portion) binds C3d. In some embodiments, the C3d binding portion (e.g. anti-C3d or anti-C3dg, or anti-iC3b portion) binds C3dg. In some embodiments, the C3d binding portion (e.g. anti-C3d or anti-C3dg, or anti-iC3b portion) binds iC3b. In some embodiments, the C3d binding portion (e.g. anti-C3d or anti-C3dg, or anti-iC3b portion) binds C3d and C3dg. In some embodiments, the C3d binding portion (e.g. anti-C3d or anti-C3dg, or anti-iC3b portion) binds C3d, C3dg, and iC3b.

In yet another embodiment, the disclosure provides a construct for monitoring or diagnosing complement activation, including: (a) a C3d binding portion including an anti-C3d antibody or antigen-binding fragment thereof (e.g. as described herein); and (b) a complement diagnostic portion including a detectable moiety.

In some embodiments, the construct disclosed herein monitors or diagnoses complement activity in the complement alternative pathway (CAP). In some embodiments, the construct disclosed herein is a fusion protein.

The present disclosure provides conjugate molecules described herein that may include two moieties or portions, e.g., the targeting moiety or portion and the active diagnostic moiety or portion, which are directly fused together by a covalent bond or fused through a linker. Such linker may include, but is not limited to, a peptide. An exemplary peptide linker is, but is not limited to, (GlySer)$_n$ (SEQ ID NO:38), wherein n=1 to 8; (GlyGlyGlySer)$_n$ (SEQ ID NO:39), wherein n=1 to 4; (GlyGlyGlyGlySer)$_n$ (SEQ ID NO:40), wherein n=1 to 8; or (GlySerSerGly)$_n$ (SEQ ID NO:41), wherein n=1 to 4. In some embodiments, the C3d binding portion and the complement diagnostic portion of the construct disclosed herein are joined directly without a linker. In some embodiments, such two portions are joined directly through a chemical bond. In other embodiments, such two portions are joined by a linker. Examples of linker sequences are known in the art, and include, for example, (Gly$_4$Ser) (SEQ ID NO:42), (Gly$_4$Ser)$_2$ (SEQ ID NO:43), (Gly$_4$Ser)$_3$ (SEQ ID NO:44), (Gly$_4$Ser)$_4$ (SEQ ID NO:45), (SerGly$_4$) (SEQ ID NO:46), (SerGly$_4$)$_2$ (SEQ ID NO:47), (SerGly$_4$)$_3$ (SEQ ID NO:48), and (SerGly$_4$)$_4$ (SEQ ID NO:49). Linking sequences can also comprise "natural" linking sequences found between different domains of complement factors. For example, VSVFPLE (SEQ ID NO:50) or EYFNKYSS (SEQ ID NO:51), the linking sequence between the first two N-terminal short consensus repeat domains of human CR2, can be used. In some embodiments, the linking sequence between the fourth and the fifth N-terminal short consensus repeat domains of human CR2 (EEIF, SEQ ID NO:52) is used.

In some embodiments, a protein (e.g. antibody or antigen-binding fragment thereof) described herein can be conjugated to a heterologous moiety. In embodiments where the heterologous moiety is a polypeptide, a fusion protein and a corresponding heterologous moiety described herein can be joined by way of fusion protein. The heterologous moiety can be, e.g., a heterologous polypeptide, a therapeutic agent (e.g., a toxin or a drug), or a detectable label or a detectable moiety such as, but not limited to, a radioactive label, an enzymatic label, a fluorescent label, a luminescent label, $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, haptens, proteins or other entities which can be made detectable. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies. Heterologous polypeptides also include polypeptides that are useful as diagnostic or detectable markers, for example, luciferase, green fluorescent protein (GFP), or chloramphenicol acetyl transferase (CAT). Where the heterologous moiety is a polypeptide, the moiety can be incorporated into a fusion protein described herein, resulting in a fusion protein.

In embodiments, the detectable moiety is a radioactive label. In embodiments, the detectable moiety is an enzymatic label. In embodiments, the detectable moiety is a fluorescent label. In embodiments, the detectable moiety is a luminescent label. In embodiments, the detectable moiety is $^{32}$P. In embodiments, the detectable moiety is a fluorescent dye. In embodiments, the detectable moiety is an electron-dense reagent. In embodiments, the detectable moiety is an enzyme (e.g., as commonly used in an ELISA). In embodiments, the detectable moiety is biotin. In embodiments, the detectable moiety is digoxigenin. In embodiments, the detectable moiety is a paramagnetic molecule. In embodiments, the detectable moiety is a paramagnetic composition. In embodiments, the detectable moiety is a paramagnetic nanoparticle. In embodiments, the detectable moiety is an ultrasmall superparamagnetic iron oxide ("USPIO") nanoparticle. In embodiments, the detectable moiety is a USPIO nanoparticle aggregate. In embodiments, the detectable moiety is a superparamagnetic iron oxide ("SPIO") nanoparticle. In embodiments, the detectable moiety is an SPIO nanoparticle aggregate. In embodiments, the detectable moiety is a monochrystalline iron oxide nanoparticle. In embodiments, the detectable moiety is a monochrystalline iron oxide. In embodiments, the detectable moiety is a nanoparticle contrast agent. In embodiments, the detectable moiety is a liposome. In embodiments, the detectable moiety is a delivery vehicle including a Gadolinium chelate ("Gd-chelate") molecule. In embodiments, the detectable moiety is Gadolinium. In embodiments, the detectable moiety is a radioisotope. In embodiments, the detectable moiety is a radionuclide (e.g. carbon-11, nitrogen-13, oxygen-15, fluorine-18, or rubidium-82). In embodiments, the detectable moiety is fluorodeoxyglucose (e.g. fluorine-18 labeled). In embodiments, the detectable moiety is a gamma ray emitting radionuclide. In embodiments, the detectable moiety is a positron-emitting radionuclide. In embodiments, the detectable moiety is radiolabeled glucose. In embodiments, the detectable moiety is radiolabeled water. In embodiments, the detectable moiety is radiolabeled ammonia. In embodiments, the detectable moiety is a biocolloid. In embodiments, the detectable moiety is a microbubble (e.g. including a microbubble shell including albumin, galactose, lipid, and/or polymers; microbubble gas core including air, heavy gas(es), perfluorcarbon, nitrogen, octafluoropropane, perflexane lipid microsphere, or perflutren). In embodiments, the detectable moiety is an iodinated contrast agent (e.g. iohexol, iodixanol, ioversol, iopamidol, ioxilan, iopromide, diatrizoate, metrizoate, or ioxaglate). In embodiments, the detectable moiety is barium sulfate. In embodiments, the detectable moiety is thorium dioxide. In embodiments, the detectable moiety is gold. In embodiments, the detectable moiety is a gold nanoparticle. In embodiments, the detectable moiety is a gold nanoparticle aggregate. In embodiments, the detectable moiety is a fluorophore. In embodiments, the detectable moiety is a two-photon fluorophore. In embodiments, the detectable moiety is a hapten. In embodiments, the detectable moiety is a protein. In embodiments, the detectable moiety is an entity which can be made detectable. In embodiments, the heterologous polypeptide is an antigenic tag (e.g., FLAG, polyhistidine, hemagglutinin (HA), glutathione-S-transferase (GST), or maltose-binding protein (MBP)) for use in purifying the antibodies. In embodiments, the heterologous polypeptide is a diagnostic or detectable marker, for example, luciferase, green fluorescent protein (GFP), or chloramphenicol acetyl transferase (CAT).

In some embodiments, the conjugates described herein are created by linkage of two independently produced polypeptide fragments, e.g., an antibody, or antigen-binding fragment thereof (e.g., a Fab fragment of an anti-C3d antibody, or antigen-binding fragment thereof) and a complement modulator polypeptide (e.g., a soluble form of CD59) or detectable moiety. Two proteins (e.g., a fusion protein described herein and a heterologous moiety or the two constituent parts of a conjugate) can, in some embodiments, be chemically cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate). In some embodiments, one or more linkers as described herein may connect an antibody or antigen binding fragment thereof (e.g. anti-C3d antibody, anti-C3dg antibody, anti-iC3b antibody, or antigen binding fragment thereof, to a detectable moiety as described herein.

In some embodiments, a conjugate described herein can contain a heterologous moiety which is chemically linked to the protein (e.g. antibody or antigen-binding fragment thereof). For example, in some embodiments, a radioactive label can be directly conjugated to the amino acid backbone of the protein (e.g. antibody or antigen-binding fragment thereof) (e.g., for use of the labeled fusion protein for in vivo imaging studies).

In some embodiments, the proteins can be modified, e.g., with a moiety that improves the stabilization and/or retention of the antibodies in circulation, e.g., in blood, serum, or other tissues. For example, a protein described herein can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the polypeptide by at least 1.5 (e.g., at least 2, 5, 10, 15, 20, 25, 30, 40, or 50 or more) fold.

In some embodiments, the proteins described herein can be glycosylated. In some embodiments, a protein described herein can be subjected to enzymatic or chemical treatment, or produced from a cell, such that the antibody has reduced or absent glycosylation. Methods for producing polypeptides with reduced glycosylation are known in the art and described in, e.g., U.S. Pat. No. 6,933,368; Wright et al. (1991) EMBO J 10(10):2717-2723; and Co et al. (1993) *Mol Immunol* 30:1361.

In a first aspect is provided an antibody conjugate including an antibody, or antigen binding fragment thereof, and a detectable moiety.

In some embodiments, the antibody, or antigen binding fragment thereof, is selected from the group consisting of any of the antibodies or antigen binding fragments described herein (e.g. including aspects, embodiments, antibody compositions and uses section above, examples, tables, figures, claims). In some embodiments, the detectable moiety is selected from the group consisting of any of the detectable moieties or labels described herein (e.g. including aspects, embodiments, detectable moieties section above, examples, tables, figures, claims). In embodiments, the antibody, or antigen binding fragment thereof, includes at least one CDR described herein. In embodiments, the antibody, or antigen binding fragment thereof, includes six CDRs described herein. In embodiments, the antibody, or antigen binding fragment thereof, includes an amino acid sequence encoded by a nucleic acid described herein. In embodiments, the antibody, or antigen binding fragment thereof, includes an amino acid sequence described herein. In embodiments, the antibody conjugate includes an amino acid sequence encoded by a nucleic acid described herein. In embodiments, the antibody conjugate includes an amino acid sequence described herein. In embodiments, the antibody conjugate includes a linker joining the antibody, or antigen-binding fragment thereof, and the detectable moiety. In embodiments, the antibody conjugate does not includes a linker joining the antibody, or antigen-binding fragment thereof, and the detectable moiety. In embodiments of the antibody conjugate, the antibody, or antigen-binding fragment thereof, and the detectable moiety are joined by a covalent bond. In embodiments, the linker is a linker described herein.

In some embodiments, the antibody, or an antigen-binding fragment thereof, is selected from the group consisting of: a polyclonal antibody a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, a bispecific antibody or antibody fragment, a monovalent antibody or antibody fragment, single chain antibody, single chain Fv fragment (scFv), Fv, Fd fragment, Fab fragment, Fab' fragment, F(ab')$_2$ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, CDR-grafted antibody or antigen-binding fragment thereof, synthetic antibody or antigen-binding fragment thereof, semi-synthetic antibody or antigen-binding fragment thereof, phage-displayed antibody or antigen-binding fragment thereof, and antibody, or antigen-binding fragment thereof, identified with a repetitive backbone array (e.g. repetitive antigen display).

In some embodiments, the antibody, or antigen-binding fragment thereof, portion of the antibody conjugate includes an anti-C3d antibody or anti-C3dg antibody or anti-iC3b antibody, or antigen-binding fragment thereof, including any of the anti-C3d/C3dg antibodies or antigen-binding fragments thereof described herein, anti-C3d antibodies or antigen-binding fragments thereof described herein, anti-C3dg antibodies or antigen-binding fragments thereof described herein, or anti-iC3b antibodies or antigen-binding fragments thereof described herein. An "anti-C3d antibody-conjugate" or "anti-C3d antibody conjugate" is a conjugate or conjugate molecule (e.g. an antibody conjugate or antibody conjugate molecule) wherein the binding portion (e.g. antibody, or antigen-binding fragment thereof, of an antibody conjugate) is an anti-C3d antibody or anti-C3dg antibody or anti-iC3b antibody, or antigen-binding fragment thereof of any of these antibodies. In some embodiments, the anti-C3d antibody conjugate includes an antibody, or antigen binding fragment thereof, selected from the group consisting of any of the antibodies or antigen binding fragments described herein (e.g. including aspects, embodiments, antibody compositions and uses section above, examples, tables, figures, claims). In some embodiments, the anti-C3d antibody conjugate includes a detectable moiety selected from the group consisting of any of the detectable moieties or labels described herein (e.g. including aspects, embodiments, detectable moieties section above, examples, tables, figures, claims). In embodiments, the anti-C3d antibody-conjugate includes an antibody, or antigen binding fragment thereof, including at least one CDR described herein. In embodiments, the anti-C3d antibody-conjugate includes an antibody, or antigen binding fragment thereof, including six CDRs described herein. In embodiments, the anti-C3d antibody-conjugate includes an antibody, or antigen binding fragment thereof, including an amino acid sequence encoded by a nucleic acid described herein. In embodiments, the anti-C3d antibody-conjugate includes an antibody, or antigen binding fragment thereof, including an amino acid sequence described herein. In embodiments, the anti-C3d antibody-conjugate includes an amino acid sequence encoded by a nucleic acid described herein. In embodiments, the anti-C3d antibody-conjugate includes an amino acid sequence described herein. In embodiments, the anti-C3d antibody conjugate includes a linker joining the binding portion (e.g. an anti-C3d antibody or anti-C3dg antibody or anti-iC3b antibody, or antigen-binding fragment thereof of any of these antibodies) and the detectable moiety. In embodiments, the anti-C3d antibody conjugate does not include a linker joining the binding portion (e.g. an anti-C3d antibody or anti-C3dg antibody or anti-iC3b antibody, or antigen-binding fragment thereof of any of these antibodies) and the detectable moiety. In embodiments of the anti-C3d antibody conjugate, the binding portion (e.g. an anti-C3d antibody or anti-C3dg antibody or anti-iC3b antibody, or antigen-binding fragment thereof of any of these antibodies) and the detectable moiety are joined by a covalent bond. In embodiments, the linker is a linker described herein.

In some embodiments, the complement diagnostic portion is a compound, composition, or protein. In some embodiments, the complement diagnostic portion is any label or detectable moiety described herein. In some embodiments, the C3d binding portion (e.g. anti-C3d portion) binds C3d. In some embodiments, the C3d binding portion (e.g. anti-C3d portion) binds C3dg. In some embodiments, the C3d binding portion (e.g. anti-C3d portion) binds iC3b. In some embodiments, the C3d binding portion (e.g. anti-C3d portion) binds C3d and C3dg. In some embodiments, the C3d binding portion (e.g. anti-C3d portion) binds C3d, C3dg, and iC3b.

In some embodiments, an antibody or antigen-binding fragment thereof described herein and including all or a portion of an amino acid sequence selected from SEQ ID NO: 12-19, 22-29, and 34-37 or expressed from a nucleic acid sequence including all or a portion of a sequence selected from SEQ ID NO: 20, 21, 30, 31, and 33 (including any of the antibodies or antigen-binding fragments thereof described herein) is an anti-C3d antibody or antigen-binding fragment thereof, anti-C3dg antibody or antigen-binding fragment thereof, anti-C3d/C3dg antibody or antigen-binding fragment thereof, anti-iC3b antibody or antigen-binding fragment thereof, antibody or antigen-binding fragment described herein, antibody described herein or antigen-binding fragment thereof, fragment described herein, antibody or antigen-binding fragment thereof provided by the disclosure, antibody or antigen-binding fragment thereof that the disclosures comprises, anti-C3d antibody or anti-C3dg antibody or anti-iC3b antibody, antigen-binding fragment thereof provided by the present disclosure, antibody or fragment thereof, antibody which binds a binding partner selected from the group consisting of C3dg and C3d and iC3b or fragments of such antibody which retain the ability to bind to its respective binding partner that is a suitable targeting moiety, antibody of the present invention or fragment thereof which retain the ability to bind to their respective binding partner and are suitable targeting moieties, isolated antibody or antigen-binding fragment thereof, as these terms are used herein, or equivalent terms used herein to describe an antibody or antigen-binding fragment of the invention (e.g. as isolated compositions, included in a conjugate, included in an antibody conjugate).

SEQ ID NO: 12-21 are amino acid or nucleic acid sequences, as appropriate, of the mouse antibody 3d8b. SEQ ID NO: 22-31 are amino acid or nucleic acid sequences, as appropriate, of the mouse antibody 3d29. SEQ ID NO: 33-37 are amino acid or nucleic acid sequences, as appropriate, of the mouse antibody 3d16. SEQ ID NO: 32 is the amino acid sequence of a 3d scFv Crry fusion protein (e.g. a construct).

In some embodiments, a pharmaceutical composition includes an antibody or antigen-binding fragment thereof described herein and a pharmaceutically-acceptable excipient. In some embodiments, the antibody described herein is a monoclonal antibody. In some embodiments, the antibody described herein is the mAb 3d8b, produced by hybridoma cell line 3d-8b/2 (ATCC Deposit PTA-10999). In some embodiments, the antibody described herein is mAb 3d9a, produced by hybridoma cell line 3d-9a/25 (ATCC Deposit PTA-10998). In some embodiments, the antibody described herein is mAb 3d29, produced by hybridoma cell line 3d-29/5/2 (ATCC Deposit PTA-11000). In some embodiments, the antibody or antigen-binding fragment thereof described in the present disclosure includes, but is not limited to, any engineered or recombinant antibody or antigen-binding fragment thereof originating from mAb 3d8b, 3d9a, 3d29, or other mAb described in this disclosure, which can be easily screened or produced by standard methods well known in the art. Generally, all these antibodies or fragments originating from mAbs in this disclosure may be designed, screened, produced and/or tested to modify, without being limiting, their binding affinity, avidity, or cross-species activity to the C3d/C3dg protein and/or iC3b protein, selectivity over C3 or other C3 fragments, or their expression pattern and solubility, stability, half-life, cross-reactivity to other proteins/targets, or other inherent activities or characteristics of these antibodies or fragments, such as the effector activity.

Described herein is a hybridoma cell selected from the group consisting of: 3d-8b/2 (ATCC Deposit PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d-3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026).

In some embodiments, an antibody or antigen-binding fragment thereof described herein is produced by one of the above-listed hybridoma cells. In some embodiments, an antibody or antigen-binding fragment thereof described herein is a humanized, primatized, or chimerized antibody including the set of six (6) CDRs of any of the antibodies produced by any of the above-listed hybridomas.

In some embodiments, the present disclosure provides an isolated nucleic acid molecule encoding the antibody or antigen-binding fragment thereof described in this disclosure. In some embodiments, the isolated nucleic acid molecule includes a nucleic acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 or SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20 or SEQ ID NO:30 respectively). In some embodiments, the isolated nucleic acid molecule includes a nucleic acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 or SEQ ID NO:31 or SEQ ID NO:33, over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21 or SEQ ID NO:31 or SEQ ID NO:33 respectively). In some embodiments, the isolated nucleic acid molecule includes a nucleic acid sequence that hybridizes to the nucleic acid consisting of SEQ ID NO:20 or SEQ ID NO:30 under moderately stringent hybridization conditions. In some embodiments, the nucleic acid sequence hybridizes to the nucleic acid consisting of SEQ ID NO:20 or SEQ ID NO:30 under stringent hybridization conditions. In some embodiments, the isolated nucleic acid molecule includes a nucleic acid sequence that hybridizes to the nucleic acid consisting of SEQ ID NO:21 or SEQ ID NO:31 or SEQ ID NO:33 under moderately stringent hybridization conditions. In some embodiments, the nucleic acid sequence hybridizes to the nucleic acid consisting of SEQ ID NO:21 or SEQ ID NO:31 or SEQ ID NO:33 under stringent hybridization conditions.

In some embodiments, is provided a nucleic acid encoding a CDR having an amino acid sequence identical to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, SEQ ID NO:29, SEQ ID NO:35, SEQ ID NO:36, or SEQ ID NO:37. In some embodiments, is provided a nucleic acid encoding a CDR having an amino acid sequence having three or less (three, two, one, or zero) amino acid mutations when compared to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, SEQ ID NO:29, SEQ ID NO:35, SEQ ID NO:36, or SEQ ID NO:37. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a CDR having an amino acid sequence identical to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, or SEQ ID NO:29. In some embodiments, is provided a nucleic acid encoding a CDR having an amino acid sequence having three or less (three, two, one, or zero) amino acid mutations when compared to SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, or SEQ ID NO:29. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a light chain variable region CDR having an amino acid sequence identical to SEQ ID NO:14, SEQ ID NO:15, SEQ ID NO:16, SEQ ID NO:24, SEQ ID NO:25, or SEQ ID NO:26. In some embodiments, is provided a nucleic acid encoding a a light chain variable region CDR having an amino acid sequence having three or less (three, two, one, or zero) amino acid mutations when compared to SEQ ID NO:14, SEQ ID NO:15, SEQ ID NO:16, SEQ ID NO:24, SEQ ID NO:25, or SEQ ID NO:26. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a heavy chain variable region CDR having an amino acid sequence identical to SEQ ID NO:17, SEQ ID NO:18, SEQ ID NO:19, SEQ ID NO:27, SEQ ID NO:28, SEQ ID NO:29, SEQ ID NO:35, SEQ ID NO:36, or SEQ ID NO:37. In some embodiments, is provided a nucleic acid encoding a heavy chain variable region CDR having an amino acid sequence having three or less (three, two, one, or zero) amino acid mutations when compared to SEQ ID NO:17, SEQ ID NO:18, SEQ ID NO:19, SEQ ID NO:27, SEQ ID NO:28, SEQ ID NO:29, SEQ ID NO:35, SEQ ID NO:36, or SEQ ID NO:37. In some embodiments, the amino acid mutations are conservative and non-conservative. In some embodiments, the amino acid mutations are conservative. In some embodiments, the amino acid mutations are non-conservative.

In some embodiments, is provided a nucleic acid encoding a heavy chain variable region CDR having an amino acid sequence identical to SEQ ID NO:17, SEQ ID NO:18, SEQ ID NO:19, SEQ ID NO:27, SEQ ID NO:28, or SEQ ID NO:29. In some embodiments, is provided a nucleic acid encoding a heavy chain variable region CDR having an amino acid sequence having three or less (three, two, one, or zero) amino acid mutations when compared to SEQ ID NO:17, SEQ ID NO:18, SEQ ID NO:19, SEQ ID NO:27, SEQ ID NO:28, or SEQ ID NO:29. In some embodiments, the amino acid mutations are conservative and non-conservative. In some embodiments, the amino acid mutations are conservative. In some embodiments, the amino acid mutations are non-conservative.

In another embodiment, the present disclosure provides a vector containing the nucleic acid sequence of an antibody, or antigen-binding fragment thereof, or CDR described herein. Such vector includes, but is not limited to, a plasmid vector, a cosmid vector, a viral vector, a shuttle vector, or any vector well known in the art for expression in prokaryotic or eukaryotic cells.

In another embodiment, the present disclosure provides a cell containing a vector containing the nucleic acid sequence of an isolated nucleic acid encoding an antibody, or antigen-binding fragment thereof, or CDR described herein. Such cell includes, for example, a prokaryotic cell or a eukaryotic cell.

In another embodiment, the disclosure features: (a) a nucleic acid encoding any one of the antibodies, antigen-binding fragments, or CDRs or constructs (e.g. conjugates, anti-C3d antibody-conjugates) described herein; (b) a vector (e.g., an expression vector) including the nucleic acid; and (c) a cell (e.g., a bacterial, plant, fungal, insect, or mammalian cell) including the vector or expression vector.

In yet another embodiment, the disclosure features a method for producing an antibody, an antigen-binding fragment of the antibody, or a CDR, or a construct (e.g. conjugates, anti-C3d antibody-conjugates) described herein. The method includes culturing the aforementioned cell under conditions suitable to allow for expression of the antibody, fragment, or construct (e.g. conjugates, anti-C3d antibody-conjugates) by the cell. The method can optionally include purifying the antibody, fragment, or construct from the cell or from the media in which the cell is cultured.

In some embodiments, the present disclosure provides a pharmaceutical composition including any of the isolated antibodies or antigen-binding fragments thereof described in this disclosure. In some embodiments, the present disclosure provides a pharmaceutical composition including a nucleic acid encoding an antibody or antigen-binding fragment thereof described in this disclosure. In some embodiments, the present disclosure provides a pharmaceutical composition including a vector containing the nucleic acid sequence of an isolated nucleic acid encoding the antibody or antigen-binding fragment thereof described in this disclosure. In some embodiments, the present disclosure provides a pharmaceutical composition including a cell containing such vector described herein. In some embodiments, the present disclosure provides a pharmaceutical composition including any of the constructs described in this disclosure. In some embodiments, the present disclosure provides a pharmaceutical composition including a conjugate described in this disclosure. In some embodiments, the present disclosure provides a pharmaceutical composition including any of the antibody conjugates described in this disclosure. In some embodiments, the present disclosure provides a pharmaceutical composition including any of the anti-C3d antibody conjugates described in this disclosure. In some embodiments, the pharmaceutical compositions include a pharmaceutically acceptable excipient.

In some embodiments, the present disclosure provides a pharmaceutical composition including any of the isolated antibodies or antigen-binding fragments thereof described in this disclosure and a therapeutically acceptable excipient. Suitable excipients are well known in the art and recited herein.

The present inventors have found that targeting of diagnostic agents or detectable moieties to particular epitopes present on the C3d and/or C3dg and/or iC3b fragment of complement is surprisingly effective in terms of localizing diagnostic agents such that they can exert optimal effects at tissue or cells which are the site of complement activation. Thus, the present inventors have isolated antibodies which bind to the C3d and/or C3dg and/or iC3b fragment of complement and used them for the targeting of diagnostic agents and detectable moieties.

In some embodiments, the disclosure features an antibody, or antigen-binding fragment thereof, that binds to an epitope in the human C3d protein. In some embodiments, the disclosure features an antibody, or antigen-binding fragment thereof, that binds to an epitope in the human C3dg protein. In some embodiments, the disclosure features an antibody, or antigen-binding fragment thereof, that binds to an epitope in the human iC3b protein. For example, the anti-C3d antibody or anti-C3dg antibody or anti-iC3b antibody can bind to an epitope within, or overlapping with, an antigenic peptide fragment of a human complement component C3d protein, or to an epitope in the human complement component C3dg protein, or to an epitope in the human complement component iC3b protein. In some embodiments, these anti-C3d antibodies or anti-C3dg antibodies or anti-iC3b antibody are monoclonal antibodies or antibody fragments maintaining the antigen-binding activity. In some embodiments, these monoclonal antibodies include those produced by hybridoma cells 3d-8b/2 (ATCC Deposit number: PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026). In some embodiments, the present disclosure provides antibodies, or antigen-binding fragments thereof, that bind to an epitope within, or overlapping with, an epitope recognized by any one of antibodies 3d8b, 3d9a, 3d29, 3d11, 3d31, 3d3, 3d15, 3d10, and 3d16. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, do not compete with at least one of antibodies 3d8b, 3d9a, 3d29, 3d11, 3d31, 3d3, 3d15, 3d10, and 3d16 for binding to C3d or C3dg or iC3b. In some embodiments, these antibodies, or antigen-binding fragments thereof, which bind to an epitope within, or overlapping with, an epitope recognized by at least one of antibodies 3d8b, 3d9a, 3d29, 3d11, 3d31, 3d3, 3d15, 3d10, and 3d16, compete with at least one (e.g. 1, 2, 3, 4, 5, 6, 7, 8, or 9) of antibodies including 3d8b, 3d9a, 3d29, 3d11, 3d31, 3d3, 3d15, 3d10, and 3d16 for binding to C3d or C3dg or iC3b. In some embodiments, these antibodies, or antigen-binding fragments thereof, which bind to an epitope within, or overlapping with, an epitope recognized by any one of antibodies 3d8b, 3d9a, 3d29, 3d11, 3d31, 3d3, 3d15, 3d10, and 3d16, inhibit at least one of antibodies 3d8b, 3d9a, 3d29, 3d11, 3d31, 3d3, 3d15, 3d10, and 3d16 from binding to C3d or C3dg or iC3b. In some embodiments, an antibody, or antigen binding fragment thereof, is an scFv. In some embodiments, the scFv is derived from any one of the antibodies 3d8b, 3d9a, 3d29, 3d11, 3d31, 3d3, 3d15, 3d10, and 3d16 (a 3d scFv). In some embodiments the scFv is a 3d8b scFv. In some embodiments, the scFv is a 3d29 scFv.

In some embodiments, the anti-C3d antibody or anti-C3dg antibody or anti-iC3b antibody, or antigen-binding fragment thereof, provided in the present disclosure can crossblock binding of another antibody or binding partner that binds to an epitope within, or overlapping with, a human complement component C3d or C3dg protein or iC3b protein. In some embodiments, the anti-C3d antibody or anti-C3dg antibody or anti-iC3b antibody, or antigen-binding fragment thereof, can crossblock binding of an antibody that binds to an epitope within, or overlapping with, a peptide fragment of a human complement component C3d protein or C3dg protein or iC3b protein.

In embodiments, are antibody-targeted nanoparticle contrast agents for non-invasive medical or diagnostic imaging applications. In certain embodiments, the antibody-targeted nanoparticle contrast agent compositions include USPIO nanoparticles or aggregates thereof. In certain embodiments, the antibody-targeted nanoparticle contrast agent compositions include antibody-targeted liposomes or other antibody-targeted delivery vehicles containing Gadolinium chelate ("Gd-chelate") molecules. Antibody-targeted nanoparticle contrast agents or compositions and antibody targeted ultrasmall super paramagnetic iron oxide ("USPIO") nanoparticles or aggregates are examples of antibody conjugates.

In another embodiment, provided herein are articles of manufacture or kits containing diagnostic compositions including an effective amount of any of the targeted diagnostic agent moieties (e.g. constructs, conjugates, anti-C3d antibody-conjugates) and instructions for their use in the methods described herein. Thus, in some embodiments, the article of manufacture includes instructions for the use of diagnostic compositions including an effective amount of a anti-C3d antibody-conjugate including a monoclonal antibody which binds to a binding partner selected from C3d and C3dg and iC3b, joined to a detectable moiety. The diagnostic compositions may further include one or more pharmaceutically acceptable excipients formulated for administration to an individual as described herein. The kit may further include means for administration, such as a syringe, inhaler or other device useful for systemic administration or local administration.

In yet another embodiment, the disclosure features an article of manufacture including: a container including a label; and a composition including any of the constructs (e.g. conjugates, anti-C3d antibody-conjugates) described herein, wherein the label indicates that the composition is to be administered to a human having, suspected of having, or at risk for developing, a complement-associated disorder, disease, or condition. The article of manufacture can include one or more additional agents.

In embodiments, is a diagnostic or monitoring kit including: (i) any of the antibodies or antigen-binding fragments thereof described herein and (ii) means for delivering the antibody or antigen-binding fragment to a human; or (ii) any of the constructs (e.g. conjugates, anti-C3d antibody-conjugates) described herein and (iv) means for delivering the construct to a human. The means can be suitable for subcutaneous delivery of the construct (e.g. conjugates, anti-C3d antibody-conjugates) to the human. The means can be suitable for intraocular delivery of the construct (e.g. conjugates, anti-C3d antibody-conjugates) to the human. The means can be suitable for intraarticular delivery of the construct (e.g. conjugates, anti-C3d antibody-conjugates) to the human.

In some of the embodiments described herein, the composition administered to the individual is a pharmaceutical composition including any of the antibody-targeted USPIO nanoparticle compositions described herein. In some of the embodiments described herein, the composition administered to the individual is a pharmaceutical composition including any of the antibody-targeted USPIO nanoparticle aggregate compositions described herein.

In some embodiments, the antibody conjugate is an anti-C3d antibody conjugate. In some embodiments, the anti-C3d antibody conjugate includes an anti-C3d antibody, or antigen binding fragment thereof. In some embodiments, the anti-C3d antibody conjugate includes an anti-C3dg antibody, or antigen binding fragment thereof. In some embodiments, the anti-C3d antibody conjugate includes an anti-iC3b antibody, or antigen binding fragment thereof. In embodiments, the anti-C3d antibody conjugate includes a linker joining the binding portion (e.g. an anti-C3d antibody or anti-C3dg antibody or anti-iC3b antibody, or antigen-binding fragment thereof of any of these antibodies) and the detectable moiety. In embodiments, the anti-C3d antibody conjugate does not includes a linker joining the binding portion (e.g. an anti-C3d antibody or anti-C3dg antibody or anti-iC3b antibody, or antigen-binding fragment thereof of any of these antibodies) and the detectable moiety. In embodiments of the anti-C3d antibody conjugate, the binding portion (e.g. an anti-C3d antibody or anti-C3dg antibody or anti-iC3b antibody, or antigen-binding fragment thereof of any of these antibodies) and the detectable moiety are joined by a covalent bond. In embodiments, the linker is a linker described herein.

In some embodiments, the anti-C3d antibody conjugate includes an antibody or an antigen-binding fragment thereof including light chain complementarity determining regions (CDR) 1, 2 and 3, wherein light chain CDR 1 is SEQ ID NO:14 including three or less amino acid mutations (e.g. 3, 2, 1, or 0) or SEQ ID NO:24 including three or less amino acid mutations (e.g. 3, 2, 1, or 0), light chain CDR 2 is SEQ ID NO:15 including three or less amino acid mutations (e.g. 3, 2, 1, or 0) or SEQ ID NO:25 including three or less amino acid mutations (e.g. 3, 2, 1, or 0) and light chain CDR 3 is SEQ ID NO:16 including three or less amino acid mutations (e.g. 3, 2, 1, or 0) or SEQ ID NO:26 including three or less amino acid mutations (e.g. 3, 2, 1, or 0); or heavy chain complementarity determining regions (CDR) 1, 2 and 3, wherein heavy chain CDR 1 is SEQ ID NO:17 including three or less amino acid mutations (e.g. 3, 2, 1, or 0) or SEQ ID NO:27 including three or less amino acid mutations (e.g. 3, 2, 1, or 0) or SEQ ID NO:35 including three or less amino acid mutations (e.g. 3, 2, 1, or 0), heavy chain CDR 2 is SEQ ID NO:18 including three or less amino acid mutations (e.g. 3, 2, 1, or 0) or SEQ ID NO:28 including three or less amino acid mutations (e.g. 3, 2, 1, or 0) or SEQ ID NO:36 including three or less amino acid mutations (e.g. 3, 2, 1, or 0) and heavy chain CDR 3 is SEQ ID NO:19 including three or less amino acid mutations (e.g. 3, 2, 1, or 0) or SEQ ID NO:29 including three or less amino acid mutations (e.g. 3, 2, 1, or 0) or SEQ ID NO:37 including three or less amino acid mutations (e.g. 3, 2, 1, or 0). In some embodiments, the mutations are non-conservative and/or conservative amino acid substitutions. In some embodiments, the mutations are conservative amino acid substitutions. In some embodiments, the mutations are non-conservative amino acid substitutions.

In some embodiments, the anti-C3d antibody conjugate includes an antibody or antigen-binding fragment thereof including light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; or heavy chain complementarity determining regions (CDR) 1, 2 and 3, wherein heavy chain CDR 1 is SEQ ID NO:17 or SEQ ID NO:27 or SEQ ID NO:35, heavy chain CDR 2 is SEQ ID NO:18 or SEQ ID NO:28 or SEQ ID NO:36 and heavy chain CDR 3 is SEQ ID NO:19 or SEQ ID NO:29 or SEQ ID NO:37. In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; or heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or SEQ ID NO:29.

In some embodiments, the anti-C3d antibody conjugate comprises an antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; and heavy chain complementarity determining regions (CDR) 1, 2 and 3, wherein heavy chain CDR 1 is SEQ ID NO:17 or SEQ ID NO:27 or SEQ ID NO:35, heavy chain CDR 2 is SEQ ID NO:18 or SEQ ID NO:28 or SEQ ID NO:36 and heavy chain CDR 3 is SEQ ID NO:19 or SEQ ID NO:29 or SEQ ID NO:37. In some embodiments, the antibody or antigen-binding fragment thereof includes light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or SEQ ID NO:26; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or SEQ ID NO:29.

In some embodiments of the anti-C3d antibody conjugate the antibody or antigen-binding fragment thereof, light chain CDR 1 is SEQ ID NO:14 including three or less amino acid mutations (e.g. 3, 2, 1, or 0), light chain CDR 2 is SEQ ID NO:15 including three or less amino acid mutations (e.g. 3, 2, 1, or 0), light chain CDR 3 is SEQ ID NO:16 including three or less amino acid mutations (e.g. 3, 2, 1, or 0), heavy chain CDR 1 is SEQ ID NO:17 including three or less amino acid mutations (e.g. 3, 2, 1, or 0), heavy chain CDR 2 is SEQ ID NO:18 including three or less amino acid mutations (e.g. 3, 2, 1, or 0), and heavy chain CDR 3 is SEQ ID NO:19 including three or less amino acid mutations (e.g. 3, 2, 1, or 0). In some embodiments of the antibody or antigen-binding fragment thereof, light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19.

In some embodiments of the anti-C3d antibody conjugate the antibody or antigen-binding fragment thereof, light chain CDR 1 is SEQ ID NO:14 including three or less amino acid mutations (e.g. 3, 2, 1, or 0), light chain CDR 2 is SEQ ID NO:15 including three or less amino acid mutations (e.g. 3, 2, 1, or 0), and light chain CDR 3 is SEQ ID NO:16 including three or less amino acid mutations (e.g. 3, 2, 1, or 0); or heavy chain CDR 1 is SEQ ID NO:17 including three or less amino acid mutations (e.g. 3, 2, 1, or 0), heavy chain CDR 2 is SEQ ID NO:18 including three or less amino acid mutations (e.g. 3, 2, 1, or 0), and heavy chain CDR 3 is SEQ ID NO:19 including three or less amino acid mutations (e.g. 3, 2, 1, or 0). In some embodiments of the antibody or antigen-binding fragment thereof, light chain CDR 1 is SEQ ID NO:14, light chain CDR 2 is SEQ ID NO:15, and light chain CDR 3 is SEQ ID NO:16; or heavy chain CDR 1 is SEQ ID NO:17, heavy chain CDR 2 is SEQ ID NO:18, and heavy chain CDR 3 is SEQ ID NO:19.

In some embodiments of the anti-C3d antibody conjugate the antibody or antigen-binding fragment thereof, light chain CDR 1 is SEQ ID NO:24 including three or less amino acid mutations (e.g. 3, 2, 1, or 0), light chain CDR 2 is SEQ ID NO:25 including three or less amino acid mutations (e.g. 3, 2, 1, or 0), light chain CDR 3 is SEQ ID NO:26 including three or less amino acid mutations (e.g. 3, 2, 1, or 0), heavy chain CDR 1 is SEQ ID NO:27 including three or less amino acid mutations (e.g. 3, 2, 1, or 0), heavy chain CDR 2 is SEQ ID NO:28 including three or less amino acid mutations (e.g. 3, 2, 1, or 0), and heavy chain CDR 3 is SEQ ID NO:29 including three or less amino acid mutations (e.g. 3, 2, 1, or 0). In some embodiments of the antibody or antigen-binding fragment thereof, light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29.

In some embodiments of the anti-C3d antibody conjugate the antibody or antigen-binding fragment thereof, light chain CDR 1 is SEQ ID NO:24 including three or less amino acid mutations (e.g. 3, 2, 1, or 0), light chain CDR 2 is SEQ ID NO:25 including three or less amino acid mutations (e.g. 3, 2, 1, or 0), and light chain CDR 3 is SEQ ID NO:26 including three or less amino acid mutations (e.g. 3, 2, 1, or 0); or heavy chain CDR 1 is SEQ ID NO:27 including three or less amino acid mutations (e.g. 3, 2, 1, or 0), heavy chain CDR 2 is SEQ ID NO:28 including three or less amino acid mutations (e.g. 3, 2, 1, or 0), and heavy chain CDR 3 is SEQ ID NO:29 including three or less amino acid mutations (e.g. 3, 2, 1, or 0). In some embodiments of the antibody or antigen-binding fragment thereof, light chain CDR 1 is SEQ ID NO:24, light chain CDR 2 is SEQ ID NO:25, and light chain CDR 3 is SEQ ID NO:26; or heavy chain CDR 1 is SEQ ID NO:27, heavy chain CDR 2 is SEQ ID NO:28, and heavy chain CDR 3 is SEQ ID NO:29. *add 35, 36, 37 with mutations and without In some embodiments of the anti-C3d antibody conjugate the antibody or an antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; or a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23 or SEQ ID NO:34. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23 or SEQ ID NO:34.

In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; or a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12 or SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13 or SEQ ID NO:23.

In some embodiments of the anti-C3d antibody conjugate the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13. In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:22. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:23. In some embodiments, the antibody or antigen-binding fragment thereof includes a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:34.

In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:12; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:13.

In some embodiments, the antibody or antigen-binding fragment thereof includes a light chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:22; and a heavy chain variable region amino acid sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:23.

In some embodiments of the anti-C3d antibody conjugate the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 or SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20 or SEQ ID NO:30 respectively). In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20). In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 30).

In some embodiments of the anti-C3d antibody conjugate the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 or SEQ ID NO:31 or SEQ ID NO:33, over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21 or SEQ ID NO:31 or SEQ ID NO:33 respectively). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:31 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 31). In some embodiments, the antibody or antigen-binding fragment thereof includes a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:33 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 33).

In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:20 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 20) and a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:21 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 21). In some embodiments, the antibody or antigen-binding fragment thereof includes a light chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:30 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 30) and a heavy chain variable region amino acid sequence expressed from a nucleic acid sequence including a sequence at least 60% (e.g. 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) identical to SEQ ID NO:31 over a continuous nucleic acid sequence of at least 20 nucleotides (e.g. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150 nucleotides or over all of SEQ ID NO: 31).

In some embodiments of the anti-C3d antibody conjugate the antibody or antigen-binding fragment thereof includes a light chain variable region amino acid sequence expressed from a nucleic acid sequence that hybridizes to the nucleic acid consisting of SEQ ID NO:20 or SEQ ID NO:30 under moderately stringent hybridization conditions. In some embodiments, the nucleic acid sequence hybridizes to the nucleic acid consisting of SEQ ID NO:20 or SEQ ID NO:30 under stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:20 under moderately stringent hybridization conditions. In some embodiments, the nucleic acid sequence hybridizes to the nucleic acid consisting of SEQ ID NO:20 under stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:30 under moderately stringent hybridization conditions. In some embodiments, the nucleic acid sequence hybridizes to the nucleic acid consisting of SEQ ID NO:30 under stringent hybridization conditions.

In some embodiments of the anti-C3d antibody conjugate the antibody or antigen-binding fragment thereof includes a heavy chain variable region amino acid sequence expressed from a nucleic acid sequence that hybridizes to the nucleic acid consisting of SEQ ID NO:21 or SEQ ID NO:31 or SEQ ID NO:33 under moderately stringent hybridization conditions. In some embodiments, the nucleic acid sequence hybridizes to the nucleic acid consisting of SEQ ID NO:21 or SEQ ID NO:31 or SEQ ID NO:33 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:21 under moderately stringent hybridization conditions. In some embodiments, the nucleic acid sequence hybridizes to the nucleic acid consisting of SEQ ID NO:21 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:31 under moderately stringent hybridization conditions. In some embodiments, the nucleic acid sequence hybridizes to the nucleic acid consisting of SEQ ID NO:31 under stringent hybridization conditions. In some embodiments, the antibody or antigen-binding fragment thereof includes a heavy chain variable region amino acid sequence expressed from a nucleic acid sequence that hybridizes to the nucleic acid consisting of SEQ ID NO:33 under moderately stringent hybridization conditions. In some embodiments, the nucleic acid sequence hybridizes to the nucleic acid consisting of SEQ ID NO:33 under stringent hybridization conditions.

In some embodiments, the antibody or antigen-binding fragment thereof includes a light chain variable region amino acid sequence expressed from a nucleic acid sequence that hybridizes to the nucleic acid consisting of SEQ ID NO:20 under moderately stringent hybridization conditions and a heavy chain variable region amino acid sequence expressed from a nucleic acid sequence that hybridizes to the nucleic acid consisting of SEQ ID NO:21 under moderately stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:20 under stringent hybridization conditions and a heavy chain variable region amino acid sequence expressed from a nucleic acid sequence that hybridizes to the nucleic acid consisting of SEQ ID NO:21 under stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:30 under moderately stringent hybridization conditions and a heavy chain variable region amino acid sequence expressed from a nucleic acid sequence that hybridizes to the nucleic acid consisting of SEQ ID NO:31 under moderately stringent hybridization conditions. In some embodiments, the antibody or antigen-binding fragment thereof includes a light chain variable region amino acid sequence expressed from a nucleic acid sequence that hybridizes to the nucleic acid consisting of SEQ ID NO:30 under stringent hybridization conditions and a heavy chain variable region amino acid sequence expressed from a nucleic acid sequence that hybridizes to the nucleic acid consisting of SEQ ID NO:31 under stringent hybridization conditions.

In some embodiments of the anti-C3d antibody conjugate the antibody or antigen-binding fragment thereof includes one or more (e.g. one, two, three, four, five, or six) CDRs encoded by the nucleic acid sequences of SEQ ID NO:20, SEQ ID NO:21, SEQ ID NO:30, or SEQ ID NO:31, having six or less (six, five, four, three, two, one, or zero) nucleotide mutations in the nucleic acid sequences encoding the one or more CDRs (e.g. one, two, three, four, five, or six). In some embodiment, the antibody or antigen-binding fragment thereof includes one or more (e.g. one, two, three, four, five, or six) CDRs encoded by the nucleic acid sequences of SEQ ID NO:20, SEQ ID NO:21, SEQ ID NO:30, or SEQ ID NO:31. In some embodiment, the antibody or antigen-binding fragment thereof includes one or more (e.g. one, two, three, four, five, or six) CDRs encoded by the CDR nucleic acid sequences of SEQ ID NO:20, SEQ ID NO:21, SEQ ID NO:30, or SEQ ID NO:31.

In some embodiments of the anti-C3d antibody conjugate the antibody or antigen-binding fragment thereof includes one or more (e.g. one, two, or three) light chain variable region CDRs encoded by the nucleic acid sequences of SEQ ID NO:20 or SEQ ID NO:30, having six or less (six, five, four, three, two, one, or zero) nucleotide mutations in the nucleic acid sequences encoding the one or more CDRs (e.g. one, two, or three). In some embodiment, the antibody or antigen-binding fragment thereof includes one or more (e.g. one, two, or three) light chain variable region CDRs encoded by the nucleic acid sequences of SEQ ID NO:20 or SEQ ID NO:30. In some embodiment, the antibody or antigen-binding fragment thereof includes one or more (e.g. one, two, or three) light chain variable region CDRs encoded by the CDR nucleic acid sequences of SEQ ID NO:20 or SEQ ID NO:30.

In some embodiments of the anti-C3d antibody conjugate the antibody or antigen-binding fragment thereof includes one or more (e.g. one, two, or three) heavy chain variable region CDRs encoded by the nucleic acid sequences of SEQ ID NO:21 or SEQ ID NO:31 or SEQ ID NO:33, having six or less (six, five, four, three, two, one, or zero) nucleotide mutations in the nucleic acid sequences encoding the one or more CDRs (e.g. one, two, or three). In some embodiment, the antibody or antigen-binding fragment thereof includes one or more (e.g. one, two, or three) heavy chain variable region CDRs encoded by the nucleic acid sequences of SEQ ID NO:21 or SEQ ID NO:31 or SEQ ID NO:33. In some embodiment, the antibody or antigen-binding fragment thereof includes one or more (e.g. one, two, or three) heavy chain variable region CDRs encoded by the CDR nucleic acid sequences of SEQ ID NO:21 or SEQ ID NO:31 or SEQ ID NO:33.

In some embodiments of the anti-C3d antibody conjugate the antibody or antigen-binding fragment thereof includes one or more (e.g. one, two, or three) heavy chain variable region CDRs encoded by the nucleic acid sequences of SEQ ID NO:21 or SEQ ID NO:31, having six or less (six, five, four, three, two, one, or zero) nucleotide mutations in the nucleic acid sequences encoding the one or more CDRs (e.g. one, two, or three). In some embodiment, the antibody or antigen-binding fragment thereof includes one or more (e.g. one, two, or three) heavy chain variable region CDRs encoded by the nucleic acid sequences of SEQ ID NO:21 or SEQ ID NO:31. In some embodiment, the antibody or antigen-binding fragment thereof includes one or more (e.g. one, two, or three) heavy chain variable region CDRs encoded by the CDR nucleic acid sequences of SEQ ID NO:21 or SEQ ID NO:31.

In some embodiments, the anti-C3d antibody conjugate includes a detectable moiety and light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or 26; or heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or 29. In some embodiments, the anti-C3d antibody conjugate includes a detectable moiety and light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or 26; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or 29.

In some embodiments of the anti-C3d antibody conjugate, light chain CDR 1 is SEQ ID NO:14, light chain CDR 2 is SEQ ID NO:15, and light chain CDR 3 is SEQ ID NO:16; or heavy chain CDR 1 is SEQ ID NO:17, heavy chain CDR 2 is SEQ ID NO:18, and heavy chain CDR 3 is SEQ ID NO:19.

In some embodiments of the anti-C3d antibody conjugate, light chain CDR 1 is SEQ ID NO:24, light chain CDR 2 is SEQ ID NO:25, and light chain CDR 3 is SEQ ID NO:26; or heavy chain CDR 1 is SEQ ID NO:27, heavy chain CDR 2 is SEQ ID NO:28, and heavy chain CDR 3 is SEQ ID NO:29.

In some embodiments of the anti-C3d antibody conjugate, light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19. In some embodiments of the anti-C3d antibody conjugate, light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29.

In some embodiments of the anti-C3d antibody conjugate, heavy chain CDR 1 is SEQ ID NO:35, heavy chain CDR 2 is SEQ ID NO:36, and heavy chain CDR 3 is SEQ ID NO:37.

In some embodiments, the anti-C3d antibody conjugate includes a detectable moiety and a light chain variable region amino acid sequence 90% identical to SEQ ID NO:12 or SEQ ID NO:22; or a heavy chain variable region amino acid sequence 90% identical to SEQ ID NO:13 or SEQ ID NO:23. In some embodiments, the anti-C3d antibody conjugate includes a light chain variable region amino acid sequence 90% identical to SEQ ID NO:12 or SEQ ID NO:22; and a heavy chain variable region amino acid sequence 90% identical to SEQ ID NO:13 or SEQ ID NO:23. In some embodiments, the anti-C3d antibody conjugate includes a light chain variable region amino acid sequence 90% identical to SEQ ID NO:12; and a heavy chain variable region amino acid sequence 90% identical to SEQ ID NO:13. In some embodiments, the anti-C3d antibody conjugate includes a light chain variable region amino acid sequence 90% identical to SEQ ID NO:22; and a heavy chain variable region amino acid sequence 90% identical to SEQ ID NO:23.

In some embodiments, the anti-C3d antibody conjugate includes a detectable moiety and a light chain variable region amino acid sequence 90% identical to SEQ ID NO:12 or SEQ ID NO:22; or a heavy chain variable region amino acid sequence 90% identical to SEQ ID NO:13 or SEQ ID NO:23 or SEQ ID NO:33. In some embodiments, the anti-C3d antibody conjugate includes a light chain variable region amino acid sequence 90% identical to SEQ ID NO:12 or SEQ ID NO:22; and a heavy chain variable region amino acid sequence 90% identical to SEQ ID NO:13 or SEQ ID NO:23 or SEQ ID NO:33.

In some embodiments, the anti-C3d antibody conjugate includes a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, single chain antibody, single chain Fv fragment (scFv), Fd fragment, Fab fragment, Fab' fragment, F(ab')2 fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, phage-displayed antibody or antigen-binding fragment thereof, or antibody, or antigen-binding fragment thereof, identified with a repetitive backbone array (e.g. repetitive antigen display). In some embodiments, the anti-C3d antibody conjugate includes a humanized antibody, or an antigen-binding fragment thereof. In some embodiments, the anti-C3d antibody conjugate includes a monoclonal antibody, or an antigen-binding fragment thereof. In some embodiments of the anti-C3d antibody conjugate, the antibody, or antigen-binding fragment thereof, preferentially binds iC3b, C3d or C3dg with at least 10 fold greater affinity than uncleaved C3. In some embodiments of the anti-C3d antibody conjugate, the antibody, or antigen-binding fragment thereof, preferentially binds iC3b, C3d or C3dg with at least 100 fold greater affinity than uncleaved C3.

In some embodiments of the anti-C3d antibody conjugate, the detectable moiety is selected from the group consisting of $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

In some embodiments of the anti-C3d antibody conjugate, the detectable moiety is $^{32}$P. In some embodiments of the anti-C3d antibody conjugate, the detectable moiety is a fluorescent dye. In some embodiments of the anti-C3d antibody conjugate, the detectable moiety is an electron-dense reagents. In some embodiments of the anti-C3d antibody conjugate, the detectable moiety is an enzyme (e.g., as commonly used in an ELISA). In some embodiments of the anti-C3d antibody conjugate, the detectable moiety is biotin. In some embodiments of the anti-C3d antibody conjugate, the detectable moiety is digoxigenin. In some embodiments of the anti-C3d antibody conjugate, the detectable moiety is a paramagnetic molecule. In some embodiments of the anti-C3d antibody conjugate, the detectable moiety is a paramagnetic nanoparticle. In some embodiments of the anti-C3d antibody conjugate, the detectable moiety is an ultrasmall superparamagnetic iron oxide ("USPIO") nanoparticle. In some embodiments of the anti-C3d antibody conjugate, the detectable moiety is a USPIO nanoparticle aggregate. In some embodiments of the anti-C3d antibody conjugate, the detectable moiety is a superparamagnetic iron oxide ("SPIO") nanoparticle. In some embodiments of the anti-C3d antibody conjugate, the detectable moiety is an SPIO nanoparticle aggregate. In some embodiments of the anti-C3d antibody conjugate, the detectable moiety is a monochrystalline iron oxide nanoparticle. In some embodiments of the anti-C3d antibody conjugate, the detectable moiety is a monochrystalline iron oxide. In some embodiments of the anti-C3d antibody conjugate, the detectable moiety is another nanoparticle contrast agent. In some embodiments of the anti-C3d antibody conjugate, the detectable moiety is a liposome or other delivery vehicle containing Gadolinium chelate ("Gd-chelate") molecules. In some embodiments of the anti-C3d antibody conjugate, the detectable moiety is Gadolinium. In some embodiments of the anti-C3d antibody conjugate, the detectable moiety is a radioisotope. In some embodiments of the anti-C3d antibody conjugate, the detectable moiety is a radionuclide (e.g. carbon-11, nitrogen-13, oxygen-15, fluorine-18, or rubidium-82). In some embodiments of the anti-C3d antibody conjugate, the detectable moiety is fluorodeoxyglucose (e.g. fluorine-18 labeled). In some embodiments of the anti-C3d antibody conjugate, the detectable moiety is any gamma ray emitting radionuclide. In some embodiments of the anti-C3d antibody conjugate, the detectable moiety is a positron-emitting radionuclide. In some embodiments of the anti-C3d antibody conjugate, the detectable moiety is radiolabeled glucose. In some embodiments of the anti-C3d antibody conjugate, the detectable moiety is radiolabeled water. In some embodiments of the anti-C3d antibody conjugate, the detectable moiety is radiolabeled ammonia. In some embodiments of the anti-C3d antibody conjugate, the detectable moiety is a biocolloid. In some embodiments of the anti-C3d antibody conjugate, the detectable moiety is a microbubble (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.). In some embodiments of the anti-C3d antibody conjugate, the detectable moiety is an iodinated contrast agent (e.g. iohexol, iodixanol, ioversol, iopamidol, ioxilan, iopromide, diatrizoate, metrizoate, ioxaglate). In some embodiments of the anti-C3d antibody conjugate, the detectable moiety is barium sulfate. In some embodiments of the anti-C3d antibody conjugate, the detectable moiety is thorium dioxide. In some embodiments of the anti-C3d antibody conjugate, the detectable moiety is gold. In some embodiments of the anti-C3d antibody conjugate, the detectable moiety is a gold nanoparticle. In some embodiments of the anti-C3d antibody conjugate, the detectable moiety is a gold nanoparticle aggregate. In some embodiments of the anti-C3d antibody conjugate, the detectable moiety is a fluorophore. In some embodiments of the anti-C3d antibody conjugate, the detectable moiety is a two-photon fluorophore. In some embodiments of the anti-C3d antibody conjugate, the detectable moiety is a hapten. In some embodiments of the anti-C3d antibody conjugate, the detectable moiety is a protein. In some embodiments of the anti-C3d antibody conjugate, the detectable moiety is a fluorescent moiety. In some embodiments of the anti-C3d antibody conjugate, the detectable moiety is selected from the group consisting of fluorescein, fluorescein isothiocyanate, and fluorescein derivatives. In some embodiments of the anti-C3d antibody conjugate, the detectable moiety is a paramagnetic moiety. In some embodiments of the anti-C3d antibody conjugate, the detectable moiety is an ultrasmall superparamagnetic iron oxide ("USPIO")

nanoparticle or aggregate thereof. In some embodiments of the anti-C3d antibody conjugate, the detectable moiety is an ultrasmall superparamagnetic iron oxide ("USPIO") nanoparticle. In some embodiments of the anti-C3d antibody conjugate, the detectable moiety is an ultrasmall superparamagnetic iron oxide ("USPIO") nanoparticle aggregate. In some embodiments of the anti-C3d antibody conjugate, the ultrasmall superparamagnetic iron oxide ("USPIO") nanoparticle aggregate is between about 10 nm and about 150 nm in diameter. In some embodiments of the anti-C3d antibody conjugate, the ultrasmall superparamagnetic iron oxide ("USPIO") nanoparticle aggregate is between about 65 nm and about 85 nm in diameter. In some embodiments of the anti-C3d antibody conjugate, the ultrasmall superparamagnetic iron oxide ("USPIO") nanoparticle aggregate is about 75 nm in diameter. In some embodiments of the anti-C3d antibody conjugate, the ultrasmall superparamagnetic iron oxide ("USPIO") nanoparticle aggregate is about 150 nm in diameter. In some embodiments of the anti-C3d antibody conjugate, the nanoparticle aggregate is coated with dextran, coated with an amphiphilic polymer, or encapsulated with phospholipid. In some embodiments of the anti-C3d antibody conjugate, the phospholipid is PEGylated. In some embodiments of the anti-C3d antibody conjugate, the PEGylated phospholipid is amine-functionalized or carboxylic acid-functionalized. In some embodiments of the anti-C3d antibody conjugate, the PEGylated, amine-functionalized phospholipid is 1,2-distearoyl-sn-glycero-3-phosphoethanolamine-PEG2000. In some embodiments of the anti-C3d antibody conjugate, the antibody or antigen binding fragment thereof is conjugated to the detectable moiety through an antibody, or antigen binding fragment, lysine amino acid. In some embodiments of the anti-C3d antibody conjugate, the antibody or antigen binding fragment thereof is conjugated to the detectable moiety through an antibody, or antigen binding fragment, lysine sidechain. In some embodiments of the anti-C3d antibody conjugate, the antibody or antigen binding fragment thereof is conjugated to the detectable moiety through an antibody, or antigen binding fragment, cysteine, glutamate, aspartate, or arginine amino acid. In some embodiments of the anti-C3d antibody conjugate, the antibody or antigen binding fragment thereof is conjugated to the detectable moiety through an antibody, or antigen binding fragment, cysteine, glutamate, aspartate, or arginine sidechain. In some embodiments of the anti-C3d antibody conjugate, the antibody or antigen binding fragment thereof is conjugated to the detectable moiety through a 4-succinimidyloxycarbonyl-α-methyl-α (2-pyridyldithio) toluene (SMPT), N-5-azido-2-nitrobenzoyloxysuccinimide, 1,4-bis-maleimidobutane, m-maleimidobenzoyl-N-hydroxysuccinimide ester, 4-[p-azidosalicylamido]butylamine, or p-azidophenyl glyoxal monohydrate. In some embodiments of the anti-C3d antibody conjugate, the antibody or antigen binding fragment thereof is connected to the detectable moiety by a reaction including a thiolated antibody or antigen binding fragment thereof and maleoyl-activated NH2-SPIO. In some embodiments of the anti-C3d antibody conjugate, the antibody or antigen binding fragment thereof is connected to the detectable moiety by a reaction including an EDC/NHS activated antibody or antigen binding fragment thereof and an NH2-SPIO, forming an amide bond. In some embodiments of the anti-C3d antibody conjugate, the antibody or antigen binding fragment thereof is connected to the detectable moiety by a reaction including an EDC/NHS activated COOH-SPIO or other activated COOH-detectable moiety and an amine on the antibody or antigen binding fragment thereof, forming an amide bond.

In embodiments of the anti-C3d antibody conjugate, the USPIO nanoparticles or aggregates thereof are between about 1 nm and about 1000 nm in diameter. In embodiments of the anti-C3d antibody conjugate, the USPIO nanoparticles or aggregates thereof are between about 5 nm and about 500 nm in diameter. In embodiments of the anti-C3d antibody conjugate, the USPIO nanoparticles or aggregates thereof are between about 10 nm and about 100 nm in diameter. In embodiments of the anti-C3d antibody conjugate, the USPIO nanoparticles or aggregates thereof are between about 50 nm and about 150 nm in diameter. In embodiments of the anti-C3d antibody conjugate, the USPIO nanoparticles or aggregates thereof are between about 65 nm and about 85 nm in diameter. In embodiments of the anti-C3d antibody conjugate, the USPIO nanoparticles or aggregates thereof are about 75 nm in diameter. In embodiments of the anti-C3d antibody conjugate, the USPIO nanoparticles or aggregates thereof are about 150 nm in diameter. In embodiments of the anti-C3d antibody conjugate, the USPIO nanoparticles or aggregates thereof are between about 1 nm and about 1000 nm in diameter and coated with amphiphilic polymer. In embodiments of the anti-C3d antibody conjugate, the USPIO nanoparticles or aggregates thereof are between about 5 nm and about 500 nm in diameter and coated with amphiphilic polymer. In embodiments of the anti-C3d antibody conjugate, the USPIO nanoparticles or aggregates thereof are between about 10 nm and about 100 nm in diameter and coated with amphiphilic polymer. In embodiments of the anti-C3d antibody conjugate, the USPIO nanoparticles or aggregates thereof are between about 50 nm and about 150 nm in diameter and coated with amphiphilic polymer. In embodiments of the anti-C3d antibody conjugate, the USPIO nanoparticles or aggregates thereof are between about 65 nm and about 85 nm in diameter and coated with amphiphilic polymer. In embodiments of the anti-C3d antibody conjugate, the USPIO nanoparticles or aggregates thereof are about 75 nm in diameter and coated with amphiphilic polymer. In embodiments of the anti-C3d antibody conjugate, the USPIO nanoparticles or aggregates thereof are about 150 nm in diameter and coated with amphiphilic polymer. In embodiments of the anti-C3d antibody conjugate, the USPIO nanoparticles or aggregates thereof are between about 1 nm and about 1000 nm in diameter and phospholipid-encapsulated. In embodiments of the anti-C3d antibody conjugate, the USPIO nanoparticles or aggregates thereof are between about 5 nm and about 500 nm in diameter and phospholipid-encapsulated. In embodiments of the anti-C3d antibody conjugate, the USPIO nanoparticles or aggregates thereof are between about 10 nm and about 100 nm in diameter and phospholipid-encapsulated. In embodiments of the anti-C3d antibody conjugate, the USPIO nanoparticles or aggregates thereof are between about 50 nm and about 150 nm in diameter and phospholipid-encapsulated. In embodiments of the anti-C3d antibody conjugate, the USPIO nanoparticles or aggregates thereof are between about 65 nm and about 85 nm in diameter and phospholipid-encapsulated. In embodiments of the anti-C3d antibody conjugate, the USPIO nanoparticles or aggregates thereof are about 75 nm in diameter and phospholipid-encapsulated. In embodiments of the anti-C3d antibody conjugate, the USPIO nanoparticles or aggregates thereof are about 150 nm in diameter and phospholipid-encapsulated.

In embodiments of the anti-C3d antibody conjugate, the USPIO nanoparticles or aggregates thereof are between about 1 nm and about 1000 nm in diameter and coated with dextran. In embodiments of the anti-C3d antibody conjugate, the USPIO nanoparticles or aggregates thereof are between about 5 nm and about 500 nm in diameter and coated with dextran.

In embodiments of the anti-C3d antibody conjugate, the USPIO nanoparticles or aggregates thereof are between about 10 nm and about 100 nm in diameter and coated with dextran. In embodiments of the anti-C3d antibody conjugate, the USPIO nanoparticles or aggregates thereof are between about 50 nm and about 150 nm in diameter and coated with dextran. In embodiments of the anti-C3d antibody conjugate, the USPIO nanoparticles or aggregates thereof are between about 65 nm and about 85 nm in diameter and coated with dextran. In embodiments of the anti-C3d antibody conjugate, the USPIO nanoparticles or aggregates thereof are about 75 nm in diameter and coated with dextran. In embodiments of the anti-C3d antibody conjugate, the USPIO nanoparticles or aggregates thereof are about 150 nm in diameter and coated with dextran.

In embodiments of the anti-C3d antibody conjugate, the phospholipid-encapsulated antibody-targeted USPIO nanoparticles or aggregates thereof are between about 1 nm and about 1000 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between about 5 nm and about 500 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between about 10 nm and about 100 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between about 50 nm and about 150 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between about 65 nm and about 85 nm in diameter and include an antibody-targeting group attached to the phospholipid coating. In embodiments of the anti-C3d antibody conjugate, the phospholipid-encapsulated antibody-targeted USPIO nanoparticles or aggregates thereof are about 75 nm in diameter and include an antibody-targeting group attached to the phospholipid coating. In embodiments of the anti-C3d antibody conjugate, the phospholipid-encapsulated antibody-targeted USPIO nanoparticles or aggregates thereof are about 150 nm in diameter and include an antibody-targeting group attached to the phospholipid coating.

In embodiments of the anti-C3d antibody conjugate, the dextran-coated antibody-targeted USPIO nanoparticles or aggregates thereof are between about 1 nm and about 1000 nm in diameter and include an antibody-targeting group attached to the dextran coating. In embodiments of the anti-C3d antibody conjugate, the dextran-coated antibody-targeted USPIO nanoparticles or aggregates thereof are between about 5 nm and about 500 nm in diameter and include an antibody-targeting group attached to the dextran coating. In embodiments of the anti-C3d antibody conjugate, the dextran-coated antibody-targeted USPIO nanoparticles or aggregates thereof are between about 10 nm and about 100 nm in diameter and include an antibody-targeting group attached to the dextran coating. In embodiments of the anti-C3d antibody conjugate, the dextran-coated antibody-targeted USPIO nanoparticles or aggregates thereof are between about 50 nm and about 150 nm in diameter and include an antibody-targeting group attached to the dextran coating. In embodiments of the anti-C3d antibody conjugate, the dextran-coated antibody-targeted USPIO nanoparticles or aggregates thereof are between about 65 nm and about 85 nm in diameter and include an antibody-targeting group attached to the dextran coating. In embodiments of the anti-C3d antibody conjugate, the dextran-coated antibody-targeted USPIO nanoparticles or aggregates thereof are about 75 nm in diameter and include an antibody-targeting group attached to the dextran coating. In embodiments of the anti-C3d antibody conjugate, the dextran-coated antibody-targeted USPIO nanoparticles or aggregates thereof are about 150 nm in diameter and include an antibody-targeting group attached to the dextran coating.

In embodiments of the anti-C3d antibody conjugate, the USPIO nanoparticles or aggregates thereof are between 1 nm and 1000 nm in diameter. In embodiments of the anti-C3d antibody conjugate, the USPIO nanoparticles or aggregates thereof are between 5 nm and 500 nm in diameter. In embodiments of the anti-C3d antibody conjugate, the USPIO nanoparticles or aggregates thereof are between 10 nm and 100 nm in diameter. In embodiments of the anti-C3d antibody conjugate, the USPIO nanoparticles or aggregates thereof are between 50 nm and 150 nm in diameter. In embodiments of the anti-C3d antibody conjugate, the USPIO nanoparticles or aggregates thereof are between 65 nm and 85 nm in diameter. In embodiments of the anti-C3d antibody conjugate, the USPIO nanoparticles or aggregates thereof are 75 nm in diameter. In embodiments of the anti-C3d antibody conjugate, the USPIO nanoparticles or aggregates thereof are 150 nm in diameter. In embodiments of the anti-C3d antibody conjugate, the USPIO nanoparticles or aggregates thereof are between 1 nm and 1000 nm in diameter and coated with amphiphilic polymer. In embodiments of the anti-C3d antibody conjugate, the USPIO nanoparticles or aggregates thereof are between 5 nm and 500 nm in diameter and coated with amphiphilic polymer. In embodiments of the anti-C3d antibody conjugate, the USPIO nanoparticles or aggregates thereof are between 10 nm and 100 nm in diameter and coated with amphiphilic polymer. In embodiments of the anti-C3d antibody conjugate, the USPIO nanoparticles or aggregates thereof are between 50 nm and 150 nm in diameter and coated with amphiphilic polymer. In embodiments of the anti-C3d antibody conjugate, the USPIO nanoparticles or aggregates thereof are between 65 nm and 85 nm in diameter and coated with amphiphilic polymer. In embodiments of the anti-C3d antibody conjugate, the USPIO nanoparticles or aggregates thereof are 75 nm in diameter and coated with amphiphilic polymer. In embodiments of the anti-C3d antibody conjugate, the USPIO nanoparticles or aggregates thereof are 150 nm in diameter and coated with amphiphilic polymer. In embodiments of the anti-C3d antibody conjugate, the USPIO nanoparticles or aggregates thereof are between 1 nm and 1000 nm in diameter and phospholipid-encapsulated. In embodiments of the anti-C3d antibody conjugate, the USPIO nanoparticles or aggregates thereof are between 5 nm and 500 nm in diameter and phospholipid-encapsulated. In embodiments of the anti-C3d antibody conjugate, the USPIO nanoparticles or aggregates thereof are between 10 nm and 100 nm in diameter and phospholipid-encapsulated. In embodiments of the anti-C3d antibody conjugate, the USPIO nanoparticles or aggregates thereof are between 50 nm and 150 nm in diameter and phospholipid-encapsulated. In embodiments of the anti-C3d antibody conjugate, the USPIO nanoparticles or aggregates thereof are between 65 nm and 85 nm in diameter and phospholipid-encapsulated. In embodiments of the anti-C3d antibody conjugate, the USPIO nanoparticles or aggregates thereof are 75 nm in diameter and phospholipid-encapsulated. In embodiments of the anti-C3d antibody conjugate, the USPIO nanoparticles or aggregates thereof are 150 nm in diameter and phospholipid-encapsulated.

In embodiments of the anti-C3d antibody conjugate, the USPIO nanoparticles or aggregates thereof are between 1 nm and 1000 nm in diameter and coated with dextran. In embodiments of the anti-C3d antibody conjugate, the USPIO nanoparticles or aggregates thereof are between 5 nm and 500 nm in diameter and coated with dextran. In embodiments of the anti-C3d antibody conjugate, the USPIO nanoparticles or aggregates thereof are between 10 nm and 100 nm in diameter and coated with dextran. In embodiments of the anti-C3d antibody conjugate, the USPIO nanoparticles or aggregates thereof are between 50 nm and 150 nm in diameter and coated with dextran. In embodiments of the anti-C3d antibody conjugate, the USPIO nanoparticles or aggregates thereof are between 65 nm and 85 nm in diameter and coated with dextran. In embodiments of the anti-C3d antibody conjugate, the USPIO nanoparticles or aggregates thereof are 75 nm in diameter and coated with dextran. In embodiments of the anti-C3d antibody conjugate, the USPIO nanoparticles or aggregates thereof are 150 nm in diameter and coated with dextran.

In embodiments of the anti-C3d antibody conjugate, the phospholipid-encapsulated antibody-targeted USPIO nanoparticles or aggregates thereof are between 1 nm and 1000 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between 5 nm and 500 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between 10 nm and 100 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between 50 nm and 150 nm in diameter and include an antibody-targeting group attached to the phospholipid coating. In embodiments of the anti-C3d antibody conjugate, the phospholipid-encapsulated antibody-targeted USPIO nanoparticles or aggregates thereof are between 65 nm and 85 nm in diameter and include an antibody-targeting group attached to the phospholipid coating. In embodiments of the anti-C3d antibody conjugate, the phospholipid-encapsulated antibody-targeted USPIO nanoparticles or aggregates thereof are 75 nm in diameter and include an antibody-targeting group attached to the phospholipid coating. In embodiments of the anti-C3d antibody conjugate, the phospholipid-encapsulated antibody-targeted USPIO nanoparticles or aggregates thereof are 150 nm in diameter and include an antibody-targeting group attached to the phospholipid coating.

In embodiments of the anti-C3d antibody conjugate, the dextran-coated antibody-targeted USPIO nanoparticles or aggregates thereof are between 1 nm and 1000 nm in diameter and include an antibody-targeting group attached to the dextran coating. In embodiments of the anti-C3d antibody conjugate, the dextran-coated antibody-targeted USPIO nanoparticles or aggregates thereof are between 5 nm and 500 nm in diameter and include an antibody-targeting group attached to the dextran coating. In embodiments of the anti-C3d antibody conjugate, the dextran-coated antibody-targeted USPIO nanoparticles or aggregates thereof are between 10 nm and 100 nm in diameter and include an antibody-targeting group attached to the dextran coating. In embodiments of the anti-C3d antibody conjugate, the dextran-coated antibody-targeted USPIO nanoparticles or aggregates thereof are between 50 nm and 150 nm in diameter and include an antibody-targeting group attached to the dextran coating. In embodiments of the anti-C3d antibody conjugate, the dextran-coated antibody-targeted USPIO nanoparticles or aggregates thereof are between 65 nm and 85 nm in diameter and include an antibody-targeting group attached to the dextran coating. In embodiments of the anti-C3d antibody conjugate, the dextran-coated antibody-targeted USPIO nanoparticles or aggregates thereof are 75 nm in diameter and include an antibody-targeting group attached to the dextran coating. In embodiments of the anti-C3d antibody conjugate, the dextran-coated antibody-targeted USPIO nanoparticles or aggregates thereof are 150 nm in diameter and include an antibody-targeting group attached to the dextran coating.

In embodiments, the USPIO has a diameter selected from the group consisting of 1, 2, 3, 4, 5, 6, 7, 8, 9, 10, 11, 12, 13, 14, and 15 nm. In embodiments, the USPIO has a diameter selected from the group consisting of about 1, 2, 3, 4, 5, 6, 7, 8, 9, 10, 11, 12, 13, 14, and 15 nm. In embodiments, the USPIO has a diameter selected from the group consisting of 1, 2, 3, 4, 5, 6, 7, 8, 9, and 10 nm. In embodiments, the USPIO has a diameter selected from the group consisting of about 1, 2, 3, 4, 5, 6, 7, 8, 9, and 10 nm. In embodiments, the USPIO has a diameter between about 1 and 15 nm. In embodiments, the USPIO has a diameter between 1 and 15 nm. In embodiments, the USPIO has a diameter between about 1 and 10 nm. In embodiments, the USPIO has a diameter between 1 and 10 nm. In embodiments, any of the USPIOs described herein may be modified as described above for USPIOs of different sizes (e.g. coated with an amphiphilic polymer, phospholipid encapsulated, coated with dextran, etc., or combinations thereof).

In embodiments of the construct (e.g. conjugate or conjugate molecule), the C3d binding portion may be any composition capable of binding (e.g. specifically binding) a C3d, C3dg, and/or iC3b protein (e.g. human C3d, C3dg, iC3b protein) (e.g. in any aspect or embodiment, in the antibody compositions and uses section above, any example, table, figure, or claim herein). In embodiments of the construct (e.g. conjugate or conjugate molecule), the complement diagnostic portion may be any detectable agent or detectable moiety capable of being used to detect complement, including any detectable agent or detectable moiety described herein (e.g. in any aspect or embodiment, in the detectable moieties section above, any example, table, figure, or claim herein).

Methods of Detecting Complement

In a second aspect is provided a method of detecting complement-mediated inflammation in an individual including: (a) administering to the individual an effective amount of an anti-C3d antibody conjugate as described herein; (b) allowing the anti-C3d antibody conjugate to bind to a C3 protein fragment within the individual thereby forming an anti-C3d antibody conjugate-C3 protein fragment complex; and (c) detecting the anti-C3d antibody conjugate-C3 protein fragment complex in the individual. In some embodiments, the C3 protein fragment is C3d or C3dg or iC3b. In embodiments, the C3 protein fragment is C3d. In embodiments, the C3 protein fragment is C3dg. In embodiments, the C3 protein fragment is iC3b. In some embodiments, the detecting includes fluorescent spectroscopy. In some embodiments, the detecting includes magnetic resonance imaging. In some embodiments, the detecting includes fluorescent spectroscopy. In some embodiments, the detecting includes fluorescent microscopy. In some embodiments, the detecting includes positron emission tomography. In some embodiments, the detecting includes computed tomography. In some embodiments, the detecting includes PET/CT. In some embodiments, the detecting includes single photon emission computed tomography. In some embodiments, the detecting includes SPECT/CT. In some embodiments, the detecting includes radiography. In some embodiments, the detecting includes X-ray imaging. In some embodiments, the detecting includes ultrasound. In some embodiments, the detecting includes two photon microscopy. In some embodiments, the detecting includes detecting the presence of a detectable moiety (e.g. any one of the detectable moieties described herein). In some embodiments, the detecting includes detecting a USPIO. In some embodiments, the detecting includes detecting a USPIO aggregate. In some embodiments, the detecting includes detecting a paramagnetic detectable moiety. In some embodiments, the detecting includes detecting an iron containing detectable moiety. In some embodiments, the complement-mediated inflammation is associated with an ocular inflammatory disease, ocular degenerative disease, or ocular autoimmune disease. In some embodiments, the complement-mediated inflammation is ocular inflammation. In some embodiments, the ocular complement-mediated inflammation is associated with age-related macular degeneration. In some embodiments, the age-related macular degeneration is wet age-related macular degeneration. In some embodiments, the age-related macular degeneration is dry age-related macular degeneration. In some embodiments, the complement-mediated inflammation is associated with cancer, ischemia reperfusion injury, inflammatory disorders, transplant rejection (cellular or antibody mediated), pregnancy-related diseases, adverse drug reactions, age-related macular degeneration, glomerulonephritis, or autoimmune or immune complex disorders. In some embodiments, the complement-mediated inflammation is associated with tissue damage resulting from cancer, ischemia reperfusion injury, inflammatory disorders, transplant rejection (cellular or antibody mediated), pregnancy-related diseases, adverse drug reactions, age-related macular degeneration, glomerulonephritis, or autoimmune or immune complex disorders. In some embodiments, the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In some embodiments, the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In some embodiments, the transplant rejection is hyperacute xenograft rejection. In some embodiments, the transplant rejection is cellular mediate. In some embodiments, the transplant rejection is antibody mediated. In some embodiments, the pregnancy-related disease is selected from the group consisting of: HELLP (Hemolytic anemia, elevated liver enzymes, and low platelet count), recurrent fetal loss, and pre-eclampsia. In some embodiments, the adverse drug reaction is selected from the group consisting of drug allergy and IL-2 induced vascular leakage syndrome. In some embodiments, the autoimmune or immune complex disorder is selected from the group consisting of myasthenia gravis, Alzheimer's disease, multiple sclerosis, rheumatoid arthritis, osteoarthritis, systemic lupus erythematosus, lupus nephritis, IgG4 associated diseases, insulin-dependent diabetes mellitus, acute disseminated encephalomyelitis, Addison's disease, antiphospholipid antibody syndrome, thrombotic thrombycytopenic purpura, autoimmune hepatitis, Crohn's disease, Goodpasture's syndromes, Graves' disease, Guillain-Barre syndrome, Hashimoto's disease, idiopathic thrombocytopenic purpura, pemphigus, Sjogren's syndrome, Takayasu's arteritis, autoimmune glomerulonephritis, membranoproliferative glomerulonephritis type II, membranous disease, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, Shiga-toxin-associated hemolytic uremic syndrome, and atypical hemolytic uremic syndrome. In some embodiments, the autoimmune or immune complex disorder is systemic lupus erythematosus. In some embodiments, the autoimmune or immune complex disorder is lupus nephritis. In some embodiments, the autoimmune or immune complex disorder is rheumatoid arthritis. In some embodiments, the autoimmune or immune complex disorder is Alzheimer's disease. In some embodiments, the autoimmune or immune complex disorder is multiple sclerosis. In some embodiments, the autoimmune or immune complex disorder is osteoarthritis. In some embodiments, the autoimmune or immune complex disorder is age-related macular degeneration. In some embodiments, the autoimmune or immune complex disorder is diabetic maculopathy. In some embodiments, the autoimmune glomerulonephritis is selected from the group consisting of immunoglobulin A nephropathy or membranoproliferative glomerularnephritis type I. In some embodiments, the individual is a mammal. In some embodiments, the mammal is a human. In some embodiments, the administering is by injection. In some embodiments, administering is parenteral, intravenous, subcutaneous, intraocular, intra-articular, or intramuscular. In some embodiments, the individual is undergoing treatment for the complement-mediated inflammation. In some embodiments the method of detecting complement-mediated inflammation is a method of monitoring the efficacy of a treatment for a complement-mediated inflammation. In some embodiments, the method of detecting complement-mediated inflammation includes a method of treating complement-mediated inflammation by administering a complement inhibitor. In some embodiments, the method of detecting complement-mediated inflammation is a companion diagnostic to a complement-mediated inflammation treatment. As used herein, the term "companion diagnostic" refers to an assay used to provide a specific therapy for a disease or condition of an individual by stratifying disease status, identifying a therapeutic treatment, tailoring dosages or administration regimens or to assess a patient's risk of a disease or condition and identify preventative or prophylactic treatments. In some embodiments, the method of detecting includes a plurality of detecting steps to monitor the progress of a treatment for a disease (e.g. as disclosed herein) or complement-mediated inflammation.

In a third aspect is provided a method of detecting complement activation in an individual including: (a) administering to the individual an effective amount of an anti-C3d antibody conjugate as described herein; (b) allowing the anti-C3d antibody conjugate to bind to a C3 protein fragment within the individual thereby forming an anti-C3d antibody conjugate-C3 protein fragment complex; and (c) detecting the anti-C3d antibody conjugate-C3 protein fragment complex in the individual. In some embodiments, the C3 protein fragment is C3d or C3dg or iC3b. In embodiments, the C3 protein fragment is C3d. In embodiments, the C3 protein fragment is C3dg. In embodiments, the C3 protein fragment is iC3b. In some embodiments, the detecting includes fluorescent spectroscopy. In some embodiments, the detecting includes magnetic resonance imaging. In some embodiments, the detecting includes fluorescent spectroscopy. In some embodiments, the detecting includes fluorescent microscopy. In some embodiments, the detecting includes positron emission tomography. In some embodiments, the detecting includes computed tomography. In some embodiments, the detecting includes PET/CT. In some embodiments, the detecting includes single photon emission computed tomography. In some embodiments, the detecting includes SPECT/CT. In some embodiments, the detecting includes radiography. In some embodiments, the detecting includes X-ray imaging. In some embodiments, the detecting includes ultrasound. In some embodiments, the detecting includes two photon microscopy. In some embodiments, the detecting includes detecting the presence of a detectable moiety (e.g. any one of the detectable moieties described herein). In some embodiments, the detecting includes detecting a USPIO. In some embodiments, the detecting includes detecting a USPIO aggregate. In some embodiments, the detecting includes detecting a paramagnetic detectable moiety. In some embodiments, the detecting includes detecting an iron containing detectable moiety. In some embodiments, the complement activation is ocular. In some embodiments, the ocular complement activation is associated with age-related macular degeneration. In some embodiments, the age-related macular degeneration is wet age-related macular degeneration. In some embodiments, the age-related macular degeneration is dry age-related macular degeneration. In some embodiments, the complement activation is associated with cancer, ischemia reperfusion injury, inflammatory disorders, transplant rejection (cellular or antibody mediated), pregnancy-related diseases, adverse drug reactions, age-related macular degeneration, glomerulonephritis, or autoimmune or immune complex disorders. In some embodiments, the complement activation is associated with tissue damage resulting from cancer, ischemia reperfusion injury, inflammatory disorders, transplant rejection (cellular or antibody mediated), pregnancy-related diseases, adverse drug reactions, age-related macular degeneration, glomerulonephritis, or autoimmune or immune complex disorders. In some embodiments, the complement activation is associated with an ocular inflammatory disease, ocular degenerative disease, or ocular autoimmune disease. In some embodiments, the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In some embodiments, the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In some embodiments, the transplant rejection is hyperacute xenograft rejection. In some embodiments, the pregnancy-related disease is selected from the group consisting of: HELLP (Hemolytic anemia, elevated liver enzymes, and low platelet count), recurrent fetal loss, and pre-eclampsia. In some embodiments, the adverse drug reaction is selected from the group consisting of drug allergy and IL-2 induced vascular leakage syndrome. In some embodiments, the autoimmune or immune complex disorder is selected from the group consisting of myasthenia gravis, Alzheimer's disease, multiple sclerosis, rheumatoid arthritis, osteoarthritis, systemic lupus erythematosus, lupus nephritis, IgG4 associated diseases, insulin-dependent diabetes mellitus, acute disseminated encephalomyelitis, Addison's disease, antiphospholipid antibody syndrome, thrombotic thrombycytopenic purpura, autoimmune hepatitis, Crohn's disease, Goodpasture's syndromes, Graves' disease, Guillain-Barre syndrome, Hashimoto's disease, idiopathic thrombocytopenic purpura, pemphigus, Sjogren's syndrome, Takayasu's arteritis, autoimmune glomerulonephritis, membranoproliferative glomerulonephritis type II, membranous disease, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, Shiga-toxin-associated hemolytic uremic syndrome, and atypical hemolytic uremic syndrome. In some embodiments, the autoimmune or immune complex disorder is systemic lupus erythematosus. In some embodiments, the autoimmune or immune complex disorder is lupus nephritis. In some embodiments, the autoimmune or immune complex disorder is rheumatoid arthritis. In some embodiments, the autoimmune or immune complex disorder is Alzheimer's disease. In some embodiments, the autoimmune or immune complex disorder is multiple sclerosis. In some embodiments, the autoimmune or immune complex disorder is osteoarthritis. In some embodiments, the autoimmune or immune complex disorder is age-related macular degeneration. In some embodiments, the autoimmune or immune complex disorder is diabetic maculopathy. In some embodiments, the autoimmune glomerulonephritis is selected from the group consisting of immunoglobulin A nephropathy or membranoproliferative glomerularnephritis type I. In some embodiments, the individual is a mammal. In some embodiments, the mammal is a human. In some embodiments, the administering is by injection. In some embodiments, administering is parenteral, intravenous, subcutaneous, intraocular, intra-articular, or intramuscular. In some embodiments, the individual is undergoing treatment for the complement activation associated disease. In some embodiments the method of detecting complement activation is a method of monitoring the efficacy of a treatment for a complement activation associated disease. In some embodiments, the method of detecting complement activation includes a method of treating a complement activation associated disease by administering a complement inhibitor. In some embodiment, the method of detecting complement activation is a companion diagnostic to a disease treatment. In some embodiments, the method of detecting includes a plurality of detecting steps to monitor the progress of a treatment for a disease (e.g. as disclosed herein) or disease.

In a fourth aspect is provided a method of detecting complement activation including (a) administering to a biological sample (e.g. biopsy, tissue, blood, blood fraction, serum, cells, all optionally from a subject or patient) an effective amount of an anti-C3d antibody conjugate as described herein; (b) allowing the anti-C3d antibody conjugate to bind to a C3 protein fragment within the biological sample thereby forming an anti-C3d antibody conjugate-C3 protein fragment complex; and (c) detecting the anti-C3d antibody conjugate-C3 protein fragment complex in the biological sample. In some embodiments, the C3 protein fragment is C3d or C3dg or iC3b. In embodiments, the C3 protein fragment is C3d. In embodiments, the C3 protein fragment is C3dg. In embodiments, the C3 protein fragment is iC3b. In some embodiments, the detecting includes fluorescent spectroscopy. In some embodiments, the detecting includes magnetic resonance imaging. In some embodiments, the detecting includes fluorescent spectroscopy. In some embodiments, the detecting includes fluorescent microscopy. In some embodiments, the detecting includes positron emission tomography. In some embodiments, the detecting includes computed tomography. In some embodiments, the detecting includes PET/CT.

In some embodiments, the detecting includes single photon emission computed tomography. In some embodiments, the detecting includes SPECT/CT. In some embodiments, the detecting includes radiography. In some embodiments, the detecting includes X-ray imaging. In some embodiments, the detecting includes ultrasound. In some embodiments, the detecting includes two photon miscroscopy. In some embodiments, the detecting includes ELISA. In some embodiments, the detecting includes in situ hybridization. In some embodiments, the detecting includes immunohistochemistry. In some embodiments, the detecting includes western blotting. In some embodiments, the detecting includes detecting the presence of a detectable moiety (e.g. any one of the detectable moieties described herein). In some embodiments, the detecting includes detecting a USPIO. In some embodiments, the detecting includes detecting a USPIO aggregate. In some embodiments, the detecting includes detecting a paramagnetic detectable moiety. In some embodiments, the detecting includes detecting an iron containing detectable moiety. In some embodiments, the method of detecting complement activation is a companion diagnostic and optionally combined with any of the methods of detecting complement in an individual described herein (e.g. complement activation or complement-mediated inflammation). In embodiments, the method of detecting complement activation is conducted using a tissue sample. In embodiments, the method of detecting complement activation is conducted using a tissue biopsy.

ADDITIONAL EMBODIMENTS

1. An isolated antibody or antigen-binding fragment thereof specifically binding to a mammalian complement component C3d or C3dg or iC3b protein, wherein the antibody or antigen-binding fragment thereof is selected from the group consisting of:

a. an isolated anti-C3d antibody or antigen-binding fragment thereof, wherein said antibody or antigen-binding fragment thereof has a binding affinity to C3d of 1.1 nM or better;

b. an isolated anti-C3d antibody or antigen-binding fragment thereof or isolated anti-C3dg antibody or antigen-binding fragment thereof or isolated anti-iC3b antibody or antigen-binding fragment thereof, wherein said antibody or antigen-binding fragment thereof binds to C3d or C3dg or iC3b with higher affinity than to complement proteins C3, C3a, C3b, C3c or C3f;

c. an isolated anti-C3d antibody or antigen-binding fragment thereof or isolated anti-C3dg antibody or antigen-binding fragment thereof or isolated anti-iC3b antibody or antigen-binding fragment thereof, wherein the antibody or antigen-binding fragment thereof binds to deposited C3 fragments;

d. an isolated anti-C3d antibody or antigen-binding fragment thereof, wherein the antibody or antigen-binding fragment thereof binds to C3d proteins of at least two species;

e. an isolated anti-C3d antibody or antigen-binding fragment thereof, wherein the antibody or antigen-binding fragment thereof competes with complement receptor 2 (CR2) for binding to C3d;

f. an isolated anti-C3d antibody or antigen-binding fragment thereof or isolated anti-C3dg antibody or antigen-binding fragment thereof or isolated anti-iC3b antibody or antigen-binding fragment thereof, wherein the antibody or antigen-binding fragment thereof does not enhance complement activation;

g. an isolated anti-C3d antibody or antigen-binding fragment thereof or isolated anti-C3dg antibody or antigen-binding fragment thereof or isolated anti-iC3b antibody or antigen-binding fragment thereof, wherein the antibody or antigen-binding fragment thereof decreases host humoral immune response;

h. an isolated antibody or an antigen-binding fragment thereof comprising light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or 26; or heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or 29;

i. an isolated antibody or an antigen-binding fragment thereof comprising light chain complementarity determining regions (CDR) 1, 2 and 3, wherein light chain CDR 1 is SEQ ID NO:14 or SEQ ID NO:24, light chain CDR 2 is SEQ ID NO:15 or SEQ ID NO:25 and light chain CDR 3 is SEQ ID NO:16 or 26; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 or SEQ ID NO:28 and heavy chain CDR 3 is SEQ ID NO:19 or 29;

j. an isolated antibody or an antigen-binding fragment thereof, wherein light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19;

k. an isolated antibody or an antigen-binding fragment thereof, wherein light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29;

l. an isolated antibody or an antigen-binding fragment thereof comprising a light chain variable region amino acid sequence 90% identical to SEQ ID NO:12 or SEQ ID NO:22; or a heavy chain variable region amino acid sequence 90% identical to SEQ ID NO:13 or SEQ ID NO:23;

m. an isolated antibody or an antigen-binding fragment thereof comprising a light chain variable region amino acid sequence 90% identical to SEQ ID NO:12 or SEQ ID NO:22; and a heavy chain variable region amino acid sequence 90% identical to SEQ ID NO:13 or SEQ ID NO:23;

n. an isolated antibody or an antigen-binding fragment thereof comprising a light chain variable region amino acid sequence 90% identical to SEQ ID NO:12; and a heavy chain variable region amino acid sequence 90% identical to SEQ ID NO:13; and o. an isolated antibody or an antigen-binding fragment thereof comprising a light chain variable region amino acid sequence 90% identical to SEQ ID NO:22; and a heavy chain variable region amino acid sequence 90% identical to SEQ ID NO:23.

2. The isolated antibody or antigen-binding fragment thereof of embodiment 1, wherein said $K_D$ is 0.5 nM or better.

3. The isolated antibody or antigen-binding fragment thereof of embodiment 1, wherein said antibody or antigen-binding fragment thereof does not bind to complement proteins C3, C3a, C3b, C3c or C3f.

4. The isolated antibody or antigen-binding fragment thereof of embodiment 1, wherein said antibody or antigen-binding fragment thereof binds to deposited C3d or C3dg or iC3b with a higher affinity than it binds to circulating intact C3, C3b, or (C3H2O).

5. The isolated antibody or antigen-binding fragment thereof of embodiment 1, wherein said mammal is a human.

6. The isolated antibody or antigen-binding fragment thereof of embodiment 1, wherein said mammal is a non-human primate selected from the group consisting of orangutan, chimpanzee, macaque, gorilla, lemur, or gibbon.

7. The isolated antibody or antigen-binding fragment thereof of embodiment 1(f), wherein said antibody or antigen-binding fragment thereof reduces complement activation.

8. The isolated antibody or antigen-binding fragment thereof of any one of embodiments 1-7, wherein said antibody or antigen-binding fragment thereof is selected from the group consisting of: a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a bispecific antibody or antibody fragment, a monovalent antibody or antibody fragment, a single chain antibody, an Fv, an Fd, an Fab, an Fab', and an F(ab')2.

9. The isolated antibody of embodiment 8, wherein said antibody is a monoclonal antibody.

10. The antibody of embodiment 9, wherein said antibody is selected from the group consisting of: i) 3db8 produced by hybridoma cell line 3d-8b/2 (ATCC Deposit PTA-10999), ii) 3d9a produced by hybridoma cell line 3d-9a/25 (ATCC Deposit PTA-10998), and iii) 3d29 produced by hybridoma cell line 3d-29/5/2 (ATCC Deposit PTA-11000).

11. A hybridoma cell selected from the group consisting of: 3d-8b/2 (ATCC Deposit PTA-10999), 3d-9a/25 (ATCC Deposit number: PTA-10998), 3d-29/5/2 (ATCC Deposit number: PTA-11000), 3d-11/14 (ATCC Deposit number: PTA-11011), 3d-31/A6/9 (ATCC Deposit number: PTA-11027), 3d-3/28/4 (ATCC Deposit number: PTA-11025), 3d-15A9 (ATCC Deposit number: PTA-11012), 3d-10/14/1 (ATCC Deposit number: PTA-11010), and 3d-16/3/3 (ATCC Deposit number: PTA-11026).

12. An isolated antibody produced by the hybridoma of embodiment 11.

13. An isolated nucleic acid molecule comprising a nucleotide sequence encoding the antibody or antigen-binding fragment thereof of any one of embodiments 1-10 and 12.\

14. An expression vector comprising the isolated nucleic acid molecule of embodiment 13.

15. A cell comprising the expression vector of embodiment 14.

16. A method for producing an antibody or antigen-binding fragment thereof, the method comprising culturing the cell of embodiment 15 under conditions suitable to allow expression of the antibody or antigen-binding fragment by the cell.

17. The method of embodiment 16, further comprising isolating the antibody or antigen-binding fragment thereof from the cell or the culture media in which the cell was cultured.

18. The isolated antibody or antigen-binding fragment thereof produced by the method of embodiment 17.

19. A pharmaceutical composition comprising the isolated antibody or antigen-binding fragment thereof of any one of embodiments 1-10, 12, or 18 and a pharmaceutically-acceptable excipient.

20. A construct comprising:
a. C3d binding portion; and
b. detectable moiety, wherein (a) and (b) are joined.

21. The construct of embodiment 20, wherein said C3d binding portion comprises said anti-C3d antibody or antigen-binding fragment thereof of any one of embodiments 1-10, 12, or 18.

22. The construct of embodiment 20 or 21, wherein said detectable moiety comprises 32P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, haptens, or proteins.

23. A method of detecting complement activation in a mammal comprising administering to said subject the construct of any one of embodiments 20-21 in an amount effective to detect complement activation in a mammal 24. A method of diagnosing or monitoring a mammal having or suspected of having a disease or wherein said disease is selected from the group consisting of: tissue damage resulting from ischemia-reperfusion injury, an inflammatory disorder, transplant rejection, a pregnancy-related disease, an adverse drug reaction, and an autoimmune or immune complex disorder, said method comprising administering to said mammal a diagnostically effective amount of the construct of any one of embodiments 20-22.

25. The method of embodiment 24, wherein said tissue damage resulting from ischemia-reperfusion injury is associated with a disorder selected from the group consisting of:
myocardial infarction, aneurysm, stroke, hemorrhagic shock, crush injury, multiple organ failure, hypovolemic shock, intestinal ischemia, spinal cord injury and traumatic brain injury.

26. The method of embodiment 24, wherein said inflammatory disorder is selected from the group consisting of: burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis.

27. The method of embodiment 24, wherein said transplant rejection is hyperacute xenograft rejection.

28. The method of embodiment 24, wherein said pregnancy-related disease is selected from the group consisting of: HELLP syndrome (Hemolytic anemia, Elevated Liver enzymes and Low Platelet count), recurrent fetal loss, and pre-eclampsia.

29. The method of embodiment 24, wherein said adverse drug reaction is selected from the group consisting of: drug allergy and IL-2 induced vascular leakage syndrome.

30. The method of embodiment 24, wherein said autoimmune or immune complex disorder is selected from the group consisting of: myasthenia gravis, Alzheimer's disease, multiple sclerosis, neuromyelitis optica, rheumatoid arthritis, IgG4 mediated/associated disease, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndromes, Graves' disease, Guillain-Barré syndrome, Hashimoto's disease, idiopathic thrombocytopenic purpura, pemphigus, Sjögren's syndrome, Takayasu's arteritis, autoimmune glomerulonephritis, membranoproliferative glomerulonephritis type II, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, and atypical hemolytic uremic syndrome.

31. The method of embodiment 30, wherein said autoimmune glomerulonephritis is selected from the group consisting of: immunoglobulin A nephropathy and membranoproliferative glomerulonephritis type I.

32. A method of diagnosing or monitoring a mammal having or suspected of having a disease wherein said disease is selected from the group consisting of: a cancer, a viral infection, a bacterial infection, a parasitic infection, and a fungal infection, said method comprising administering to said mammal the construct of embodiment 20-22 in an amount effective to detect complement activation in said mammal 33. The method of any one of embodiments 23 to 32, wherein said mammal is a human.

34. An article of manufacture comprising:
(a) a container comprising a label; and
(b) a composition comprising the construct of any one of embodiments 20-22, wherein the label indicates that the composition is to be administered to a human having, suspected of having, or at risk for developing, a complement-associated disorder.

35. An anti-C3d antibody conjugate comprising a detectable moiety and light chain complementarity determining regions (CDR) 1, 2 and 3, wherein light chain CDR 1 is SEQ ID NO:14, light chain CDR 2 is SEQ ID NO:15 and light chain CDR 3 is SEQ ID NO:16; or heavy chain complementarity determining regions (CDR) 1, 2 and 3, wherein heavy chain CDR 1 is SEQ ID NO:17 or SEQ ID NO:27, heavy chain CDR 2 is SEQ ID NO:18 and heavy chain CDR 3 is SEQ ID NO:19 or 29.

36. The anti-C3d antibody conjugate of embodiment 35, comprising a detectable moiety and light chain complementarity determining regions (CDR) 1, 2 and 3, wherein light chain CDR 1 is SEQ ID NO:14, light chain CDR 2 is SEQ ID NO:15 and light chain CDR 3 is SEQ ID NO:16; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 and heavy chain CDR 3 is SEQ ID NO:19 or 29.

37. The anti-C3d antibody conjugate of embodiment 36, wherein light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19.

38. The anti-C3d antibody conjugate of embodiment 36, wherein light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29.

39. An anti-C3d antibody conjugate comprising a detectable moiety and a light chain variable region amino acid sequence 90% identical to SEQ ID NO:12 or SEQ ID NO:22; or a heavy chain variable region amino acid sequence 90% identical to SEQ ID NO:13 or SEQ ID NO:23.

40. The anti-C3d antibody conjugate of embodiment 39 comprising a light chain variable region amino acid sequence 90% identical to SEQ ID NO:12 or SEQ ID NO:22; and a heavy chain variable region amino acid sequence 90% identical to SEQ ID NO:13 or SEQ ID NO:23.

41. The anti-C3d antibody conjugate of embodiment 40 comprising a light chain variable region amino acid sequence 90% identical to SEQ ID NO:12; and a heavy chain variable region amino acid sequence 90% identical to SEQ ID NO:13.

42. The anti-C3d antibody conjugate of embodiment 40 comprising a light chain variable region amino acid sequence 90% identical to SEQ ID NO:22; and a heavy chain variable region amino acid sequence 90% identical to SEQ ID NO:23.

43. The anti-C3d antibody conjugate of any one of embodiments 35 to 42, comprising a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, single chain antibody, single chain Fv fragment (scFv), Fd fragment, Fab fragment, Fab' fragment, F(ab')$_2$ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, or phage-displayed antibody or antigen-binding fragment thereof, or antibody, or antigen-binding fragment thereof, identified with repetitive antigen array or antigen binding fragment thereof 44. The anti-C3d antibody conjugate of any one of embodiments 35 to 43, comprising a humanized antibody, or an antigen-binding fragment thereof.

45. The anti-C3d antibody conjugate of any one of embodiments 35 to 44, comprising a monoclonal antibody, or an antigen-binding fragment thereof.

46. The anti-C3d antibody conjugate of any one of embodiments 35 to 45, wherein the antibody, or antigen-binding fragment thereof, preferentially binds iC3b, C3d or C3dg with at least 10 fold greater affinity than uncleaved C3.

47. The anti-C3d antibody conjugate of any one of embodiments 35 to 46, wherein the antibody, or antigen-binding fragment thereof, preferentially binds iC3b, C3d or C3dg with at least 100 fold greater affinity than uncleaved C3.

48. The anti-C3d antibody conjugate of any one of embodiments 35 to 47, wherein said detectable moiety is selected from the group consisting of $^{32}$P, a fluorescent dye, an electron-dense reagent, an enzyme, biotin, digoxigenin, a paramagnetic molecule, a paramagnetic nanoparticle, an ultrasmall superparamagnetic iron oxide ("USPIO") nanoparticle, a USPIO nanoparticle aggregate, a superparamagnetic iron oxide ("SPIO") nanoparticle, an SPIO nanoparticle aggregate, a standard superparamagnetic iron oxide ("SSPIO"), an SSPIO nanoparticle aggregate, a polydisperse superparamagnetic iron oxide ("PSPIO"), a PSPIO nanoparticle aggregate, a monochrystalline SPIO, a monochrystalline SPIO aggregate, a monochrystalline iron oxide nanoparticle, a monochrystalline iron oxide, another nanoparticle contrast agent, a liposome or other delivery vehicle comprising Gadolinium chelate ("Gd-chelate") molecules, Gadolinium, a radioisotope, a radionuclide, carbon-11, nitrogen-13, oxygen-15, fluorine-18, rubidium-82, fluorodeoxyglucose, a gamma ray emitting radionuclide, a positron-emitting radionuclide, radiolabeled glucose, radiolabeled water, radiolabeled ammonia, a biocolloid, a microbubble, an iodinated contrast agent, barium sulfate, thorium dioxide, gold, a gold nanoparticle, a gold nanoparticle aggregate, a fluorophore, a two-photon fluorophore, a hapten, a protein, and a fluorescent moiety.

49. The anti-C3d antibody conjugate of embodiment 48, wherein said fluorescent moiety is selected from the group consisting of fluorescein, fluorescein isothiocyanate, and a fluorescein derivative.

50. The anti-C3d antibody conjugate of any one of embodiments 35 to 48, wherein said detectable moiety is a paramagnetic moiety.

51. The anti-C3d antibody conjugate of embodiment 50, wherein said paramagnetic moiety is an ultrasmall superparamagnetic iron oxide ("USPIO") nanoparticle or aggregate thereof 52. The anti-C3d antibody conjugate of embodiment 51, wherein said paramagnetic moiety is an ultrasmall superparamagnetic iron oxide ("USPIO") nanoparticle aggregate.

53. The anti-C3d antibody conjugate of embodiment 52, wherein said ultrasmall superparamagnetic iron oxide ("USPIO") nanoparticle aggregate is between about 10 nm and about 150 nm in diameter.

54. The anti-C3d antibody conjugate of embodiment 52, wherein said ultrasmall superparamagnetic iron oxide ("USPIO") nanoparticle aggregate is between about 65 nm and about 85 nm in diameter.

55. The anti-C3d antibody conjugate of embodiment 52, wherein said ultrasmall superparamagnetic iron oxide ("USPIO") nanoparticle aggregate is about 75 nm in diameter.

56. The anti-C3d antibody conjugate of embodiment 52, wherein said ultrasmall superparamagnetic iron oxide ("USPIO") nanoparticle aggregate is about 150 nm in diameter.

57. The anti-C3d antibody conjugate of embodiment 52, wherein said ultrasmall superparamagnetic iron oxide ("USPIO") nanoparticle aggregate is coated with dextran, coated with an amphiphilic polymer, or encapsulated with phospholipid.

58. The anti-C3d antibody conjugate of embodiment 57, wherein the phospholipid is PEGylated.

59. The anti-C3d antibody conjugate of embodiment 58, wherein the PEGylated phospholipid is amine-functionalized or carboxylic acid-functionalized.

60. The anti-C3d antibody conjugate of embodiment 59, wherein the PEGylated, amine-functionalized phospholipid is 1,2-distearoyl-sn-glycero-3-phosphoethanolamine-PEG2000.

61. The anti-C3d antibody conjugate of any one of embodiments 35 to 60, wherein the antibody, or antigen-binding fragment thereof, is conjugated to the detectable moiety through a lysine amino acid.

62. The anti-C3d antibody conjugate of embodiment 61, wherein the antibody, or antigen-binding fragment thereof, is conjugated to the detectable moiety through a lysine sidechain.

63. The anti-C3d antibody conjugate of any one of embodiments 35 to 60, wherein the antibody, or antigen-binding fragment thereof, is conjugated to the detectable moiety through a cysteine, glutamate, aspartate, or arginine amino acid.

64. The anti-C3d antibody conjugate of embodiment 63, wherein the antibody, or antigen-binding fragment thereof, is conjugated to the detectable moiety through a cysteine, glutamate, aspartate, or arginine sidechain.

65. The anti-C3d antibody conjugate of any one of embodiments 35 to 60, wherein the antibody, or antigen-binding fragment thereof, is conjugated to the detectable moiety a) through a 4-succinimidyloxycarbonyl-α-methyl-α (2-pyridyldithio) toluene (SMPT), N-5-azido-2-nitrobenzoyloxysuccinimide, 1,4-bis-maleimidobutane, m-maleimidobenzoyl-N-hydroxysuccinimide ester, 4-[p-azidosalicylamido]butylamine, or p-azidophenyl glyoxal monohydrate; or b) through a reaction comprising a thiolated antibody, or antigen binding fragment thereof, and a maleoyl-activated amine of the detectable moiety; EDC/NHS-activated antibody, or antigen binding fragment thereof, and an amine of the detectable moiety; or EDC/NHS-activated carboxylic acid of the detectable moiety and an amine of the antibody, or antigen binding fragment thereof 66. A method of detecting complement-mediated inflammation in an individual comprising: (a) administering to said individual an effective amount of an anti-C3d antibody conjugate of any one of embodiments 35 to 65; (b) allowing said anti-C3d antibody conjugate to bind to a C3 protein fragment within said individual thereby forming an anti-C3d antibody conjugate-C3 protein fragment complex; and (c) detecting said anti-C3d antibody conjugate-C3 protein fragment complex in said individual.

67. The method of embodiment 66, wherein said C3 protein fragment is C3d or C3dg or iC3b.

68. The method of any one of embodiments 66 to 67, wherein said detecting comprises fluorescent spectroscopy.

69. The method of any one of embodiments 66 to 67, wherein said detecting comprises magnetic resonance imaging, computed tomography, positron emission tomography, single photon emission computed tomography, ultrasonography, or radiography.

70. The method of any one of embodiments 66 to 69, wherein said complement-mediated inflammation is ocular inflammation.

71. The method of embodiment 70, wherein said ocular complement-mediated inflammation is associated with age-related macular degeneration.

72. The method of embodiment 71, wherein said age-related macular degeneration is wet age-related macular degeneration.

73. The method of embodiment 71, wherein said age-related macular degeneration is dry age-related macular degeneration.

74. The method of any one of embodiments 66 to 70, wherein said complement-mediated inflammation is associated with tissue damage resulting from cancer, an ischemia reperfusion injury, an inflammatory disorder, transplant rejection (cellular or antibody mediated), a pregnancy-related disease, an adverse drug reaction, age-related macular degeneration, glomerulonephritis, or an autoimmune or immune complex disorder.

75. The method of embodiment 74, wherein the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury.

76. The method of embodiment 74, wherein the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis.

77. The method of embodiment 74, wherein the transplant rejection is hyperacute xenograft rejection.

78. The method of embodiment 74, wherein the pregnancy-related disease is selected from the group consisting of: HELLP (Hemolytic anemia, elevated liver enzymes, and low platelet count), recurrent fetal loss, and pre-eclampsia.

79. The method of embodiment 74, wherein the adverse drug reaction is selected from the group consisting of drug allergy and IL-2 induced vascular leakage syndrome.

80. The method of embodiment 74, wherein the autoimmune or immune complex disorder is selected from the group consisting of myasthenia gravis, Alzheimer's disease, multiple sclerosis, neuromyelitis optica, rheumatoid arthritis, osteoarthritis, systemic lupus erythematosus, lupus nephritis, IgG4 associated diseases, insulin-dependent diabetes mellitus, acute disseminated encephalomyelitis, Addison's disease, antiphospholipid antibody syndrome, thrombotic thrombycytopenic purpura, autoimmune hepatitis, Crohn's disease, Goodpasture's syndromes, Graves' disease, Guillain-Barre syndrome, Hashimoto's disease, idiopathic thrombocytopenic purpura, pemphigus, Sjogren's syndrome, Takayasu's arteritis, autoimmune glomerulonephritis, membranoproliferative glomerulonephritis type II, membranous disease, paroxysmal nocturnal hemoglobinuria, age-related macular degeneration, diabetic maculopathy, uveitis, retinal degeneration disorders, diabetic nephropathy, focal segmental glomerulosclerosis, ANCA associated vasculitis, hemolytic uremic syndrome, Shiga-toxin-associated hemolytic uremic syndrome, and atypical hemolytic uremic syndrome.

81. The method of embodiment 80, wherein the autoimmune glomerulonephritis is selected from the group consisting of immunoglobulin A nephropathy or membranoproliferative glomerularnephritis type I.

82. The method of any one of embodiments 66 to 81, wherein said individual is a mammal.

83. The method of embodiment 82, wherein said mammal is a human.

84. The method of any one of embodiments 66 to 83, wherein said administering is by injection.

85. The method of embodiment 84, wherein said injection is parenteral, intravenous, subcutaneous, intraocular, intra-articular, or intramuscular.

Unless otherwise defined, all technical and scientific terms used herein have the same meaning as commonly understood by one of ordinary skill in the art to which this disclosure pertains. In case of conflict, the present document, including definitions, will control. Exemplary methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., compositions and methods for treating or preventing or detecting or monitoring a complement-associated disorder, will be apparent from the description, the examples, and from the claims.

EXAMPLES

Example 1

It has become increasingly apparent that covalent decoration of inflamed tissues with the complement C3 fragments iC3b, C3 dg and C3d provides a unique "flag" or "target" to which therapeutic or diagnostic agents can be directed. Described herein are monoclonal antibodies having utility as molecular imaging probes for the non-invasive detection of tissue-bound C3 fragments in various tissue, including the kidney and retina. Following extensive in vitro and in vivo analyses, a subset of the mAbs described herein were shown to possess unique characteristics that in aggregate prove that these mAbs can be used to identify in vivo sites of complement activation. This capability enables the antibodies to direct linked diagnostic modules to these sites. For example, the antibodies could direct contrast agents to sites of inflammation that are then detectable by MRI, positron emission tomography (PET), ultrasound, and/or optical imaging devices. Described herein are antibodies, including nucleotide and derived protein sequences of the key antigen combining sites. Also included are data demonstrating that ScFv generated using these sequences compete with the originally described monoclonal antibody, showing their interrelationships.

During activation of the complement system the C3 protein is cleaved, and C3 activation fragments are covalently fixed to nearby tissues. Tissue-bound C3 fragments are a durable sign of this process and are commonly used as biomarkers of tissue inflammation. These fragments have been exploited as addressable binding ligands for targeted therapeutics and diagnostic agents. We have generated novel murine monoclonal antibodies to human C3d (the final C3 degradation fragment generated during complement activation). We screened these antibodies to determine whether any of them bind to epitopes on C3d that are not present or exposed on intact C3. Three of the antibodies (clones 3d8b, 3d9a, and 3d29) preferentially bound to the iC3b, C3dg, and C3d fragments in solution, but do not bind to intact C3 or C3b. The same three clones also bound to tissue-bound C3 activation fragments when injected systemically. Using mouse models of renal and retinal disease, we confirmed that the antibodies accumulated at sites of C3 fragment deposition within the glomerulus, the renal tubulointerstitium, and the eye after systemic injection. To detect antibodies bound within the eye, we used optical imaging and observed accumulation of the antibodies within retinal lesions in a model of choroidal neovascularization (CNV). Our results demonstrate that imaging methods that utilize these antibodies may provide a sensitive means of detecting and monitoring tissue inflammation.

3d scFv and 3d scFv-Complement Inhibitors Construction and Expression 3d 29scFv and 3d8bscFv Purification.

Figure 19:
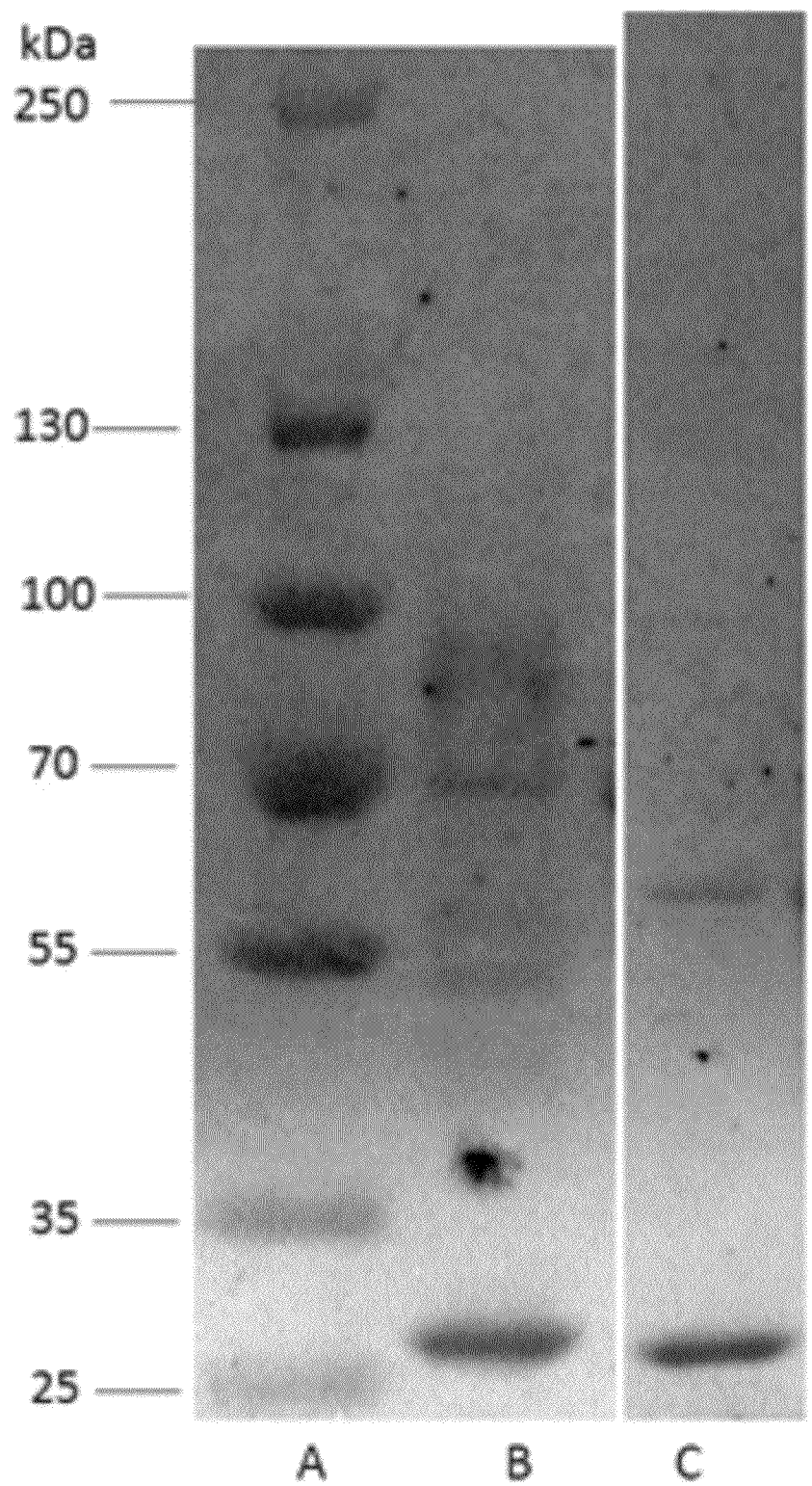
FIG. 19. SDS-PAGE of 3d29 scFv and 3d8b scFv. Lane A: Protein Ladder, Lane B: 3d29scFv; Lane C: 3d8b scFv.

Positive clones of 3dscFv CHO cells were cultured and amplified in HyperFlask cell culture vessel. Supernatant were collected and filtered, followed by loading on HisPur columns. After adjust the washing and elution condition, scFv were purified with almost 90% purity, see FIG. 19.

3d8bscFv and 3d29 scFv Block Test.

Figure 20:
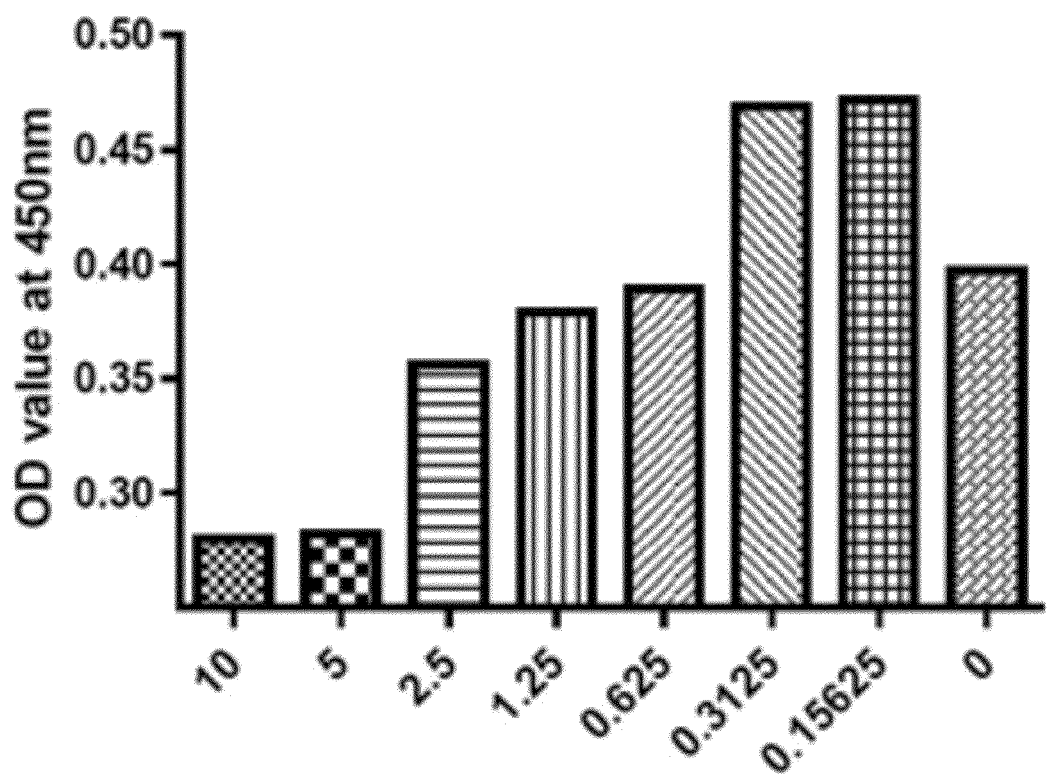
FIG. 20. 3d8b scFv block test.
Figure 21:
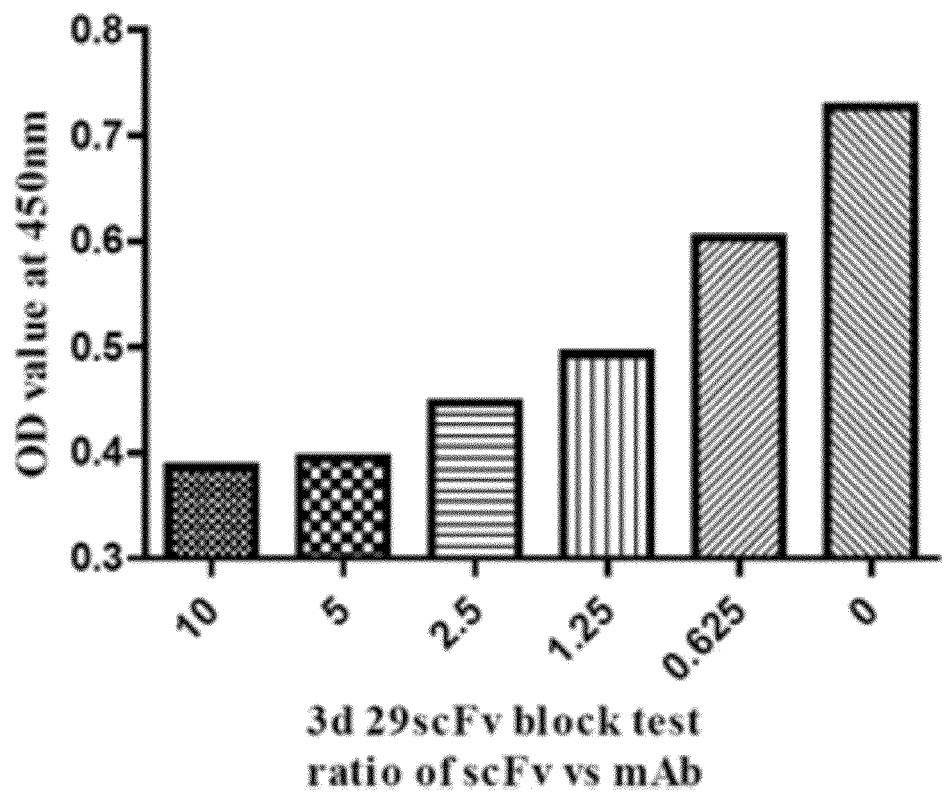
FIG. 21. 3d29 scFv block test.

3d antigen were coated on the plates (10 ng/well) 4° C. overnight. Plates were blocked for 1 hr at RT with ELISA blocking buffer. After washing, a serial dilution of 3dscFv were incubated with the antigen plates 4° C. overnight. After 5 times wash, a serial dilation of 3dmA b were incubated on the plates for 2 hrs at RT followed by 5 times wash. Anti-mouse IgG Fc-HRP were used as secondardy Ab. After 5 times wash, add TMB solution to each well, incubate for 5-10 min, add equal volume of stopping solution (2 M H2SO4) and read the optical density at 450 nM, see FIGS. 20 and 21.

3dscFv-Crry Cloning and Positive Clones Selected.

Primers were designed to amplify 3d8bscFv and Crry separately. 3' primer for 3d8b have 25 by sequence the same as the 5' primer for Crry. After overlapping 2 fragments, 3' primer for 3d8b and 5' primer for Crry were used to amplify 3dscFvCrry fusion gene. 3d8bscFv-Crry fusion gene was cloned into pEE14.1 vector at the sites of HindIII and EcorI, see FIG. 22.

Transfection and Positive Clone Selection.

Figure 23:
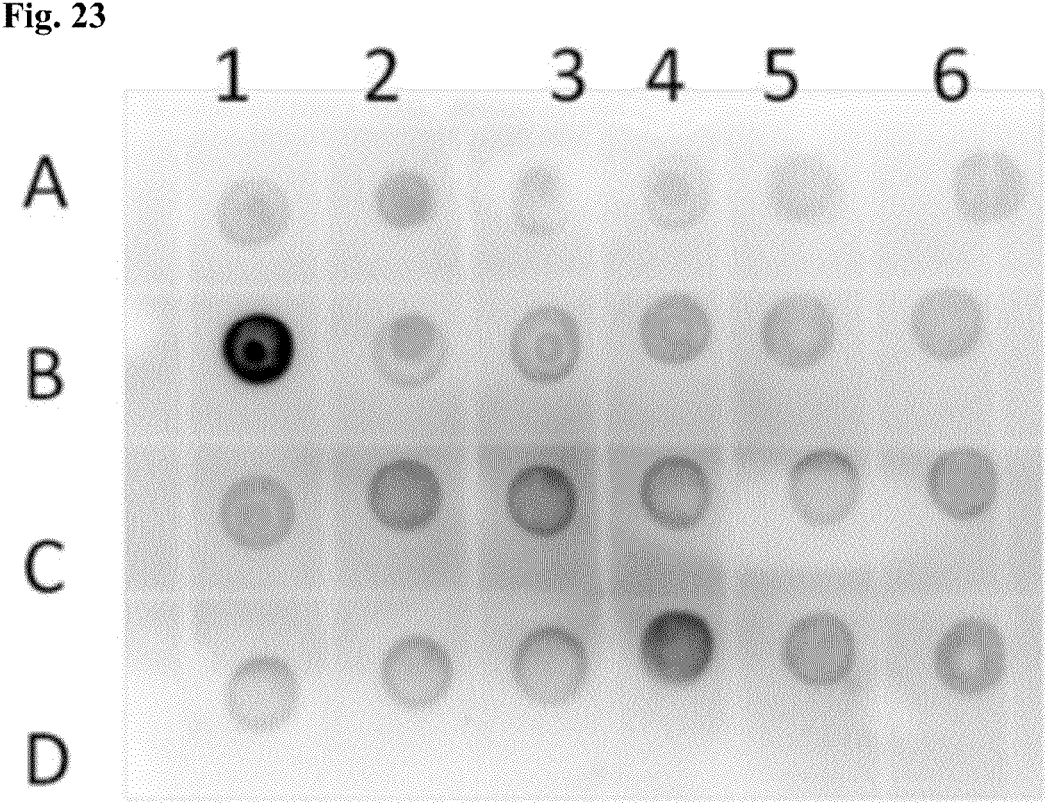
FIG. 23. Dot blot to select the positive clones of 3d8bscFv-Crry.

PEE14.1/3d8bscFv-Crry was sequenced with right sq. PEE14.1/3d8bscFv-Crry-1 was transfected into CHO cells. 48 hrs after transfection, CHO/PEE14.1/3d8bscFv-Crry were transferred to MSX selection medium and after 3-4 weeks culture, cell clone were moved to 24 wells, followed with clone selection by Dot-blot, see FIG. 23. 5 µl of cultured supernatant were loaded on NC membrane followed by 2% of BSA block at RT for 1 hr. Anti-6×His HRP:1:1000 4° C. overnight. A6 of CHO supernatant was used as negative control. Based on the result, B1 and D4 were selected as positive clones for further culture and selection, see FIG. 23.

3d8bscFv-FH cloning and sequencing.

Primers were designed to amplify 3d8bscFv and FH separately. 3' primer for 3d8b have 25 by sequence the same as the 5' primer for FH. After overlapping 2 fragments, 3' primer for 3d8b and 5' primer for FH were used to amplify 3dscFv-FH fusion gene. 3d8bscFv-FH fusion gene was cloned into pEE14.1 vector at the sites of HindIII and EcorI. pEE3d8bFH-5 have been confirmed with right sequence. The plasmid has been transfected into CHO cells for further selection.

Example 2

Ongoing work will further define the biodistribution, pharmacokinetics, and methods of tagging the antibodies with different reporter moieties for visual, radiologic and other means of detection. We have confirmed that the antibodies can be radiolabeled for detection by PET, and the radiolabeled antibodies retain greater than 95% of their immunoreactivity. The affinity constants for the labeled antibodies were:

| Clone | Kd |
|---|---|
| 29 | 0.43 nM |
| 9a | 0.62 nM |
| 8b | 0.38 nM |

Data collected indicates that the antibodies can successfully be conjugated to the surface of an MRI contrast agent (e.g. iron oxide nanoparticles), and fluorescently labeled antibody can be detected in the retina using optical imaging methods.

Figure 10A:
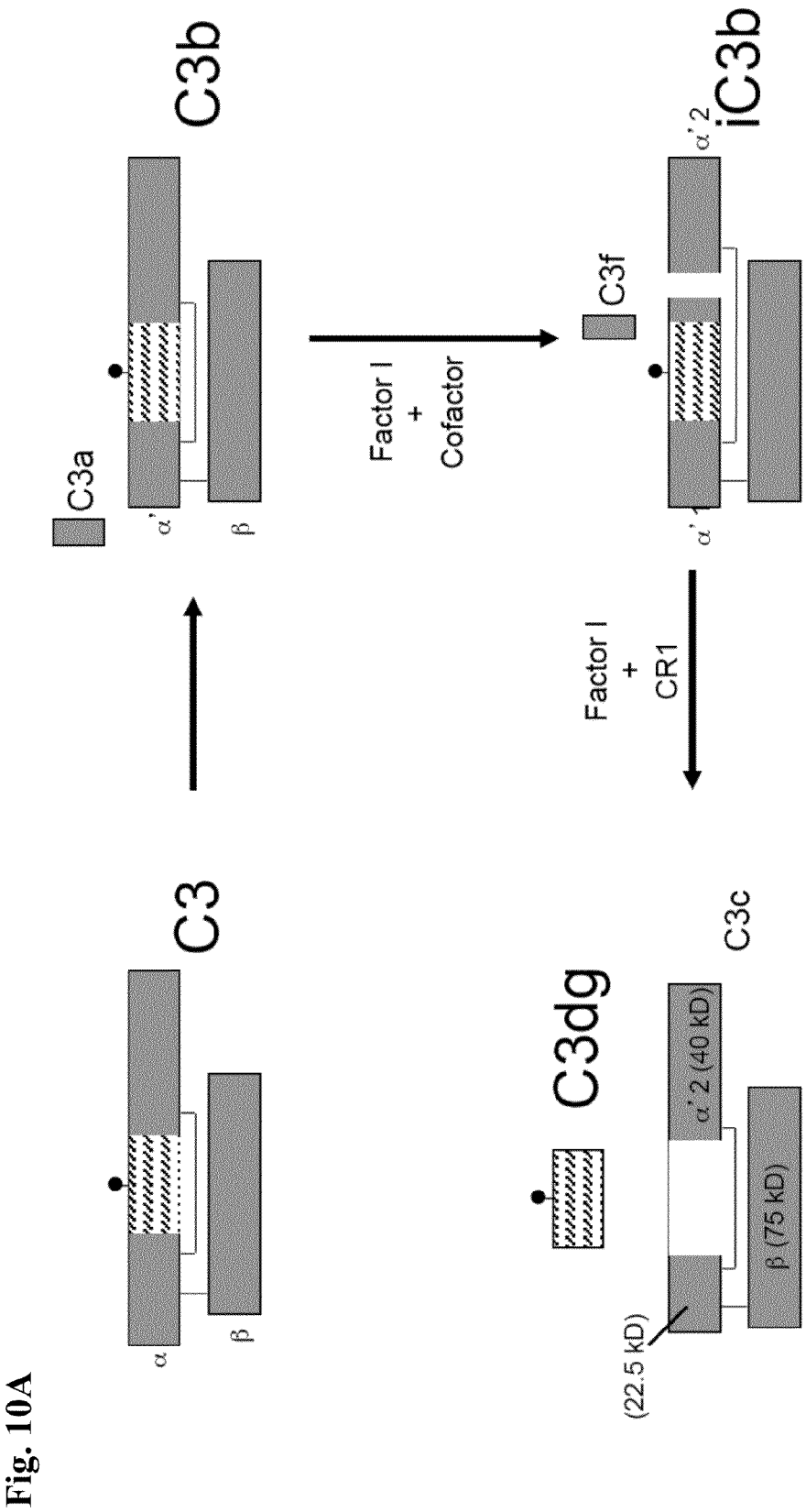
FIGS. 10A-10B. Metabolism of C3 to iC3b and C3d during complement activation.
Figure 10B:
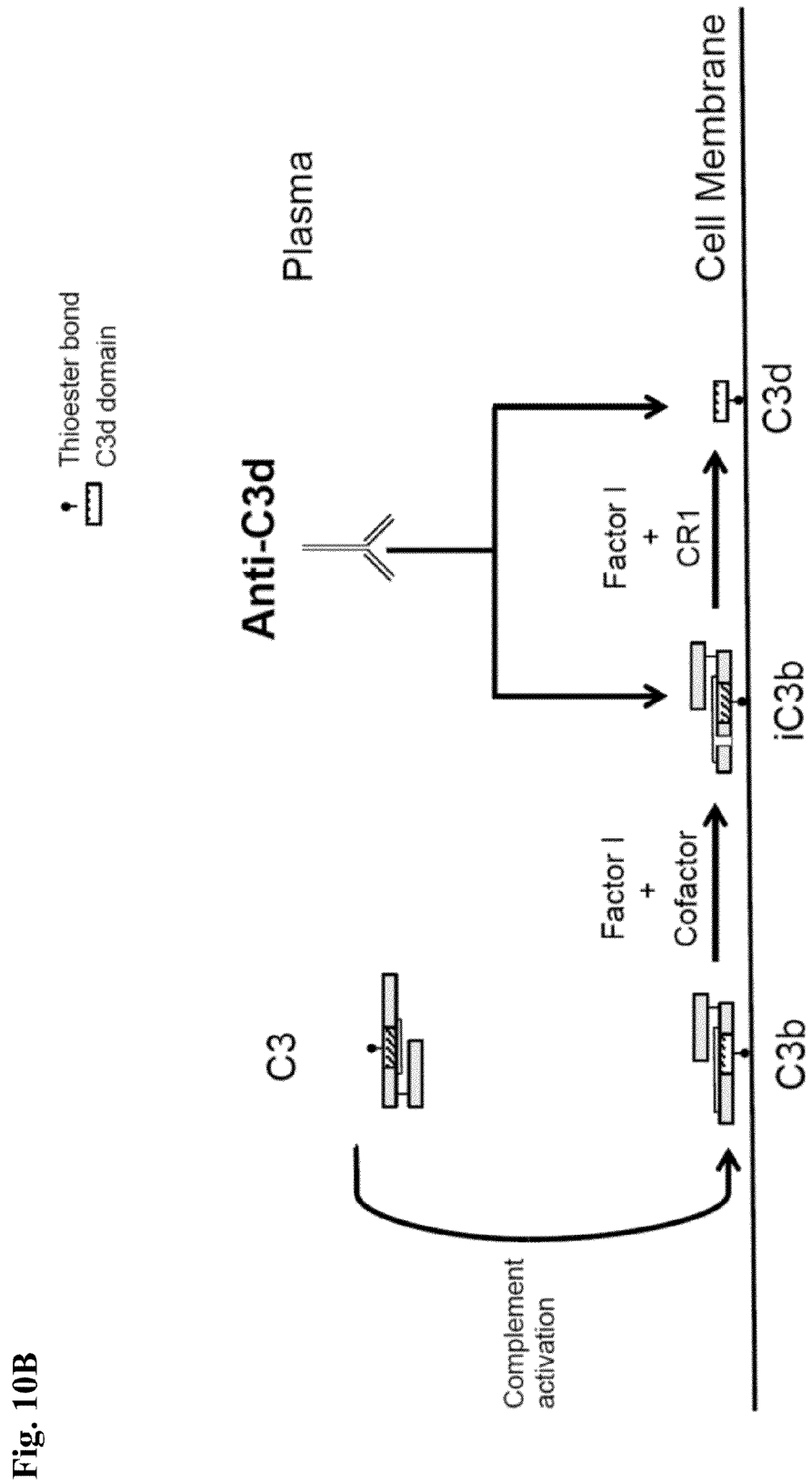

The complement system is an important arm of the innate immune system, providing critical protection against invasive pathogens (Ricklin, D., Hajishengallis, G., Yang, K., and Lambris, J. D. 2010. Complement: a key system for immune surveillance and homeostasis. Nat Immunol 11:785-797). Complement activation also contributes to the pathogenesis of numerous autoimmune and inflammatory diseases (Walport, M. J. 2001. Complement. Second of two parts. N Engl J Med 344:1140-1144). During the course of complement activation, the C3 protein undergoes proteolytic cleavage at several different sites (FIG. 10). The cleavage fragments are fixed to nearby tissues through a covalent linkage between a thioester site on C3 and hydroxyl groups on receptor surfaces (Serkova, N. J., Renner, B., Larsen, B. A., Stoldt, C. R., Hasebroock, K. M., Bradshaw-Pierce, E. L., Holers, V. M., and Thurman, J. M. 2010. Renal inflammation: targeted iron oxide nanoparticles for molecular MR imaging in mice. Radiology 255:517-526; Law, S. K., and Dodds, A. W. 1997. The internal thioester and the covalent binding properties of the complement proteins C3 and C4. Protein Sci 6:263-274). Thus, the deposition of C3 fragments on tissue surfaces constitutes a durable signal of tissue inflammation. For this reason, tissue-bound C3 fragments are commonly used as biomarkers of immune activation. Renal biopsies, for example, are routinely immunostained for C3 fragments, and the detection of glomerular C3 fragments serves as a sensitive and robust indicator of disease activity (Schulze, M., Pruchno, C. J., Burns, M., Baker, P. J., Johnson, R. J., and Couser, W. G. 1993. Glomerular C3c localization indicates ongoing immune deposit formation and complement activation in experimental glomerulonephritis. Am J Pathol 142:179-187).

Because tissue-bound C3 fragments reflect local inflammation, they have also been exploited as addressable binding ligands for targeted therapeutics and diagnostic agents (Serkova, N. J., Renner, B., Larsen, B. A., Stoldt, C. R., Hasebroock, K. M., Bradshaw-Pierce, E. L., Holers, V. M., and Thurman, J. M. 2010. Renal inflammation: targeted iron oxide nanoparticles for molecular MR imaging in mice. Radiology 255:517-526; Atkinson, C., Song, H., Lu, B., Qiao, F., Burns, T. A., Holers, V. M., Tsokos, G. C., and Tomlinson, S. 2005. Targeted complement inhibition by C3d recognition ameliorates tissue injury without apparent increase in susceptibility to infection. J Clin Invest 115:2444-2453; Sargsyan, S. A., Serkova, N. J., Renner, B., Hasebroock, K. M., Larsen, B., Stoldt, C., McFann, K., Pickering, M. C., and Thurman, J. M. 2012. Detection of glomerular complement C3 fragments by magnetic resonance imaging in murine lupus nephritis. Kidney Int 81:152-159; Rohrer, B., Long, Q., Coughlin, B., Wilson, R. B., Huang, Y., Qiao, F., Tang, P. H., Kunchithapautham, K., Gilkeson, G. S., and Tomlinson, S. 2009. A targeted inhibitor of the alternative complement pathway reduces angiogenesis in a mouse model of age-related macular degeneration. Invest Ophthalmol Vis Sci 50:3056-3064; Rohrer, B., Coughlin, B., Bandyopadhyay, M., and Holers, V. M. 2012. Systemic Human CR2-Targeted Complement Alternative Pathway Inhibitor Ameliorates Mouse Laser-Induced Choroidal Neovascularization. J Ocul Pharmacol Ther). These targeted agents have employed recombinant forms of complement receptor-2 (CR2), a protein that can discriminate between intact C3 in the plasma and tissue-bound C3 fragments. The rationale for this approach is that systemically administered agents can be delivered to sites of inflammation through their affinity with the iC3b and C3d fragments. By directing therapeutic agents to molecular targets, one can achieve a high degree of local activity for the drug while minimizing its systemic side-effects (Webb, S. 2011. Pharma interest surges in antibody drug conjugates. Nat Biotechnol 29:297-298) We have also used a CR2-targeted contrast agent to detect tissue-bound C3 fragments and renal disease activity by magnetic resonance imaging (Serkova, N. J., Renner, B., Larsen, B. A., Stoldt, C. R., Hasebroock, K. M., Bradshaw-Pierce, E. L., Holers, V. M., and Thurman, J. M. 2010. Renal inflammation: targeted iron oxide nanoparticles for molecular MR imaging in mice. Radiology 255:517-526; Sargsyan, S. A., Serkova, N. J., Renner, B., Hasebroock, K. M., Larsen, B., Stoldt, C., McFann, K., Pickering, M. C., and Thurman, J. M. 2012. Detection of glomerular complement C3 fragments by magnetic resonance imaging in murine lupus nephritis. Kidney Int 81:152-159). Although specific for the cleaved forms of C3, CR2-targeted agents may bind these fragments with a relatively low affinity [reported values range from 1-10 µM at physiologic ionic strength (Guthridge, J. M., Rakstang, J. K., Young, K. A., Hinshelwood, J., Aslam, M., Robertson, A., Gipson, M. G., Sarrias, M. R., Moore, W. T., Meagher, M., et al. 2001. Structural studies in solution of the recombinant N-terminal pair of short consensus/complement repeat domains of complement receptor type 2 (CR2/CD21) and interactions with its ligand C3dg. *Biochemistry* 40:5931-5941; Isenman, D. E., Leung, E., Mackay, J. D., Bagby, S., and van den Elsen, J. M. 2010. Mutational analyses reveal that the staphylococcal immune evasion molecule Sbi and complement receptor 2 (CR2) share overlapping contact residues on C3d: implications for the controversy regarding the CR2/C3d cocrystal structure. *J Immunol* 184:1946-1955). Higher affinity targeting vectors for epitopes on the cleaved forms of C3 could potentially deliver therapeutic and diagnostic agents to sites of inflammation with even greater efficiency.

Well-characterized monoclonal antibodies to tissue-bound C3 fragments thus have many biomedical applications. They could be used as in vivo delivery vehicles for new therapeutic and diagnostic agents. They could also potentially modulate the biologic functions of the C3 fragments. For example they could block the interaction of the C3 fragments with CRs 1-4 or with other proteins that bind C3, such as the complement inhibitor factor H. Such antibodies could also be useful for identifying specific C3 fragments (e.g. C3b, iC3b, C3dg, and C3d) and quantifying their relative abundance. There are, however, several barriers to the generation of such antibodies by standard methods. Like CR2, the antibodies must recognize epitopes of cleaved C3 that are not exposed on intact C3 (which circulates at a concentration of 1-2 mg/mL). This is feasible, however, since internal regions of C3d (and likely also iC3b and C3dg) are exposed by a conformational change in C3 during its activation (Janssen, B. J., Christodoulidou, A., McCarthy, A., Lambris, J. D., and Gros, P. 2006. Structure of C3b reveals conformational changes that underlie complement activity. *Nature* 444:213-216). Another difficulty is that standard methods for generating and cloning hybridomas may expose the hybridoma cells to C3 and C3 fragments in serum-containing media, or to C3 synthesized by cells, such as macrophages, that are used in the cultures. C3 in the media could mask positive hybridoma clones or affect the growth of such clones through cross-linkage of the B cell receptors.

We have used novel methods to overcome these difficulties and have developed nine murine monoclonal antibodies to human C3d that cross-react with both mouse and cynomologous C3d. Three of these high-affinity antibodies discriminate the cleaved forms of C3 from the intact C3 protein. Furthermore, our studies demonstrate that these antibodies can be used to target tissue sites of complement activation in vivo despite high levels of intact C3 in the circulation. We report herein the methods that we used to develop these monoclonal antibodies to C3d, and the evidence that these reagents target tissue-bound C3d in vivo.

Example 3

Development of Murine mAbs to Recombinant Human C3d

During complement activation C3 undergoes a conformational change that exposes a thioester bond (Serkova, N. J., Renner, B., Larsen, B. A., Stoldt, C. R., Hasebroock, K. M., Bradshaw-Pierce, E. L., Holers, V. M., and Thurman, J. M. 2010. Renal inflammation: targeted iron oxide nanoparticles for molecular MR imaging in mice. *Radiology* 255:517-526; Janssen, B. J., Christodoulidou, A., McCarthy, A., Lambris, J. D., and Gros, P. 2006. Structure of C3b reveals conformational changes that underlie complement activity. *Nature* 444: 213-216). The thioester domain (TED) of C3 rotates during the conversion of C3 into C3b, altering the orientation of the TED on the surface of the molecule (Janssen, B. J., Christodoulidou, A., McCarthy, A., Lambris, J. D., and Gros, P. 2006. Structure of C3b reveals conformational changes that underlie complement activity. *Nature* 444:213-216). This region of C3b remains exposed during the subsequent cleavages that generate iC3b, C3dg, and finally C3d (FIG. 10). In order to generate mAbs to epitopes on this region of C3 we produced recombinant human C3d (Guthridge, J. M., Rakstang, J. K., Young, K. A., Hinshelwood, J., Aslam, M., Robertson, A., Gipson, M. G., Sarrias, M. R., Moore, W. T., Meagher, M., et al. 2001. Structural studies in solution of the recombinant N-terminal pair of short consensus/complement repeat domains of complement receptor type 2 (CR2/CD21) and interactions with its ligand C3dg. *Biochemistry* 40:5931-5941) and immunized mice bearing a targeted deletion of the C3 gene [C3−/− mice; (Wessels, M. R., Butko, P., Ma, M., Warren, H. B., Lage, A. L., and Carroll, M. C. 1995. Studies of group B streptococcal infection in mice deficient in complement component C3 or C4 demonstrate an essential role for complement in both innate and acquired immunity. *Proc Natl Acad Sci USA* 92:11490-11494)]. Although C3−/− mice have impaired humoral immunity (Wessels, M. R., Butko, P., Ma, M., Warren, H. B., Lage, A. L., and Carroll, M. C. 1995. Studies of group B streptococcal infection in mice deficient in complement component C3 or C4 demonstrate an essential role for complement in both innate and acquired immunity. *Proc Natl Acad Sci USA* 92:11490-11494), they developed a strong antibody response to the C3d immunogen (data not shown).

Figure 11A:
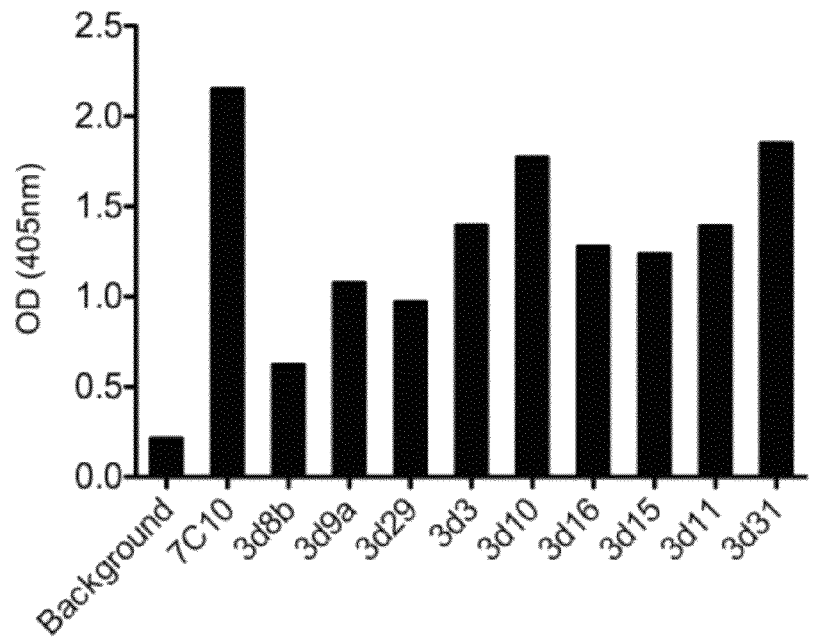
FIGS. 11A-11D. Generation of monoclonal antibodies that recognize C3 activation fragments. Anti-human C3d hybridomas were generated.

Two fusions were performed using splenocytes of mice with high antibody titers to C3d, but both fusions failed to yield any reactive clones. Because the desired hybridoma cells were specific for C3d, we hypothesized that the failure to generate any clones was because C3 fragments generated by serum in the tissue culture media or from macrophages used in the cloning process bound to the B cell receptors of reactive cells. This could potentially lead to apoptosis of the cells or interfere with the screening ELISA assay. Therefore, a third fusion was performed in which hybridoma cells were grown in serum-free media formulations. Because macrophages also have the capacity to synthesize all of the proteins of the alternative complement pathway and generate C3 fragments (Strunk, R. C., Kunke, K. S., and Giclas, P. C. 1983. Human peripheral blood monocyte-derived macrophages produce haemolytically active C3 in vitro. *Immunology* 49:169-174), the feeder cells used during cloning were obtained by peritoneal lavage of C3−/− mice. Single cell clones were generated and screened against C3d by ELISA, and nine clones with strong reactivity were identified (FIG. 11A).

To confirm that the antibodies reacted with C3d and not with a contaminant in the immunogen, the antibodies were tested against the C3d using a sandwich ELISA in which the recombinant C3d was captured with a polyclonal anti-C3d capture antibody (Table 2). To test reactivity of the clones against murine C3d we performed indirect and sandwich ELISAs using recombinant murine C3d. We also performed direct ELISAs to test binding of the antibodies to recombinant human C3d from a second construct, purified human C3d, and to recombinant cynomologous C3d. The nine clones all showed strong reactivity against all of these targets (Table 2)

Example 4

Specificity of Clones 3d8b, 3d9, and 3d29 for C3 Activation Fragments

Figure 11B:
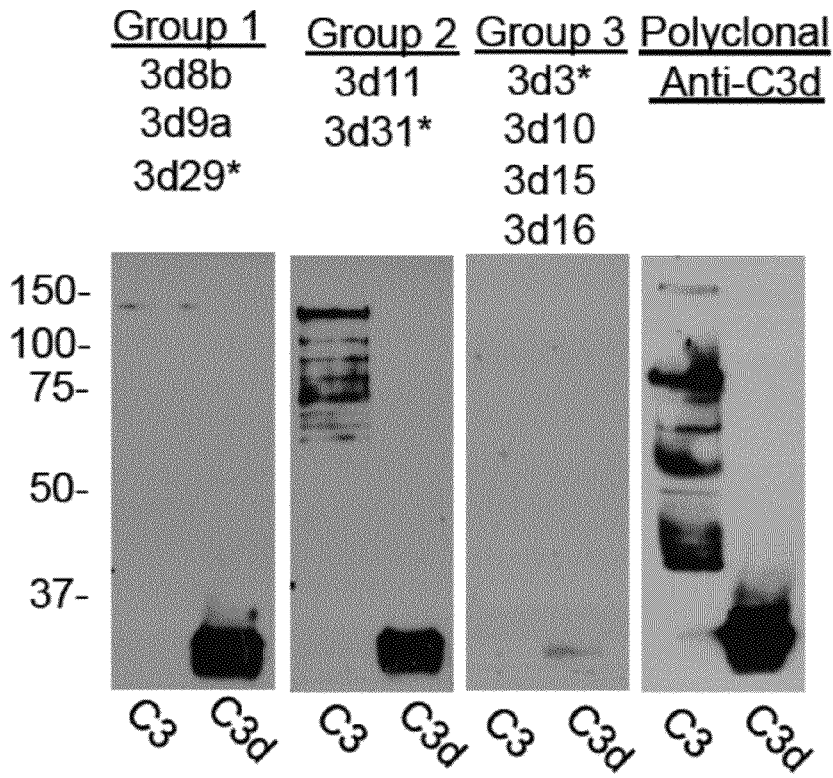
Figure 11C:
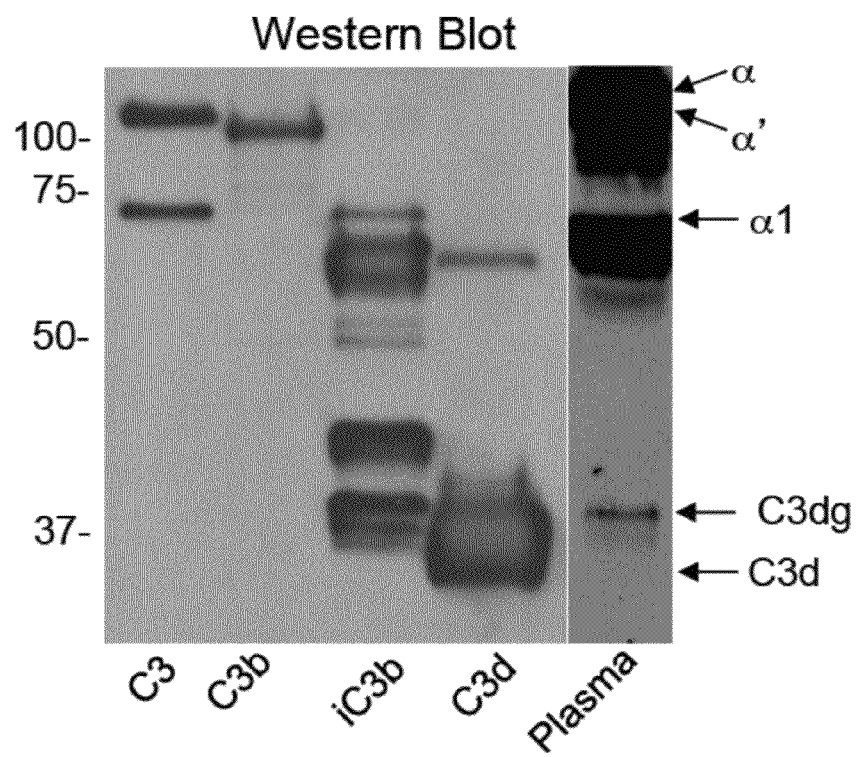

Western blot analysis of C3 and C3d was performed under denaturing conditions and the blots were probed with the nine anti-C3d clones. Although one would expect epitopes recognized in denatured C3d to also be exposed on the intact C3a chain in its denatured form, the antibodies demonstrated differential recognition of C3 and C3d in this assay (FIG. 11B). The antibodies displayed three distinct binding patterns by Western blot analysis: strong binding to C3d without binding to C3 (Group I), strong binding to C3 and C3d (Group II), or weak binding to both proteins (Group III). Clone 3d11 recognized all of the C3 fragments by Western blot analysis (FIG. 11C).

Figure 11D:
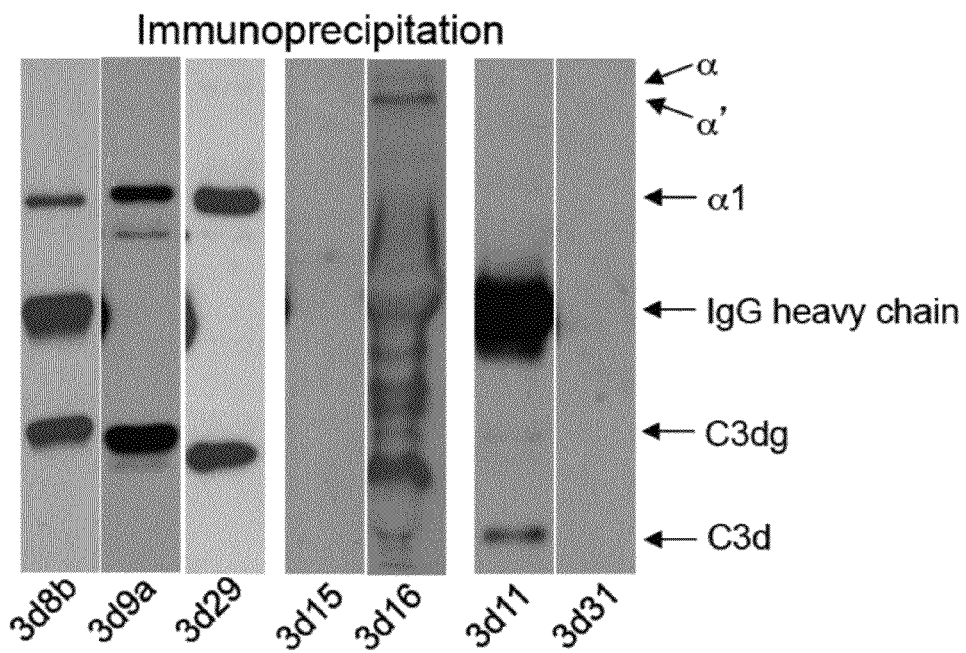

To test the binding of the antibodies to the different C3 fragments in their native form, immunoprecipitation reactions were performed using activated plasma that contained a mixture of the various C3 fragments (FIG. 11D). The antibodies in Group I (clones 3d8b, 3d9, and 3d29) pulled-down the iC3b and C3dg fragments. Clone 11 (Group II) pulled down C3d. Clone 16 (Group III) pulled-down C3, iC3b, C3dg, and C3d.

Figure 12A:
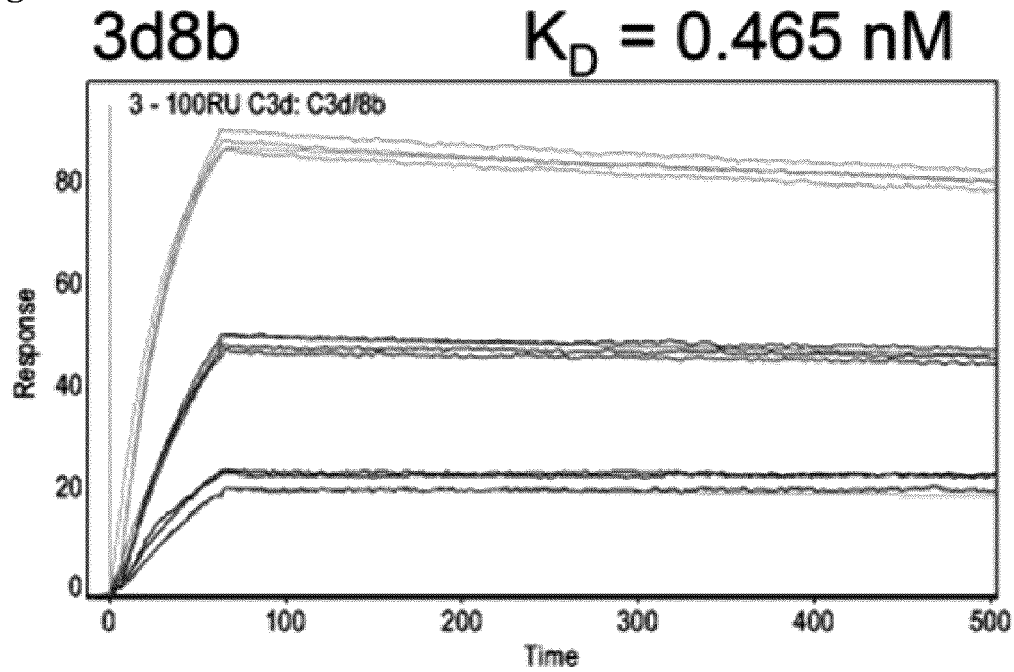
FIGS. 12A-12C. Surface plasmon resonance of clones 3d8b (FIG. 12A), 3d9a (FIG. 12B), and 3d29 (FIG. 12C) against recombinant human C3d demonstrate high affinity binding. Surface plasmon resonance was performed using recombinant human C3d fixed to a CM5 chip. The antibodies demonstrated high affinity binding, and $K_D$s are shown for each result.
Figure 12B:
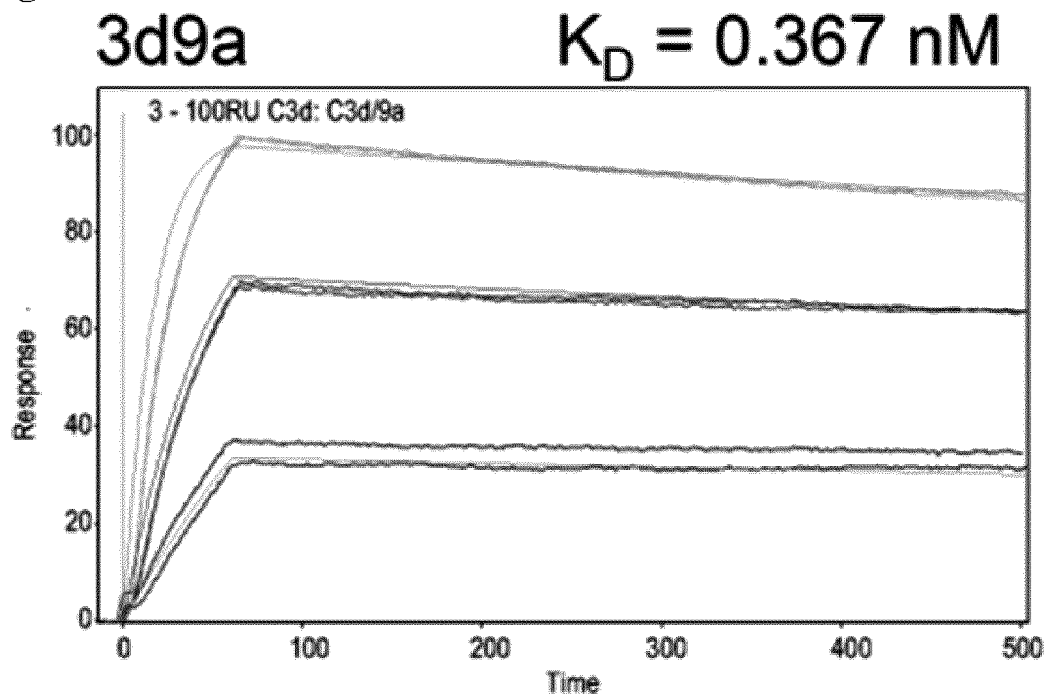
Figure 12C:
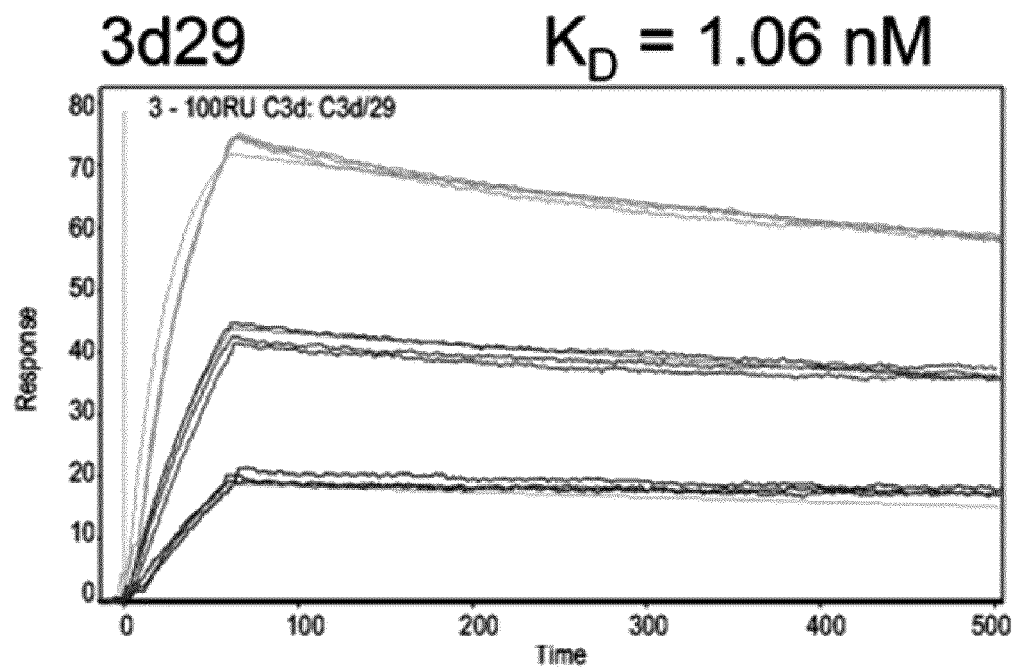

The affinity of clones 3d8b, 3d9, and 3d29 for C3d were tested by surface plasmon resonance (FIG. 12). The measured affinities were: 3d29: KD=1.06 nM; 3d9a: KD=0.367 nM; 3d8b: KD=0.465 nM.

Example 5

Effects of Anti-C3d mAbs on Surface-Bound C3 Convertase Activity

Figure 13A:
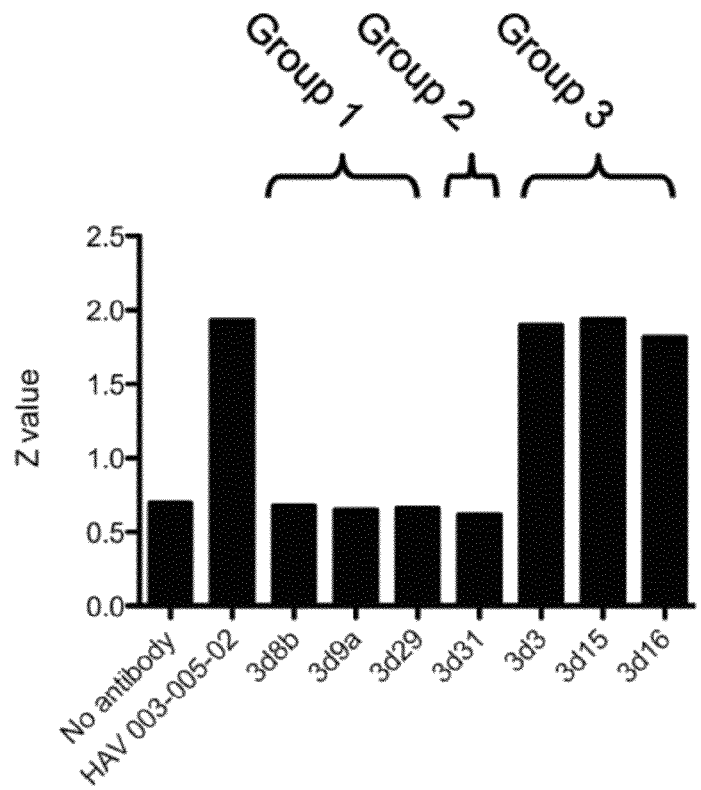
FIGS. 13A-13E. Clones 3d3, 3d15, and 3d16 stabilize the C3 convertase on sheep erythrocytes. Sheep erythrocytes were sensitized with antibody and opsonized with human C3b. They were than treated with factor B, factor D, and properdin to generate AP C3-convertases (C3bBbP) on the cell surfaces. One µg of antibody was added to a 150 µl reaction mix, and the cells were used immediately (FIG. 13A and FIG. 13C) or incubated for 2 hours (FIG. 13B and FIG. 13D).
Figure 13B:
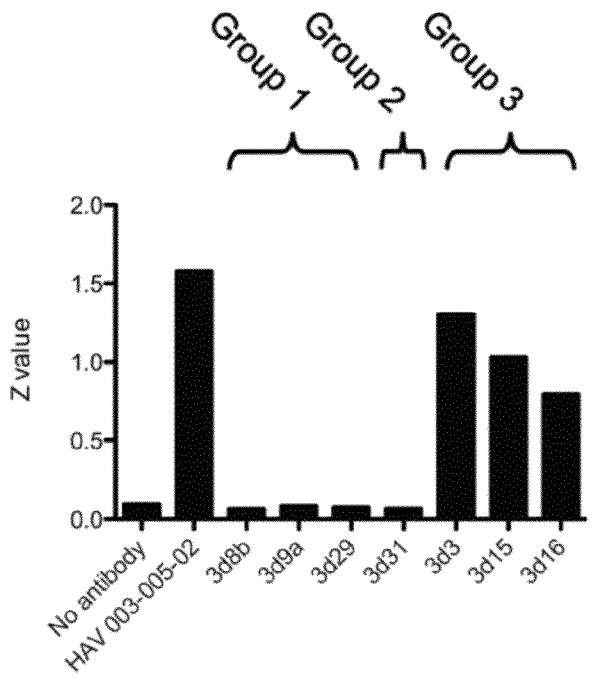

The alternative pathway C3-convertase is comprised of C3b in complex with the factor B fragment Bb and the fluid phase protein properdin (P). While C3bBbP dissociation occurs spontaneously (T ½~5-10 min), this process is greatly accelerated by the fluid phase complement regulator factor H. This latter reaction plays a critical role in protecting cells and tissues from complement-mediated damage and in preserving C3 homeostasis. Certain anti-C3 autoantibodies, referred to as C3 nephritic factors (C3Nef), stabilize the alternative pathway C3 convertase and confer to it resistance to factor H, thus permitting uncontrolled complement activation (Daha, M. R., Fearon, D. T., and Austen, K. F. 1976. C3 nephritic factor (C3NeF): stabilization of fluid phase and cell-bound alternative pathway convertase. *J Immunol* 116:1-7). To assess whether the anti-C3d antibodies have C3Nef-like activity, we first incubated C3bBbP complexes pre-assembled on sheep erythrocytes with the anti-C3d antibodies or with buffer alone for various times. We then quantified the hemolytic activity of the remaining convertases. (FIG. 13A). The group I clones (3d8b, 3d9a, and 3d29) did not have any effect on erythrocyte lysis, nor did the group II clone 3d31. The loss of hemolysis activity due to spontaneous convertase dissociation during the incubation period in these samples was comparable to that of the control cells. In contrast, the group III clones (3d3, 3d15, 3d16) stabilized the convertase, causing greater erythrocyte lysis immediately (FIG. 13A) and after a 2 hour incubation (FIG. 13B). In all cases, hemolysis was absolutely dependent on the presence of factor B in the pre-assembly step (FIGS. 13C and D), thus confirming that the alternative pathway C3-convertase mediated the Group III effects. EGTA was included as a calcium chelator, thus precluding the involvement of the other complement activation pathways in the process.

Figure 13C:
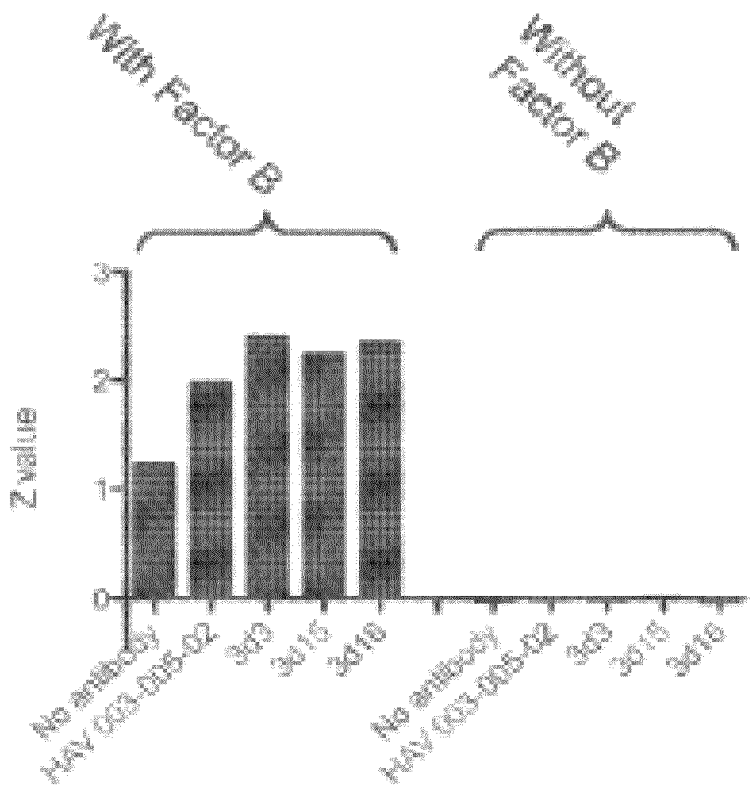
Figure 13D:
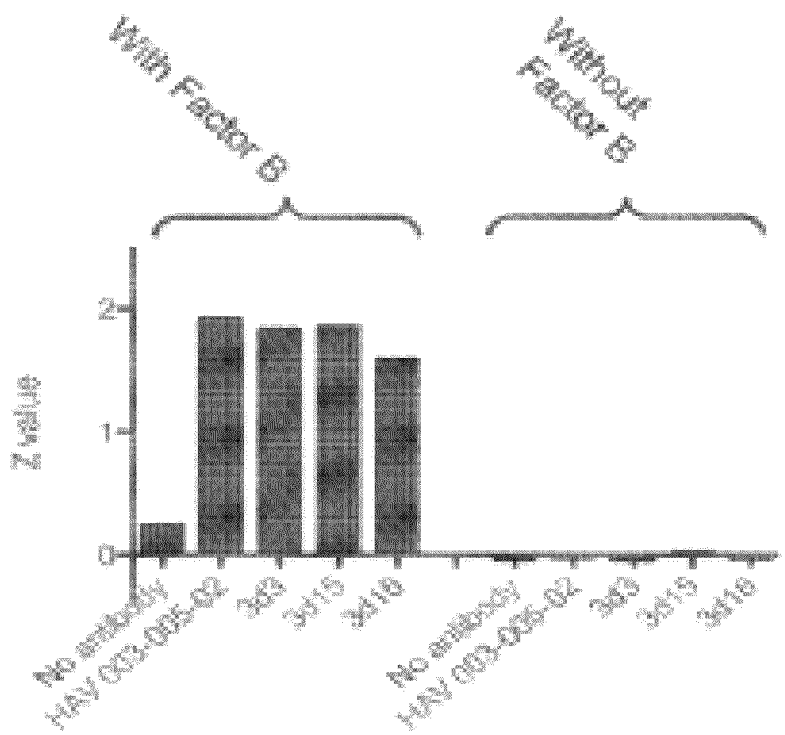
Figure 13E:
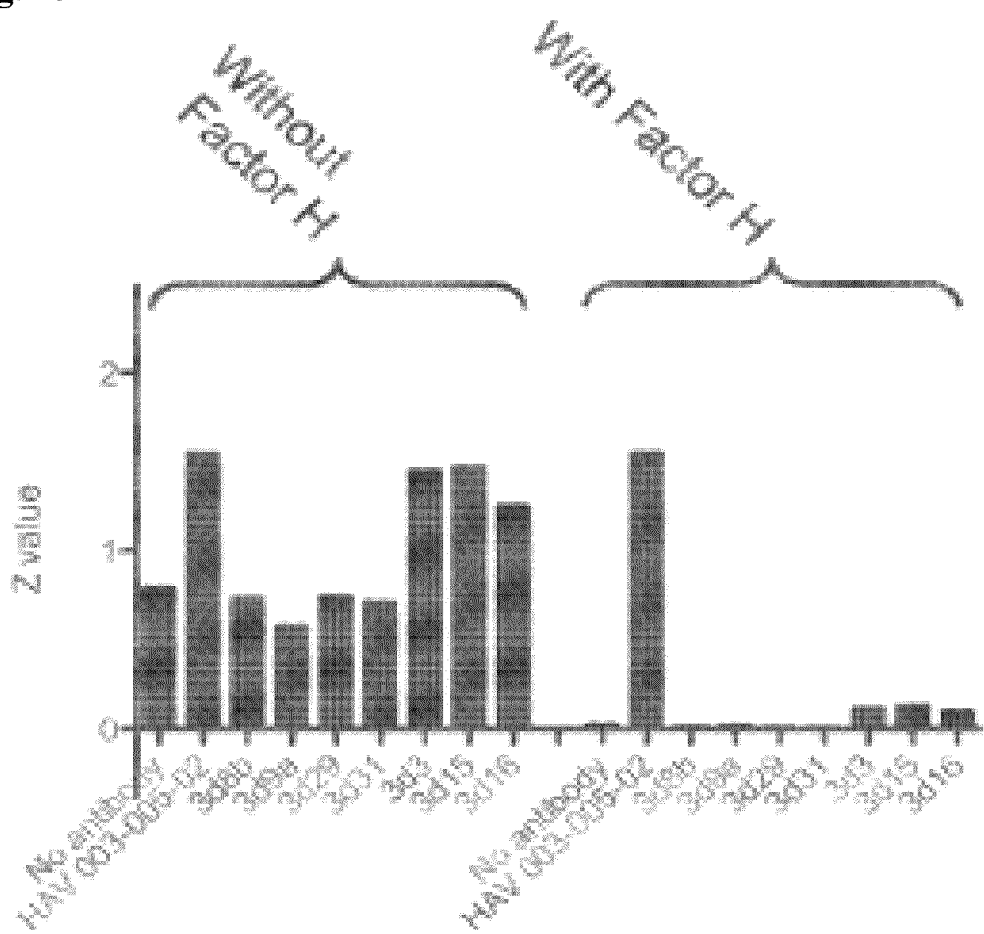
Figure 14:
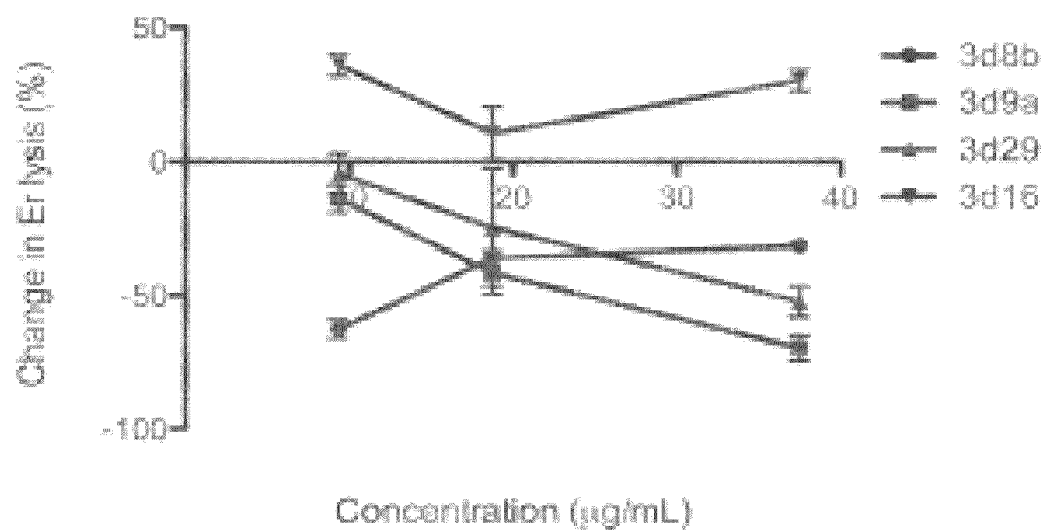
FIG. 14. Clones 3d8b, 3d9a, and 3d29 do not increase alternative pathway activation on rabbit erythrocytes. Varying amounts of clones 3d8b, 3d9a, 3d29, and 3d16 were added to an alternative pathway lysis assay (AH50) in which rabbit erythrocytes are incubated with human serum. An increase in lysis was observed in reactions containing 3d16, but not in reactions to which 3d8b, 3d9a, or 3d29 had been added.

We also examined the impact of the anti-C3d antibodies on factor H activity. Factor H is an alternative pathway regulatory protein that limits alternative pathway activation by accelerating the decay of the C3-convertase (Weiler, J. M., Daha, M. R., Austen, K. F., and Fearon, D. T. 1976. Control of the amplification convertase of complement by the plasma protein beta1H. *Proc Natl Acad Sci USA* 73:3268-3272) or by serving as a co-factor for factor I mediated cleavage (inactivation) of C3b (Pangburn, M. K., Schreiber, R. D., and Muller-Eberhard, H. J. 1977. Human complement C3b inactivator: isolation, characterization, and demonstration of an absolute requirement for the serum protein beta1H for cleavage of C3b and C4b in solution. *J Exp Med* 146:257-270). The addition of factor H inhibited lysis of the erythrocytes in reactions containing each of the anti-C3d antibodies, indicating that none of the antibodies blocked the factor H binding site on the surface of C3b (FIG. 13E). This is consistent with recent data indicating that the binding site on C3b for the amino-terminal four SCRs of FH (CFH1-4), which harbor the factor I cofactor and C3bBb decay acceleration activities of FH, lies outside the TED domain (which approximates to the C3d cleavage product) (Wu, J., Wu, Y. Q., Ricklin, D., Janssen, B. J., Lambris, J. D., and Gros, P. 2009. *Structure of complement fragment C3b-factor H and implications for host protection by complement regulators.* Nat Immunol 10:728-733).

Finally, the antibodies were tested in an alternative pathway hemolysis assay using normal human serum and rabbit erythrocytes. This is a standard assay for measuring alternative pathway activity on activator surfaces. Even when clones 3d8b, 3d9a, and 3d29 were added to the reaction mix at high concentrations they did not increase lysis of the erythrocytes. Conversely, the addition of clone 16 at high concentrations did increase hemolysis.

Example 6

Effect of Anti-C3d mAbs on Binding of C3d by CR2

Figure 15A:
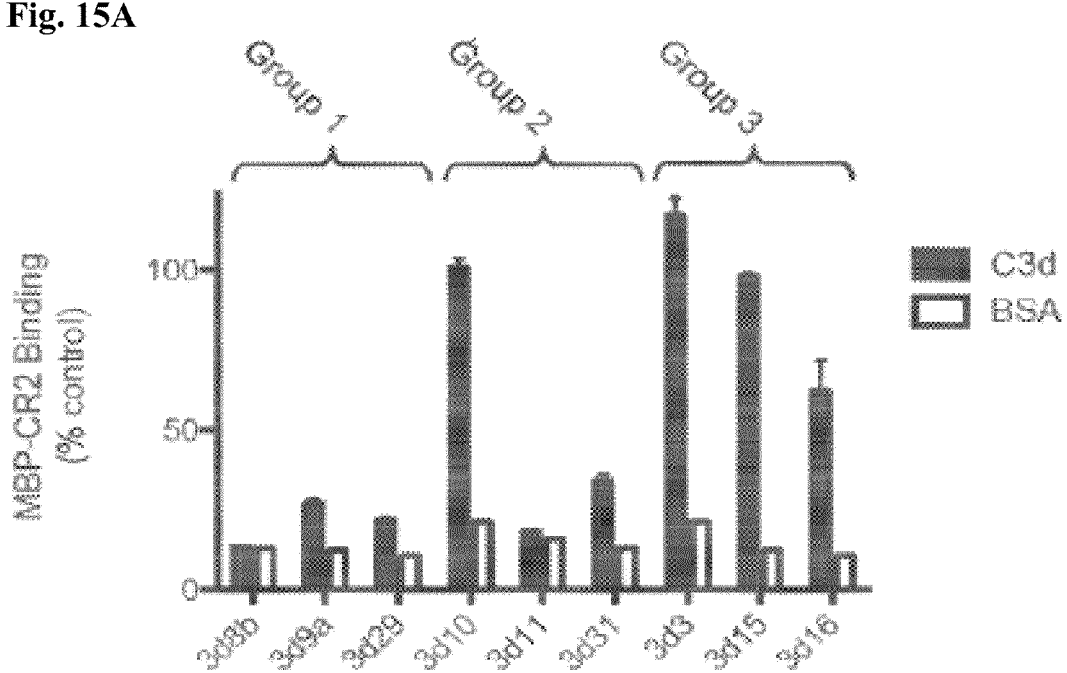
FIGS. 15A-15D. Blockade of the CR2-C3d interaction by anti-C3d mAbs.
Figure 15B:
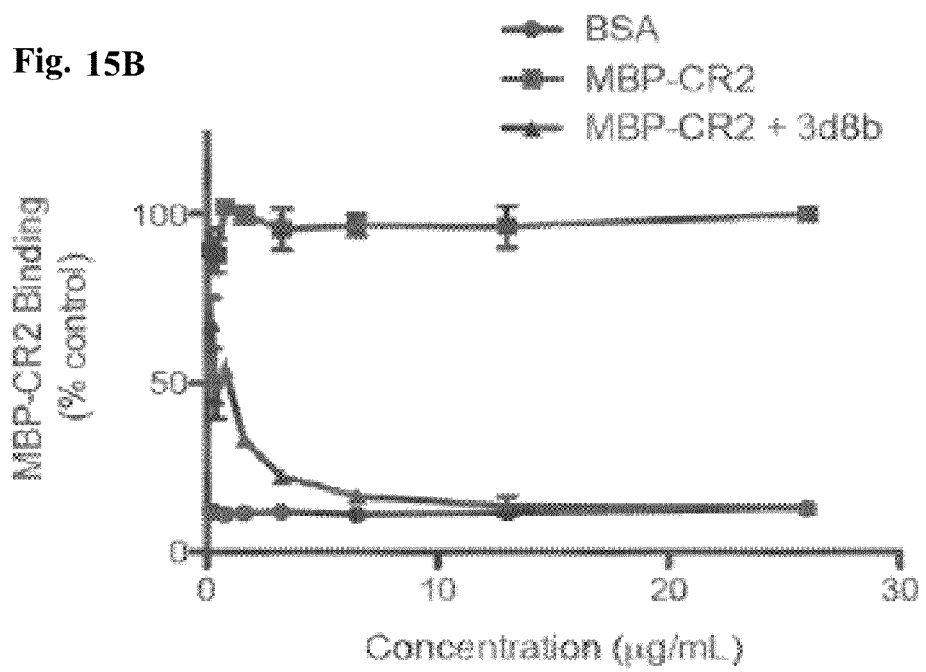
Figure 15C:
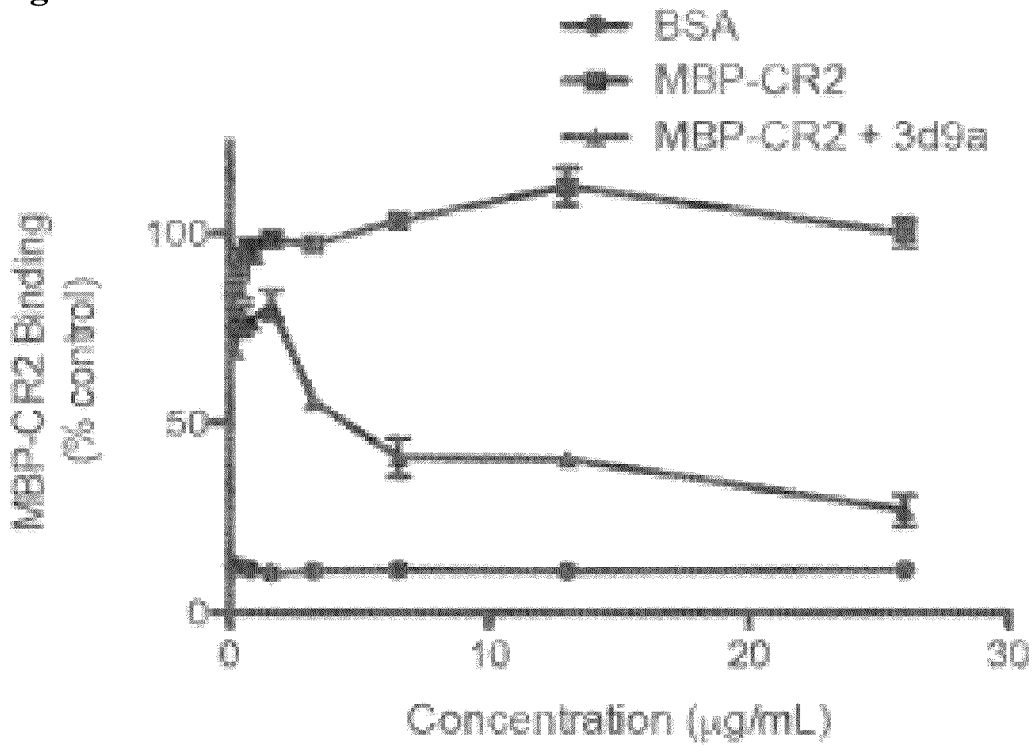
Figure 15D:
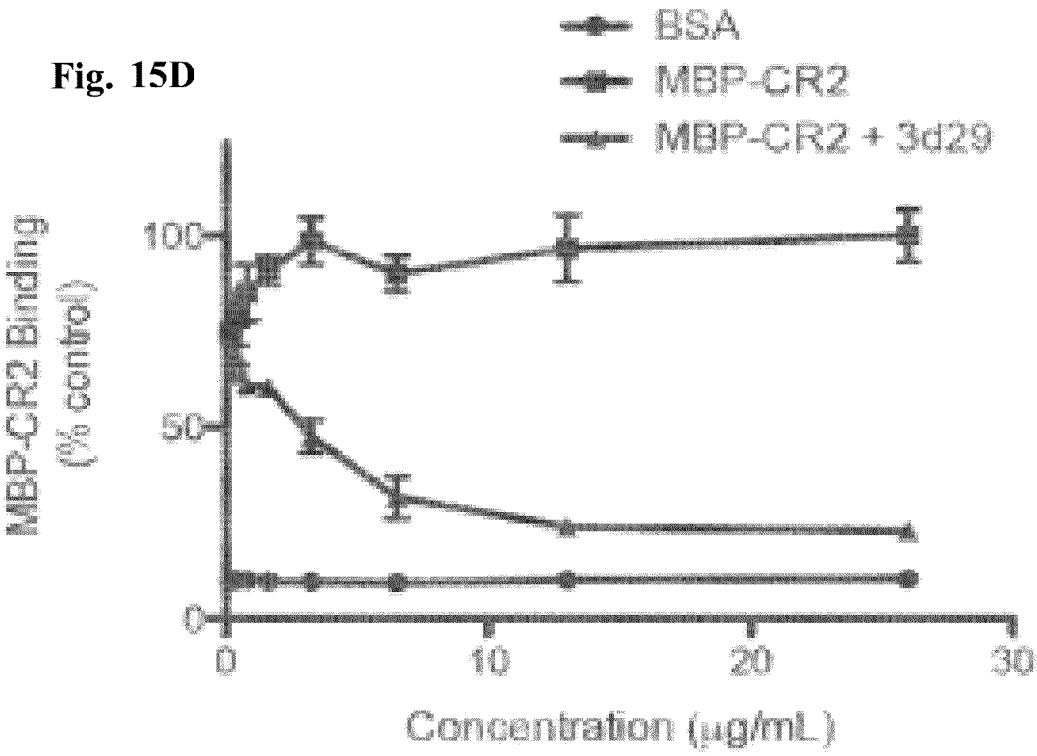

C3d is a ligand for CR2, which is expressed on B cells and follicular dendritic cells. Recognition of C3d by CR2 on B cells lowers the threshold for B cell activation by the B cell receptor (Lyubchenko, T., dal Porto, J., Cambier, J. C., and Holers, V. M. 2005. Coligation of the B cell receptor with complement receptor type 2 (CR2/CD21) using its natural ligand C3dg: activation without engagement of an inhibitory signaling pathway. *J Immunol* 174:3264-3272). Consequently, signaling by CR2 is important in the development of the humoral immune response and autoimmunity. We tested whether the mAbs to C3d would block this interaction (FIG. 15). Using an in vitro CR2-C3d binding assay, we found that clones 3d8b, 3d9a, 3d11, 3d29, and 3d31 blocked CR2 from binding C3d. Dose response curves for the group 1 antibodies demonstrated nearly complete inhibition of CR2 by 3d8b at high concentrations (FIG. 15B). Clones 3d9a and 3d29 achieved approximately 80% inhibition of binding by CR2 when added at high concentrations (FIGS. 13C-D). These results raise the possibility that the antibodies may have immunomodulatory function.

Example 7

Binding of Anti-C3d mAbs to Surface-Bound C3 Activation Fragments In Vitro

To assess the ability of the mAbs to bind native C3 fragments bound to activating surfaces, zymosan particles were opsonized with C3 fragments by incubation with serum (Thurman, J. M., Kraus, D. M., Girardi, G., Hourcade, D., Kang, H. J., Royer, P. A., Mitchell, L. M., Giclas, P. C., Salmon, J., Gilkeson, G., et al. 2005. A novel inhibitor of the alternative complement pathway prevents antiphospholipid antibody-induced pregnancy loss in mice. *Mol Immunol*

Figure 16A:
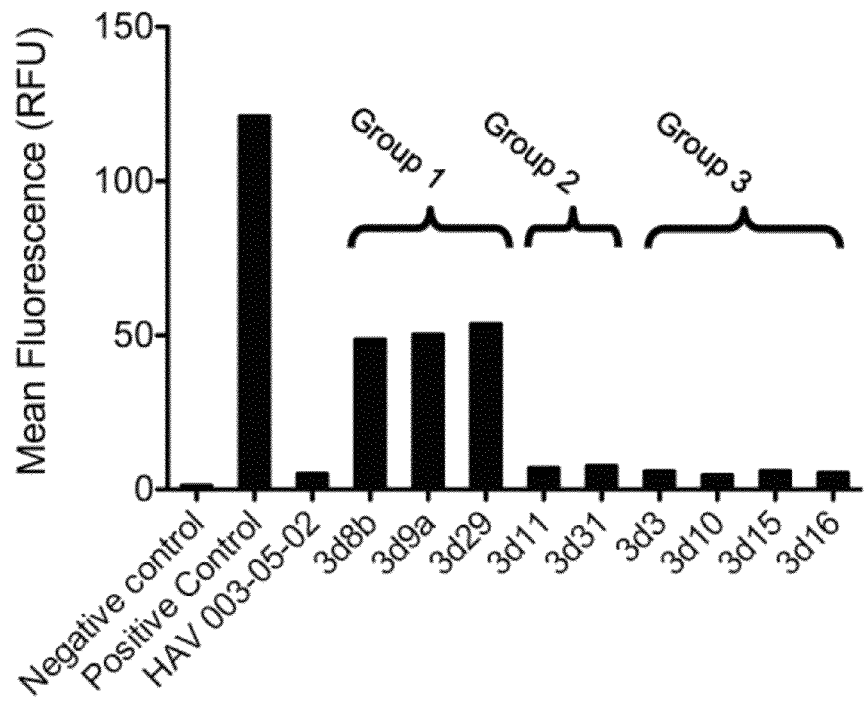
FIGS. 16A-16B. Clones 3d8b, 3d9a, and 3d29 bind to mouse C3 fragments generated in vitro and in vivo.
Figure 16B:
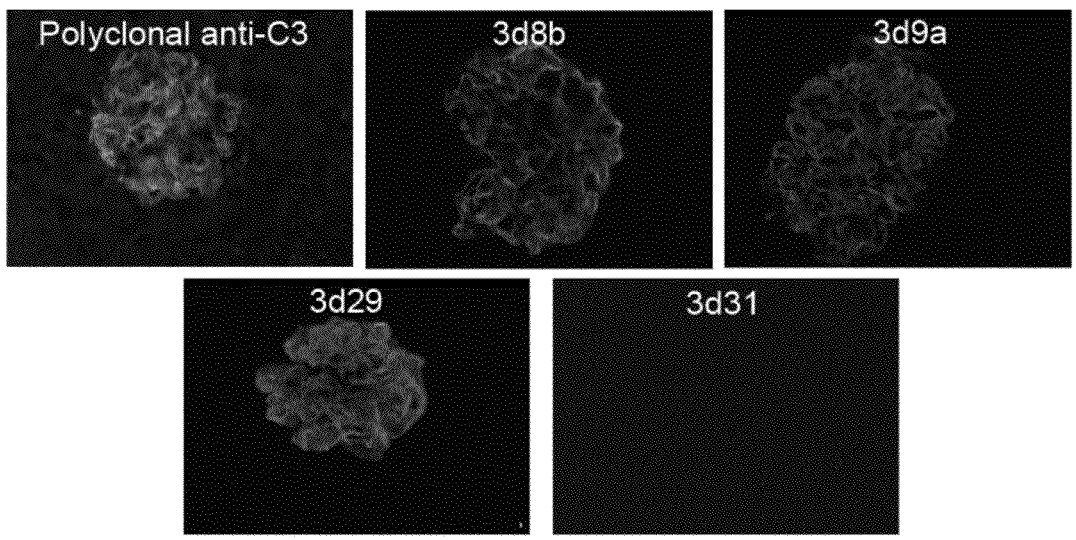
Figure 17A:
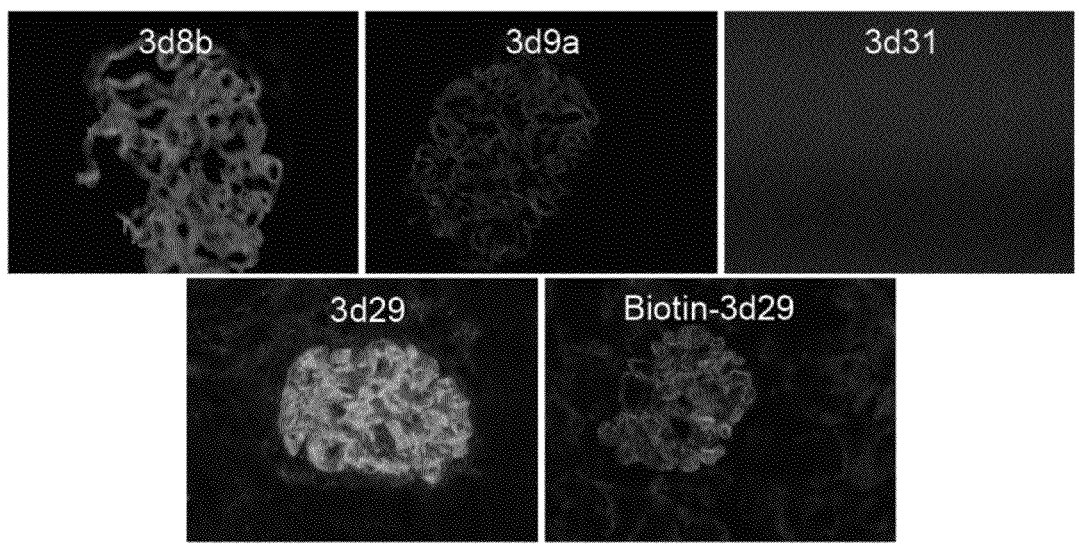
FIGS. 17A-17B. Clones 3d8b, 3d9a (3d9), and 3d29 target tissue-bound C3 fragments after systemic in vivo injection.
Figure 17B:

42:87-97). The particles were then incubated with the antibodies, and bound antibodies were detected by flow cytometry (FIG. 16A). Clones 8b, 9a, and 29 bound to the opsonized zymosan particles, whereas the other clones did not. To test the binding of these antibodies to C3 deposits in tissues, sections were made from the kidneys of factor H deficient mice. These glomeruli of these mice are characterized by glomerulonephritis and have abundant deposits of the C3 activation fragments iC3b and C3dg/C3d (Paixao-Cavalcante, D., Hanson, S., Botto, M., Cook, H. T., and Pickering, M. C. 2009. Factor H facilitates the clearance of GBM bound iC3b by controlling C3 activation in fluid phase. *Mol Immunol* 46:1942-1950; Pickering, M. C., Cook, H. T., Warren, J., Bygrave, A. E., Moss, J., Walport, M. J., and Botto, M. 2002. Uncontrolled C3 activation causes membranoproliferative glomerulonephritis in mice deficient in complement factor H. *Nat Genet* 31:424-428). Clones 8b, 9a, and 29 bound to the acetone-fixed sections in a pattern indistinguishable from that obtained using a polyclonal antibody to C3 (FIG. 16B).

Example 8

In Vivo Targeting of Anti-C3d mAbs to Tissue Sites of Complement Activation

Next, we sought to determine whether the antibodies would bind to tissue-bound C3 fragments when injected in vivo. The antibodies were injected intravenously into fH−/− mice, which do not have glomerular deposits of endogenous IgG (Pickering, M. C., Cook, H. T., Warren, J., Bygrave, A. E., Moss, J., Walport, M. J., and Botto, M. 2002. Uncontrolled C3 activation causes membranoproliferative glomerulonephritis in mice deficient in complement factor H. Nat Genet 31:424-428). After 24 hours the kidneys were harvested and immunostained for IgG (FIG. 16A). Clones 8b, 9a, and 29 were readily detected along the glomerular basement membrane in a pattern indistinguishable from that of the C3 fragments, demonstrating that they bound to C3 deposits in the glomerular capillary wall after intravenous injection. To confirm that we were not detecting endogenous deposits of IgG, clone 3d29 was biotinylated and injected into fH−/− mice. Glomerular binding of the antibody was detected using streptavidin-FITC.

C3 fragments are ordinarily deposited along the tubular basement membrane of wild-type mice (Thurman, J. M., Ljubanovic, D., Edelstein, C. L., Gilkeson, G. S., and Holers, V. M. 2003. Lack of a functional alternative complement pathway ameliorates ischemic acute renal failure in mice. *J Immunol* 170:1517-1523). Tubular C3 deposits are not seen in fH−/− mice, likely because most C3 is consumed in the fluid phase in these mice (Guthridge, J. M., Rakstang, J. K., Young, K. A., Hinshelwood, J., Aslam, M., Robertson, A., Gipson, M. G., Sarrias, M. R., Moore, W. T., Meagher, M., et al. 2001. Structural studies in solution of the recombinant N-terminal pair of short consensus/complement repeat domains of complement receptor type 2 (CR2/CD21) and interactions with its ligand C3dg. *Biochemistry* 40:5931-5941). No IgG was detected along the tubular basement membrane of fH−/− mice injected with the anti-C3d antibodies. However, when biotinylated 3d29 was injected into wild-type mice, it was detected along the tubular basement membrane and co-localized with the C3 deposits. These results indicate that 3d8b, 3d9a, and 3d29 target and bind to tissue deposits of C3 activation fragments in the glomeruli of nephritic mice and in the tubulointerstitium of unmanipulated wild-type mice.

Example 9

In Vivo Imaging Anti-C3d mAbs Targeted to Ocular Sites of Complement Activation

To test whether the targeted antibodies could be visualized in vivo, we turned to a system amenable to optical imaging, the eye. Complement activation is involved in pathology of age-related macular degeneration (AMD). Complement components, including C3 (Hageman, G. S., Luthert, P. J., Victor Chong, N. H., Johnson, L. V., Anderson, D. H., and Mullins, R. F. 2001. An integrated hypothesis that considers drusen as biomarkers of immune-mediated processes at the RPE-Bruch's membrane interface in aging and age-related macular degeneration. *Prog Retin Eye Res* 20:705-732), anaphlatoxins C3a and C5a (Nozaki, M., Raisler, B. J., Sakurai, E., Sarma, J. V., Barnum, S. R., Lambris, J. D., Chen, Y., Zhang, K., Ambati, B. K., Baffi, J. Z., et al. 2006. Drusen complement components C3a and C5a promote choroidal neovascularization. *Proc Natl Acad Sci USA* 103:2328-2333) as well as components of the membrane attack complex (Hageman, G. S., Luthert, P. J., Victor Chong, N. H., Johnson, L. V., Anderson, D. H., and Mullins, R. F. 2001. An integrated hypothesis that considers drusen as biomarkers of immune-mediated processes at the RPE-Bruch's membrane interface in aging and age-related macular degeneration. *Prog Retin Eye Res* 20:705-732) have been found to be present in pathological structures in AMD (e.g., drusen, Bruch's membrane), and single polymorphisms in complement genes pose as risk factors for AMD (Leveziel, N., Tilleul, J., Puche, N., Zerbib, J., Laloum, F., Querques, G., and Souied, E. H. 2011. Genetic factors associated with age-related macular degeneration. *Ophthalmologica* 226:87-102). AMD results in vision loss from either atrophy of the retinal pigmented epithelium (RPE) followed by loss of photoreceptors, or choroidal neovascularization (CNV) followed by loss of photoreceptors (Brown et al., 2005). The latter process can be mimicked in mice by damaging the blood retina barrier using laser photocoagulation, which triggers ingrowth of choroidal blood vessels into the subretinal space in a complement-dependent way (Rohrer et al., 2009; Rohrer et al., 2011). Likewise, complement deposition has been shown to occur at the site of injury (Nozaki et al., 2006; Rohrer et al., 2009). Utilizing the systemic CR2 targeting strategy, we have shown that complement inhibition delivered in this fashion (CR2-fH) can ameliorate CNV (Rohrer et al., 2009; Rohrer et al., 2012).

Figure 18A:
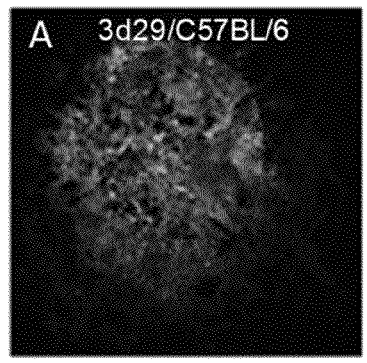
FIGS. 18A-18G. Clones 3d29 binds in vitro to tissue-bound C3 fragments in the retina in a model of choroidal neovascularization. Four laser spots in each eye were created by Argon laser photocoagulation.
Figure 18B:
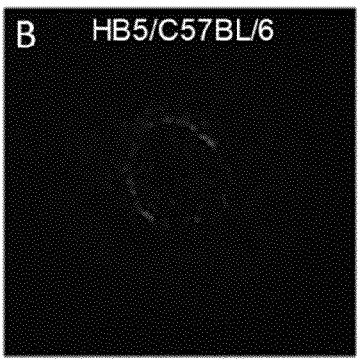
Figure 18C:
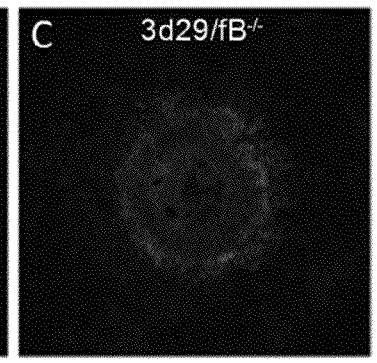

Here we tested whether we can directly image sites of complement activation in the RPE/choroid of laser-damaged mice, using the anti-C3d mAbs. First, we tested which of antibodies recognize C3d epitopes in the CNV lesion sites in flatmounted eyes. Since fluorescently labeled antibodies will be required for the in-vivo imaging, only FITC-labeled antibodies were tested. Of the FITC-labeled mAbs, clone 29 demonstrated the best binding to the CNV lesion in lightly fixed tissues (4% paraformaldehyde) (FIG. 18A). Since complement factor B knockout mice (fB−/−) show no increase in C3 in the RPE/choroid in response to the lesion and fail to develop significant CNV (Rohrer et al., 2009), fB−/− mice were used as negative controls for FITC-labeled mAb binding (FIG. 18B). An isotype control antibody (HB5) was also tested in order to confirm specificity of binding by 3d29 (FIG. 18C).

Figure 18D:
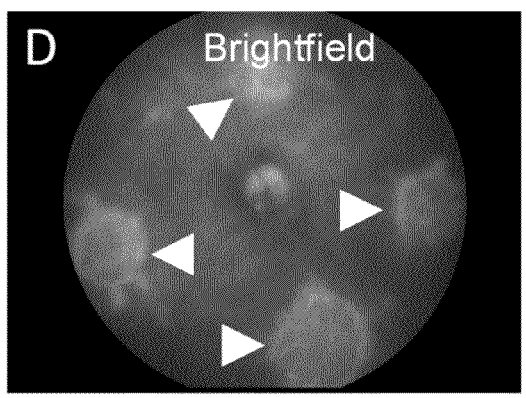
Figure 18E:
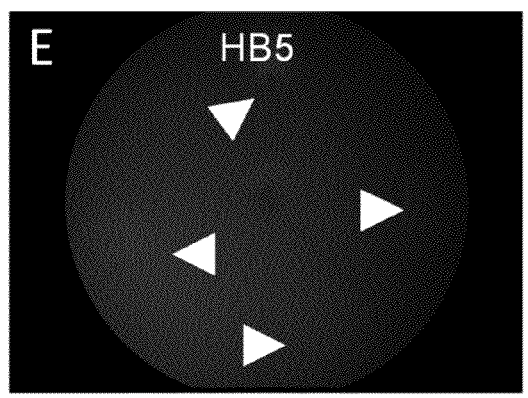
Figure 18F:
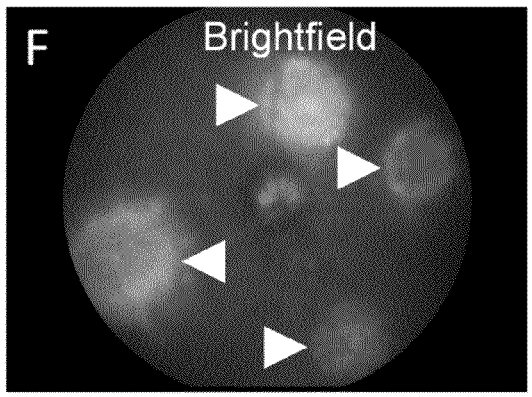
Figure 18G:
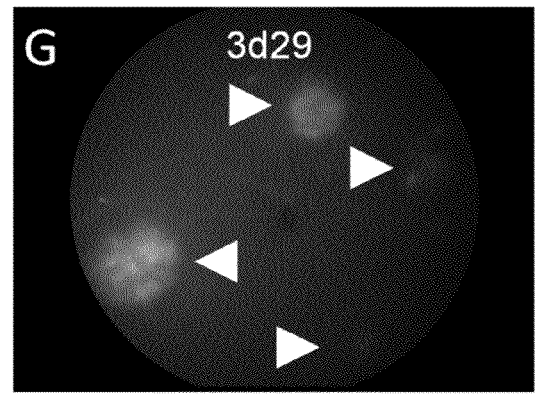

For in vivo imaging, CNV lesions were generated and FITC-labeled 3d29 or HB5 was injected intravenously on day 3 after CNV induction, a time point previously shown to correspond to the peak of C3 expression within the lesion (Rohrer et al., 2009) Animals were imaged 6, 24 and 48 hours after the injection, using fundus imaging. The CNV lesions are readily apparent in brighfield images as depigmented areas (FIG. 18D, F). At the early time points (6 and 24 hrs), both antibodies produced increased but indistinguishable fluorescence in the lesions. By 48 hours, diffuse background fluorescence is detected in control antibody—(FIG. 18E, E') in comparison to the punctate pattern revealed in 3d29 mAb-injected mice (FIG. 18G, G'). These results indicate that 3d29 is retained in RPE/choroid tissue deposits of C3 activation fragments at the posterior pole of CNV-lesioned mice at a high enough concentration that it can be visualized in the living eye using conventional imaging techniques.

Example 10

Analysis

This report describes the development of three monoclonal antibodies (the group I antibodies 3d8b, 3d9a, and 3d29) to the C3 activation fragment C3d that do not bind to intact C3 in its native conformation. These are antibodies that recognize an epitope on iC3b and C3d that is either generated or exposed during complement activation. To successfully create these antibodies we made several modifications to standard methods of hybridoma fusion: the hybridoma cells were grown under serum-free conditions and macrophages from C3−/− mice were used as feeder cells during the cloning process. This approach allowed the generation of nine mAbs to human C3d that also reacted with murine and cynomologous C3d.

Three of the nine antibodies demonstrated strong binding to SDS-denatured C3d, but little binding to denatured C3. The same three antibodies pulled-down iC3b and C3dg from a mixture that also contained intact C3, but the antibodies did not pull-down the intact C3 protein. These three clones also bound to C3 fragments on the surface of opsonized zymosan particles in vitro, demonstrating the ability to bind surface bound C3 fragments. Certain anti-C3 antibodies are known to stabilize C3-convertases, effectively amplifying complement activation. The three clones that target tissue-bound C3 fragments did not have any activating activity using several different in vitro assays. One of the other clones (clone 3d16), however, increased rabbit erythrocyte lysis in an assay of alternative pathway activation, and, along with other Group III antibodies, stabilized C3 convertases that were preassembled on sheep red blood cells. None of the antibodies described here prevented factor H mediated dissociation of the C3 convertase.

When mice with glomerulonephritis were injected with clones 3d8b, 3d9a, or 3d29, the antibodies accumulated at the site of C3 deposits within the glomeruli, demonstrating that the antibodies can be used to target tissue-bound iC3b and C3d at this location. When injected into wild-type mice these antibodies bound to C3 fragments deposited along the tubular basement membrane (which have deposition of C3 fragments at baseline). Because C3 fragments are present in the circulation of fH−/− mice and wild-type mice have high circulating levels of intact C3, this experiment verified that the clones 8b, 9a, and 29 preferentially bind to the tissue-bound iC3b and C3d activation fragments even in the presence of circulating C3 and C3 fragments.

The high affinity of these antibodies for C3d and the ability to deliver agents to sites of C3d deposition in vivo potentially make them invaluable tools for the development of diagnostic and therapeutic agents. The detection of glomerular C3 deposition is critical for the accurate diagnosis of glomerulonephritis, and renal biopsy tissue is routinely stained for C3. We have developed an MRI-based method for the non-invasive detection of glomerular C3 and these high-affinity antibodies may improve the sensitivity of this method. In the current study we demonstrated that FITC-labeled 3d29 was visualized in live animals using conventional fluorescence imaging. This enabled us to non-invasively detect C3d deposits within the RPE/choroid of mice with CNV. Finally, targeted complement inhibitors have also demonstrated great promise for the treatment of inflammatory diseases (Atkinson, C., Song, H., Lu, B., Qiao, F., Burns, T. A., Holers, V. M., Tsokos, G. C., and Tomlinson, S. 2005. Targeted complement inhibition by C3d recognition ameliorates tissue injury without apparent increase in susceptibility to infection. *J Clin Invest* 115:2444-2453; Sekine, H., Kinser, T. T., Qiao, F., Martinez, E., Paulling, E., Ruiz, P., Gilkeson, G. S., and Tomlinson, S. 2011. The benefit of targeted and selective inhibition of the alternative complement pathway for modulating autoimmunity and renal disease in MRL/lpr mice. *Arthritis Rheum* 63:1076-1085; Song, H., He, C., Knaak, C., Guthridge, J. M., Holers, V. M., and Tomlinson, S. 2003. Complement receptor 2-mediated targeting of complement inhibitors to sites of complement activation. *J Clin Invest* 111:1875-1885). These antibodies may provide a high-affinity targeting vector for delivery of novel therapeutic agents to sites of tissue inflammation.

In addition to their ability to direct diagnostic and therapeutic agents to sites of tissue-bound iC3b and C3dg/C3d in vivo, these antibodies may also be useful for modulating the biologic functions of complement. Clones 3d8b, 3d9a, and 3d29 blocked the binding of C3d by CR2. Given the important role of C3d-CR2 signaling in the adaptive immune response these antibodies may have immunomodulatory activity outside of the complement system.

We screened the antibodies against a panel of C3d mutants to identify the exact epitope on C3d. The antibodies may recognize complex epitopes. Similarly, all nine of the clones recognized all forms of C3 when screened by ELISA, possibly because adherence of C3 and C3b to ELISA plates caused exposure of the target epitopes that would otherwise have been hidden. Possible methods to detect the binding site of these antibodies include co-crystal structure studies (Wu, J., Wu, Y. Q., Ricklin, D., Janssen, B. J., Lambris, J. D., and Gros, P. 2009. Structure of complement fragment C3b-factor H and implications for host protection by complement regulators. *Nat Immunol* 10:728-733) or nuclear magnetic resonance (Kovacs, J. M., Hannan, J. P., Eisenmesser, E. Z., and Holers, V. M. 2009. Mapping of the C3d ligand binding site on complement receptor 2 (CR2/CD21) using nuclear magnetic resonance and chemical shift analysis. *J Biol Chem* 284:9513-9520). Identification of the binding site for each antibody may help predict biologic functions of the antibodies, as one may then predict interactions of the C3 molecules that will be interrupted by the antibodies.

In conclusion, we have successfully generated mAbs to C3 activation fragments. Three of the antibodies recognize the activated forms of C3 (iC3b and C3dg/C3d) but do not bind to intact C3 in its native state. We have demonstrated that these antibodies can successfully target tissue-bound C3 fragments in vivo, in spite of high circulating levels of intact C3. Antibodies specific to tissue-bound C3 activation fragments may be employed for targeted delivery of therapeutic and diagnostic agents to sites of tissue inflammation. Radiologic methods of detecting these antibodies could provide an important new tool for detecting and monitoring tissue inflammation. We have demonstrated that fluorescently labeled antibody was detected in live animals with CNV. Now that therapeutic complement inhibitors have been approved for clinical use (Rother, R. P., Rollins, S. A., Mojcik, C. F., Brodsky, R. A., and Bell, L. 2007. Discovery and development of the complement inhibitor eculizumab for the treatment of paroxysmal nocturnal hemoglobinuria. *Nat Biotechnol* 25:1256-1264), non-invasive methods of detecting complement activation within tissues will be particularly important.

Example 11

Experimental Methods

Recombinant Human C3d.

Recombinant human C3d was used as an immunogen for antibody generation. It was also used as a target antigen in ELISA binding studies, and Western blot analysis. The C3d was generated using the pGEX expression system (GE Healthcare) in *E. coli* as previously described (Hannan, J. P., Young, K. A., Guthridge, J. M., Asokan, R., Szakonyi, G., Chen, X. S., and Holers, V. M. 2005. Mutational analysis of the complement receptor type 2 (CR2/CD21)-C3d interaction reveals a putative charged SCR1 binding site for C3d. *J Mol Biol* 346:845-858). Briefly, ampicillin-resistant colonies were expanded to 1 liter in Luria-Bertani (LB) broth. The cultures were grown at 37° C. until an A600 of 0.3 was achieved. Cultures were induced with 0.3 mM isopropyl-β-D-thiogalactoside at 30° C. overnight before harvesting by centrifugation. Harvested pellets were resuspended in glutathione S-transferase column buffer (50 mM Tris-HCl, pH 8.0, 250 mM NaCl, 1 mM EDTA) and lysed by sonication. Lysate was clarified by centrifugation and applied to a GStrap column (GE Biosciences). C3d was cleaved from the column by digesting with 50 units of thrombin overnight at 4° C. and subsequently purified by size exclusion chromatography. Purity of C3d was verified using SDS-PAGE. A second form of recombinant human C3d was also produced as previously described (Kulik, L., Marchbank, K. J., Lyubchenko, T., Kuhn, K. A., Liubchenko, G. A., Haluszczak, C., Gipson, M. G., Boackle, S. A., and Holers, V. M. 2007. Intrinsic B cell hypo-responsiveness in mice prematurely expressing human CR2/CD21 during B cell development. *Eur J Immunol* 37:623-633).

Recombinant Murine C3d.

Murine C3d was cloned from murine cDNA using a forward primer containing a BamH I restriction site (5' cgc gga tcc gcg get gtg gac ggg gag 3') (SEQ ID NO:53) and a reverse primer containing an EcoR I restriction site (5' ccg gaa ttc cgg tca tca acg get ggg gag gtg 3') (SEQ ID NO:54). The amplified fragment was inserted into pGEX vector and generated by the same methods as was the human C3d. The murine C3d was used as a target antigen in ELISA binding studies.

Recombinant CR2 SCR1-2.

Recombinant Maltose-binding protein (MBP-) tagged CR2 SCR1-2 (MBP-CR2) comprising residues 1-133 of wild-type CR2 and encompassing the first two SCR modules were expressed in *E. coli* as previously described (Szakonyi, G., Klein, M. G., Hannan, J. P., Young, K. A., Ma, R. Z., Asokan, R., Holers, V. M., and Chen, X. S. 2006. Structure of the Epstein-Barr virus major envelope glycoprotein. Nat Struct Mol Biol 13:996-1001; Young, K. A., Chen, X. S., Holers, V. M., and Hannan, J. P. 2007. Isolating the Epstein-Barr virus gp350/220 binding site on complement receptor type 2 (CR2/CD21). *J Biol Chem* 282:36614-36625; Young, K. A., Herbert, A. P., Barlow, P. N., Holers, V. M., and Hannan, J. P. 2008. Molecular basis of the interaction between complement receptor type 2 (CR2/CD21) and Epstein-Barr virus glycoprotein gp350. J Virol 82:11217-11227). Briefly, MBP-CR2 SCR1-2-transformed colonies of *E. coli* BL21 were expanded to 4 liters in LB media and grown at 37° C. until an A600 of 0.3 was obtained. Cultures were then induced with 0.3 mM IPTG at 20° C. overnight before harvesting by centrifugation. Resulting cell pellets were re-suspended in a column buffer comprising 20 mM Tris-HCl (pH 7.4), 0.2 M NaCl, and 1 mM EDTA prior to lysis by sonication. The resulting lysate was clarified by centrifugation and recombinant MBP-CR2 initially purified by successive amylose-affinity and size exclusion chromatography steps. Finally, the recombinant MBP-CR2 was applied to a C3d-affinity column, generated by binding GST-tagged C3d to a GSTrap column (GE Biosciences) and eluted with a linear NaCl gradient. The resulting protein was then concentrated, buffer-exchanged into PBS (1.6 mM $MgCl_2$, 0.9 mM KCl, 0.5 mM $KH_2PO_4$, 45.6 mM NaCl, 2.7 mM $Na_2HPO_4$) and the purity tested by SDS-PAGE.

Purified Complement Proteins.

Binding studies were also performed using commercially available purified complement proteins (C3, C3b, iC3b, and C3d; all from CompTech).

Example 12

Detectable Moieties and Conjugation to Antibodies, or Antigen-Binding Fragments Thereof Nanoparticles of 30 nm in diameter, polyethylene glycol (PEG)-coated, amine (#SHA-30-05) or carboxylic acid group (#SHP-30-10) reactive-site containing SPIO, were purchased from Ocean NanoTech, LLC. Amine containing SPIO are termed here as NH2-SPIO, and carboxylic acid containing SPIO are termed here as COOH-SPIO. Purified C3d protein was prepared. Chimeric molecule CR2-Fc (Fc from mouse IgG1, binds iC3b and C3d), mouse antibody C3d29 (isotype IgG2a, binds C3d), and mouse antibody 171 (used as a non-specific control, isotype IgG1) were purified from respective hybridoma lines as per protocols described previously. The conjugation chemicals 1-ethyl-3-[3-dimethylaminopropyl] carbodiimide hydrochloride (EDC; #22980), N-hydroxysuccinimide (NHS; #24500), hydroxylamine hydrochloride (hydroxylamine HCl; #26103), and N-succinimidyl-S-acetylthioacetate (SATA; #26102) were purchased from ThermoScientific. N-Maleoyl-β-alanine was from Sigma-Aldrich (#394815), phosphate buffered saline (PBS) was from Invitrogen (#10010-023), and PD-minitrap G-25 columns were from GE Healthcare (#28-9180-07). Anti-mouse-IgG-fluorescein isothiocyante (FITC) secondary antibody, binding all isotypes of mouse IgG, was purchased from Jackson ImmunoResearch (#115-095-164). The suspension Chinese hamster ovary (CHO) cells were purchased and maintained in CHO medium (Invitrogen #12651) and 1% penicillin/streptomycin (Invitrogen, #15140) at 37° C. and 5% $CO_2$. Adherent CHO cells from . . . , and maintained in Dulbecco's Modified Eagles Medium medium (DMEM; Invitrogen, #21063), 10% fetal calf serum (HyClone), and 1% penicillin/streptomycin, at 37° C. and 5% $CO_2$. Bicinchoninic acid (BCA) protein assay kit was purchased from Pierce (#23227), hydrochloric acid was from Fisher Scientific (#A1445I-212), hydrogen peroxide was from Sigma (#H-1009), potassium thiocyanate was from Sigma (#P-3048), paraformaldehyde from Sigma (PFA; #158127), N,N-dimethylformamide from Sigma (DMF; #D-8654), 96-well plates from Costar (#3690), 6-well plates from Croning (#), bovine serum albumin (BSA) from Fisher Scientific (BP1600-100), 1-Step UltraTMB substrate from ThermoScientific (#34028), normal mouse serum from Valley Biomedical (#AS3054C57BL).

Conjugation of SPIO

Three conjugation reactions were set up: 1) thiolated protein binding maleoyl-activated NH2-SPIO (named hereafter as "maleoyl" method of conjugation); 2) EDC/NHS activated proteins binding NH2-SPIO (named hereafter as "EDC/NHS/NH2" conjugation method); and 3) EDC/NHS activated COOH-SPIO binding proteins (named hereafter as "EDC/NHS" conjugation method). For maleoyl method, 200 µg of proteins in PBS were reacted with 5 µl of 8 mg/ml SATA in DMF for 30 min, then hydroxylamine HCl was added at final concentration of 50 mM and reacted for 1 h. The proteins were purified through the PD-minitrap columns as per manufacturer's protocol. The purified proteins were immediately reacted with NH2-SPIO containing 100 µg of $Fe^{3+}$ and activated for 10 min at 55° C. with N-Maleoyl-β-alanine and EDC, each at 0.1 nmole. For EDC/NHS/NH2 method, 200 µg of respective proteins were activated for 15 min at room temperature with EDC/NHS mixture, each at 0.4 nmole, and then added to NH2-SPIO containing 100 µg of $Fe^{3+}$. For EDC/NHS method, COOH—SPIO containing 250 µg of $Fe^{3+}$ were activated for 15 min at room temperature with EDC/NHS, each at 0.8 nmole, and added to 500 µg of proteins. For all three methods, the proteins and respective SPIO were reacted for 2 h at room temperature, under constant mixing. The SPIO were then washed three times with PBS, and resuspended in PBS after a brief (3-10 s) sonication (model W-380, Ultrasonics Inc.). The conjugated SPIO were stored at 4° C.

Example 13

Animal Models

Mice and Animal Models.

To generate monoclonal antibodies to C3d, mice with a targeted deletion of the C3 gene were immunized with recombinant human C3d. These mice were generated as previously described (Wessels, M. R., Butko, P., Ma, M., Warren, H. B., Lage, A. L., and Carroll, M. C. 1995. Studies of group B streptococcal infection in mice deficient in complement component C3 or C4 demonstrate an essential role for complement in both innate and acquired immunity. *Proc Natl Acad Sci USA* 92:11490-11494). C57BL/6 wild-type mice were used for some in vivo experiments, and serum was collected from these mice for in vitro assays that required murine complement proteins. Mice with targeted deletion of the gene for factor H gene were generated as previously described (Pickering, M. C., Cook, H. T., Warren, J., Bygrave, A. E., Moss, J., Walport, M. J., and Botto, M. 2002. Uncontrolled C3 activation causes membranoproliferative glomerulonephritis in mice deficient in complement factor H. *Nat Genet* 31:424-428). Kidney section from these mice were used to test binding of the anti-C3d antibodies to tissue-bound C3 fragments in vitro, and fH−/− mice were injected with purified anti-C3d antibodies to test binding of the antibodies to tissue-bound C3 fragments in vivo. Mice with targeted deletion of the gene for complement factor B gene were used as a negative control for binding of the FITC-labeled anti-C3d antibodies to CNV lesions (Matsumoto, M., Fukuda, W., Circolo, A., Goellner, J., Strauss-Schoenberger, J., Wang, X., Fujita, S., Hidvegi, T., Chaplin, D. D., and Colten, H. R. 1997. Abrogation of the alternative complement pathway by targeted deletion of murine factor B. *Proc Natl Acad Sci USA* 94:8720-8725).

To induce CNV lesions, 3-month-old mice were anesthetized (xylazine and ketamine, 20 and 80 mg/kg, respectively) and pupils were dilated (2.5% phenylephrine HCl and 1% atropine sulfate). Argon laser photocoagulation (532 nm, 100 µm spot size, 0.1 s duration, 100 mW) was used to generate four laser spots in each eye surrounding the optic nerve, using a handheld coverslip as a contact lens (Rohrer et al., 2009). For tail-vein injections, the vein was vasodilated by heat, a 25-G needle was inserted and a volume of 100 µL injected. The dosing and treatment schedule is outlined in the results section. The CNV model and fundus imaging were performed in accordance with the ARVO Statement for the Use of Animals in Ophthalmic and Vision Research and were approved by the University Animal Care and Use Committee.

Immunization Protocol and Hybridoma Generation.

The humoral immune response to the immunizations was assessed by ELISA using the C3d as the target. The mice developed high titers of anti-C3d antibodies after three injections of 60-100 µg of protein (the first injection in complete Freund's adjuvant and the second injection using incomplete Freund's adjuvant). The mice were then injected intra-peritoneally with 100 µg of C3d, and after 24 hours the spleen was harvested for fusion to Sp2/0 hybridoma cells (Kulik, L., Fleming, S. D., Moratz, C., Reuter, J. W., Novikov, A., Chen, K., Andrews, K. A., Markaryan, A., Quigg, R. J., Silverman, G. J., et al. 2009. Pathogenic natural antibodies recognizing annexin IV are required to develop intestinal ischemia-reperfusion injury. *J Immunol* 182:5363-5373). To prevent exposure of the anti-C3d hybridomas to C3d during the cloning process, the cells were grown in serum free media supplemented with hypoxanthine-aminopterin-thymidine (HAT) (Sigma-Aldrich, St. Louis, Mo.), and peritoneal macrophages from C3−/− mice were used as the feeder cells during this process. Single cell clones were generated, and specificity of the clones for C3d was confirmed by ELISA, as described below.

Example 14

Assays

C3d ELISAs.

To assess reactivity of antibodies against C3d, ELISAs were performed using purified forms of C3 activation fragments from several different sources (see Reagents section above). Direct ELISAs were performed by affixing 30-50 ng of the C3 fragment to the ELISA plate overnight at 4° C. The plates were blocked with 1% bovine serum albumin in PBS for 2 hours at room temperature. Bound antibodies were then detected with HRP-conjugated anti-mouse IgG (MP Biomedicals, Solon, Ohio). Sandwich ELISAs were performed by incubating polyclonal anti-human C3d antibody (Dako USA, Carpinteria, Calif.) to the ELISA plates in order to capture the C3d. Binding of the antibodies to the captured C3d was then detected as above.

C3d-CR2/Anti-C3d Monoclonal Antibody Competition Assay.

Plates were incubated overnight at 4° C. with wild-type C3d at a concentration of 5 µg/ml, in a 50 mM sodium bicarbonate buffer (pH 8.8). After coating, plates were blocked utilizing 1% BSA in PBS, pH 7.4 for one hour at room temperature. Plates were then washed three times using PBS-Tween 20 (0.05%). 10 µg/ml of recombinant wild-type MBP-CR2 were added to half of the C3d-coated wells to act as a positive control. To the other half of the C3d-coated wells 10 µg/ml of recombinant wild-type MBP-CR2 additionally containing one of the following anti-C3d monoclonal antibodies: 3d8B; 3d31; 3d15; 3d9a; 3d11; 3d16; 3d10; 3d3 and 3d29 at concentrations ranging from 1.625-26 µg/ml in PBS was added. After a one hour incubation period the plates were washed and the plates were than incubated with commercially available HRP-conjugated anti-MBP MBP-CR2 (New England Biolabs) according to the manufacturers instructions. After one hour, binding of MBP-CR2 SCR1-2 to the plate-bound C3d was detected with 2,2'-azinobis(3-ethylbenzthiazoline-6-sulfonic acid) (ABTS).

Western Blot Analysis and Pull-Down Studies.

Western blot analysis was performed by running 1 µg of purified complement protein was resolved by electrophoresis with a 10% Bis-Tris polyacrylamide gel (Invitrogen, Carlsbad, Calif.) under denaturing conditions, and was then transferred to a nitrocellulose membrane. C3 fragments were then detected by incubating the membrane with 25 µg of each antibody for 1 hour at room temperature, and bound antibody was detected with HRP-conjugated anti-mouse IgG.

Complement Assays

Zymosan Activation Assay.

Zymosan particles were opsonized with murine C3 fragments by incubating the particles with complement sufficient mouse serum as previously described (Thurman, J. M., Kraus, D. M., Girardi, G., Hourcade, D., Kang, H. J., Royer, P. A., Mitchell, L. M., Giclas, P. C., Salmon, J., Gilkeson, G., et al. 2005. A novel inhibitor of the alternative complement pathway prevents antiphospholipid antibody-induced pregnancy loss in mice. *Mol Immunol* 42:87-97). The particles were incubated with 2 µg of purified anti-C3d antibody, and bound antibody was detected with FITC-conjugated antimouse IgG (MP Biotech). The samples were analyzed by flow cytometry, and were compared to a positive control [C3 deposition detected with a polyclonal anti-mouse C3 (MP Biomedicals)] or with a negative control (no serum added).

Alternative Pathway Hemolytic Assay.

This assay was performed as previously described (Thurman, J. M., Kraus, D. M., Girardi, G., Hourcade, D., Kang, H. J., Royer, P. A., Mitchell, L. M., Giclas, P. C., Salmon, J., Gilkeson, G., et al. 2005. A novel inhibitor of the alternative complement pathway prevents antiphospholipid antibody-induced pregnancy loss in mice. *Mol Immunol* 42:87-97). Briefly, rabbit erythrocytes (Colorado Serum Company, Denver, Colo.) were washed and then resuspeneded in a solution of 1.1% NaCl, 0.0025% Na-5,5 diethyl barbiturate, pH 7.35, 8 mM EGTA, 2 mM MgCl2. (GVB/Mg/EGTA). Fifty µl of this suspension was added to human serum (5 to 100 µl), and buffer solution was added to bring the final volume up to 150 µl. Erythrocytes in buffer without serum were used as a negative control, and erythrocytes added to 100 µl of distilled water were used as positive controls (complete lysis). Samples were incubated at 37° C. for 30 minutes with occasional shaking to keep the cells in suspension. The reactions were stopped by adding 1.5 ml of cold PBS and the samples were spun at 1000×g for five minutes. The optical density of each supernatant was read at 415 nm using a spectrophotometer (Biorad, Hercules, Calif.). We determined the concentration of serum that caused ~50% lysis of the erythrocytes. The reactions were then repeated with the addition of 0 to 40 µg of each antibody. The percent lysis for each reaction was compared to serum alone, and the change in lysis was reported as a percentage.

Buffers.

$DGVB^{2+}$: 1 mM MgCl2, 0.15 mM CaCl2, 71 mM NaCl, 0.1% (w/v) gelatin, 2.5%(w/v) dextrose, and 2.47 mM sodium 5',5"-diethyl barbiturate (pH 7.35); Mg2+ EGTA buffer: 10 mM $Na_2EGTA$, 7 mM MgCl2, 59 mM NaCl, 0.083% (w/v) gelatin, 2.075% (w/v) dextrose and 2.05 mM sodium 5',5"-diethyl barbiturate (pH 7.3-7.6); 10 mM EDTA buffer: 10 mM $Na_2EDTA$, 128 mM NaCl, 0.1% (w/v) gelatin, and 4.45 mM sodium 5',5"-diethyl barbiturate (pH 7.35); 40 mM EDTA buffer: 40 mM $Na_2EDTA$, 85 mM NaCl, 0.1% (w/v) gelatin, and 2.96 mM sodium 5',5"-diethyl barbiturate (pH 7.35).

Preparation of Cell-Bound C3b.

Ab-sensitized sheep erythrocytes (EA cells, 5 ml, 5×10⁸/ml) obtained from CompTech were washed twice and resuspended in 5 ml of $DGVB^{2+}$ buffer, mixed with 37.5 µg of human C1 in 5 ml of $DGVB^{2+}$, and incubated for 15 min at 30°. The resulting cells (EAC1) were washed twice and resuspended in 5 ml of $DGVB^{2+}$, mixed with 50 µg of human C4 suspended in 5 ml of $DGVB^{2+}$, and incubated for 15 min at 30°. These cells (EAC1, 4) were washed twice and suspended in 5 ml of $DGVB^{2+}$, mixed with 250 µg of human C3 and 5 µg of human C2 suspended in 5 ml of $DGVB^{2+}$, and incubated for 30 min at 30°. The resulting cells (EAC1, 4, 2, 3) were washed and resuspended in 5 ml of 10 mM EDTA buffer and incubated at 37° C. for 2 h to allow dissociation of the active classical pathway convertases. The resulting C3b-coated cells were washed twice in 5 ml 10 mM EDTA buffer, twice in 5 ml of 10 mM Mg2+ EGTA buffer, and resuspended in 10 mM Mg2+ EGTA buffer to a final concentration of 1×10⁸/ml. They were stored at 4° C. and used within a week.

Effects of Anti-C3 mAbs on the Activity of Cell-Bound C3bBbP Complexes.

C3b-coated sheep erythrocytes were prepared as described (Hourcade, D. E., Wagner, L. M., and Oglesby, T. J. 1995. Analysis of the short consensus repeats of human complement factor B by site-directed mutagenesis. *J Biol Chem* 270:19716-19722; Whaley, K. 1985. Measurement of complement. In Methods in Complement for Clinical Immunologists. K. Whaley, editor. New York: Churchill Livingstone. 77-139). 100 uL of C3b-coated sheep erythrocytes, 50 uL of purified factor D (5 ng in Mg2+ EGTA buffer), 50 uL of properdin (P; 45 ng in Mg2+ EGTA buffer), and 50 uL of factor B (3-5 ng in Mg2+ EGTA buffer) were mixed together and incubated at 30° C. for 30 min. In some cases, the factor B was replaced by 50 ml of in Mg2+EGTA buffer. Samples were chilled to 4° C. and treated with 150 uL 40 mM EDTA buffer (40 mM $Na_2EDTA$, 85 mM NaCl, 0.1% (w/v) gelatin, and 2.96 mM sodium 5',5"-diethyl barbiturate, pH 7.35), containing in some cases 1 ug of mouse anti-human C3d mAb. Samples were then incubated for 0-3 hr at 30° C. to permit spontaneous C3bBbP dissociation. In some cases this incubation was undertaken with or without 400 ug the addition of factor H and for 30 min to assess factor H-dependent convertase decay acceleration. Functional convertases were then quantified by adding 150 uL of a 1/20 dilution of guinea pig serum (Colorado Serum, Denver, Colo.) in 40 mM EDTA buffer to all samples followed by incubation at 37° C. for 60 min. Additional samples included cell lysis controls in which cells were treated with 450 ul of distilled water alone and a negative control in which cells were treated with 450 ul of $DGVB^{2+}$ buffer alone. All samples were then centrifuged and the $OD_{414}$ of the supernatants determined. Hemolytic activity levels were expressed as Z values, the average number of lytic sites per red blood cell, calculated from the expression $Z=-\ln(1-y)$, where y is the proportion of lysed cells. Each determination was the average of duplicate points. All complement proteins were of human origin and purchased from CompTech (Tyler TX).

Immunofluorescence Microscopy.

For immunofluorescence microscopy, sagittal sections of the kidneys were snap frozen in OCT compound (Sakura Finetek, U.S.A., Inc.). Five µm sections were cut with a cryostat and stored at −80° C. until used. The slides were later fixed with acetone and stained with antibody to mouse C3 or mouse IgG. The slides were then counterstained with hematoxylin (Vector Laboratories, Inc.) and viewed using an Olympus BX51 microscope. When used for tissue staining, the anti-C3d antibodies were used at a concentration of 2 µg/mL.

For immunofluorescence microscopy of RPE/choroid, flatmount preparations were incubated with FITC-labeled antibodies. In brief, eyes were collected and immersion-fixed in 4% paraformaldehyde for 30 min at 4° C. after which the anterior chamber, lens and retina were removed. The eyecups were incubated in blocking solution (3% bovine serum albumin, 10% normal goat serum, and 0.4% Triton-X in tris-buffered saline) for one hour followed by anti-C3d antibodies (1:100 of 1 µg/mL solution) overnight at 4° C. in blocking solution. Following extensive washing, eyecups were flattened using four relaxing cuts, coverslips were applied with Fluoromount (Southern Biotechnology Associates, Inc., Birmingham, Ala.), and slides were examined by confocal microscopy (Leica TCS SP2 AOBS, Leica Bannockburn, Ill.).

Fundus Imaging.

Fundus imaging was performed using the Micron III retinal imaging microscope (Phoenix Research Laboratories Inc, Pleasanton, Calif.) which is based on a custom optical system with a 300-W xenon light source and a three-chip CCD camera, operating at 30 frames/sec in linear/diagnostic mode. For imaging, mice were anesthetized, pupils dilated as described above and secured in the imaging cradle. Optical contact between the cornea of the mouse and the lens of the optical system was established through a drop of methylcellulose. A fundus photograph is obtained using bright field imaging to focus the CNV lesions, after which the mode is switched to FITC fluorescent imaging (excitation at 490 nm). JPEG images were exported to Photoshop to assemble photos and to extract images of individual lesions. To improve visualization of individual lesions, contrast enhancement using identical parameters for control and experimental images was applied.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCES

SEQ ID NO: 1 [amino acid sequence of human membrane cofactor protein (MCP)]:
MEPPGRRECPFPSWRFPGLLLAAMVLLLYSFSDACEEPPTFEAMELI

GKPKPYYEIGERVDYKCKKGYFYIPPLATHTICDRNHTWLPVSDDAC

YRETCPYIRDPLNGQAVPANGTYEFGYQMHFICNEGYYLIGEEILYC

ELKGSVAIWSGKPPICEKVLCTPPPKIKNGKHTFSEVEVFEYLDAVT

YSCDPAPGPDPFSLIGESTIYCGDNSVWSRAAPECKVVKCRFPVVEN

GKQISGFGKKFYYKATVMFECDKGFYLDGSDTIVCDSNSTWDPPVPK

CLKVLPPSSTKPPALSHSVSTSSTTKSPASSASGPRPTYKPPVSNYP

GYPKPEEGILDSLDVWVIAVIVIAIVVGVAVICVVPYRYLQRRKKKG

TYLTDETHREVKFTSL

SEQ ID NO: 2 [amino acid sequence of human decay accelerating factor (DAF/CD55)]:
MTVARPSVPAALPLLGELPRLLLLVLLCLPAVWGDCGLPPDVPNAQP

ALEGRTSFPEDTVITYKCEESFVKIPGEKDSVICLKGSQWSDIEEFC

NRSCEVPTRLNSASLKQPYITQNYFPVGTVVEYECRPGYRREPSLSP

KLTCLQNLKWSTAVEFCKKKSCPNPGEIRNGQIDVPGGILFGATISF

SCNTGYKLFGSTSSFCLISGSSVQWSDPLPECREIYCPAPPQIDNGI

IQGERDHYGYRQSVTYACNKGFTMIGEHSIYCTVNNDEGEWSGPPPE

CRGKSLTSKVPPTVQKPTTVNVPTTEVSPTSQKTTTKTTTPNAQATR

STPVSRTTKHFHETTPNKGSGTTSGTTRLLSGHTCFTLTGLLGTLVT

MGLLT

SEQ ID NO: 3 [amino acid sequence of mouse decay accelerating factor (DAF/CD55)]:
MIRGRAPRTRPSPPPPLLPLLSLSLLLLSPTVRGDCGPPPDIPNARP

ILGRHSKFAEQSKVAYSCNNGFKQVPDKSNIVVCLENGQWSSHETFC

EKSCVAPERLSFASLKKEYLNMNFFPVGTIVEYECRPGFRKQPPLPG

KATCLEDLVWSPVAQFCKKKSCPNPKDLDNGHINIPTGILFGSEINF

TABLE 2

| Clone name | Class/ subclass | Direct ELISA - Recombinant human C3d | Sandwich ELISA - Recombinant human C3d | Direct ELISA - human C3d purified from plasma | Direct ELISA - Biotinylated recombinant C3d on streptavidin ELISA plate | Direct ELISA - Biotinylated recombinant C3d, purified via HIS tag | Direct ELISA - Recombinant murine C3d | Sandwich ELISA - Recombinant murine C3d | Direct ELISA - Recombinant cynomologous C3d |
|---|---|---|---|---|---|---|---|---|---|
| 3d3 | IgG1 | +++ | +++ | +++ | +++ | +++ | +++ | +++ | |
| 3d8b | IgG2b | ++ | +++ | +++ | +++ | +++ | +++ | + | |
| 3d9a | IgG2a/c | +++ | +++ | +++ | +++ | +++ | +++ | + | |
| 3d10 | IgG1 | ++ | +++ | +++ | +++ | +++ | + | +++ | |
| 3d11 | IgG1 | +++ | +++ | +++ | +++ | + | +++ | + | |
| 3d15 | IgG2a/c | ++ | +++ | +++ | +++ | +++ | +++ | +++ | |
| 3d16 | IgG1 | ++ | +++ | ++ | +++ | +++ | ++ | ++ | |
| 3d29 | IgG2a/c | +++ | +++ | +++ | +++ | ++ | +++ | + | |
| 3d31 | IgG2a/c | +++ | +++ | +++ | +++ | + | +++ | − | |

SCNPGYRLVGVSSTFCSVTGNTVDWDDEFPVCTEIHCPEPPKINNGI

MRGESDSYTYSQVVTYSCDKGFILVGNASIYCTVSKSDVGQWSSPPP

RCIEKSKVPTKKPTINVPSTGTPSTPQKPTTESVPNPGDQPTPQKPS

TVKVSATQHVPVTKTTVRHPIRTSTDKGEPNTGGDRYIYGHTCLITL

TVLHVMLSLIGYLT

SEQ ID NO: 4 [amino acid sequence of human
CD59 protein]:
MGIQGGSVLFGLLLVLAVFCHSGHSLQCYNCPNPTADCKTAVNCSSD

FDACLITKAGLQVYNKCWKFEHCNFNDVTTRLRENELTYYCCKKDLC

NFNEQLENGGTSLSEKTVLLLVTPFLAAAWSLHP

SEQ ID NO: 5 [amino acid sequence of mouse
CD59A protein]:
MRAQRGLILLLLLLAVFCSTAVSLTCYHCFQPVVSSCNMNSTCSPDQ

DSCLYAVAGMQVYQRCWKQSDCHGEIIMDQLEETKLKFRCCQFNLCN

KSDGSLGKTPLLGTSVLVAILNLCFLSHL

SEQ ID NO: 6 [amino acid sequence of mouse
CD59B protein]:
MRAQRGLILLLLLLAVFCSTAVSLKCYNCFQFVSSCKINTTCSPNLD

SCLYAVAGRQVYQQCWKLSDCNSNYIMSRLDVAGIQSKCCQWGLCNK

NLDGLEEPNNAETSSLRKTALLGTSVLVAILKFCF

SEQ ID NO: 7 [amino acid sequence of mouse
complement receptor 1-related gene/protein
y (Crry)]:
MEVSSRSSEPLDPVWLLVAFGRGGVKLEVLLLFLLPFTLGELRGGLG

KHGHTVHREPAVNRLCADSKRWSGLPVSAQRPFPMGHCPAPSQLPSA

KPINLTDESMFPIGTYLLYECLPGYIKRQFSITCKQDSTWTSAEDKC

IRKQCKTPSDPENGLVHVHTGIQFGSRINYTCNQGYRLIGSSSAVCV

ITDQSVDWDTEAPICEWIPCEIPPGIPNGDFFSSTREDFHYGMVVTY

RCNTDARGKALFNLVGEPSLYCTSNDGEIGVWSGPPPQCIELNKCTP

PPYVENAVMLSENRSLFSLRDIVEFRCHPGFIMKGASSVHCQSLNKW

EPELPSCFKGVICRLPQEMSGFQKGLGMKKEYYYGENVTLECEDGYT

LEGSSQSQCQSDGSWNPLLAKCVSRSISGLIVGIFIGIIVFILVIIV

FIWMILKYKKRNTTDEKYKEVGIHLNYKEDSCVRLQSLLTSQENSST

TSPARNSLTQEVS

SEQ ID NO: 8 [amino acid sequence of human
complement receptor 1 (CR1)]:
MGASSPRSPEPVGPPAPGLPFCCGGSLLAVVVLLALPVAWGQCNAPE

WLPFARPTNLTDEFEFPIGTYLNYECRPGYSGRPFSIICLKNSVWTG

AKDRCRRKSCRNPPDPVNGMVHVIKGIQFGSQIKYSCTKGYRLIGSS

SATCIISGDTVIWDNETPICDRIPCGLPPTITNGDFISTNRENFHYG

SVVTYRCNPGSGGRKVFELVGEPSIYCTSNDDQVGIWSGPAPQCIIP

NKCTPPNVENGILVSDNRSLFSLNEVVEFRCQPGFVMKGPRRVKCQA

LNKWEPELPSCSRVCQPPPDVLHAERTQRDKDNFSPGQEVFYSCEPG

YDLRGAASMRCTPQGDWSPAAPTCEVKSCDDFMGQLLNGRVLFPVNL

QLGAKVDFVCDEGFQLKGSSASYCVLAGMESLWNSSVPVCEQIFCPS

PPVIPNGRHTGKPLEVFPFGKAVNYTCDPHPDRGTSFDLIGESTIRC

TSDPQGNGVWSSPAPRCGILGHCQAPDHFLFAKLKTQTNASDFPIGT

SLKYECRPEYYGRPFSITCLDNLVWSSPKDVCKRKSCKTPPDPVNGM

VHVITDIQVGSRINYSCTTGHRLIGHSSAECILSGNAAHWSTKPPIC

QRIPCGLPPTIANGDFISTNRENFHYGSVVTYRCNPGSGGRKVFELV

GEPSIYCTSNDDQVGIWSGPAPQCIIPNKCTPPNVENGILVSDNRSL

FSLNEVVEFRCQPGFVMKGPRRVKCQALNKWEPELPSCSRVCQPPPD

VLHAERTQRDKDNFSPGQEVFYSCEPGYDLRGAASMRCTPQGDWSPA

APTCEVKSCDDFMGQLLNGRVLFPVNLQLGAKVDFVCDEGFQLKGSS

ASYCVLAGMESLWNSSVPVCEQIFCPSPPVIPNGRHTGKPLEVFPFG

KAVNYTCDPHPDRGTSFDLIGESTIRCTSDPQGNGVWSSPAPRCGIL

GHCQAPDHFLFAKLKTQTNASDFPIGTSLKYECRPEYYGRPFSITCL

DNLVWSSPKDVCKRKSCKTPPDPVNGMVHVITDIQVGSRINYSCTTG

HRLIGHSSAECILSGNTAHWSTKPPICQRIPCGLPPTIANGDFISTN

RENFHYGSVVTYRCNLGSRGRKVFELVGEPSIYCTSNDDQVGIWSGP

APQCIIPNKCTPPNVENGILVSDNRSLFSLNEVVEFRCQPGFVMKGP

RRVKCQALNKWEPELPSCSRVCQPPPEILHGEHTPSHQDNFSPGQEV

FYSCEPGYDLRGAASLHCTPQGDWSPEAPRCAVKSCDDFLGQLPHGR

VLFPLNLQLGAKVSFVCDEGFRLKGSSVSHCVLVGMRSLWNNSVPVC

EHIFCPNPPAILNGRHTGTPSGDIPYGKEISYTCDPHPDRGMTFNLI

GESTIRCTSDPHGNGVWSSPAPRCELSVRAGHCKTPEQFPFASPTIP

INDFEFPVGTSLNYECRPGYFGKMFSISCLENLVWSSVEDNCRRKSC

GPPPEPFNGMVHINTDTQFGSTVNYSCNEGFRLIGSPSTTCLVSGNN

VTWDKKAPICEIISCEPPPTISNGDFYSNNRTSFHNGTVVTYQCHTG

PDGEQLFELVGERSIYCTSKDDQVGVWSSPPPRCISTNKCTAPEVEN

AIRVPGNRSFFSLTEIIRFRCQPGFVMVGSHTVQCQTNGRWGPKLPH

CSRVCQPPPEILHGEHTLSHQDNFSPGQEVFYSCEPSYDLRGAASLH

CTPQGDWSPEAPRCTVKSCDDFLGQLPHGRVLLPLNLQLGAKVSFVC

DEGFRLKGRSASHCVLAGMKALWNSSVPVCEQIFCPNPPAILNGRHT

GTPFGDIPYGKEISYACDTHPDRGMTFNLIGESSIRCTSDPQGNGVW

SSPAPRCELSVPAACPHPPKIQNGHYIGGHVSLYLPGMTISYTCDPG

YLLVGKGFIFCTDQGIWSQLDHYCKEVNCSFPLFMNGISKELEMKKV

YHYGDYVTLKCEDGYTLEGSPWSQCQADDRWDPPLAKCTSRAHDALI

VGTLSGTIFFILLIIFLSWIILKHRKGNNAHENPKEVAIHLSQGGS

SVHPRTLQTNEENSRVLP

SEQ ID NO: 9 [amino acid sequence of human
factor H]:
MRLLAKIICLMLWAICVAEDCNELPPRRNTEILTGSWSDQTYPEGTQ

AIYKCRPGYRSLGNVIMVCRKGEWVALNPLRKCQKRPCGHPGDTPFG

-continued

| SEQUENCES |
|---|

TFTLTGGNVFEYGVKAVYTCNEGYQLLGEINYRECDTDGWTNDIPIC
EVVKCLPVTAPENGKIVSSAMEPDREYHFGQAVRFVCNSGYKIEGDE
EMHCSDDGFWSKEKPKCVEISCKSPDVINGSPISQKIIYKENERFQY
KCNMGYEYSERGDAVCTESGWRPLPSCEEKSCDNPYIPNGDYSPLRI
KHRTGDEITYQCRNGFYPATRGNTAKCTSTGWIPAPRCTLKPCDYPD
IKHGGLYHENMRRPYFPVAVGKYYSYYCDEHFETPSGSYWDHIHCTQ
DGWSPAVPCLRKCYFPYLENGYNQNYGRKFVQGKSIDVACHPGYALP
KAQTTVTCMENGWSPTPRCIRVKTCSKSSIDIENGFISESQYTYALK
EKAKYQCKLGYVTADGETSGSITCGKDGWSAQPTCIKSCDIPVFMNA
RTKNDFTWFKLNDTLDYECHDGYESNTGSTTGSIVCGYNGWSDLPIC
YERECELPKIDVHLVPDRKKDQYKVGEVLKFSCKPGFTIVGPNSVQC
YHFGLSPDLPICKEQVQSCGPPPELLNGNVKEKTKEEYGHSEVVEYY
CNPRFLMKGPNKIQCVDGEWTTLPVCIVEESTCGDIPELEHGWAQLS
SPPYYYGDSVEFNCSESFTMIGHRSITCIHGVWTQLPQCVAIDKLKK
CKSSNLIILEEHLKNKKEFDHNSNIRYRCRGKEGWIHTVCINGRWDP
EVNCSMAQIQLCPPPPQIPNSHNMTTTLNYRDGEKVSVLCQENYLIQ
EGEEITCKDGRWQSIPLCVEKIPCSQPPQIEHGTINSSRSSQESYAH
GTKLSYTCEGGFRISEENETTCYMGKWSSPPQCEGLPCKSPPEISHG
VVAHMSDSYQYGEEVTYKCFEGFGIDGPAIAKCLGEKWSHPPSCIKT
DCLSLPSFENAIPMGEKKDVYKAGEQVTYTCATYYKMDGASNVTCIN
SRWTGRPTCRDTSCVNPPTVQNAYIVSRQMSKYPSGERVRYQCRSPY
EMFGDEEVMCLNGNWTEPPQCKDSTGKCGPPPPIDNGDITSFPLSVY
APASSVEYQCQNLYQLEGNKRITCRNGQWSEPPKCLHPCVISREIME
NYNIALRWTAKQKLYSRTGESVEFVCKRGYRLSSRSHTLRTTCWDGK
LEYPTCAKR

SEQ ID NO: 10 [amino acid sequence of mouse factor H]:
MRLSARIIWLILWTVCAAEDCKGPPPRENSEILSGSWSEQLYPEGTQ
ATYKCRPGYRTLGTIVKVCKNGKWVASNPSRICRKKPCGHPGDTPFG
SFRLAVGSQFEFGAKVVYTCDDGYQLLGEIDYRECGADGWINDIPLC
EVVKCLPVTELENGRIVSGAAETDQEYYFGQVVRFECNSGFKIEGHK
EIHCSENGLWSNEKPRCVEILCTPPRVENGDGINVKPVYKENERYHY
KCKHGYVPKERGDAVCTGSGWSSQPFCEEKRCSPPYILNGIYTPHRI
IHRSDDEIRYECNYGFYPVTGSTVSKCTPTGWIPVPRCTLKPCEFPQ
FKYGRLYYEESLRPNFPVSIGNKYSYKCDNGFSPPSGYSWDYLRCTA
QGWEPEVPCVRKCVFHYVENGDSAYWEKVYVQGQSLKVQCYNGYSLQ
NGQDTMTCTENGWSPPPKCIRIKTCSASDIHIDNGFLSESSSIYALN
RETSYRCKQGYVTNTGEISGSITCLQNGWSPQPSCIKSCDMPVFENS
ITKNTRTWFKLNDKLDYECLVGFENEYKHTKGSITCTYYGWSDTPSC -continued

| SEQUENCES |
|---|

YERECSVPTLDRKLVVSPRKEKYRVGDLLEFSCHSGHRVGPDSVQCY
HFGWSPGFPTCKGQVASCAPPLEILNGEINGAKKVEYSHGEVVKYDC
KPRFLLKGPNKIQCVDGNWTTLPVCIEEERTCGDIPELEHGSAKCSV
PPYHHGDSVEFICEENFTMIGHGSVSCISGKWTQLPKCVATDQLEKC
RVLKSTGIEAIKPKLTEFTHNSTMDYKCRDKQEYERSICINGKWDPE
PNCTSKTSCPPPPQIPNTQVIETTVKYLDGEKLSVLCQDNYLTQDSE
EMVCKDGRWQSLPRCIEKIPCSQPPTIEHGSINLPRSSEERRDSIES
SSHEHGTTFSYVCDDGFRIPEENRITCYMGKWSTPPRCVGLPCGPPP
SIPLGTVSLELESYQHGEEVTYHCSTGFGIDGPAFIICEGGKWSDPP
KCIKTDCDVLPTVKNAIIRGKSKKSYRTGEQVTFRCQSPYQMNGSDT
VTCVNSRWIGQPVCKDNSCVDPPHVPNATIVTRTKNKYLHGDRVRYE
CNKPLELFGQVEVMCENGIWTEKPKCRDSTGKCGPPPPIDNGDITSL
SLPVYEPLSSVEYQCQKYYLLKGKKTITCTNGKWSEPPTCLHACVIP
ENIMESHNIILKWRHTEKIYSHSGEDIEFGCKYGYYKARDSPPFRTK
CINGTINYPTCV

SEQ ID NO: 11 [amino acid sequence of CVF from *Naja kaouthia*]:
MERMALYLVAALLIGFPGSSHGALYTLITPAVLRTDTEEQILVEAHG
DSTPKQLDIFVHDFPRKQKTLFQTRVDMNPAGGMLVTPTIEIPAKEV
STDSRQNQYVVVQVTGPQVRLEKVVLLSYQSSFLFIQTDKGIYTPGS
PVLYRVFSMDHNTSKMNKTVIVEFQTPEGILVSSNSVDLNFFWPYNL
PDLVSLGTWRIVAKYEHSPENYTAYFDVRKYVLPSFEVRLQPSEKFF
YIDGNENFHVSITARYLYGEEVEGVAFVLFGVKIDDAKKSIPDSLTR
IPIIDGDGKATLKRDTFRSRFPNLNELVGHTLYASVTVMTESGSDMV
VTEQSGIHIVASPYQIHFTKTPKYFKPGMPYELTVYVTNPDGSPAAH
VPVVSEAFHSMGTTLSDGTAKLILNIPLNAQSLPITVRTNHGDLPRE
RQATKSMTAIAYQTQGGSGNYLHVAITSTEIKPGDNLPVNFNVKGNA
NSLKQIKYFTYLILNKGKIFKVGRQPRRDGQNLVTMNLHITPDLIPS
FRFVAYYQVGNNEIVADSVWVDVKDTCMGTLVVKGDNLIQMPGAAMK
IKLEGDPGARVGLVAVDKAVYVLNDKYKISQAKIWDTIEKSDFGCTA
GSGQNNLGVFEDAGLALTTSTNLNTKQRSAAKCPQPANRRRRSSVLL
LDSNASKAAEFQDQDLRKCCEDVMHENPMGYTCEKRAKYIQEGDACK
AAFLECCRYIKGVRDENQRESELFLARDDNEDGFIADSDIISRSDFP
KSWLWLTKDLTEEPNSQGISSKTMSFYLRDSITTWVVLAVSFTPTKG
ICVAEPYEIRVMKVFFIDLQMPYSVVKNEQVEIRAILHNYVNEDIYV
RVELLYNPAFCSASTKGQRYRQQFPIKALSSRAVPFVIVPLEQGLHD
VEIKASVQEALWSDGVRKKLKVVPEGVQKSIVTIVKLDPRAKGVGGT
QLEVIKARKLDDRVPDTEIETKIIIQGDPVAQIIENSIDGSKLNHLI
ITPSGCGEQNMIRMAAPVIATYYLDTTEQWETLGINRRTEAVNQIVT
GYAQQMVYKKADHSYAAFTNRASSSWLTAYVVKVFAMAAKMVAGISH

EIICGGVRWLILNRQQPDGAFKENAPVLSGTMQGGIQGAEEEVYLTA

FILVALLESKTICNDYVNSLDSSIKKATNYLLKKYEKLQRPYTTALT

AYALAAADQLNDDRVLMAASTGRDHWEEYNAHTHNIEGTSYALLALL

KMKKFDQTGPIVRWLTDQNFYGETYGQTQATVMAFQALAEYEIQMPT

HKDLNLDITIELPDREVPIRYRINYENALLARTVETKLNQDITVTAS

GDGKATMTILTFYNAQLQEKANVCNKFHLNVSVENIHLNAMGAKGAL

MLKICTRYLGEVDSTMTIIDISMLTGFLPDAEDLTRLSKGVDRYISR

YEVDNNMAQKVAVIIYLNKVSHSEDECLHFKILKHFEVGFIQPGSVK

VYSYYNLDEKCTKFYHPDKGTGLLNKICIGNVCRCAGETCSSLNHQE

RIDVPLQIEKACETNVDYVYKTKLLRIEEQDGNDIYVMDVLEVIKQG

TDENPRAKTHQYISQRKCQEALNLKVNDDYLIWGSRSDLLPTKDKIS

YIITKNTWIERWPHEDECQEEEFQKLCDDFAQFSYTLTEFGCPT

SEQ ID NO: 12 [amino acid sequence of 3d8B
light chain variable region]
DVLMTQTPLTLSVTIGQPASISCKSSQSLLDSDGKTYLNWLLQRPGQ

SPKRLIYLVSKLDSGVPDRFTGSGSGTDFTLKISRVEAEDLGVYYCW

QGTHFPRTFGGGTKLEIK

SEQ ID NO: 13 [amino acid sequence of 3d8B
heavy chain variable region]
EVQLQQSGPVLVKPGASVKMSCKASGYTFTNYYINWVKQSHGKSLEW

IGVINPYNGGTSYNQKFKGKATLTVDKSSSTAYMELNSLTSEDSAVY

FCSSPYWGQGTSVTVSS

SEQ ID NO: 14 [amino acid sequence of CDR1
3d8B light chain variable region]
QSLLDSDGKTY SEQ ID NO: 15 [amino acid sequence of CDR2
3d8B light chain variable region]
LVS SEQ ID NO: 16 [amino acid sequence of CDR3
3d8B light chain variable region]
WQGTHFPRT SEQ ID NO: 17 [amino acid sequence of CDR1
3d8B heavy chain variable region]
GYTFTNYY SEQ ID NO: 18 [amino acid sequence of CDR2
3d8B heavy chain variable region]
INPYNGGT SEQ ID NO: 19 [amino acid sequence of CDR3
3d8B heavy chain variable region]
SSPY SEQ ID NO: 20 [nucleic acid sequence of 3d8b
light chain variable region]
GATGTTTTGATGACCCAAACTCCACTCACTTTGTCGGTTACCATTGG ACAACCAGCCTCCATCTCTTGCAAGTCAAGT<u>CAGAGCCTCTTAGATA</u>

<u>GTGATGGAAAGACATATTT</u>GAATTGGTTGTTACAGAGGCCAGGCCAG

TCTCCAAAGCGCCTAATCTAT<u>CTGGTGTCT</u>AAACTGGACTCTGGAGT

CCCTGACAGGTTCACTGGCAGTGGATCAGGGACAGATTTCACACTGA

AAATCAGCAGAGTGGAGGCTGAGGATTTGGGAGTTTATTATTGC<u>TGG</u>

<u>CAAGGTACACATTTTCCTCGGAC</u>GTTCGGTGGAGGCACCAAGCTGGA

AATCAAA

SEQ ID NO: 21 [nucleic acid sequence of 3d8b
heavy chain variable region]
GAGGTTCAGCTTCAGCAGTCTGGACCTGTGCTGGTGAAGCCTGGGGC TTCAGTGAAGATGTCCTGTAAGGCTTCT<u>GGATACACATTCACTAACT</u>

<u>ACTAT</u>ATAAACTGGGTGAAGCAGAGCCATGGAAAGAGCCTTGAGTGG

ATTGGAGTT<u>ATTAATCCTTACAACGGTGGTACT</u>AGCTACAACCAGAA

GTTCAAGGGCAAGGCCACATTGACTGTTGACAAGTCCTCCAGCACAG

CCTACATGGAGCTCAACAGCCTGACATCTGAGGACTCTGCAGTCTAT

TTCTGT<u>TCAAGTCCCTAC</u>TGGGGTCAAGGAACCTCAGTCACCGTCTC

CTCA

SEQ ID NO: 22 [amino acid sequence of 3d29
light chain variable region]
DVLMTQTPLTLSVTIGQPASISCKSSQSLLDSDGKTYLNWLLQRPGQ

SPKRLIYLVSKLESGVPDRFTGSGSGTDFTLEISRVEAEDLGVYYCW

QGTHFPRTFGGGTKLEIK

SEQ ID NO: 23 [amino acid sequence of 3d29
heavy chain variable region]
EVQLQQSGPVLVKPGASVKMSCKASGYTFTDYYMNWVKQSHGKSLEW

IGVINPYNGGTSYNQKFKGKATLTVDKSSRTAYMELNSLTSEDSAVY

YCSRGGPYWGQGTTLTVSS

SEQ ID NO: 24 [amino acid sequence of CDR 1
3d29 light chain variable region]
QSLLDSDGKTY SEQ ID NO: 25 [amino acid sequence of CDR2
3d29 light chain variable region]
LVS SEQ ID NO: 26 [amino acid sequence of CDR3
3d29 light chain variable region]
WQGTHFPRT SEQ ID NO: 27 [amino acid sequence of CDR1
3d29 heavy chain variable region]
GYTFTDYY SEQ ID NO: 28 [amino acid sequence of CDR2
3d29 heavy chain variable region]
INPYNGGT SEQ ID NO: 29 [amino acid sequence of CDR3
3d29 heavy chain variable region]
SRGGPY SEQ ID NO: 30 [nucleic acid sequence of 3d29
light chain variable region]
GATGTTTTGATGACCCAAACTCCACTCACTTTGTCGGTTACCATTGG ACAACCAGCCTCCATCTCTTGCAAGTCAAGT<u>CAGAGCCTCTTAGATA</u>

<u>GTGATGGAAAGACATATTT</u>GAATTGGTTGTTACAGAGGCCAGGCCAG

TCTCCAAAGCGCCTAATCTAT<u>CTGGTGTCT</u>AAACTGGAATCTGGAGT

CCCTGACAGGTTCACTGGCAGTGGATCAGGGACAGATTTCACACTGG

AAATCAGCAGAGTGGAGGCTGAGGATTTGGGAGTTTATTATTGC<u>TGG</u>

CAAGGTACACATTTTCCTCGGACGTTCGGTGGAGGCACCAAGCTGGA

AATCAAA

SEQ ID NO: 31 [nucleic acid sequence of 3d29
heavy chain variable region]
GAGGTTCAGCTGCAGCAGTCTGGACCTGTGCTGGTGAAGCCTGGGGC

TTCAGTGAAGATGTCCTGTAAGGCTTCTGGATACACATTCACTGACT

ACTATATGAATTGGGTGAAGCAGAGCCATGGAAAGAGCCTTGAGTGG

ATTGGAGTTATTAATCCTTACAACGGTGGTACTAGTTACAATCAGAA

GTTCAAGGGCAAGGCCACATTGACTGTTGATAAGTCCTCCCGCACAG

CCTACATGGAGCTCAACAGCCTGACATCTGAGGACTCTGCAGTCTAT

TATTGTTCAAGAGGGGCCCCTACTGGGGCCAAGGCACCACTCTCAC

AGTCTCCTCA

SEQ ID NO: 32 [amino acid sequence of 3d
scFv Crry fusion]
MPMGSLQPLATLYLLGMLVASVLAHHHHHHIEGREVKLVESGGGLVQ

PGSSMKLSCTTSGFTFSDYYMAWVRQVPEKGLEWVANINYDGSSAYY

LDSFKSRFTISRDNEKNILYLQMSSLKSEDTATYYCARGDWFVYWGQ

GTLVTVSAGGGGSGGGGSGGGGSDIQMTQSPSSMSASLGERVTITCK

ASQDINSYLNWFQQKPGKSPKTLIFRANRLVDGVPSRFSGSGSGQDY

SLTISSLEFEDVGIYYCLQYAEFPFTFGSGTKLEIKIEGRGGGGSGG

GGSCPAPSQLPSAKPINLTDESMFPIGTYLLYECLPGYIKRQFSITC

KQDSTWTSAEDKCIRKQCKTPSDPENGLVHVHTGIQFGSRINYTCNQ

GYRLIGSSSAVCVITDQSVDWDTEAPICEWIPCEIPPGIPNGDFFSS

TREDFHYGMVVTYRCNTDARGKALFNLVGEPSLYCTSNDGEIGVWSG

PPPQCIELNKCTPPPYVENAVMLSENRSLFSLRDIVEFRCHPGFIMK

GASSVHCQSLNKWEPELPSCFKGVICRLPQEMSGFQKGLGMKKEYYY

GENVTLECEDGYTLEGSSQSQCQSDGSWNPLLAKCVSRSI

SEQ ID NO: 33 [nucleic acid sequence of 3d16
heavy chain variable region]
GAGGTCCAGCTGCAGCAATCTGGAGCTGAGCTGGTAAGGCCTGGGAC

TTCAGTGAAGGTGTCCTGCAAGGCTTCTGGATACGCCTTCGCTCACT

ACTTGATAGAATGGGTAAAGCAGAGGCCTGGACAGGGCCTTGAGTGG

ATTGGCGTGATTAATCCTGGAACTGATGGCACTAACTACAATGAGAA

GTTCAAGGGCAAGGCAACACTGACTGCAGACAAATCCTCCAGCACTG

CCTACATGCACCTCAGCAGCCTGACATCTGAGGACTCTGCGGTCTAT

TTCTGTGCAAGAGAGGAACTGGGGTTTGCTTACTGGGGCCAAGGGAC

TCTGGTCACTGTCTCTGCA

SEQ ID NO: 34 [amino acid sequence of 3d16
heavy chain variable region]
EVQLQQSGAELVRPGTSVKVSCKASGYAFAHYLIEWVKQRPGQGLEW

IGVINPGTDGTNYNEKFKGKATLTADKSSSTAYMHLSSLTSEDSAVY

FCAREELGFAYWGQGTLVTVSA

SEQ ID NO: 35 [amino acid sequence of CDR1
3d16 heavy chain variable region]
GYAFAHYL SEQ ID NO: 36 [amino acid sequence of CDR2
3d16 heavy chain variable region]
INPGTDGT SEQ ID NO: 37 [amino acid sequence of CDR3
3d16 heavy chain variable region]
AREELGFAY

What is claimed is:

1. An anti-C3d antibody conjugate, comprising a detectable moiety and light chain complementarity determining regions (CDR) 1, 2 and 3, wherein light chain CDR 1 is SEQ ID NO:14, light chain CDR 2 is SEQ ID NO:15 and light chain CDR 3 is SEQ ID NO:16; and heavy chain complementarity determining regions (CDR) 1, 2 and 3, wherein heavy chain CDR 1 is SEQ ID NO:17 or SEQ ID NO:27, heavy chain CDR 2 is SEQ ID NO:18 and heavy chain CDR 3 is SEQ ID NO:19 or 29.

2. The anti-C3d antibody conjugate of claim 1, wherein light chain CDR 1 is SEQ ID NO:14, light chain CDR 2 is SEQ ID NO:15, light chain CDR 3 is SEQ ID NO:16, heavy chain CDR 1 is SEQ ID NO:17, heavy chain CDR 2 is SEQ ID NO:18, and heavy chain CDR 3 is SEQ ID NO:19.

3. The anti-C3d antibody conjugate of claim 1, wherein light chain CDR 1 is SEQ ID NO:24, light chain CDR 2 is SEQ ID NO:25, light chain CDR 3 is SEQ ID NO:26, heavy chain CDR 1 is SEQ ID NO:27, heavy chain CDR 2 is SEQ ID NO:28, and heavy chain CDR 3 is SEQ ID NO:29.

4. The anti-C3d antibody conjugate of claim 1, comprising a monoclonal antibody or antigen-binding fragment thereof, chimerized or chimeric antibody or antigen-binding fragment thereof, humanized antibody or antigen-binding fragment thereof, deimmunized human antibody or antigen-binding fragment thereof, fully human antibody or antigen-binding fragment thereof, single chain antibody, single chain Fv fragment (scFv), Fd fragment, Fab fragment, Fab' fragment, F(ab')$_2$ fragment, diabody or antigen-binding fragment thereof, minibody or antigen-binding fragment thereof, triabody or antigen-binding fragment thereof, domain antibody or antigen-binding fragment thereof, camelid antibody or antigen-binding fragment thereof, dromedary antibody or antigen-binding fragment thereof, or phage-displayed antibody or antigen-binding fragment thereof, or antibody, or antigen-binding fragment thereof, identified with repetitive antigen array or antigen binding fragment thereof.

5. The anti-C3d antibody conjugate of claim 1, comprising a humanized antibody, or an antigen-binding fragment thereof.

6. The anti-C3d antibody conjugate of claim 1, wherein the antibody, or antigen-binding fragment thereof, preferentially binds iC3b, C3d or C3dg with at least 10 fold greater affinity than uncleaved C3.

7. The anti-C3d antibody conjugate of claim 1, wherein said detectable moiety is selected from the group consisting of $^{32}$P, a fluorescent dye, an electron-dense reagent, an enzyme, biotin, digoxigenin, a paramagnetic molecule, a paramagnetic nanoparticle, an ultrasmall superparamagnetic iron oxide ("USPIO") nanoparticle, a USPIO nanoparticle aggregate, a superparamagnetic iron oxide ("SPIO") nanoparticle, an SPIO nanoparticle aggregate, a standard superparamagnetic iron oxide ("SSPIO"), an SSPIO nanoparticle aggregate, a polydisperse superparamagnetic iron oxide ("PSPIO"), a PSPIO nanoparticle aggregate, a monochrystalline SPIO, a monochrystalline SPIO aggregate, a monochrystalline iron oxide nanoparticle, a monochrystalline iron oxide, another nanoparticle contrast agent, a liposome or other delivery vehicle comprising Gadolinium chelate ("Gd-chelate") molecules, Gadolinium, a radioisotope, a radionuclide, carbon-11, nitrogen-13, oxygen-15, fluorine-18, rubidium-82, fluorodeoxyglucose, a gamma ray emitting radionuclide, a positron-emitting radionuclide, radiolabeled glucose, radiolabeled water, radiolabeled ammonia, a biocolloid, a microbubble, an iodinated contrast agent, barium sulfate, thorium dioxide, gold, a gold nanoparticle, a gold nanoparticle aggregate, a fluorophore, a two-photon fluorophore, a hapten, a protein, and a fluorescent moiety.

8. The anti-C3d antibody conjugate of claim 1, wherein said detectable moiety is a paramagnetic moiety.

9. The anti-C3d antibody conjugate of claim 8, wherein said paramagnetic moiety is an ultrasmall superparamagnetic iron oxide ("USPIO") nanoparticle or aggregate thereof.

10. The anti-C3d antibody conjugate of claim 9, wherein said paramagnetic moiety is an ultrasmall superparamagnetic iron oxide ("USPIO") nanoparticle aggregate.

11. The anti-C3d antibody conjugate of claim 10, wherein said nanoparticle aggregate is coated with dextran, coated with an amphiphilic polymer, or encapsulated with phospholipid.

12. The anti-C3d antibody conjugate of claim 1, wherein the antibody, or antigen-binding fragment thereof, is conjugated to the detectable moiety through a lysine amino acid.

13. The anti-C3d antibody conjugate of claim 1, wherein the antibody, or antigen-binding fragment thereof, is conjugated to the detectable moiety through a cysteine, glutamate, aspartate, or arginine amino acid.

14. The anti-C3d antibody conjugate of claim 1, wherein the antibody, or antigen-binding fragment thereof, is conjugated to the detectable moiety a) through a 4-succinimidyloxycarbonyl-α-methyl-α (2-pyridyldithio) toluene (SMPT), N-5-azido-2-nitrobenzoyloxysuccinimide, 1,4-bis-maleimidobutane, m-maleimidobenzoyl-N-hydroxysuccinimide ester, 4-[p-azidosalicylamido]butylamine, or p-azidophenyl glyoxal monohydrate; or b) through a reaction comprising a thiolated antibody, or antigen binding fragment thereof, and a maleoyl-activated amine of the detectable moiety; EDC/NHS-activated antibody, or antigen binding fragment thereof, and an amine of the detectable moiety; or EDC/NHS-activated carboxylic acid of the detectable moiety and an amine of the antibody, or antigen binding fragment thereof.

15. A method of detecting complement-mediated inflammation in an individual comprising: (a) administering to said individual an effective amount of an anti-C3d antibody conjugate of claim 2; (b) allowing said anti-C3d antibody conjugate to bind to a C3 protein fragment within said individual thereby forming an anti-C3d antibody conjugate-C3 protein fragment complex; and (c) detecting said anti-C3d antibody conjugate-C3 protein fragment complex in said individual.

16. The method of claim 15, wherein said detecting comprises fluorescent spectroscopy.

17. The method of claim 15, wherein said detecting comprises magnetic resonance imaging, computed tomography, positron emission tomography, single photon emission computed tomography, ultrasonography, or radiography.

18. The method of claim 15, wherein said complement-mediated inflammation is ocular inflammation.

19. The method of claim 18, wherein said ocular complement-mediated inflammation is associated with age-related macular degeneration.

20. The method of claim 15, wherein said complement-mediated inflammation is associated with tissue damage resulting from cancer, an ischemia reperfusion injury, an inflammatory disorder, transplant rejection (cellular or antibody mediated), a pregnancy-related disease, an adverse drug reaction, age-related macular degeneration, glomerulonephritis, or an autoimmune or immune complex disorder.

* * * * *